(12) United States Patent
Mundt et al.

(10) Patent No.: US 11,261,464 B2
(45) Date of Patent: *Mar. 1, 2022

(54) PROMOTERS

(71) Applicant: Boehringer Ingelheim Vetmedica GmbH, Ingelheim am Rhein (DE)

(72) Inventors: Alice Mundt, Isernhagen (DE); Andreas Gallei, Wedemark (DE); Ramesh Koukuntla, Ames, IA (US); Robert Barry Mandell, Collins, IA (US); Kristina Rehmet, Hannover (DE); Eric Martin Vaughn, Ames, IA (US)

( * ) Notice: Subject to any disclaimer, the term of this patent is extended or adjusted under 35 U.S.C. 154(b) by 741 days.

This patent is subject to a terminal disclaimer.

(21) Appl. No.: 15/706,892

(22) Filed: Sep. 18, 2017

(65) Prior Publication Data

US 2018/0080047 A1 Mar. 22, 2018

(30) Foreign Application Priority Data

Sep. 20, 2016 (EP) ..................................... 16189780

(51) Int. Cl.

| C12N 15/861 | (2006.01) |
|---|---|
| C07K 14/005 | (2006.01) |
| A61K 39/12 | (2006.01) |
| C12N 7/04 | (2006.01) |
| C12N 15/85 | (2006.01) |
| C12N 15/86 | (2006.01) |
| A61K 39/00 | (2006.01) |

(52) U.S. Cl.
CPC .......... *C12N 15/8613* (2013.01); *A61K 39/12* (2013.01); *C07K 14/005* (2013.01); *C12N 7/045* (2013.01); *C12N 15/85* (2013.01); *C12N 15/86* (2013.01); *A61K 2039/51* (2013.01); *A61K 2039/543* (2013.01); *A61K 2039/545* (2013.01); *A61K 2039/552* (2013.01); *C12N 2710/00034* (2013.01); *C12N 2710/00043* (2013.01); *C12N 2710/00045* (2013.01); *C12N 2710/10044* (2013.01); *C12N 2710/10062* (2013.01); *C12N 2710/16034* (2013.01); *C12N 2710/16734* (2013.01); *C12N 2710/16744* (2013.01); *C12N 2760/12034* (2013.01); *C12N 2760/16134* (2013.01)

(58) Field of Classification Search
CPC ........ C12N 7/045; C12N 15/85; C12N 15/86; C12N 15/8613; C07K 14/005; A61K 39/12

See application file for complete search history.

(56) References Cited

U.S. PATENT DOCUMENTS

| 3,857,423 | A | 12/1974 | Ronca, Jr. | |
|---|---|---|---|---|
| 5,616,326 | A | 4/1997 | Spibey | |
| 5,820,868 | A | 10/1998 | Mittal et al. | |
| 5,851,521 | A | 12/1998 | Branellec et al. | |
| 6,090,393 | A | 7/2000 | Fischer | |
| 6,110,735 | A | 8/2000 | Chartier et al. | |
| 6,127,175 | A | 10/2000 | Vigne et al. | |
| 6,156,567 | A | 12/2000 | Fischer | |
| 6,193,983 | B1 | 2/2001 | Crabb et al. | |
| 6,261,807 | B1 | 7/2001 | Crouzet et al. | |
| 6,294,377 | B1 | 9/2001 | Haddada et al. | |
| 6,420,170 | B1 | 7/2002 | Perricaudet et al. | |
| 6,669,942 | B2 | 12/2003 | Perricaudet et al. | |
| 7,037,723 | B1 | 5/2006 | Helibronn | |
| 7,744,900 | B2 | 6/2010 | Dubensky, Jr. et al. | |
| 8,119,396 | B2 | 2/2012 | Eloit et al. | |
| 10,329,586 | B2 * | 6/2019 | Gallei | A61K 48/00 |
| 10,619,169 | B2 * | 4/2020 | Mundt | C12N 15/86 |
| 10,626,414 | B2 * | 4/2020 | Gallei | A61P 37/04 |
| 2001/0014319 | A1 | 8/2001 | Denefle et al. | |
| 2002/0006395 | A1 | 1/2002 | Perricaudet et al. | |
| 2003/0096787 | A1 | 5/2003 | Perricaudet et al. | |
| 2003/0100116 | A1 | 5/2003 | Kremer et al. | |
| 2004/0109873 | A1 | 6/2004 | Neubauer et al. | |
| 2011/0091490 | A1 | 4/2011 | Okazaki et al. | |
| 2011/0110892 | A1 | 5/2011 | Desrosiers | |
| 2011/0236419 | A1 | 9/2011 | Audonnet et al. | |
| 2018/0080043 | A1 | 3/2018 | Mundt et al. | |
| 2018/0080044 | A1 | 3/2018 | Gallei et al. | |
| 2018/0080045 | A1 | 3/2018 | Gallei et al. | |
| 2018/0080047 | A1 | 3/2018 | Mundt et al. | |

FOREIGN PATENT DOCUMENTS

| EP | 0512017 B1 | 6/1997 |
|---|---|---|
| EP | 1118670 A1 | 7/2001 |
| EP | 0736100 B1 | 3/2002 |

(Continued)

OTHER PUBLICATIONS

Madin et al.; Established Kidney Cell Lines of Normal Adult Bovine and Ovine Origin; Proceedings of the Society for Experimental Biology and Medicine, vol. 98, No. 3, pp. 574-576, published: Jul. 1, 1958 (Year: 1958).*

Van Olphen et al., "Generation of infectious genome of bovine adenovirus type 3 by homologous recombination in bacteria." Journal of Virological Methods, vol. 77, 1999, pp. 125-129.

Von Einem et al. "In vitro and in vivo characterization of equine herpesvirus type 1 (EHV-1) mutants devoid of the viral chemokine-binding glycoprotein G (gG)." Virology, vol. 362, 2007, pp. 151-162.

(Continued)

*Primary Examiner* — Antonio Galisteo Gonzalez
(74) *Attorney, Agent, or Firm* — Steffan Finnegan

(57) ABSTRACT

The present invention relates to the field of (vector) vaccines, and especially to novel promoter sequences, expression cassettes and vectors, which are suitable to express genes of interest, especially antigen encoding sequences. The viral vectors of the present invention are useful for producing an immunogenic composition or vaccine.

14 Claims, 33 Drawing Sheets

Specification includes a Sequence Listing.

(56) References Cited

FOREIGN PATENT DOCUMENTS

| EP | 0979101 B1 | 10/2010 |
|---|---|---|
| JP | 2019531724 | 11/2019 |
| KR | 20050055689 | 6/2005 |
| WO | 199111525 A2 | 8/1991 |
| WO | 199522607 A1 | 8/1995 |
| WO | 199800166 A1 | 1/1998 |
| WO | 200008165 A1 | 2/2000 |
| WO | 0142481 A2 | 6/2001 |
| WO | 2004009802 | 1/2004 |
| WO | 2007081336 A1 | 7/2007 |
| WO | 2007115059 A2 | 10/2007 |
| WO | 2018054822 A1 | 3/2018 |
| WO | 2018054837 A1 | 3/2018 |
| WO | 2018054840 A1 | 3/2018 |
| WO | 2018057441 | 3/2018 |
| WO | 2018057441 A1 | 3/2018 |

OTHER PUBLICATIONS

Xue et al., "Vaccination with a modified-live bovine viral diarrhea virus (BVDV) type 1a vaccine completely protected calves against challenge with BVDV type 1b strains." Vaccine, vol. 29, 2011, pp. 70-76.
Yang et al., "Complete protection of cats against feline panleukopenia virus challenge by a recombinant canine adenovirus type 2 expressing VP2 from FPV." Vaccine, vol. 26, 2008, pp. 1482-1487.
Zhang et al., "Oral vaccination of dogs (Canis familiaris) with baits containing the recombinant rabies-canine adenovirus type-2 vaccine confers long-lasting immunity against rabies." Vaccine, vol. 26, 2008, pp. 345-350.
Babiuk et al, "Adenoviruses as vectors for delivering vaccines to mucosal surfaces." Journal of Biotechnology, vol. 83, 2000, pp. 105-113.
Bangari et al. "Development of nonhuman adenoviruses as vaccine vectors." Vaccine, vol. 24, No. 7, Feb. 2006, pp. 849-862.
Bouet-Cararo et al., "Canine adenoviruses elicit both humoral and cell-mediated immune responses against rabies following immunisation of sheep." Vaccine, vol. 29, 2011, pp. 1304-1310.
Bru et al., "An Update on Canine Adenovirus Type 2 and Its Vectors." Viruses, vol. 2, 2010, pp. 2134-2153.
Brun et al., "Antigen delivery systems for veterinary vaccine development Viral-vector based delivery systems." Vaccine, vol. 26, 2008, pp. 6508-6528.
Chapman et al., "Effect of intron a human cytomegalovirus (Towne) immediate-early gene on heterologous expression in mammalian cells." Nucleic Acids Research, vol. 19, No. 14, 1991, pp. 3979-3986.
Chartier et al., "Efficient Generation of Recombinant Adenovirus Vectors by Homologous Recombination in *Escherichia coli*." Journal of Virology, vol. 70, No. 7, Jul. 1996, pp. 4805-4810.
Chengalvala et al, "Adenovirus vectors for gene expression." Current Opinion in Biotechnology, vol. 2, No. 5, Oct. 1991, pp. 718-722.
Dai et al., "Cellular and humoral immune responses to adenoviral vectors containing factor IX gene: Tolerization of factor IX and vector antigens allows for long-term expression." Proceedings of the National Academy of Sciences, vol. 92, Feb. 1995, pp. 1401-1405.
De Turiso et al., "Recombinant Vaccine for Canine Parvovirus in Dogs." Journal of Virology, vol. 66, No. 5, May 1992, pp. 2748-2753.
Dong et al., "Systematic Analysis of Repeated Gene Delivery into Animal Lungs with a Recombinant Adenovirus Vector." Human Gene Therapy, vol. 7, No. 3, Feb. 10, 1996, pp. 319-331.
Fallaux et al., "New Helper Cells and Matched Early Region 1-Deleted Adenovirus Vectors Prevent Generation of Replication-Competent Adenoviruses." Human Gene Therapy, vol. 9, Sep. 1, 1998, pp. 1909-1917.

Fischer et al., "Vaccination of puppies born to immune dams with a canine adenovirus-based vaccine protects against a canine distemper virus challenge." Vaccine, vol. 20, 2002, pp. 3485-3497.
Ghosh-Choudhury et al., "Human adenovirus cloning vectors based on infectious bacterial plasmids." Gene, vol. 50, Nos. 1-3, 1986, pp. 161-171.
Haj-Ahmad et al., "Development of a helper-independent human adenovirus vector and its use in the transfer of the herpes simplex virus thymidine kinase gene." Journal of Virology, vol. 57, No. 1, Jan. 1986, pp. 267-274.
Henderson et al., "Oral immunization of raccoons and skunks with a canine adenovirus recombinant rabies vaccine." Vaccine, vol. 27, 2009, pp. 7194-7197.
Hsu et al., "Efficacy of adenovirus-vectored respiratory syncytial virus vaccines in a new ferret model." Vaccine, vol. 12, No. 7, 1994, pp. 607-612.
Hu et al., "Experimental immunization of cats with a recombinant rabies-canine adenovirus vaccine elicits a long-lasting neutralizing antibody response against rabies." Vaccine, vol. 25, 2007, pp. 5301-5307.
Hu et al., "Prevention of rabies virus infection in dogs by a recombinant canine adenovirus type-2 encoding the rabies virus glycoprotein." Microbes and Infection, vol. 8, 2006, pp. 1090-1097.
Huang et al., "Glycoprotein G deletion mutants of equine herpesvirus 1 (EHV1; equine abortion virus) and EHV4 (equine rhinopneumonitis virus)." Archives of Virology, vol. 150, 2005, pp. 2583-2592.
Imler, Jean-Luc, "Adenovirus vectors as recombinant viral vaccines." Vaccine, vol. 13, No. 13, 1995, pp. 1143-1151.
International Search Report and Written Opinion for PCT/EP2017/073481 dated Dec. 7, 2017.
Kapoor et al., "A nonessential glycoprotein is coded by early region E3 of adenovirus type 7." Virology, vol. 112, No. 2, Jul. 30, 1981, pp. 780-784.
Kelly et al., "Use of Nondefective Adenovirus-Simian Virus 40 Hybrids for Mapping the Simian Virus 40 Genome." Journal of Virology, vol. 12, No. 3, Sep. 1973, pp. 643-652.
Kremer et al., "Canine Adenovirus Vectors: an Alternative for Adenovirus-Mediated Gene Transfer." Journal of Virology, vol. 74, No. 1, 2000, pp. 505-512.
Levrero et al., "Defective and nondefective adenovirus vectors for expressing foreign genes in vitro and in vivo." Gene, vol. 101, No. 2, May 30, 1991, pp. 195-202.
Li et al., "A single immunization with a recombinant canine adenovirus expressing the rabies virus G protein confers protective immunity against rabies in mice." Virology, vol. 356, 2006, pp. 147-154.
Linné, Tommy, "Differences in the E3 regions of the canine adenovirus type 1 and type 2." Virus Research, vol. 23, Nos. 1-2, Apr. 1992, pp. 119-113.
Liu et al., "Efficacy and safety of a live canine adenovirus-vectored rabies virus vaccine in swine." Vaccine, vol. 26, 2008, pp. 5368-5372.
Lubeck et al., "Immunogenicity and efficacy testing in chimpanzees of an oral hepatitis B vaccine based on live recombinant adenovirus." Proceedings of the National Academy of Sciences USA, vol. 86, No. 17, Sep. 1989, pp. 6763-6767.
Ma et al., "An Equine Herpesvirus Type 1 (EHV-1) Expressing VP2 and VP5 of Serotype 8 Bluetongue Virus (BTV-8) Induces Protection in a Murine Infection Model." PLoS ONE, vol. 7, No. 4, Apr. 2012, e34425, pp. 1-9.
Massie et al., "New adenovirus vectors for protein production and gene transfer." Cytotechnology, vol. 28, 1998, pp. 53-64.
Mittal et al., "Pathology and immunogenicity in the cotton rat (*Sigmodon hispidus*) model after infection with a bovine adenovirus type 3 recombinant virus expressing the firefly luciferase gene." Journal of General Virology, vol. 77, 1996, pp. 1-9.
Morin et al., "Recombinant adenovirus induces antibody response to hepatitis B virus surface antigen in hamsters." Proceedings of the National Academy of Sciences, USA, vol. 84, Jul. 1987, pp. 4626-4630.

(56) References Cited

OTHER PUBLICATIONS

Morrison et al., "Generation of E3-Deleted Canine Adenoviruses Expressing Canine Parvovirus Capsid by Homologous Recombination in Bacteria." Virology, vol. 293, 2002, pp. 26-30.

Nagesha et al., "Analysis of the nucleotide sequence of five genese at the left end of the unique short region of the equine herpesvirus 4 genome." Archives of Virology, vol. 128, 1993, pp. 143-154.

Natuk et al., "Immunogenicity of Recombinant Human Adenovirus-Human Immunodeficiency Virus Vaccines in Chimpanzees." AIDS Research and Human Retroviruses, vol. 9, No. 5, May 1993, pp. 395-404.

Prevec et al., "Use of Human Adenovirus-based Vectors for Antigen Expression in Animals." Journal of General Virology, vol. 70, 1989, pp. 429-434.

Reddy et al., "Development of porcine adenovirus-3 as an expression vector." Journal of General Virology, vol. 80, 1999, pp. 563-570.

Said et al., "An equine herpesvirus 1 (EHV-1) vectored H1 vaccine protects against challenge with swine-origin influenza virus H1N1." Veterinary Microbiology, vol. 154, 2011, pp. 113-123.

Said et al., "Recombinant equine herpesvirus 1 (EHV-1) vaccine protects pigs against challenge with influenza A (H1N1)pmd09". Virus Research, vol. 173, 2013, pp. 371-376.

Said, Abdelrahman, "Development of a vectored equine herpesvirus type 1 (EHV-1) vaccine against pandemic influenza A virus (09/H1N1)." Inaugural-Dissertation, Berlin, 2013, Journal-Nr: 3637, pp. 1-83. [Accessed at: http://www.diss.fu-berlin.de/diss/servlets/MCRFileNodeServlet/FUDISS_derivate_000000013293/Said_online.pdf retrieved on Mar. 8, 2017].
Saito et al., "Construction of nondefective adenovirus type 5 bearing a 2.8-kilobase hepatitis B virus DNA near the right end of its genome." Journal of Virology, vol. 54, No. 3, Jun. 1985, pp. 711-719.
Shibata et al., "Nucleotide Sequence of E1 Region of Canine Adenovirus Type 2." Virology, vol. 172, 1989, pp. 460-467.
Spibey et al., "Identification and nucleotide sequence of the early region 1 from canine adenovirus types 1 and 2." Virus Research, vol. 14, No. 3, Nov. 1989, pp. 241-255.
Spibey et al., "Molecular Cloning and Restriction Endonuclease Mapping of Two Strains of Canine Adenovirus Type 2." Journal of General Virology, vol. 70, 1989, pp. 165-172.
Tartaglia et al., "Protection of Cats against Feline Leukemia Virus by Vaccination with a Canarypox Virus Recombinant, ALVAC-FL." Journal of Virology, vol. 67, N. 4, Apr. 1993, pp. 2370-2375.
Telford et al., "The DNA sequence of equine herpesvirus-4." Journal of General Virology, vol. 79, 1998, pp. 1197-1203.
Trapp et al. "Potential of Equine Herpesvirus 1 as a Vector for Immunization." Journal of Virology, vol. 79, No. 9, May 2005, pp. 5445-5454.
Van De Walle et al., "Analysis of the Herpesvirus Chemokine-binding Glycoprotein G Residues Essential for Chemokine Binding and Biological Activity." The Journal of Biological Chemistry, vol. 384, No. 9, Feb. 27, 2009, pp. 5968-5976.
Telford, E. A. et al., NCBI Reference Sequence [online], Apr. 23, 2010, Database Accession No. NC_001844.
Equine herpesvirus 4 strain NS80567, complete genome, NCBI GenBank: AF030027.1 (May 21, 1998).

* cited by examiner

FIG. 3
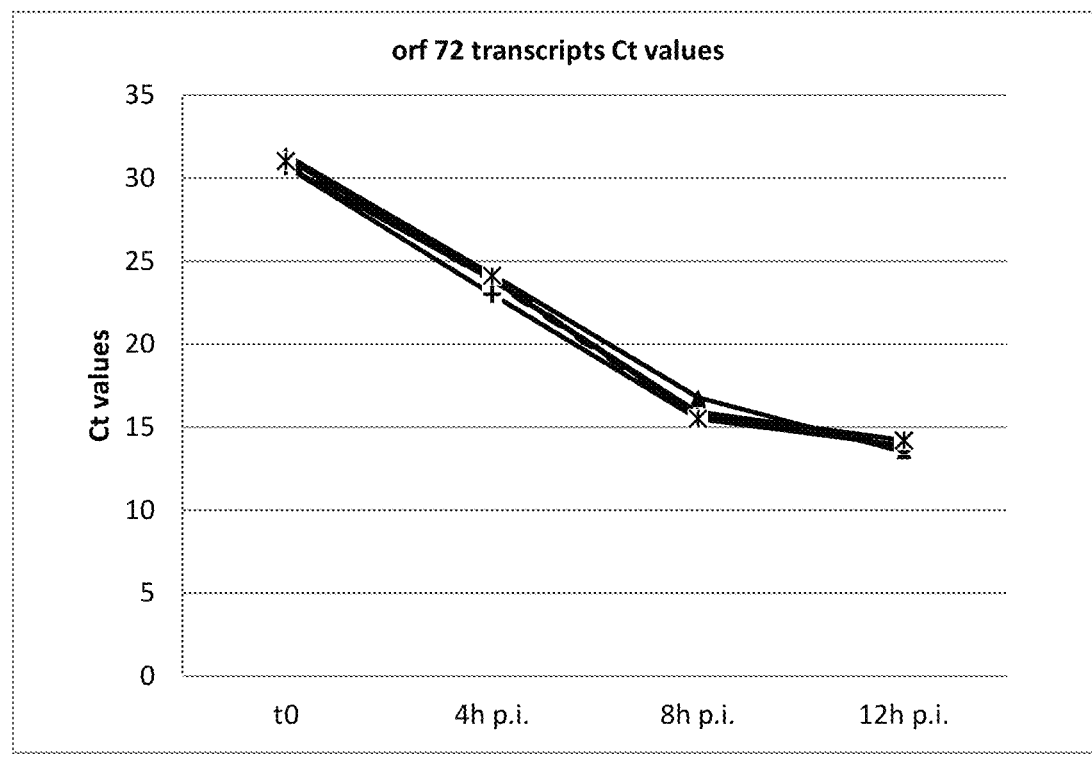
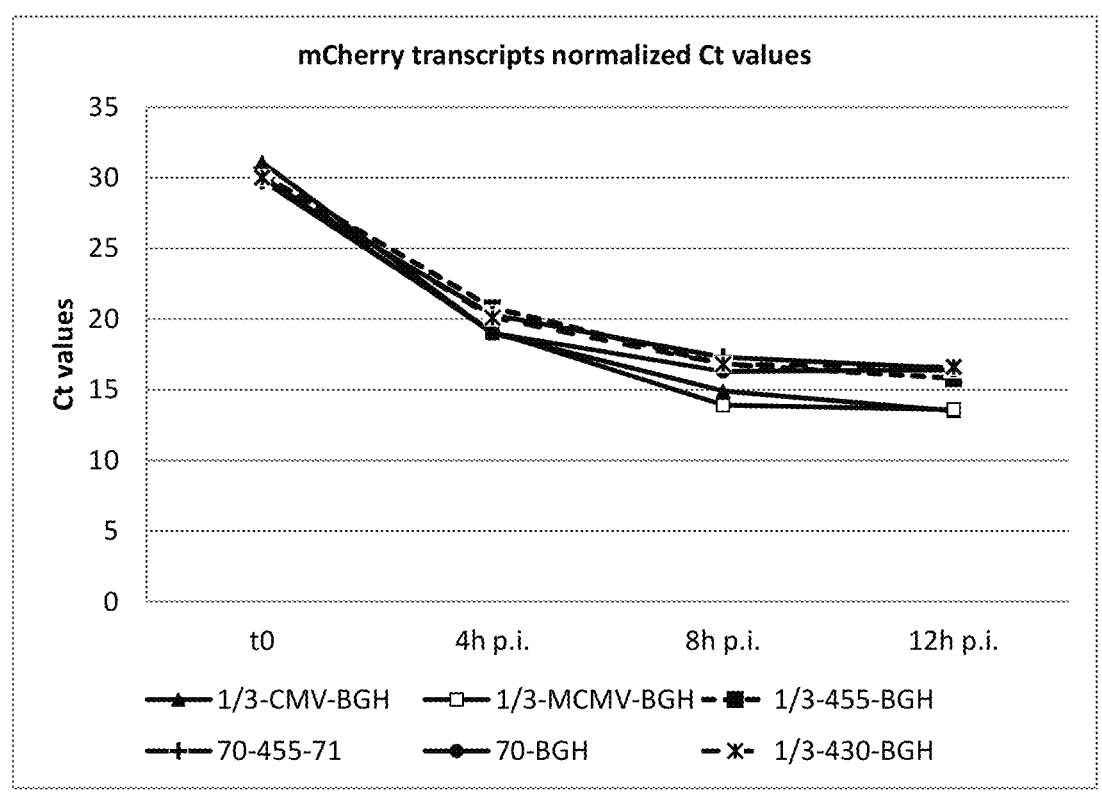

| | 1/3-CMV-BGH (V) | 1/3-MCMV-BGH (V) | 1/3-455-BGH (V) | 70-455-71 (V) | 70-egGp-BGH (V) | 1/3-430-BGH (V) | | 1/3-CMV-BGH (P) | 1/3-MCMV-BGH (P) | 1/3-455-BGH (P) | 70-455-71 (P) | 70-egGp-BGH (P) | 1/3-430-BGH (P) |
|---|---|---|---|---|---|---|---|---|---|---|---|---|---|
| 4 h p.i. | 5.46 | 5.17 | 4.95 | 5.19 | 5.43 | 5.96 | | 11.2 | 11.1 | 9.4 | 9.9 | 11.2 | 10.1 |
| 8 h p.i. | 7.77 | 10.42 | 8.06 | 9.05 | 9.06 | 9.9 | | 15.3 | 16.3 | 13.4 | 12.9 | 13.9 | 13.4 |
| 12 h p.i. | 8.04 | 10.67 | 8.39 | 9.93 | 9.48 | 9.1 | | 16.7 | 16.6 | 14.4 | 13.7 | 13.8 | 13.6 |

FIG. 5

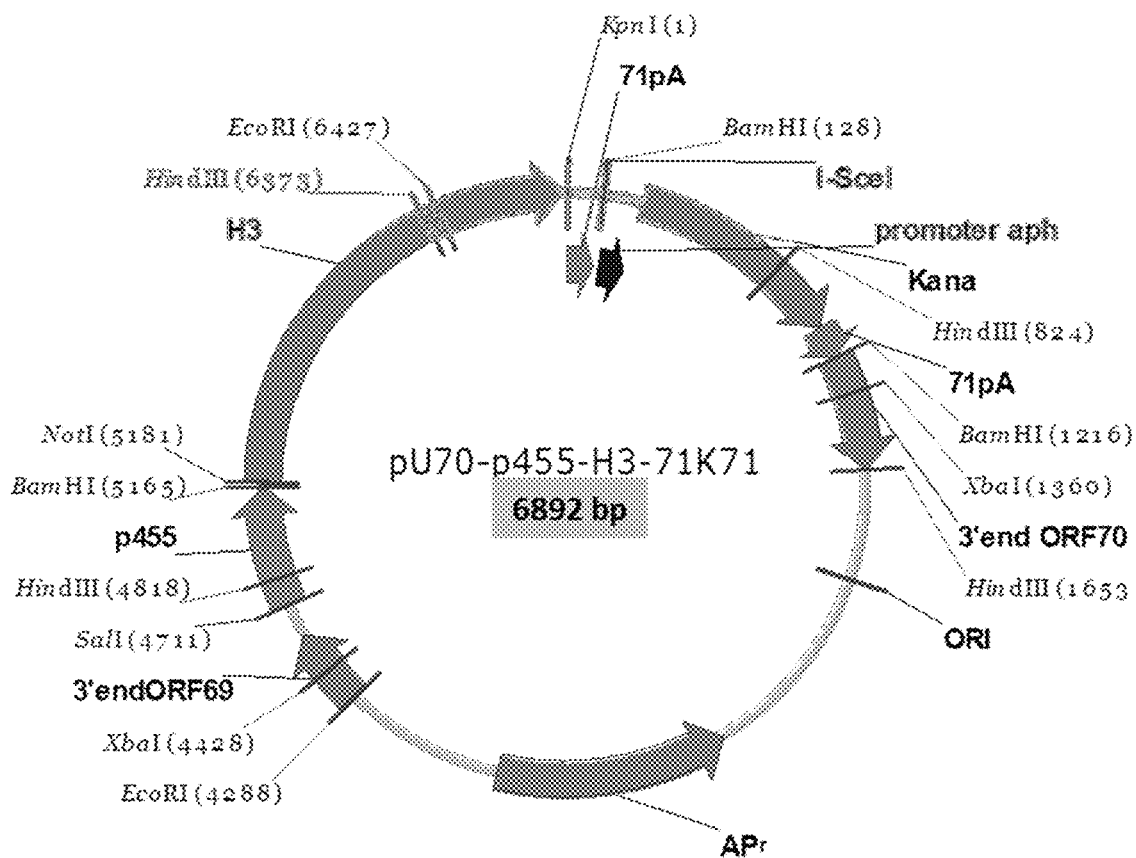

| | |
|---|---|
| 3'end ORF69 | viral genomic DNA sequence flanking the insertion site upstream |
| 3'end ORF70 | viral genomic DNA sequence flanking the insertion site downstream |
| p455 | promoter driving expression of transgene |
| H3 | transgene (IAV hemagglutinin) |
| 71pA | polyadenylation sequence |
| I-Sce1 | cleavage site for I-Sce1 |
| promoter aph | prokaryotic promoter driving expression of Kanamycin-resistence gene |
| Kana | Kanamycine resistance orf |
| ORI | origin of replication of

FIG. 7 rEHV-1 RacH-SE70-455-H3

Anti-H3 monoclonal antibody

FIG. 8

1: rEHV-1 RacH-SE-70-p455-H3 P5 infected cells
2: rEHV-1 RacH-SE-70-p455-H3 P10 infected cells
3: rEHV-1 RacH-SE-70-p455-H3 P15 infected cells
4: rEHV-1 RacH-SE-70-p455-H3 P20 infected cells
5: rEHV-1 RacH-mC70 infected cells
6: non-infected cells FIG. 9
A.
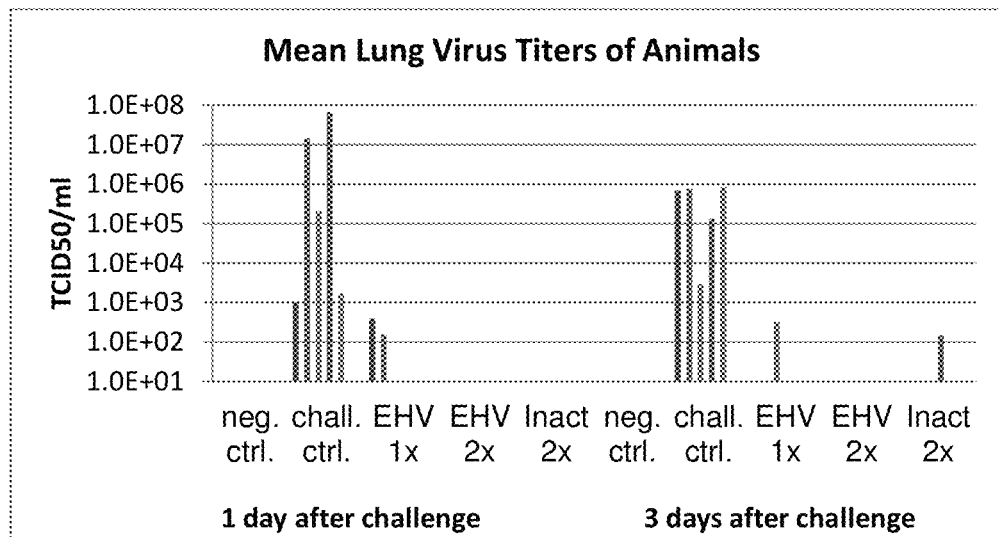
B.
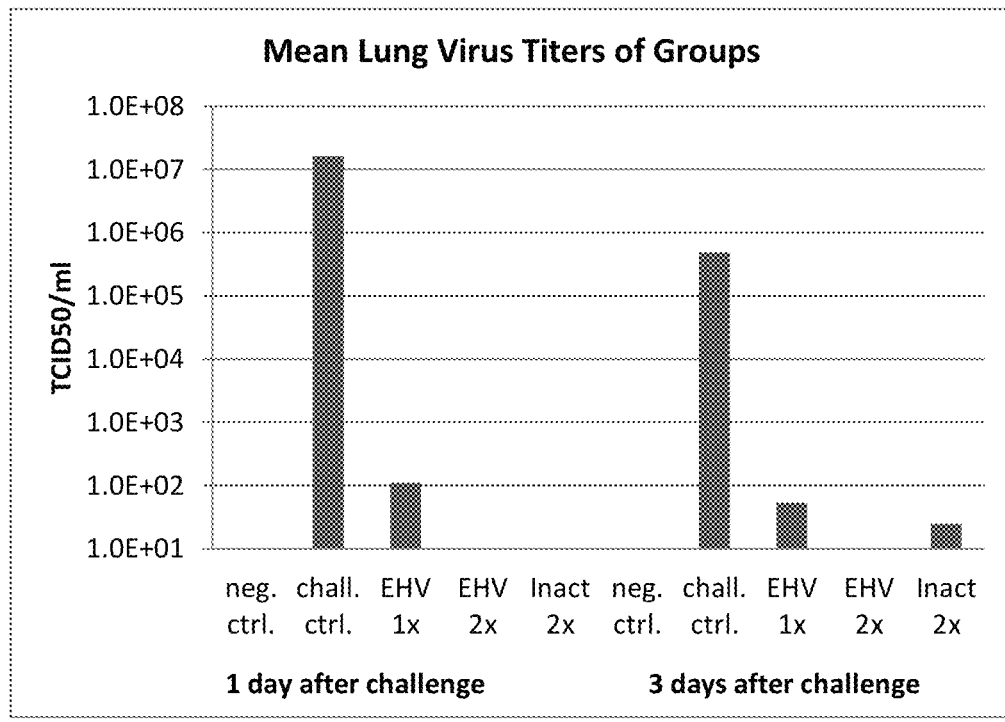

| | |
|---|---|
| Flank A | viral genomic DNA sequence flanking the insertion site upstream |
| Flank B | viral genomic DNA sequence flanking the insertion site downstream |
| p430 | promoter driving expression of the transgene |
| H1av | transgene (IAV hemagglutinin) |
| BGHpA | polyadenylation sequence |
| I

FIG. 12

| Western blot | IFA |
|---|---|
| H1av  SE  mock | H1av – infected VERO-cells |

Markers: 250, 150, 100, 75, 50, 37

Anti H1 polyclonal antibody PA-34929

Anti-H1 monoclonal antibody C102

H1av = rEHV-1 RacH-SE1/3-430-H1av
SE = rEHV-RacH-SE (control)
mock = uninfected cells (control)

| Recombinant virus | Mean CAV-2 Protein | CAV-2 Infected Cells (%) | Mean VP2 Protein | VP2 Expressing Cells (%) |
|---|---|---|---|---|
| CAV2 CMVie BRSV F | 518113 | 48.47 | n/a | 0.23 |
| CAV2 CMVie CPV VP2 (Despl) | 656218 | 62.21 | 178929 | 2.61 |
| CAV2 CMVie CPV VP2 (Gen0.95) | 697527 | 63.99 | 164591 | 2.59 |

| Recombinant virus | Mean CAV-2 Protein | CAV-2 Infected Cells (%) | Mean VP2 Protein | VP2 Expr. Cells (%) | Mean VP2 Protein | VP2 Expr. Cells (%) |
|---|---|---|---|---|---|---|
| CAV2 CMVie BRSV F | 249037 | 16.13 | 47389 | 0.80 | n/a | 0.45 |
| CAV2 gG430 CPV VP2 (Despl) | 265134 | 18.28 | 151824 | 18.20 | 260564 | 14.17 |
| CAV2 gG430 CPV VP2 (Gen0.95) | 292271 | 32.82 | 136458 | 28.31 | 221600 | 19.68 |
| CAV2 MCP455 CPV VP2 (Gen0.95) | 248349 | 24.65 | 188663 | 35.78 | 292102 | 29.73 |
| | Anti-CAV2-FITC pAb | | Anti-CPV VP2-FITC | | Anti-CPV VP2 pAb | |

| PBS dilution | | | | | | | |
|---|---|---|---|---|---|---|---|
| 1/64 | 1/32 | 1/16 | 1/8 | 1/4 | 1/2 | 1 | |
|  |  |  |  |  |  |  | CAV-2 CMVie BRSV F |
|  |  | ● | ● | ● | ● | ● | CAV-2 gG430 CPV VP2 (Despl) (sup/lysate) |
|  |  |  |  |  | ● | ● | CAV-2 gG430 CPV VP2 (Gen0.95) (sup/lysate) |
|  | ● | ● | ● | ● | ● | ● | CAV-2 MCP CPV VP2 (Gen0.95) (sup/lysate) |

B

| | Supernatants/lysates from recombinant virus-infected cells | | | |
|---|---|---|---|---|
| Rec. Virus | CAV-2 CMVie BRSV F | CAV-2 gG430 CPV VP2 (Despl) | CAV-2 gG430 CPV VP2 (Gen0.95) | CAV-2 MCP CPV VP2 (Gen0.95) |
| Dilution 1 | - | ++++ | ++ | ++++ |
| 0.5 | - | +++ | + | ++++ |
| 0.25 | - | +++ | + | ++++ |
| 0.125 | - | +++ | + | ++++ |
| 0.0625 | - | ++ | +/- | +++ |
| 0.0312 | - | + | - | ++ |
| 0.0156 | - | +/- | - | + |

FIG. 18

| Recombinant virus | Mean CAV-2 Protein | CAV-2 Infected Cells (%) | Mean RabG Protein | rabG Expressing Cells (%) |
|---|---|---|---|---|
| CAV2 gG430 CPV VP2 (Gen0.95) | 516801 | 46.22 | n/a | 0.63 |
| Original CAV2 CMVie RabG (n) | 375281 | 16.79 | 33298 | 1.58 |
| CAV2 MCP455 RabG (n) | 542598 | 54.41 | 90294 | 14.22 |
| | Anti-CAV2-FITC pAb | | Anti-RabG-FITC | |

FIG. 19
A
IFA for CPV VP2 expression in infected AI-ST 2015 cells
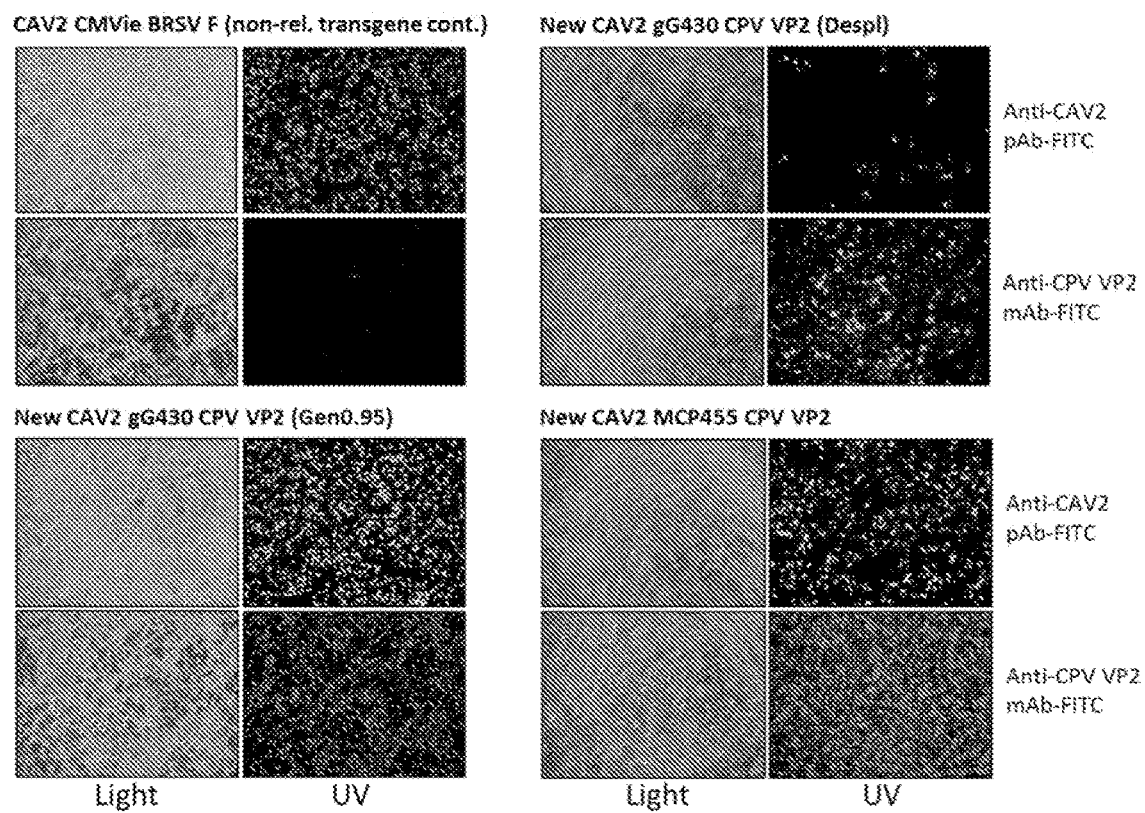
B
IFA for RabG expression in AI-ST 2015 cells.
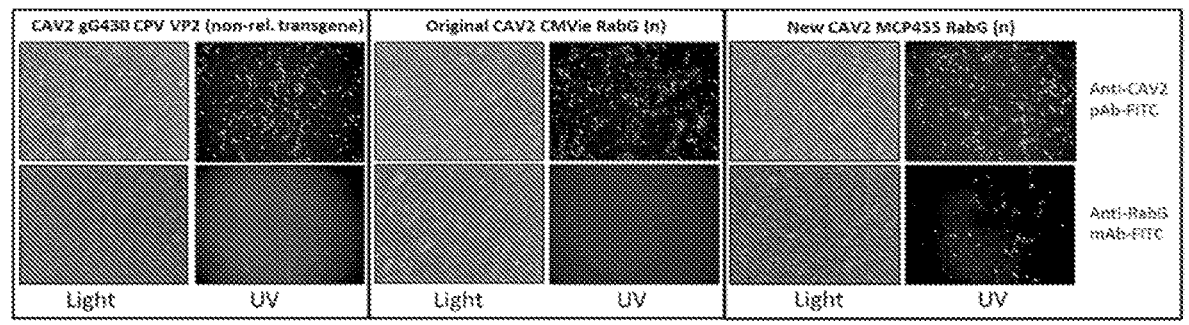

C
IFA for RabG expression in BIVI 2011 MDCK cells – dual stain for RabG and CAV-2

FIG. 21

Lung Scores of Groups (Bar chart showing percentages from 0.00% to 12.00% for groups: neg. ctrl. day 1, neg. ctrl. day 3, chall. ctrl. day 1, chall. ctrl. day 3, 1x EHV-1 day 1, 1x EHV-1 day 3, 2x EHV-1 day 1, 2x EHV-1 day 3, 2x killed day 1, 2x killed day 3)

FIG. 22

Reciprocal SN Titers of Animals (Bar chart with y-axis log scale from 20 to 5120 for groups: neg ctrl., chall. ctrl, 1x EHV-1, 2x EHV-1, 2x killed)

IL-1ß-ELISA from BALF

FIG. 25

*Kpn* I (1)
BGHpA (2-226)
*Hin* dIII (202)
*Bam* HI (226)
I-SceI
H1hu (4972-6666)
promoter aph (249-371)
Kana (372-1184)
*Hin* dIII (902)
BGHpA (1194-1417)
*Hin* dIII (4982)
*Bam* HI (1418)
*Not* I (4966)
Flank B (1430-1655)
pU1-3-p430-H1hu BGHKBGH
6671 bp
p430 (4533-4962)
I-CeuI
*Sal* I (4527)
*Hin* dIII (1668)
Flank A (4359-4519)
I-CeuI
*Eco* RI (4823)
*Sca* I (3120)

| | |
|---|---|
| Flank A | viral genomic DNA sequence flanking the insertion site upstream |
| Flank B | viral genomic DNA sequence flanking the insertion site downstream |
| p430 | promoter driving expression of the transgene |
| H1hu | transgene (IAV hemagglutinin) |
| BGHpA | polyadenylation sequence |
| I-Sce1 | cleavage site for I-Sce1 |
| I-Ceu 1 | cleavage site for I-Ceu1 |
| promoter aph | prokaryotic promoter driving expression of Kanamycin-resistence gene |
| Kana | Kanamycine resistance orf |
| ScaI, EcoRI, SalI, NotI, HindIII, KpnI, BamHI indicate restriction endonuclease cleavage sites | |

FIG. 26

Plasmid map: pU70-p455-H1pdm 71K71, 6892 bp

Features labeled on map:
- Kpn I (1)
- 71pA (2-226)
- Bam HI (128)
- promoter aph (151-273)
- Kana (274-1089)
- Hin dIII (824)
- 71pA (1090-1214)
- Bam HI (1216)
- Xba I (1360)
- 3'end orf70 (1221-165)
- Hin dIII (1663)
- Sca I (3385)
- Eco RI (4288)
- Xba I (4428)
- upstream orf70 (4293-4709)
- Sal I (4711)
- Hin dIII (4818)
- p455 (4714-5168)
- Bam HI (5165)
- Not I (5181)
- Eco RI (5771)
- H1pdm (5187-6887)
- Eco RI (6694)

| | |
|---|---|
| 3'end ORF69 | viral genomic DNA sequence flanking the insertion site upstream |
| 3'end ORF70 | viral genomic DNA sequence flanking the insertion site downstream |
| p455 | promoter driving expression of transgene |
| H1pdm | transgene (IAV hemagglutinin) |
| 71pA | polyadenylation sequence |
| I-Sce1 | cleavage site for I-Sce1 |
| promoter aph | prokaryotic promoter driving expression of Kanamycin-resistence gene |
| Kana | Kanamycine resistance orf |

ScaI, EcoRI, SalI, NotI, HindIII, KpnI, BamHI, XbaI indicate restriction endonuclease cleavage sites

FIG. 29

Neutralizing capacities of mice sera to 100 TCID50 of IAV

(Bar chart: reciprocal serum dilution, y-axis from 1 to 1024, log scale. Bars for H3N2: PatViB-1, PatViB-2, PatViB-3, PatViB-4, PatViB-5; Bars for H1avN1: PatViB-1, PatViB-2, PatViB-3, PatViB-4, PatViB-5, PatVi3-1, PatVi3-2, PatVi3-3, PatVi3-4, PatVi3-5.)

FIG. 30 pU70-455-SBVGc 71K71@1
6124 bp

Features: p455, Not I (1), signal peptide, SBVGc, GS-linker, TM-anchor, Kpn I (945), 71pA, promoter aph, Kana, 71pA, Xba I (2304), 3'end US4, Xba I (5372), upstream US4, Sal I (5655)

FIG. 31

A unvaccinated control rEHV-SBV-Gc

FIG. 31 (Cont'd)

B unvaccinated control rEHV-SBV-Gc

FIG. 32 rEHV-SBV-Gc

PROMOTERS

SEQUENCE LISTING

The Sequence Listing associated with this application is provided in text format in lieu of a paper copy, and is hereby incorporated by reference into the specification. The name of the text file containing the Sequence Listing is 01-3202-US-1-SEQ.txt. The text file is 74,813 bytes; it was created on 14 Sep. 2017; and it is being submitted electronically via EFS-Web, concurrent with the filing of the specification.

BACKGROUND OF THE INVENTION

A. Field of the Invention

The present invention relates to the field of (vector) vaccines, and especially to novel promoter sequences, expression cassettes and vectors, which are suitable to express genes of interest, especially antigen encoding sequences. The viral vectors of the present invention are useful for producing an immunogenic composition or vaccine.

B. Background and Description of the Related Art

The horse pathogen Equid Alphaherpesvirus 1 (Equine abortion virus, EHV-1) belongs to the genus *Varicellovirus* in the subfamily Alphaherpesvirinae in the family Herpesviridae in the order Herpesvirales. It is a large, enveloped virus with a double-stranded DNA genome of approximately 150,000 base pairs. Other important members of the subgenus *Varicellovirus* are the Human Alphaherpesvirus 3 (Varicella Zoster Virus), Suid Alphaherpesvirus 1 (Pseudorabies virus), Bovine Alphaherpesvirus 1 (Infectious Bronchitis Virus), and Equid Alphaherpes Virus 4 (Equine Rhinopneumitis Virus, EHV-4) (Virus Taxonomy: 2015 Release EC 47, London, UK, July 2015; Email ratification 2016 (MSL #30)) EHV-1 and EHV-4 are endemic and affecting horses throughout the world. While EHV-4 causes a mostly mild infection of the upper respiratory tract, EHV-1 can cause systemic infection with a range of diseases from respiratory symptoms to abortion and lethal myeloencephalopathy depending on the strain and the immunological status of the host. Two licensed modified live vaccines (MLV) against EHV-1 are currently available in the USA and Europe, respectively, RHINOMUNEO™ (Boehringer Ingelheim) and PREVACCINOLO™ (MSD). Both contain the classically attenuated EHV-1 RacH strain, which was passaged 256 times in porcine epithelial cells for attenuation (Ma et al. 2013). The mechanism of attenuation has been investigated on the molecular level. Osterrieder et al. (1996) showed that RacH lacks the two genomic copies of orf67 and that restoration of one copy was sufficient to restore virulence. In addition, RacH carries a 1283 bp deletion removing more than 90% of the coding sequence of orf1 which encodes an immunosuppressive viral protein. Other mutations might also influence attenuation, but have not been investigated in detail, so far. All this makes RacH a very safe vaccine strain as a reversion to virulence by passaging in vaccinated animals is highly unlikely, if possible at all.

An *E. coli* bacterial artificial chromosome (BAC) harboring the entire genome of the Equid Alphaherpes Virus 1 (EHV-1) vaccine strain RacH (pRacH-SE) is known as a platform for vector vaccine development. It has been shown that EHV-1 RacH-based vector vaccines are able to elicit immunity in several mammalian species including pigs, cattle, and dogs (Rosas et al. 2007, Rosas et al. 2008, Trapp et al. 2005, Said et al. 2013). Genes coding for antigenic proteins of pathogens can be expressed by recombinant EHV-1 RacH. The EHV-1-RacH genome is manipulated in its BAC form in *E. coli* and tailored to express additional proteins usually by inserting transgene expression cassettes (Tischer et al., 2010). Upon transfection of pRacH-SE DNA in cultured permissive cells, EHV-1 replication is initiated by cellular transcription factors. Activity of the viral DNA polymerase leads to deletion of all BAC-vector related sequences and restoration of the EHV-1 RacH genome to its original state. Infectious virus is generated which is indistinguishable from RacH.

When pRacH-SE is manipulated in *E. coli* e.g. by insertion of transgene expression cassettes, virus reconstituted after transfection in permissive cells will carry the modification and will express the additional gene. The recombinant EHV-1 RacH can be used as a vector vaccine.

However, the amount of transgenic protein expressed without an additional exogenous promoter is usually relatively low. Thus, there is an unmet need for additional promoters that can be used to express transgenic proteins from such a vector, especially the recombinant EHV-1 RacH.

Wild-type EHV-1 strains possess three open reading frames (orf) called orf1, orf 2 and orf3 at one end of the long unique segment of their genome (sequence coordinates 1298-3614; FIG. 2). Orf1 and orf3 are serially arranged on one strand of the DNA while orf 2 is encoded by the complementary strand. The vaccine strain RacH has a 1283 bp deletion in that region affecting orfs 1 and 2 indicating that these genes are non-essential for viral replication. For this reason the site serves as a transgene insertion site. Using the Human cytomegalovirus immediate-early gene 1 promoter-enhancer (Boshart et al. 1985), transgenes have been reported to be efficiently expressed from the orf1/3 insertion site. In such studies the bovine growth hormone polyadenylation signal (BGH) was used to stabilize the transcripts for better expression (Ma et al. 2012; Said et al. 2013). Although there is no evidence that HCMV can induce tumors in humans, a theoretical risk cannot be excluded. Before the HCMV-IE enhancer was described (Boshart et 1. 1985) the majority of strong enhancers were discovered in the genomes of known oncogenic viruses like Simian Virus 40, polyoma viruses or Moloney murine sarcoma virus. While the extremely strong and non-tissue specific HCMV and MCMV (Mouse cytomegalovirus) IE promoters-enhancers are very well suited for a variety of research activities, they might not represent the first choice of promoter for transgenic vector vaccines in general. In particular the risk of accidental exposure of persons vaccinating animals could be viewed by the regulatory authorities as a hurdle for licensing a vaccine.

SUMMARY OF THE INVENTION

In order to avoid any such obstacles the present invention provides new regulatory nucleic acid sequences/promoter sequences for transgene expression, especially within the context of vector vaccines and especially within the context of the EHV-1 vector.

Thus, the solution to the above described technical problem is achieved by the description and the embodiments characterized in the claims and the invention in its different aspects is implemented according to the claims.

The present invention provides new regulatory nucleic acid sequences/promoter sequences for transgene expression, immunogenic compositions, vaccines, and related methods that overcome deficiencies in the art.

Established promoter sequences widely used to drive high levels of transgene expression in various vector systems including herpesviruses are the promoter sequences of immediate-early genes of HCMV (Boshart et al. 1985; Foecking and Hofstetter 1986) or the mouse cytomegalovirus (MCMV; Dorsch-Hasler et al. 1985) or strong promoters of oncogenic viruses like simian virus 40 (SV40), e.g. the SV40 large T-antigen promoter and many more (e.g. Kim et al. 1990). Such strong promoters were preferred by cell biologists because they function autonomously in various cell culture systems. In the context of viral replication an infected cell is transformed by viral functions into a virus-replicating machine. The biology of replication and morphogenesis of herpesviruses is well understood. After infection, only very few genes (α-genes) are transcribed and translated into the immediate-early proteins (IEp). These IEp are transcriptional activators for the β-genes encoding viral enzymes like the DNA polymerase and many others. The start of the viral genome replication marks the beginning of the late phase of viral replication where β- and γ-genes are being transcribed that encode for the viral structural proteins (Fields, 2013). For improved vector vaccines, however, none of the autonomous strong promoters described above is seen as an option, in particular the ones derived from oncogenic viruses have a disadvantageous safety profile. Thus, there is a need to provide promoters with high activity in the context of viral replication like those of EHV-1β- and γ-genes. Since it is not possible to use an identical DNA sequence twice in one vector molecule without running the risk of internal homologous recombination and thus genetic instability, the present invention provides new alternative promoter sequences derived from the published genomic sequence of EHV-4 (Equid Alphaherpesvirus 4 strain NS80567, complete genome, Accession AF030027, Version AF030027.1 GI:2605950, date 21 May 1998). Sequence identity of the genes with EHV-1 genes is in the range of 55 to 84%.

The present invention provides two new promoters: p430 and p455, which are shown to be functional in the background of rEHV1-RacH replication in cell cultures, and also in animals (pigs and mice). Activity levels of the two new promoters during the viral replication cycle appear to be very similar as deduced from in vitro promoter kinetic experiments.

These properties allow creation of recombinant vector vaccines based on EHV-1 RacH expressing two different antigens in parallel with similar efficiency. If a vaccine target consists of two different pathogens application of the two new promoters in two insertion sites combined with two polyadenylation sequences can reduce cost of goods significantly and represents a clear advantage over a vector expressing only one antigenic component.

The present invention provides two new promoters: 4pgG600 and 4pMCP600, and derivatives of shorter lengths thereof, which are shown to be functional after transient transfection in cell cultures or in the background of rEHV1-RacH replication in cell cultures.

Additionally, the new promoter sequences provided by the present invention are shown to be efficient in other vector backgrounds like canine adenovirus (CAdV) as well.

Importantly, the rescue of recombinant CAdV was not achieved when either the CAG or CMV5 promoter sequences were present in the expression cassettes located in the E3 region. This appears to be sequence-specific as the size of the expression cassettes had not exceeded observed experimental genome size limitations. Thus, the new EHV-4 derived promoter sequences of the present invention such as p430 and p455 not only facilitate transgene expression, but also support the crucial step of viral rescue and are, therefore, advantageous in view of prior art promoter sequences.

DETAILED DESCRIPTION OF THE INVENTION

The present invention solves the problems inherent in the prior art and provides a distinct advance in the state of the art.

Generally, the present invention provides a promoter sequence/regulatory nucleic acid sequence comprising 4pgG600 (SEQ ID No. 1) or 4pMCP600 (SEQ ID No. 2) or the complementary nucleotide sequences thereof or a functional fragment or functional derivative thereof or the complementary nucleotide sequences thereof, wherein said promoter sequence leads to expression of a nucleotide sequence of interest, preferably a gene of interest, more preferably an antigen encoding sequence.

In a specific aspect the functional fragment or derivative has a length of 550 nucleotides, preferably 500, 490, 480, 470, 460, 455, 450, 445, 440, 435, 434, 433, 432, 431, 430 nucleotides, most preferably 455 or 430 nucleotides. In another aspect the functional fragment or derivative has a length of between 430 to 550 nucleotides, 430 to 500 nucleotides, or 430 to 480 nucleotides. Preferably the functional fragment has a sequence identity and/or homology or sequence identity of 70%, 80%, 85%, preferably 90%, 91%, 92%, 93%, 94%, more preferably 95%, 96%, 97%, 98%, 99%, 99.1%, 99.2%, 99.3%, 99.4%, 99.5%, 99.6%, 99.7%, 99.8%, 99.9%. In a specific aspect the expression is increased.

In a specific aspect the functional fragment is a truncation of 4pgG600 (SEQ ID No. 1) or the complementary nucleotide sequence thereof, preferably the sequence identity is (at least) 72% over entire length (or higher). Preferably, the functional fragment of 4pgG600 (SEQ ID No. 1) is the fragment designated p430 (SEQ ID NO:3). In another aspect the sequence identity is (at least) 70%, 80%, 85%, preferably 90%, 91%, 92%, 93%, 94%, more preferably 95%, 96%, 97%, 98%, 99%, 99.1%, 99.2%, 99.3%, 99.4%, 99.5%, 99.6%, 99.7%, 99.8%, 99.9%.

In a further specific aspect the functional fragment is a truncation of 4pMCP600 (SEQ ID No. 2) or the complementary nucleotide sequence thereof, preferably the sequence identity is (at least) 78% over entire length (or higher). Preferably, the functional fragment of 4pMCP600 (SEQ ID No. 2) is the fragment designated p455 (SEQ ID NO:4). In another aspect the sequence identity is (at least) 70%, 80%, 85%, preferably 90%, 91%, 92%, 93%, 94%, more preferably 95%, 96%, 97%, 98%, 99%, 99.1%, 99.2%, 99.3%, 99.4%, 99.5%, 99.6%, 99.7%, 99.8%, 99.9%.

The present invention further provides a promoter sequence/regulatory nucleic acid sequence comprising p430 (SEQ ID No. 3) or p455 (SEQ ID No. 4) or the complementary nucleotide sequences thereof or a functional fragment or functional derivative thereof or the complementary nucleotide sequences thereof, wherein said promoter sequence leads to expression of a nucleotide sequence of interest, preferably a gene of interest, more preferably an antigen encoding sequence. Preferably the functional fragment has a sequence homology or sequence identity of 70%, 80%, 85%, preferably 90%, 91%, 92%, 93%, 94%, more preferably 95%, 96%, 97%, 98%, 99%, 99.1%, 99.2%, 99.3%, 99.4%, 99.5%, 99.6%, 99.7%, 99.8%, 99.9%. In a specific aspect the expression is increased.

The present invention further concerns an expression cassette comprising a promoter sequence/regulatory nucleic acid sequence selected from the group consisting of: 4pgG600 (SEQ ID No. 1) and 4pMCP600 (SEQ ID No. 2) and the complementary nucleotide sequences thereof and a functional fragment and a functional derivative thereof and the complementary nucleotide sequences thereof, and p430 (SEQ ID No. 3) and p455 (SEQ ID No. 4) and the complementary nucleotide sequences thereof and a functional fragment thereof, and a functional derivative thereof, and the complementary nucleotide sequences thereof, wherein the promoter sequence is operably linked to a sequence of interest, preferably a gene of interest or an antigen encoding sequence, more preferably a heterologous and/or exogenous sequence of interest, gene of interest or antigen encoding sequence, wherein said promoter sequence/regulatory nucleic acid sequence leads to expression of a nucleotide sequence of interest, preferably a gene of interest, more preferably an antigen encoding sequence, whereby said promoter sequence is preferably a heterologous promoter sequence/regulatory nucleic acid sequence, more preferably an exogenous promoter sequence/regulatory nucleic acid sequence. In a specific aspect the expression is increased.

In a specific aspect the expression cassette is a recombinant, heterologous and/or exogenous expression cassette. In another specific aspect the promoter sequence/regulatory nucleic acid sequence is a recombinant, heterologous and/or exogenous promoter sequence/regulatory nucleic acid sequence.

The present invention further concerns a vector such as a viral vector or viral construct comprising the expression cassette according to the present invention. Preferably said vector is useful for producing an immunogenic composition or vaccine.

In another aspect the present invention concerns a vector such as a viral vector or viral construct comprising an expression cassette comprising a promoter sequence/regulatory nucleic acid sequence selected from the group consisting of: 4pgG600 (SEQ ID No. 1) and 4pMCP600 (SEQ ID No. 2) and the complementary nucleotide sequences thereof and a functional fragment and a functional derivative thereof and the complementary nucleotide sequences thereof, and p430 (SEQ ID No. 3) and p455 (SEQ ID No. 4) and the complementary nucleotide sequences thereof and a functional fragment thereof, and a functional derivative thereof, and the complementary nucleotide sequences thereof,
wherein the promoter sequence is operably linked to a sequence of interest, preferably a gene of interest or an antigen encoding sequence, more preferably a heterologous and/or exogenous sequence of interest, gene of interest or antigen encoding sequence,
wherein said promoter sequence/regulatory nucleic acid sequence leads to expression of a nucleotide sequence of interest, preferably a gene of interest, more preferably an antigen encoding sequence,
whereby said promoter sequence is preferably a heterologous promoter sequence/regulatory nucleic acid sequence, more preferably an exogenous promoter sequence/regulatory nucleic acid sequence. In a specific aspect the expression is increased. Preferably said vector is useful for producing an immunogenic composition or vaccine.

The present invention further concerns a heterologous (expression) vector such as a viral vector or a plasmid for DNA vaccination comprising a regulatory nucleic acid/promoter sequence comprising 4pgG600 (SEQ ID No. 1) and/or 4pMCP600 (SEQ ID No. 2) or the complementary nucleotide sequences thereof or a functional fragment or a functional derivative thereof or the complementary nucleotide sequences thereof, or p430 (SEQ ID No. 3) and/or p455 (SEQ ID No. 4) or the complementary nucleotide sequences thereof or a functional fragment thereof, or a functional derivative thereof, or the complementary nucleotide sequences thereof, wherein said regulatory nucleic acid/promoter sequence leads to the transcription or expression of a sequence of interest, a gene of interest, or an antigen encoding sequence. In a specific aspect the transcription or expression of said sequence of interest, gene of interest, or antigen encoding sequence is increased. Preferably said vector is useful for producing an immunogenic composition or vaccine.

In a specific aspect the vector is a recombinant, heterologous and/or exogenous vector. In another specific aspect the promoter sequence/regulatory nucleic acid sequence is a recombinant, heterologous and/or exogenous promoter sequence/regulatory nucleic acid sequence.

In a specific aspect of the expression cassette according to the present invention and/or of the vector according to the present invention, the functional fragment or derivative (of the promoter sequence/regulatory nucleic acid sequence) has a sequence homology or sequence identity of 70%, 80%, 85%, preferably 90%, 91%, 92%, 93%, 94%, more preferably 95%, 96%, 97%, 98%, 99%, 99.1%, 99.2%, 99.3%, 99.4%, 99.5%, 99.6%, 99.7%, 99.8%, 99.9%.

In another specific aspect of the expression cassette according to the present invention and/or of the vector according to the present invention, the functional fragment or derivative (of the promoter sequence/regulatory nucleic acid sequence) has a length of 550 nucleotides, preferably 500, 490, 480, 470, 460, 455, 450, 445, 440, 435, 434, 433, 432, 431, 430 nucleotides, most preferably 455 or 430 nucleotides. In another specific aspect of the expression cassette according to the present invention and/or of the vector according to the present invention, the functional fragment or derivative (of the promoter sequence/regulatory nucleic acid sequence) has a length of between 430 to 550 nucleotides, 430 to 500 nucleotides, or 430 to 480 nucleotides. In yet another specific aspect of the expression cassette according to the present invention and/or of the vector according to the present invention, the functional fragment or derivative (of the promoter sequence/regulatory nucleic acid sequence) has a sequence homology or sequence identity of 70%, 80%, 85%, preferably 90%, 91%, 92%, 93%, 94%, more preferably 95%, 96%, 97%, 98%, 99%, 99.1%, 99.2%, 99.3%, 99.4%, 99.5%, 99.6%, 99.7%, 99.8%, 99.9%.

In a further specific aspect of the expression cassette according to the present invention and/or of the vector according to the present invention, the functional fragment or derivative (of the promoter sequence/regulatory nucleic acid sequence) is a truncation of 4pgG600 (SEQ ID No. 1) or the complementary nucleotide sequence thereof, preferably the sequence identity is (at least) 72% over entire length (or higher). Preferably, said functional fragment of 4pgG600 (SEQ ID No. 1) is the fragment designated p430 (SEQ ID NO: 3).

In a further specific aspect of the expression cassette according to the present invention and/or of the vector according to the present invention, the functional fragment or derivative (of the promoter sequence/regulatory nucleic acid sequence) is a truncation of 4pMCP600 (SEQ ID No. 2) or the complementary nucleotide sequence thereof, preferably the sequence identity is (at least) 78% over entire length (or higher). Preferably, said functional fragment of 4pMCP600 (SEQ ID No. 2) is the fragment designated p455 (SEQ ID NO:4).

In a further specific aspect of the expression cassette according to the present invention and/or of the vector according to the present invention, whereby said expression cassette and/or said vector comprises one or more further regulatory sequences such as a termination signal, a polyadenylation signal or a regulatory element like IRES and/or 2a peptide.

In a specific aspect the vector according to the present invention is a heterologous and/or exogenous vector.

In another specific aspect of the present invention the vector according to the present invention is a viral vector, preferably selected from the group consisting of herpes viridae such as Equid Alphaherpesvirus 1 (EHV-1), Equid Alphaherpesvirus 4 (EHV-4) and other Varicelloviruses like Suid Alphaherpesvirus 1 (Pseudorabies virus, PrV) and Bovine Alphaherpesvirus 1 (Bovine Herpesvirus 1, BHV-1), Adenoviridae (AdV) such as CAdV (Canine Adenovirus), Adeno-associated viridae, Baculoviridae, Lentiviridae such as Retroviruses, and Poxviridae. In a more specific aspect said viral vector is a member of the family Herpesviridae, preferably of the genus Alphaherpesvirinae, more preferably of the subgenus *Varicellovirus*, most preferably said vector is Equid Alphaherpesvirus 1 (EHV-1).

The present invention further concerns a method of producing a vector, preferably a viral vector, comprising: a) Providing a promoter sequence and/or regulatory nucleic acid sequence according to the present invention, b) Integrating said promoter sequence from step a) into a vector backbone derived from a virus, which is selected from the group consisting of: Herpesviridae such as EHV-1, EHV-4, Varicelloviruses like Suid Alphaherpesvirus 1 (Pseudorabies virus, PrV) and Bovine Alphaherpesvirus 1 (Bovine Herpesvirus 1, BHV-1), Adenoviridae (AdV) such as CAdV (Canine Adenovirus), Parvoviridae like Adeno-associated viruses, Baculoviridae, Retroviridae, and Poxviridae, preferably said vector backbone is derived from a herpes virus, more preferably said vector backbone is EHV-1 or EHV-4.

The present invention further concerns a eukaryotic host cell line, characterized in that it is permissive to replication of the vector according to the present invention, preferably said host cell line is a mammalian cell line or an insect cell line, most preferably it is a PK/WRL cell line, a RK13 cell line, a MDBK cell line, a ST cell line, an AI-ST cell line, a VERO cell line, a Sf9 cell line, a Sf21, a Sf plus cell line, a MDCK cell line, and/or derivatives thereof.

The present invention further concerns a method of preparing a host cell, characterized by the following steps: a) infecting the eukaryotic host cell line according to claim 21 with the vector according to claims 9 to 19, cultivating the infected cells under suitable conditions, c) optionally harvesting said host cell.

The mammalian host cell lines as listed above are generally cultivated in plastic tissue culture vessels submerged in medium for mammalian cell culture such as Minimal Essential Medium (MEM) supplemented with Earle's salts and fetal bovine serum. The mammalian cell lines are kept in an incubator at 37° C. in regular atmosphere supplemented with 5% CO2 and approximately 80% humidity. The insect cell lines are cultivated in plastic tissue culture vessels submerged in insect cell culture medium and are kept at 27° C. in regular atmosphere in an incubator.

The present invention further concerns the use of a nucleic acid sequence comprising 4pgG600 (SEQ ID No. 1) or 4pMCP600 (SEQ ID No. 2) or the complementary nucleotide sequences thereof or a functional fragment or a functional derivative thereof or the complementary nucleotide sequences thereof, as a promotor sequence, wherein said nucleic acid sequence leads to expression of a nucleotide sequence of interest, preferably a gene of interest, more preferably an antigen encoding sequence. In a specific aspect the expression is increased.

The present invention further concerns the use of a nucleic acid sequence comprising 4pgG600 (SEQ ID No. 1) or 4pMCP600 (SEQ ID No. 2) or the complementary nucleotide sequences thereof or a functional fragment or a functional derivative thereof or the complementary nucleotide sequences thereof, as a regulatory nucleic acid sequence, wherein said nucleic acid sequence leads to expression of a nucleotide sequence of interest, preferably a gene of interest, more preferably an antigen encoding sequence. In a specific aspect the expression is increased.

The present invention further concerns the use of a nucleic acid sequence comprising p430 (SEQ ID No. 3) or p455 (SEQ ID No. 4) or the complementary nucleotide sequences thereof or a functional fragment or a functional derivative thereof or the complementary nucleotide sequences thereof, as a promotor sequence, wherein said nucleic acid sequence leads to expression of a nucleotide sequence of interest, preferably a gene of interest, more preferably an antigen encoding sequence. In a specific aspect the expression is increased.

The present invention further concerns the use of a nucleic acid sequence comprising p430 (SEQ ID No. 3) or p455 (SEQ ID No. 4) or the complementary nucleotide sequences thereof or a functional fragment or a functional derivative thereof or the complementary nucleotide sequences thereof, as a regulatory nucleic acid sequence, wherein said nucleic acid sequence leads to expression of a nucleotide sequence of interest, preferably a gene of interest, more preferably an antigen encoding sequence. In a specific aspect the expression is increased.

The present invention further concerns a kit consisting of a vector according to the present invention, a host cell(s), optionally transfection reagent(s), and an instruction leaflet.

The present invention further concerns the use of the vector according to the present invention or the eukaryotic host cell line according to the present invention or the eukaryotic host cell according to the present invention for the manufacture of an immunogenic composition or vaccine, optionally using a M.O.I. of 0.01 to 0.001.

Especially for the use of a viral vector the mammalian host cell lines are generally cultivated and grown to confluency or subconfluency depending on the cell line. The viral vector is mixed with an appropriate amount of fresh culture medium and diluted to result in a multiplicity of infection (m.o.i.) of 0.001 to 0.01. The cell culture medium is removed from the host cells and replaced with the medium containing the diluted viral vector. The such inoculated cell cultures are incubated at 37° C./5% CO2 for approximately 2 to 4 days depending on the cell line. Replication of the viral vector in the cells results in cytopathic effect (CPE) and eventual destruction and death of the cells. The material is collected and stored at −80° C. Viral titers are determined.

The present invention further concerns an immunogenic composition comprising: a) the expression cassette according to the present invention, and/or b) the vector according to the present invention, and/or c) a polypeptide expressed by the expression cassette according to the present invention and/or a polypeptide expressed by the vector according to the present invention, such as a virus, a modified live virus, a virus like particle (VLP) or the like, and d) optionally a pharmaceutical- or veterinary-acceptable carrier or excipient, preferably said carrier is suitable for oral, intradermal, intramuscular or intranasal application.

In a specific aspect said immunogenic composition comprises a virus. In another specific aspect said immunogenic composition comprises an infectious virus.

The present invention further concerns a vaccine or pharmaceutical composition comprising: a) the expression cassette according to the present invention and/or b) the vector according to the present invention, and/or c) a polypeptide expressed by the expression cassette according to the present invention and/or a polypeptide expressed by the vector according to the present invention, such as a modified live virus, a virus like particle (VLP) or the like, and d) a pharmaceutical- or veterinary-acceptable carrier or excipient, preferably said carrier is suitable for oral, intradermal, intramuscular or intranasal application, e) optionally said vaccine further comprises an adjuvant.

The present invention furthermore concerns a method for the preparation of an immunogenic composition or a vaccine for reducing the incidence or the severity of one or more clinical signs associated with or caused by an infection, comprising the following steps: a) Infecting the eukaryotic host cell line according to the present invention with the vector according to the present invention, b) cultivating the infected cells under suitable conditions, c) harvesting infected cells and/or vector and/or virus components, d) optionally purifying the harvest of step c) and, e) admixing said harvest with a pharmaceutically acceptable carrier.

Method of Treatment

The present invention further concerns the immunogenic composition according to the present invention or the vaccine according to the present invention for use in a method of reducing or preventing the clinical signs or disease caused by an infection with a pathogen in an animal or for use in a method of treating or preventing an infection with a pathogen in an animal, preferably said animal is a food producing animal such as swine or cattle.

The present invention further provides a method for immunizing an animal such as a food producing animal comprising administering to such animal an immunogenic composition or vaccine as described herein.

The present invention further concerns a method of immunizing an animal such as a food producing animal including swine against a clinical disease caused by a pathogen in said animal, said method comprising the step of administering to the animal the immunogenic composition according to the present invention or the vaccine according to the present invention, whereby said immunogenic composition or vaccine fails to cause clinical signs of infection but is capable of inducing an immune response that immunizes the animal against pathogenic forms of said pathogen.

In a specific aspect, immunization results in lessening of the incidence of the particular virus infection in a herd or in the reduction in the severity of clinical signs caused by or associated with the particular virus infection.

Further, the immunization of a food producing animal in need with the immunogenic compositions as provided herewith, results in preventing infection of a food producing animal by virus infection. Even more preferably, immunization results in an effective, long-lasting, immunological-response against said virus infection. It will be understood that the said period of time will last more than 2 months, preferably more than 3 months, more preferably more than 4 months, more preferably more than 5 months, more preferably more than 6 months. It is to be understood that immunization may not be effective in all animals/subjects immunized. However, the term requires that a significant portion of animals/subjects of a herd are effectively immunized.

The present invention provides a method for the treatment or prophylaxis of clinical signs caused by a virus in an animal such as a food producing animal of need, the method comprising administering to the animal a therapeutically effective amount of an immunogenic composition or vaccine as described herein.

Preferably, the clinical signs are reduced by at least 50%, even more preferably by at least 60%, still more preferably by at least 70%, even more preferably by at least 80%, even more preferably by at least 90%, still more preferably by at least 95% most preferably by 100% in comparison to an animal that is not treated (not immunized) but subsequently infected by the particular Swine Influenza A virus.

The present invention further concerns a kit for vaccinating an animal, preferably a food producing animal such as swine or cattle, against a disease associated with and/or reducing the incidence or the severity of one or more clinical signs associated with or caused by a pathogen in an animal comprising: a) a dispenser capable of administering a vaccine to said animal; and b) the immunogenic composition according to the present invention or the vaccine according to the present invention, and c) optionally an instruction leaflet.

Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

The practice of the present invention will employ, unless otherwise indicated, conventional techniques of virology, molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like.

Molecular Biology Definitions

The term "vector" as it is known in the art refers to a polynucleotide construct, typically a plasmid or a bacterial artificial chromosome, used to transmit genetic material to a host cell. Vectors can be, for example, bacteria, viruses, phages, bacterial artificial chromosomes, cosmids, or plasmids. A vector as used herein can be composed of or contain either DNA or RNA. In some embodiments, a vector is composed of DNA. In some embodiments a vector is an infectious virus. Such a viral vector contains a viral genome which was manipulated in a way that it carries a foreign gene which has no function in the replication of the viral vector neither in cell culture nor in a host animal. According to specific aspects of the present disclosure a vector may be used for various aspects such as mere transmission of genetic material, for the transfection of host cells or organisms, for use as vaccines, e.g. DNA vaccines or for gene expression purposes. Gene expression is a term describing the biosynthesis of a protein in a cell as directed by a specific polynucleotide sequence called gene. In a specific aspect a vector may be an "expression vector", which is a vector that is capable of directing the expression of a protein encoded by one or more genes carried by the vector when it is present in the appropriate environment.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018; Paoletti, "Applications of pox virus vectors to vaccination: An update," PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector, "Molecular and Cellular Biology March 1984, Vol. 4, No. 3, p. 406; EPAO 370 573; U.S. Pat. No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675, 556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Felgner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589, 466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

The term "viral vector" describes a genetically modified virus which was manipulated by recombinant DNA technique in a way so that its entry into a host cell results in a specific biological activity, e.g. the expression of a transgene carried by the vector. In a specific aspect the transgene is an antigen. A viral vector may or may not be replication competent in the target cell, tissue, or organism.

Generation of a viral vector can be accomplished using any suitable genetic engineering techniques well known in the art, including, without limitation, the standard techniques of restriction endonuclease digestion, ligation, transformation, plasmid purification, DNA sequencing, transfection in cell cultures, for example as described in Sambrook et al. (Molecular Cloning: A Laboratory Manual. Cold Spring Harbor Laboratory Press, N.Y. (1989)) or K. Maramorosch and H. Koprowski (Methods in Virology Volume VIII, Academic Press Inc. London, UK (2014)).

A viral vector can incorporate sequences from the genome of any known organism. The sequences can be incorporated in their native form or can be modified in any way to obtain a desired activity. For example, the sequences can comprise insertions, deletions or substitutions.

A viral vector can include coding regions for two or more proteins of interest. For example, the viral vector can include the coding region for a first protein of interest and the coding region for a second protein of interest. The first protein of interest and the second protein of interest can be the same or different. In some embodiments, the viral vector can include the coding region(s) for a third or a fourth protein of interest. The third and the fourth protein of interest can be the same or different. The total length of the two or more proteins of interest encoded by one viral vector can vary. For example, the total length of the two or more proteins can be at least about 200 amino acids. At least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer.

Preferred viral vectors include herpes virus vectors such as derived from EHV-1 or EHV-4 or other varicelloviruses like PrV (Pseudorabies virus) or BHV-1 (Bovine Herpesvirus 1).

According to specific aspects of the present disclosure, the term "viral vector" or alternatively "viral construct" refers to a recombinant viral construct derived from a virus, which is selected from the families of Herpesviridae such as EHV-1, EHV-4 or other Varicelloviruses like Suid Alphaherpesvirus 1 (Pseudorabies virus, PrV) and Bovine Alphaherpesvirus 1 (Bovine Herpesvirus 1, BHV-1), Adenoviridae (AdV) such as CAdV (Canine Adenovirus, van Regenmortel et al.), Parvoviridae like Adeno-associated viruses, Baculoviridae, Retroviridae, or Poxviridae. www.ictvonline.org/virustaxonomy.asp Virus Taxonomy: 2015 Release EC 47, London, UK, July 2015; Email ratification 2016 (MSL #30). Preferred viral vectors include Herpes virus vectors such as derived from EHV-1 or EHV-4 or other Varicelloviruses like PrV (Pseudorabies virus) or BHV-1 (Bovine Alphaherpesvirus 1).

The terms "viral vector" and "viral construct" can be used interchangeably.

The term "construct," as used herein, refers to a recombinant nucleic acid such as a plasmid, a BAC, or a recombinant virus that has been artificially generated.

The term "plasmid" refers to cytoplasmic DNA that replicates independently of the bacterial chromosome within a bacterial host cell. In a specific aspect of the present invention the term "plasmid" and/or "transfer plasmid" refers to an element of recombinant DNA technology useful for construction of e.g. an expression cassette for insertion into a viral vector. In another specific aspect the term "plasmid" may be used to specify a plasmid useful for DNA vaccination purposes.

As used herein, the terms "nucleic acid" and "polynucleotide" are interchangeable and refer to any nucleic acid.

The term "nucleic acid", "nucleic acid sequence", "nucleotide sequence", "polynucleotide", "polynucleotide sequence", "RNA sequence" or "DNA sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. The nucleic acid sequences of the present invention can be prepared using standard techniques well known to one of skill in the art.

The terms "nucleic acid" and "polynucleotide" also specifically include nucleic acids composed of bases other than the five biologically occurring bases (adenine, guanine, thymine, cytosine and uracil).

The terms "regulatory nucleic acid", "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, promoter sequences, core elements required for basic interaction of RNA polymerase and transcription factors, upstream elements, enhancers, and response elements. Exemplary regulatory elements in prokaryotes include promoters, operator sequences and ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry sites (IRES), picornaviridal 2A sequences, and the like, that provide for and/or regulate expression of a coding sequence and/or production of an encoded polypeptide in a host cell.

An "internal ribosome entry site" or "IRES" describes a sequence which functionally promotes translation initiation independent from the gene 5' of the IRES and allows two cistrons (open reading frames) to be translated from a single transcript in an animal cell. The IRES provides an independent ribosome entry site for translation of the open reading frame immediately downstream of it. Unlike bacterial mRNA which can be polycistronic, i.e., encode several different polypeptides that are translated sequentially from the mRNAs, most mRNAs of animal cells are monocistronic and code for the synthesis of only one polypeptide. With a polycistronic transcript in a eukaryotic cell, translation would initiate from the 5' most translation initiation site, terminate at the first stop codon, and the transcript would be released from the ribosome, resulting in the translation of only the first encoded polypeptide in the mRNA. In a eukaryotic cell, a polycistronic transcript having an IRES operably linked to the second or subsequent open reading frame in the transcript allows the sequential translation of that downstream open reading frame to produce the two or more polypeptides encoded by the same transcript. The IRES can be of varying length and from various sources, e.g. Encephalomyocarditis virus (EMCV), picornaviruses (e.g. Foot-and-mouth disease virus, FMDVor Polio virus (PV), or Hepatitis C virus (HCV). Various IRES sequences and their use in vector construction have been described and are well known in the art. The downstream coding sequence is operably linked to the 3'end of the IRES at any distance that will not negatively affect the expression of the downstream gene. The optimum or permissible distance between the IRES and the start of the downstream gene can be readily determined by varying the distance and measuring expression as a function of the distance The term "2a" or "2a peptide" means short oligopeptide sequences, described as 2a and '2a-like', serve as linkers which are able to mediate a co-translational cleavage between proteins by a process defined as ribosomal-skipping. Such 2a and '2a-like' sequences (from Picornaviridae and other viruses or cellular sequences) can be used to concatenate multiple gene sequences into a single gene, ensuring their co-expression within the same cell (see Luke and Ryan, 2013).

As used herein, the term "promoter" or "promoter sequence" means a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and animals such as mammals (including horses, pigs, cattle and humans), birds or insects. A promoter can be inducible, repressible, and/or constitutive. Inducible promoters initiate increased levels of transcription from DNA under their control in response to some change in culture conditions, such as a change in temperature (Ptashne, 2014). Examples of promoters well known to the person skilled in the art are for example SV40 large T, HCMV and MCMV immediate early gene 1, human elongation factor alpha promoter, baculovirus polyhedrin promoter.

As used herein in the context of the present invention the term promoter refers especially to a functional fragment e.g. a truncation of 4pgG600 (SEQ ID No. 1) or the complementary nucleotide sequence thereof, preferably the sequence identity is (at least) 72% over entire length (or higher). Furthermore, as used herein in the context of the present invention the term promoter refers especially to a functional fragment, e.g. a truncation of 4pMCP600 (SEQ ID No. 2) or the complementary nucleotide sequence thereof, preferably the sequence identity is (at least) 78% over entire length (or higher). Most preferably "promoter" refers to p430 (SEQ ID NO.:3) or p455 (SEQ ID NO.: 4). As further used herein in the context of the present invention the term promoter refers especially to a functional derivative of p430 (SEQ ID NO.:3) or p455 (SEQ ID NO.: 4) or 4pgG600 (SEQ ID No. 1) or 4pMCP600 (SEQ ID No. 2) having for example a small substitution, mutation or inversion such that the sequence identity is 70%, 80%, 85%, 90%, 95%, 99% identical or homologous.

The terms "p430", "gG 430" and "430" are used synonymously and interchangeably throughout the specification, figures, sequence listing etc. The terms "p455", "MCP 455" and "455" are used synonymously and interchangeably throughout the specification, figures, sequence listing etc.

The term "enhancer" denotes a polynucleotide sequence which in the cis location acts on the activity of a promoter and thus stimulates the transcription of a gene or coding sequence functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled artisan will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. The human CMV enhancer is one of the strongest enhancers identified hitherto. One example of an inducible enhancer is the metallothionein enhancer, which can be stimulated by glucocorticoids or heavy metals.

The term "complementary nucleotide sequences" describes one strand of the two paired strands of polynucleotides such as DNA or RNA. The nucleotide sequence of the complementary strand mirrors the nucleotide sequence of its paired strand so that for each adenosin it contains a thymin (or uracil for RNA), for each guanine a cytosin, and vice versa. The complementary nucleotide sequence of e.g. 5'-GCATAC-3' is 3'-CGTATG-5' or for RNA 3'-CGUAUG-5'.

The terms "gene", "gene of interest", as used herein have the same meaning and refer to a polynucleotide sequence of any length that encodes a product of interest. The gene may further comprise regulatory sequences preceding (5' non-coding or untranslated sequences) and following (3' non-coding or untranslated sequences) the coding sequence. The selected sequence can be full length or truncated, a fusion or tagged gene, and can be a cDNA, a genomic DNA, or a DNA fragment. It is generally understood that genomic DNA encoding for a polypeptide or RNA may include non-coding regions (i.e. introns) that are spliced from mature messenger RNA (mRNA) and are therefore not present in cDNA encoding for the same polypeptide or RNA. It can be the native sequence, i.e. naturally occurring form(s), or can be mutated, or comprising sequences derived from different sources or otherwise modified as desired. These modifications include codon optimizations to optimize codon usage in the selected host cell or tagging. Furthermore they can include removal or additions of cis-acting sites such as (cryptic) splice donor, acceptor sites and branch points, polyadenylation signals, TATA-boxes, chi-sites, ribosomal entry sites, repeat sequences, secondary structures (e.g. stem loops), binding sites for transcription factors or other regulatory factors, restriction enzyme sites etc. to give just a few, but not limiting examples. The selected sequence can encode a secreted, cytoplasmic, nuclear, membrane bound or cell surface polypeptide.

The term "nucleotide sequence of interest" as used herein is a more general term than gene of interest as it does not necessarily comprise a gene but may comprise elements or parts of a gene or other genetic information, e.g. on (origin of replication). A nucleotide sequence of interest may be any DNA or RNA sequence independently of whether it comprises a coding sequence or not.

"Open reading frame" or "ORF" refers to a length of nucleic acid sequence, either DNA or RNA, that comprises a translation start signal or initiation codon, such as an ATG or AUG, and a termination codon and can be potentially translated into a polypeptide sequence.

The term "transcription" describes the biosynthesis of mRNA in a cell.

The term "expression" as used herein refers to transcription and/or translation of a nucleic acid sequence within a host cell. According to specific aspects of the present invention the term "expression" refers to transcription and/or translation of a heterologous and/or exogenous nucleic acid sequence within a host cell. The level of expression of a desired product in a host cell may be determined on the basis of either the amount of corresponding RNA or mRNA that is present in the cell, or the amount of the desired polypeptide encoded by the selected sequence. For example, mRNA transcribed from a selected sequence can be quantitated by Northern blot hybridization, ribonuclease RNA protection, in situ hybridization to cellular RNA or by RTqPCR (reverse transcription followed by quantitative PCR). Proteins expressed from a selected sequence can be quantitated by various methods, e.g. by ELISA, by Western blotting, by radioimmunoassays, by immunoprecipitation, by assaying for the biological activity of the protein, or by immunostaining of the protein followed by FACS analysis.

The term "expression cassette" or "transcription unit" or "expression unit" defines a region within a vector, construct or polynucleotide sequence that contains one or more genes to be transcribed, wherein the nucleotide sequences encoding the transcribed gene(s) as well as the polynucleotide sequences containing the regulatory elements contained within an expression cassette are operably linked to each other. They are transcribed from a promoter and transcription is terminated by at least one polyadenylation signal. In one specific aspect, they are transcribed from one single promoter. As a result, the different genes are at least transcriptionally linked. More than one protein or product can be transcribed and expressed from each transcription unit (multicistronic transcription unit). Each transcription unit will comprise the regulatory elements necessary for the transcription and translation of any of the selected sequences that are contained within the unit. And each transcription unit may contain the same or different regulatory elements. For example, each transcription unit may contain the same terminator, IRES element or introns may be used for the functional linking of the genes within a transcription unit. A vector or polynucleotide sequence may contain more than one transcription unit.

By the term "increased expression", "increased titer or productivity" or "improved expression or productivity" is meant the increase in expression, synthesis or secretion of a heterologous and/or exogenous sequence introduced into a host cell, for example of a gene coding for a therapeutic protein, by comparison with a suitable control, for example a protein encoded by a cDNA versus a protein encoded by an intron-containing gene. There is increased titer or productivity if a cell according to the invention is cultivated according to a method according to the invention described here, and if this cell has at least a 1.2-fold, a 1.5-fold, a two-fold, a three-fold, a four-fold or a five-fold increase in specific productivity or titer. There is also increased titer or productivity if a cell according to the invention is cultivated according to a method according to the invention described here, and if this cell has at least a 1.2-fold or at least a 1.5-fold or at least a two-fold or at least a three-fold increase in specific productivity or titer. There is also in particular increased titer or productivity if a cell according to the invention is cultivated according to a method according to the invention described here, and if this cell has at least a 1.2-fold to five-fold, preferably a 1.5-fold to five-fold, more preferably—two-fold to five-fold particularly preferably a three-fold to five-fold increase in specific productivity or titer. "Increased expression" may mean as well that more cells are actually expressing the gene/sequence of interest. For example increased expression may mean that the new promoters of the present invention are active for a longer period of time during the viral replication cycle relative to other promoters.

An increased expression, titer or productivity may be obtained by using a heterologous vector according to the invention. This may be combined with other approaches such as a FACS-assisted selection of recombinant host cells which contain, as additional selectable marker, one or more fluorescent proteins (e.g. GFP) or a cell surface marker. Other methods of obtaining increased expression, and a combination of different methods may also be used, are based for example on the use of cis-active elements for manipulating the chromatin structure (e.g. LCR, UCOE, EASE, isolators, S/MARs, STAR elements), on the use of (artificial) transcription factors, treatment of the cells with natural or synthetic agents for up-regulating endogenous or heterologous and/or exogenous gene expression, improving the stability (half-life) of mRNA or the protein, improving the initiation of mRNA translation, increasing the gene dose by the use of episomal plasmids (based on the use of viral sequences as replication origins, e.g. SV40, polyoma, adenovirus, EBV or BPV), the use of amplification-promoting sequences or in vitro amplification systems based on DNA concatemers.

An assay to measure "increased expression" is LC-MS/MS-based protein measurements such as multiple reaction monitoring (MRM); antibody-based detection methods such as Western blot, dot blot, or Immunodiffusion, and flow cytometry; and measures of biological activity by hemagglutination assay.

"Promoter activity" is measured indirectly by quantification of mRNA transcribed under control of the respective promoter. mRNA is quantified by RTqPCR relative to an endogenous standard.

The term "viral titer" is a measure of infectious units per volume of a virus preparation. Viral titer is an endpoint in a biological procedure and is defined as the dilution at which a certain proportion of tests carried out in parallel show an effect (Reed and Muench, 1938). Specifically the tissue culture infectious dose fifty per milliliter (TCID50/ml) gives the dilution of a virus preparation at which 50% of a number of cell cultures inoculated in parallel with that dilution are infected.

"Transcription-regulatory elements" normally comprise a promoter upstream of the gene sequence to be expressed, transcription initiation and termination sites and a polyadenylation signal.

The term "transcription initiation site" refers to a nucleic acid in the construct corresponding to the first nucleic acid incorporated into the primary transcript, i.e. the mRNA precursor. The transcription initiation site may overlap with the promoter sequences.

The "termination signal" or "terminator" or "polyadenylation signal" or "polyA" or transcription termination site" or "transcription termination element" is a signal sequence which causes cleavage at a specific site at the 3'end of the eukaryotic mRNA and post-transcriptional incorporation of a sequence of about 100-200 adenine nucleotides (polyA tail) at the cleaved 3'end, and thus causes RNA polymerase to terminate transcription. The polyadenylation signal comprises the sequence AATAAA about 10-30 nucleotides upstream of the cleavage site and a sequence located downstream. Various polyadenylation elements are known such as tk polyA, SV40 late and early polyA, BGH polyA (described for example in U.S. Pat. No. 5,122,458) or hamster growth hormone polyA (WO2010010107).

"Translation regulatory elements" comprise a translation initiation site (AUG), a stop codon and a polyA signal for each individual polypeptide to be expressed. An internal ribosome entry site (IRES) may be included in some constructs. In order to optimize expression it may be advisable to remove, add or alter 5'- and/or 3'-untranslated regions of the nucleic acid sequence to be expressed to eliminate any potentially extra inappropriate alternative translation initiation codons or other sequences that may interfere with or reduce expression, either at the level of transcription or translation. Consensus ribosome binding sites (Kozak sequence) can be inserted immediately upstream of the start codon to enhance translation and thus expression. Increased A/U contents around this ribosome binding site further a more efficient ribosome binding.

By definition, every polynucleotide sequence or every gene inserted in a host cell and the respective protein or RNA encoded thereby is referred to as "exogenous", "exogenous sequence", "exogenous gene", "exogenous coding sequence", with respect to the host cell, when it comes from a different (virus) species. Accordingly, the EHV-4 based promoters of the present invention are exogenous in view of an EHV-1 viral vector or CAdV viral vector. As used herein in respect to a sequence or gene of interest such as an antigen the term "exogenous" means that said sequence or gene of interest, specifically said antigen is expressed out of its natural species context. Accordingly, the H3 antigen from swine IAV is one example (see example 3) of an exogenous antigen in respect to the EHV-1 vector. Any non-equid sequence or gene of interest such as a non-equid antigen is therefore an exogenous sequence or gene of interest or antigen according to a specific aspect of the present invention.

By definition, every polynucleotide sequence or every gene inserted in a host cell and the respective protein or RNA encoded thereby is referred to as "heterologous, "heterologous sequence", "heterologous gene", "heterologous coding sequence", "transgene" or "heterologous protein" with respect to the host cell. This applies even if the sequence to be introduced or the gene to be introduced is identical to an endogenous sequence or an endogenous gene of the host cell. For example, an EHV-4 promoter sequence introduced into an EHV-4 viral vector at a different site or in modified form than in the EHV-4 wild type virus is by definition a heterologous sequence. As used herein in respect to a sequence or gene of interest such as an antigen, the term "heterologous" means that said sequence or gene of interest, specifically said antigen, is expressed out of its natural subspecies context. Accordingly, any non-EHV-1 specific sequence or gene of interest such as an antigen, for example an antigen from any Equid alphaherpesvirus except EHV-1, e.g. EHV-3, EHV-8, is therefore a heterologous sequence or gene of interest or antigen according to a specific aspect of the present invention.

The term "non-naturally occurring" means any sequence or gene of interest such as an antigen, which is not occurring in this context naturally, such as a hybrid sequence or a sequence or gene of interest such as an antigen from a different species, or sequence or gene of interest such as an antigen, which is not a product of nature due to artificial mutation, insertion, deletion or the like.

The term "recombinant" is used exchangeably with the terms "non-naturally occurring", "heterologous" and "exogenous" throughout the specification of this present invention. Thus, a "recombinant" protein is a protein expressed from a either a heterologous or an exogenous polynucleotide sequence. The term recombinant as used with respect to a virus, means a virus produced by artificial manipulation of the viral genome. A virus comprising a heterologous or an exogenous sequence such as an exogenous antigen encoding sequence is a recombinant virus. The term recombinant virus and the term non-naturally occurring virus are used interchangeably.

Thus, the term "heterologous vector" means a vector that comprises a heterologous or an exogenous polynucleotide sequence. The term "recombinant vector" means a vector that comprises a heterologous or a recombinant polynucleotide sequence.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

Furthermore, within the scope of the present description the terms "functional linking", "functionally linked" or "operably linked" means that two or more nucleic acid sequences or sequence elements are positioned in a way that permits them to function in their intended manner. For example, a promoter/enhancer or terminator is functionally linked to a coding gene sequence if it is able to control or modulate the transcription of the linked gene sequence in the cis position. Generally, but not necessarily, the DNA sequences that are functionally linked are contiguous and, where necessary to join two polypeptide coding regions or in the case of a secretion signal peptide, contiguous and in reading frame. However, although an operably linked promoter is generally located upstream or an operably linked terminator is generally located downstream of the coding sequence, it is not necessarily contiguous with it. Enhancers do not have to be contiguous as long as they increase the transcription of the coding sequence. For this they can be located upstream or downstream of the coding sequence and even at some distance. A polyadenylation site is operably linked to a coding sequence if it is located at the 3'end of the coding sequence in a way that transcription proceeds through the coding sequence into the polyadenylation signal. Linking is accomplished by recombinant methods known in the art, e.g. by ligation at suitable restriction sites or blunt ends or by using fusion PCR methodology. Synthetic oligonucleotide linkers or adapters can be used in accord with conventional practice if suitable restriction sites are not present.

Accordingly, the term "functional fragment" or a "functional derivative" of a promoter sequence means that the fragment or derivative still effects promoter activity. Functional assays of how to assess promoter activity are well known to one of ordinary skill in the art (Bustin 2000, Nolan et al. 2006). An exemplary embodiment of such a functional assay includes e.g. a promoter kinetics experiment. Cells infected with vector viruses carrying expression cassettes where a promoter or fragment thereof directs transcription of a reporter transgene are incubated for different times. Total RNA is prepared from samples collected at different times after infection. After destruction of contaminating DNA by DNAse I digestion, the RNA is reverse transcribed. One replicate sample is processed with addition of reverse transcriptase (RT), the second replicate is processed without addition of RT in order to demonstrate successful removal of contaminating DNA from the RNA preparation. The resulting cDNA is purified and used as template in a conventional PCR. Only the samples processed with the addition of RT shall produce a PCR product. These cDNAs can then be used for qPCR with primers for the reporter transgene and in parallel with primers for an essential gene of the viral vector (internal standard gene), the transcription of which provides an internal standard for the efficiency of infection and replication. qPCR values of the reporter are normalized between the different constructs and times after infection using the qPCR values of the internal standard gene. This allows an interpretation of promoter activities of different promoters and fragments thereof.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a comparable polypeptide or polynucleotide having 95% sequence homology with a reference sequence, 85%, preferably 90%, 91%, 92%, 93%, 94%, even more preferably 95%, 96%, 97%, 98%, 99%, 99.9% of the amino acid residues or nucleotides in the reference sequence must match or comprise a conservative substitution with another amino acid or nucleotide. Alternatively, a number of amino acids or nucleotides up to 15%, preferably up to 10%, 9%, 8%, 7%, 6%, even more preferably up to 5%, 4%, 3%, 2%, 1%, 0.1% of the total amino acid residues or nucleotides, not including conservative substitutions, in the reference sequence may be inserted into the reference sequence. Preferably the homolog sequence comprises at least a stretch of 50, even more preferred of 100, even more preferred of 250, even more preferred of 500 nucleotides.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, 91%, 92%, 93%, 94%, even more preferably 95%, 96%, 97%, 98%, 99%, 99.9% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, 91%, 92%, 93%, 94%, even more preferably 95%, 96%, 97%, 98%, 99%, 99.9% identity relative to the reference nucleotide sequence, up to 15%, preferably 10%, 9%, 8%, 7%, 6%, even more preferably 5%, 4%, 3%, 2%, 10%, 0.10% of the nucleotides in the reference sequence may be deleted or substituted with another nucleotide, or a number of nucleotides up to 15%, preferably 10%, 9%, 8%, 7%, 6%, even more preferably 5%, 4%, 3%, 2%, 1%, 0.1% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, 91%, 92%, 93%, 94%, even more preferably 95%, 96%, 97%, 98%, 99% sequence identity to a reference amino acid sequence, it is intended that the given amino acid sequence of the polypeptide is identical to the reference sequence except that the given polypeptide sequence may include up to 15, preferably up to 10, 9, 8, 7, 6, even more preferably up to 5, 4, 3, 2, 1 amino acid alterations per each 100 amino acids of the reference amino acid sequence. In other words, to obtain a given polypeptide sequence having at least 85%, preferably 90%, 91%, 92%, 93%, 94%, even more preferably 95%, 96%, 97%, 98%, 99% sequence identity with a reference amino acid sequence, up to 15%, preferably up to 10%, 9%, 8%, 7%, even more preferably up to 5%, 4%, 3%, 2%, 1% of the amino acid residues in the reference sequence may be deleted or substituted with another amino acid, or a number of amino acids up to 15%, preferably up to 10%, 9%, 8%, 7%, even more preferably up to 5%, 4%, 3%, 2%, 1% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "sequence identity" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package, using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information.

EHV-1 and EHV-4/Recombinant Vector Technology Definitions

The term "equid" or "equine" or "equin" means of or belonging to the family Equidae, which includes the horses, asses, and zebras, preferably horses. In addition, the term "equid" or "equine" or "equin" encompasses also hybrids of members of the family Equidae (e.g. mules, hinnies, etc.).

A "Herpes virus" or "Herpes virus vector" refers to a species in the family Herpesviridae in the order Herpesvirales.

The term "Equid herpes virus vector" or "Equid herpes virus" or "EHV" means a member of the family Herpesviridae affecting horses. To date eight different species of equid herpesviruses have been identified, five belonging to the subfamily Alphaherpesvirinae (EHV-1, EHV-3, EHV-4, EHV-8 und EHV-9) and three to the Gammaherpesvirinae. Virus Taxonomy: 2015 Release EC 47, London, UK, July 2015; Email ratification 2016 (MSL #30)

The term "EHV-1" means Equid Alphaherpesvirus 1, a member of the subgenus *Varicellovirus* in the genus Alphaherpesvirinae in the family Herpesviridae. A non-limiting reference sequence for EHV-1 would be for example the wild-type EHV-1 strain ab4 (Genbank accession number AY665713.1) or the RacH (Hubert 1996).

The term EHV-4 means Equid Alphaherpesvirus 4, a member of the subgenus *Varicellovirus* in the genus Alphaherpesvirinae in the family Herpesviridae.

The term "CAdV" or "CAV" or "CAV2" or "CAV-2" refers to canine adenovirus type 2, a member of the genus Mastadenovirus of the family Adenoviridae. Formerly, the terms Canine adenovirus 1 (CAV-1 or CAV1) and canine adenovirus 2 (CAV-2 or CAV2) were used to specify 2 different species of Mastadenoviruses. However, according to the newer taxonomy (www.ictvonline.org/virustaxonomy.asp Virus Taxonomy: 2015 Release EC 47, London, UK, July 2015; Email ratification 2016 (MSL #30) the term canine adenovirus (CAdV) now encompasses both species CAV-2 and CAV-1.

The term "inserted into ORF70" means that a DNA fragment was inserted into the genomic DNA at a location encoding the Equid Alphaherpesvirus 1 open reading frame 70. In a specific aspect of the present invention the insertion referred to resulted in a deletion of the 801 5' basepairs of ORF70 leaving the remaining 423 bp of the 3'end intact but abolishing expression of the orf70 gene product glycoprotein G. The glycoprotein G of several Alphaherpesviruses including EHV-1 was shown to be secreted from infected cells and function as an immunomodulatory protein by binding pro-inflammatory cytokines. Abolishment of its expression in the viral vector should increase the immunogenicity of the viral infection as compared to a wild-type EHV-1 with intact glycoprotein G expression.

The term "inserted into ORF1/3" means that a DNA fragment was inserted in the viral genome at a position where by accidental deletion over passaging during the attenuation procedure of the vaccine strain EHV-1 RacH a 1283 bp fragment comprising 90% of ORF1 and the entire ORF2 were lost. This insertion site was chosen because the likelihood that expression of a transgene from this location would interfere with viral replication was expected to be extremely low.

Vaccine Definitions

An "immunogenic or immunological composition" refers to a composition of matter that comprises at least one antigen, or immunogenic portion thereof, that elicits an immunological response in the host of a cellular or antibody-mediated immune response to the composition.

The term "antigen" used herein is well understood in the art and includes substances which are immunogenic, i.e., immunogens, as well as substances which induce immunological unresponsiveness, or anergy, i.e., a lack of reactions by the body's defense mechanisms to foreign substances. As used herein, the term "antigen" is intended to mean full length proteins as well as peptide fragments thereof containing or comprising epitope.

The term "food producing animal" means animals which are used for human consumption such as swine, cattle, poultry, fish and the like, preferably food producing animal means swine and cattle, most preferably swine. The term "food producing animal" excludes, Equidae such as horses.

An "immunogenic composition" as used herein can refer to a polypeptide or a protein, such as for example a viral surface protein that elicits an immunological response as described herein. The term "immunogenic fragment" or "immunogenic portion" refers to a fragment or truncated and/or substituted form of a protein or polypeptide that includes one or more epitopes and thus elicits the immunological response described herein. In general, such truncated and/or substituted forms, or fragments will comprise at least six contiguous amino acids from a full-length protein. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are all incorporated by reference herein.)

The term "vaccine" as used herein refers to a pharmaceutical composition comprising at least one immunologically active component that induces an immunological response in an animal and possibly but not necessarily one or more additional components that enhance the immunological activity of the active component. A vaccine may additionally comprise further components typical to pharmaceutical compositions. By way of distinction the immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of the organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian, or other species plus optionally subsequent isolation and purification procedures, or by induction of the synthetic processes in the animal needing a vaccine by direct incorporation of genetic material using suitable pharmaceutical compositions (polynucleotide vaccination). A vaccine may comprise one or simultaneously more than one of the elements described above. As used within specific aspects of the present invention "vaccine" refers to a live vaccine or live virus, also called recombinant vaccine. In another specific aspect of the present invention "vaccine" refers to an inactivated or killed virus including virus like particles (VLPs). Thus, a vaccine may be a subunit vaccine or a killed (KV) or inactivated vaccine.

The term "Multiplicity of Infection (M.O.I.)" describes how many infectious units, e.g. TCID50, of a virus preparation are used per cell to infect cultured cells. For example, a M.O.I. of 0.01 means that for every 100 cells in a culture vessel one infectious unit is inoculated.

The term "DNA vaccination" or "polynucleotide vaccination" means direct inoculation of genetic material using suitable pharmaceutical compositions.

Various physical and chemical methods of inactivation are known in the art. The term "inactivated" refers to a previously virulent or non-virulent virus or bacterium that has been irradiated (ultraviolet (UV), X-ray, electron beam or gamma radiation), heated, or chemically treated to inactivate or kill such virus or bacterium while retaining its immunogenicity. Suitable inactivating agents include beta-propiolactone, binary or beta- or acetyl-ethyleneimine, gluteraldehyde, ozone, and formalin (formaldehyde).

For inactivation by formalin or formaldehyde, formaldehyde is typically mixed with water and methyl alcohol to create formalin. The addition of methyl alcohol prevents degradation or cross reaction during the in activation process. One embodiment uses about 0.1 to 1% of a 37% solution of formaldehyde to inactivate the virus or bacterium. It is critical to adjust the amount of formalin to ensure that the material is inactivated but not so much that side effects from a high dosage occur.

More particularly, the term "inactivated" in the context of a virus means that the virus is incapable of replication in vivo or in vitro and, respectively, the term "inactivated" in the context of a bacterium means that the bacterium is incapable of reproduction in vivo or in vitro. For example, the term "inactivated" may refer to a virus that has been propagated in vitro, and has then been inactivated using chemical or physical means so that it is no longer capable of replicating. In another example, the term "inactivated" may refer to a bacterium that has been propagated, and then inactivated using chemical or physical means resulting in a suspension of the bacterium, fragments or components of the bacterium, such as resulting in a bacterin which may be used as a component of a vaccine.

As used herein, the terms "inactivated", "killed" or "KV" are used interchangeably.

The term "live vaccine" refers to a vaccine comprising either a living organism or a replication competent virus or viral vector.

A "pharmaceutical composition" essentially consists of one or more ingredients capable of modifying physiological, e.g., immunological functions, of the organism it is administered to, or of organisms living in or on the organism. The term includes, but is not restricted to, antibiotics or antiparasitics, as well as other constituents commonly used to achieve certain other objectives such as, but not limited to, processing traits, sterility, stability, feasibility to administer the composition via enteral or parenteral routes such as oral, intranasal, intravenous, intramuscular, subcutaneous, intradermal, or other suitable route, tolerance after administration, or controlled release properties. One non-limiting example of such a pharmaceutical composition, solely given for demonstration purposes, could be prepared as follows: cell culture supernatant of an infected cell culture is mixed with a stabilizer (e.g., spermidine and/or bovine serum albumin (BSA) and the mixture is subsequently lyophilized or dehydrated by other methods. Prior to vaccination, the mixture is then rehydrated in aqueous (e.g., saline, phosphate buffered saline (PBS) or non-aqueous solutions (e.g., oil emulsion, aluminum-based adjuvant).

As used herein, "pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed.Stewart-Tull, D. E. S.), John Wiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of CARBOPOL® 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Attenuation" means reducing the virulence of a pathogen. In the present invention "attenuation" is synonymous with "avirulent". In the present invention, an attenuated virus is one in which the virulence has been reduced so that it does not cause clinical signs of infection but is capable of inducing an immune response in the target animal, but may also mean that the clinical signs are reduced in incidence or severity in animals infected with the attenuated virus, especially the EHV-1 RacH viral vector as claimed, in comparison with a "control group" of animals infected with non-attenuated virus or pathogen and not receiving the attenuated virus. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent pathogen such as for example an attenuated viral vector as claimed, especially the EHV-1 (preferably RacH) viral vector as claimed, is suitable for the generation of a modified live vaccine (MLV) or modified live immunogenic composition.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Particularly, an effective amount refers to colony forming units (CFU) per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

An "immune response" or "immunological response" means, but is not limited to, the development of a cellular and/or antibody-mediated immune response to the (immunogenic) composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

"Protection against disease", "protective immunity", "functional immunity", "reduction of clinical symptoms", "induction/production of neutralizing antibodies and/or serum conversion", and similar phrases, means a partial or complete response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection are lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of malaria. Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge the infectious agent.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

The term "reduction of viremia" induced by a virus means, but is not limited to, the reduction of virus entering the bloodstream of an animal, wherein the viremia level, i.e. the number of virus DNA or RNA copies per mL of blood serum or the number of plaque forming colonies per deciliter of blood serum, is reduced in the blood serum of animals receiving the composition of the present invention by at least 50% in comparison to animals not receiving the composition and may become infected. More preferably, the viremia level is reduced in animals receiving the composition of the present invention by at least 90%, preferably by at least 99.9%, more preferably by at least 99.99%, and even more preferably by at least 99.999%.

As used herein, the term "viremia" is particularly understood as a condition in which virus particles reproduce and/or circulate in the bloodstream of an animal, in particular of a mammal, a bird, or of an insect.

"Safety" refers to the absence of adverse consequences in a vaccinated animal following vaccination, including but not limited to: potential reversion of a virus-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit-directly or indirectly-, an immune response in said animal.

"Mortality", in the context of the present invention, refers to death caused by an infection, and includes the situation where the infection is so severe that an animal is euthanized to prevent suffering and provide a humane ending to its life.

Formulations

The subject to which the composition is administered is preferably an animal, including but not limited to cattle, horses, sheep, pigs, poultry (e.g. chickens), goats, cats, dogs, hamsters, mice and rats, most preferably the mammal is a swine.

The formulations of the invention comprise an effective immunizing amount of one or more immunogenic compositions and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Methods of Treatment

Preferred routes of administration include but are not limited to intranasal, oral, intradermal, and intramuscular. Administration in drinking water, most preferably in a single dose, is desirable. The skilled artisan will recognize that compositions of the invention may also be administered in one, two or more doses, as well as, by other routes of administration. For example, such other routes include subcutaneously, intracutaneously, intraperitoneally, intracutaneously, and depending on the desired duration and effectiveness of the treatment, the compositions according to the invention may be administered once or several times, also intermittently, for instance on a daily basis for several days, weeks or months and in different dosages such as about $10^3$ to $10^8$ TCID50 (see viral titer above). In a specific aspect of the present invention the dosage is about $10^3$ to $10^8$ TCID50, especially for live virus/live vaccine.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to a mammal, especially a pig. Associated with such container(s) can be a notice in the form prescribed by a governmental agency regulating the manufacture, use or sale of pharmaceuticals or biological products, which notice reflects approval by the agency of manufacture, use or sale for human administration.

Sequences Overview

The following sequences are detailed and disclosed hereby in the present invention:
Promoters:
SEQ ID NO: 1 EHV-4 600 bp desoxyribonucleic acid sequence 4pgG600
SEQ ID NO: 2 EHV-4 600 bp desoxyribonucleic acid sequence 4pMCP600
SEQ ID NO: 3 EHV-4 430 bp desoxyribonucleic acid sequence pG430
SEQ ID NO: 4 EHV-4 449 bp desoxyribonucleic acid sequence p455
SEQ ID NO: 5 primer no 1130 specific for orf72
SEQ ID NO: 6 primer no 1131 specific for orf72
SEQ ID NO: 7 primer no. 1079 specific for mCherry
SEQ ID NO: 8 primer no. 1080 specific for mCherry
Insertion Site:
SEQ ID NO: 9 Artificial sequence nucleic acid PCR primer 1017 for the orf70 insertion region
SEQ ID NO: 10 Artificial sequence nucleic acid PCR primer 1018 for the orf70 insertion region
SEQ ID NO: 11 Artificial sequence nucleic acid PCR primer 1007 for the orf1/3 insertion region
SEQ ID NO: 12 Artificial sequence nucleic acid PCR primer 1008 for the orf1/3 insertion region
SEQ ID NO: 13 left (Up70) flanking region (417 bp)
SEQ ID NO: 14 right (Up71) flanking region (431 bp)
SEQ ID NO: 15 flanking region left (up orf70) in the wild-type EHV-1 strain ab4 (Genbank accession number AY665713.1), located at nucleotides 127264-127680
SEQ ID NO: 16 flanking region right (up orf71) in the wild-type EHV-1 strain ab4 (Genbank accession number AY665713.1), located at nucleotides 128484-128913
SEQ ID NO: 17 truncated flanking region in the RED system: left (Up70) flanking region (283 bp)=identical to the 3' 283 bp of the 417 bp "classical" flanking region
SEQ ID NO: 18 truncated flanking region in the RED system: right (Up71) flanking region (144 bp)=identical to the 5' 144 bp of the 431 bp "classical" flanking region
SEQ ID NO: 19 Deleted portion in the wild-type ab4 (Genbank accession number AY665713.1) genome sequence, nt 127681-128482
SEQ ID NO: 20 Deleted portion in the RacH genome sequence (no nt numbers available because complete genome sequence not known)

Plasmid/Vector Sequences:
SEQ ID NO: 21 Nucleotide sequence of transfer plasmid pU-mC70-BGH
SEQ ID NO.: 22 Nucleotide sequence of transfer vector pU70-p455-71K71
SEQ ID NO.: 23 Nucleotide sequence of transfer plasmid pU70-p455-H3-71K71
SEQ ID NO.: 24 Nucleotide sequence of transfer vector pU-1-3-p430-BGHKBGH
SEQ ID NO.: 25 Nucleotide sequence of transfer plasmid pU1-3-p430-H1av-BGHKBGH
Hemagglutinin Sequences
SEQ ID NO:26 hemagglutinin [Influenza A virus (A/swine/Italy/116114/2010(H1N2))]
GenBank: ADR01746.1 H1pdm
SEQ ID NO:27 hemagglutinin [Influenza A virus (A/swine/Italy/7680/2001(H3N2))]
GenBank: ABS50302.2 H3:
SEQ ID NO:28 hemagglutinin [Influenza A virus (A/swine/Gent/132/2005(H1N1))]
GenBank: AFR76623.1 H1av:
SEQ ID NO:29 hemagglutinin [Influenza A virus (A/swine/Italy/4675/2003(H1N2))]
GenBank: ADK98476.1* H1hu
*Please note that amino acid 531 (X, stop codon, was changed by the inventors to I):
SBV Construct Sequences
SEQ ID NO:30 GS linker sequence
SEQ ID NO: 31 Synthesized DNA sequence including restriction sites for subcloning
SEQ ID NO:32 DNA fragment used for RED recombination to generate pRacH-SE-70-455-SBVGc
SEQ ID NO:33 up70 F primer
SEQ ID NO:34 up71 R primer
SEQ ID NO:35 seq455-F1 primer
SEQ ID NO:36 SBV Gc F1 primer
SEQ ID NO:37 SBV Gc R1 primer

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3. qPCR results of a promoter kinetics experiment. The graph in A. shows the kinetics of the transcription of orf72, encoding for the essential glycoprotein D. These data were used to normalize the data of the transcription kinetics of mCherry (graph in B).

FIG. 5. Plasmid map of the transfer plasmid for insertion of the expression cassette p455-H3-71 into orf70 of EHV-1

RacH. 3'end ORF69: viral genomic DNA sequence flanking the insertion site upstream; 3'end ORF70: viral genomic DNA sequence flanking the insertion site downstream; p455: promoter driving expression of transgene; H3: transgene (IAV hemagglutinin); 71 pA: polyadenylation sequence; I-ScelI: cleavage site for I-ScelI; promoter aph: prokaryotic promoter driving expression of Kanamycin-resistance gene; Kana: Kanamycine resistance orf; ORI: origin of replication of plasmid vector: Apr: Ampicillin-resistance gene; EcoRI, SalI, NotI, HindIII, KpnI, BamHI, XbaI indicate restriction endonuclease cleavage sites.

Figure 6:
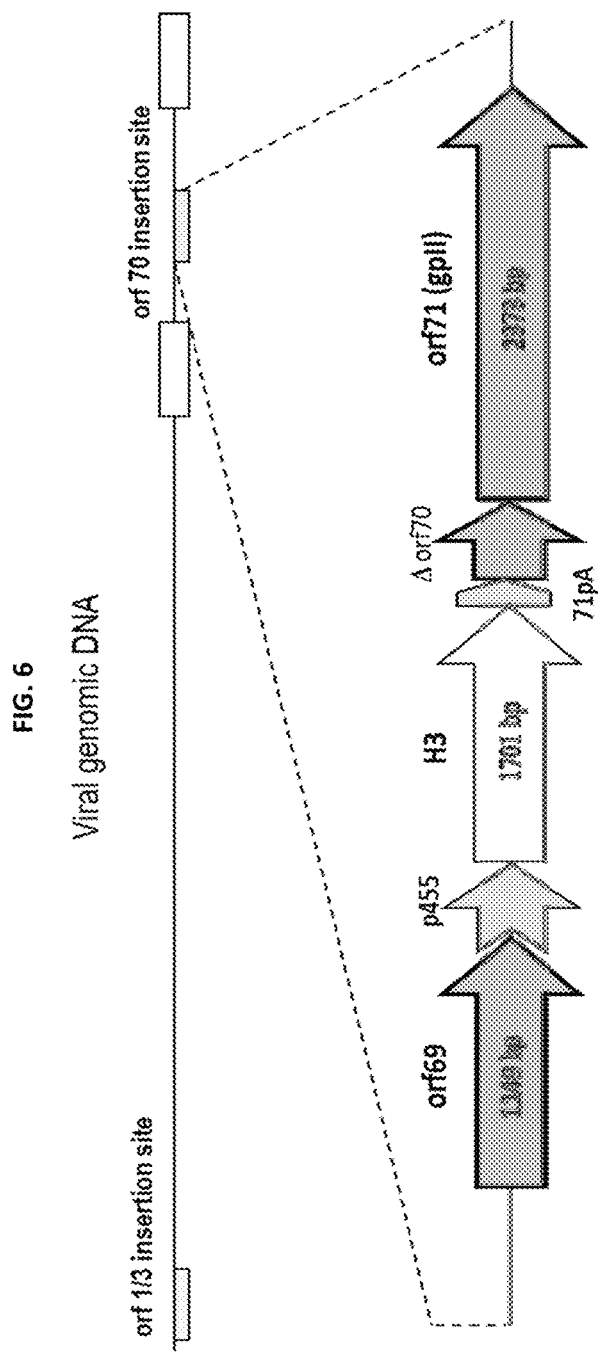

FIG. 6. Schematic illustration of the genome of rEHV-1 RacH-SE-70-p455-H3 with the orf70 insertion region enlarged. orf69: open reading frame number 69 upstream of the insertion site in orf70; p455: new promoter described herein, see e.g. example 1; H3: transgene Influenza Virus hemagglutinin; 71 pA: new polyadenylation sequence; Δorf70: remainder of orf70 containing the promoter for orf71, which encodes the structural viral glycoprotein II (gpII).

Figure 7:
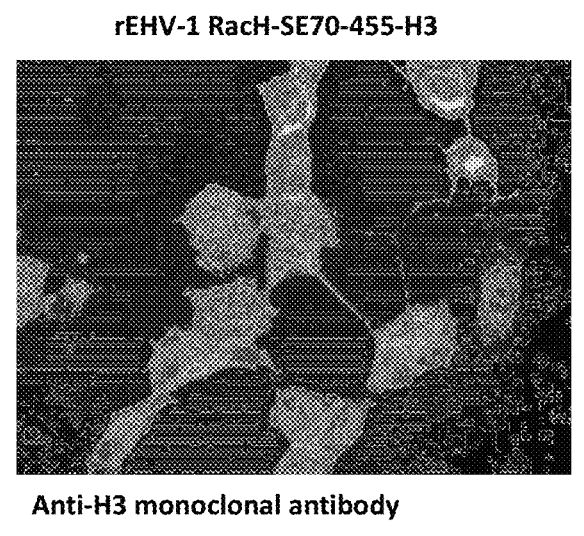

FIG. 7. Indirect immunofluorescence assay: Indirect immunofluorescence assay of VERO-cells infected with rEHV-1 RacH-SE-70-p455-H3 24 h p.i. cells were fixed with ethanol and air-dried. Using a commercial monoclonal antibody against H3 as primary antibody and a FITC-conjugated rabbit-anti mouse IgG as secondary antibody, H3 was shown in cells infected with the recombinant EHV-1 RacHSE-70-p455-H3 by fluorescence microscopy.

FIG. 8. Western blot: Western blot of cells infected with different passages of rEHV-1 RacH-SE-70-p455-H3 or a control rEHV-1 RacH-SE or mock-infected. The blot on the left was incubated with a monoclonal antibody Ai2G7 directed to gpII of EHV-1. The replica blot on the right was incubated with a commercial rabbit hyperimmune serum against Influenza A hemagglutinin H3 (PA5-34930). Annotation of lanes: 1: rEHV-1 RacH-SE-70-p455-H3 P5 infected cells; 2: rEHV-1 RacH-SE-70-p455-H3 P10 infected cells; 3: rEHV-1 RacH-SE-70-p455-H3 P15 infected cells; 4: rEHV-1 RacH-SE-70-p455-H3 P20 infected cells; 5: rEHV-1 RacH-mC70 infected cells: 6: non-infected cells FIG. 9. Virus Titers: Graphs showing viral loads of lung samples of vaccinated or non-vaccinated pigs after challenge. A) Mean lung virus titers of Animals. B) Mean lung virus Titers of Groups. Inact=commercially available inactivated vaccine EHV=rEHV-1 RacH-SE-70-p455-H3.

Figure 10:
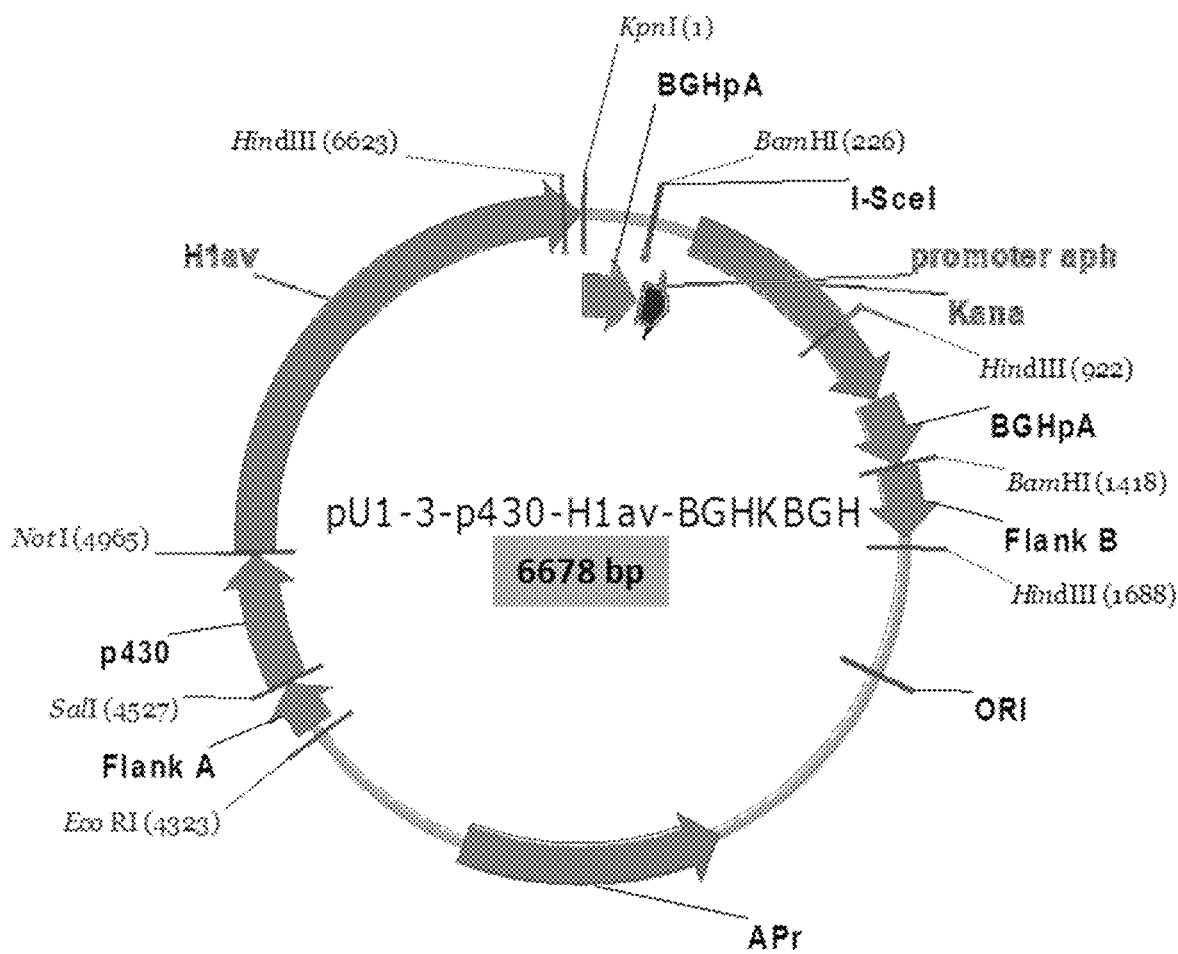

FIG. 10. Plasmid map of the transfer plasmid for insertion of the expression cassette p430-H1av-BGH into orf1/3 of EHV-1 RacH. Flank A: viral genomic DNA sequence flanking the insertion site upstream; Flank B: viral genomic DNA sequence flanking the insertion site downstream; p430: promoter driving expression of the transgene; H1av: transgene (IAV hemagglutinin); BGHpA: polyadenylation sequence; I-ScelI: cleavage site for I-ScelI; promoter aph: prokaryotic promoter driving expression of Kanamycin-resistance gene; Kana: Kanamycine resistance orf; ORI: origin of replication of plasmid vector; Apr: Ampicillin-resistance gene; EcoRI, SalI, NotI, HindIII, KpnI, BamHI indicate restriction endonuclease cleavage sites.

Figure 11:
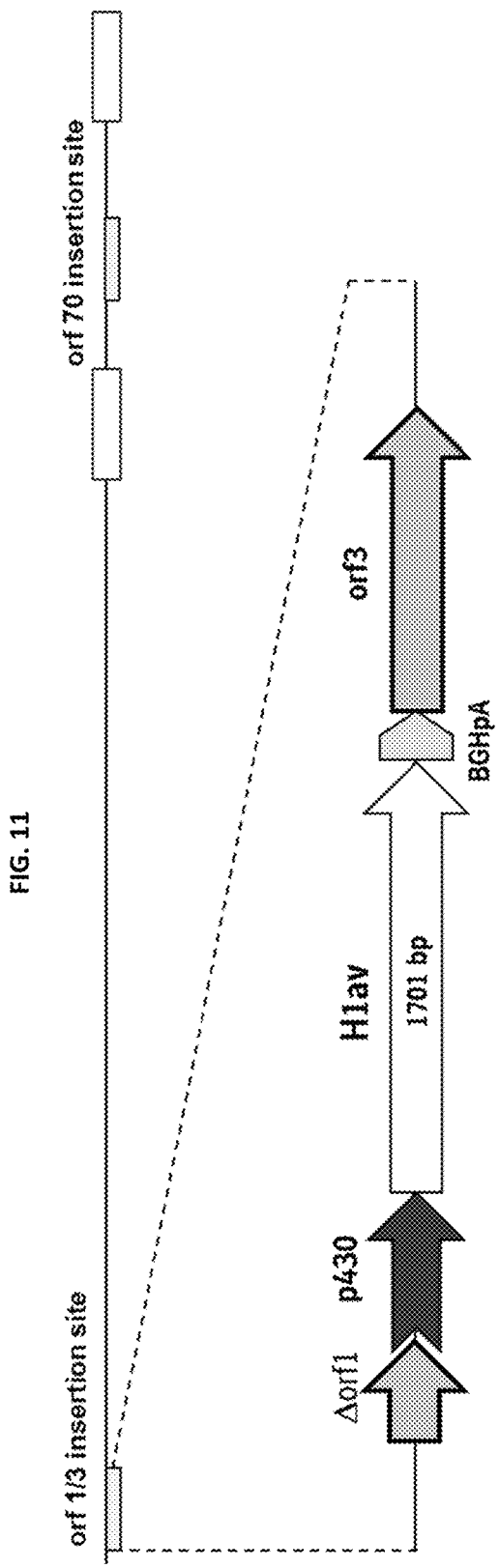

FIG. 11. Schematic illustration of the genome of rEHV-1 RacH-SE-1/3-p430-H1av with the orf1/3 insertion region enlarged. Δorf1: Remaining portion of open reading frame 1 upstream of the insertion site; p430: new promoter described herein, see e.g. example 1; H1av: transgene Influenza Virus hemagglutinin; BGHpA: bovine growth hormone polyadenylation sequence; orf3:open reading frame 3 downstream of insertion site.

FIG. 12. Western blot and immunofluorescence of cells infected with rEHV-1 RacH-SE-1/3-p430-H1av showing expression of the transgene. H1av=rEHV-1 RacH-SE1/3-p430-H1av; SE=rEHV-RacH-SE (control); mock=uninfected cells (control).

Figure 13:
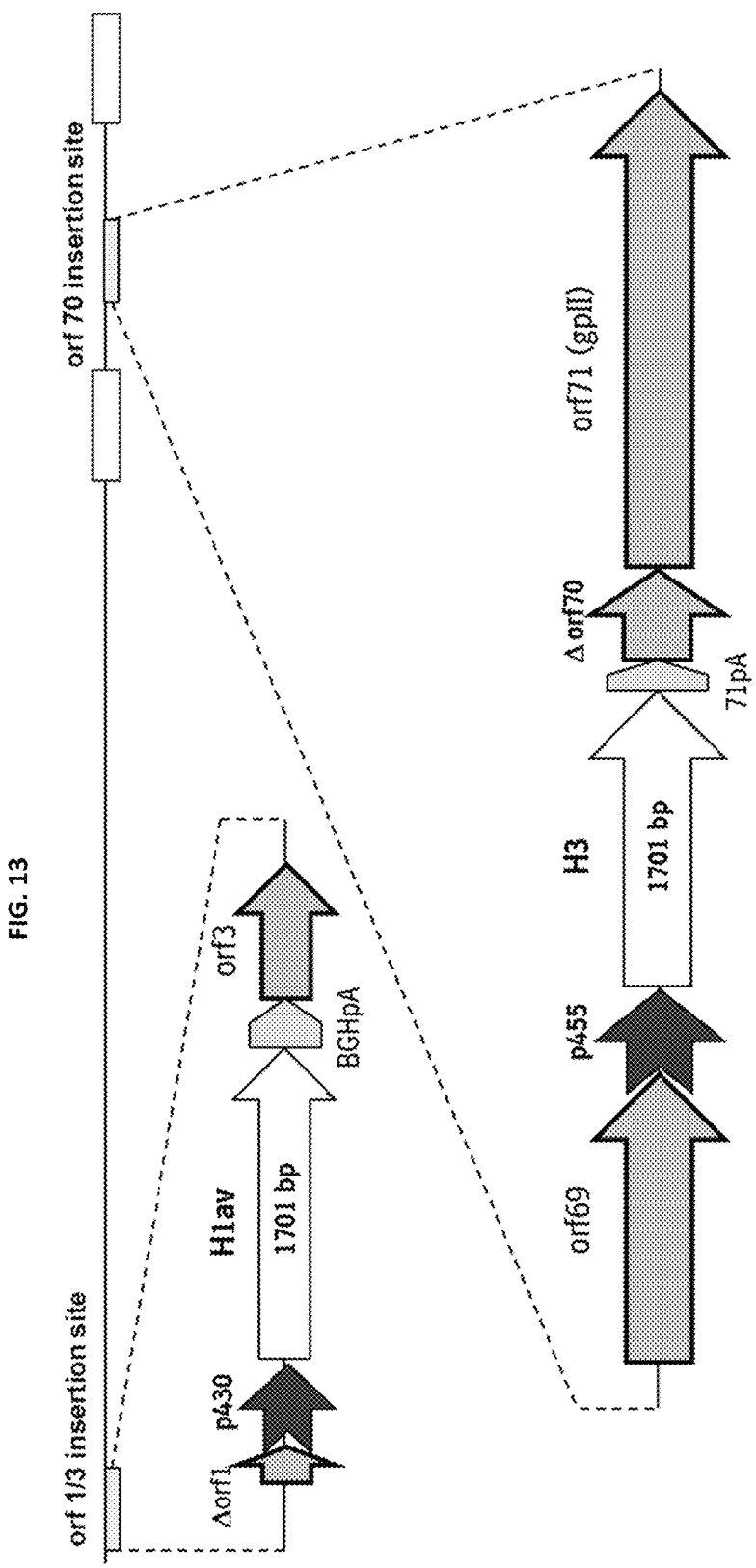

FIG. 13. Schematic illustration of the genome of rEHV-1 RacH-SE-1/3-p430-H1av-70-p455-H3 (rEHV-1-RacH-SE B) with the two insertion regions enlarged. Δorf1: Remaining portion of open reading frame 1 upstream of the insertion site; p430: new promoter; H1av: transgene Influenza Virus hemagglutinin; BGHpA: bovine growth hormone polyadenylation sequence; orf3:open reading frame 3 downstream of insertion site. orf69: open reading frame 69 upstream of the insertion site in orf70; p455: new promoter; H3: transgene Influenza Virus hemagglutinin; 71 pA: new polyadenylation sequence; Δorf70: remainder of orf70 containing the promoter for orf71, which encodes the structural viral glycoprotein II (gpII).

Figures 14, 15, 16:
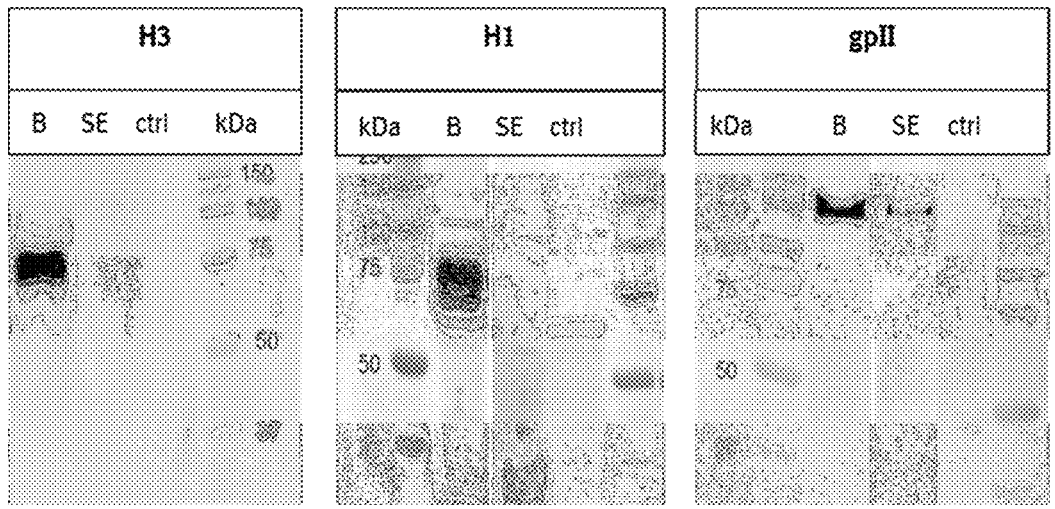

FIG. 14. Western blot: Western blot of cells infected with rEHV-1 RacH-SE-1/3-p430-H1av-70-455-H3 (B), empty vector rEHV-1 RacH-SE (SE), or mock-infected (ctrl). Replica blots were incubated with either a commercial rabbit hyperimmune serum (PA-34930) to H3 (H3), a commercial rabbit hyperimmune serum (PA-34929) to H1 (H1), or a monoclonal antibody Ai2G7 to EHV-1 gpII (gpII).

FIG. 15. Flow Cytometric Analysis of CAV2 CMVie CPV VP2-infected AI-ST 2015 cells: 72 h post-infection.

FIG. 16. rCAV-2 with New EHV-4 Promoters: Flow Cytometric Analysis of Infected AI-ST 2015 cells: 48 h post-infection.

FIG. 17. rCAV-2 with New EHV-4 Promoters: Dot Blot Analysis of CPV VP2 Protein Expression in Infected E1B MDCK (new rCAV-2) cells. 1°=1/50 a-CPV-FITC mAb (VMRD); 2°=1/1.000 Goat-a-mouse IgG-peroxidase (JIR). A) Original dot blot data; B) Semi-quantitative data generated from dot blot: For quantification, dot blots are analyzed using ImageJ software (Burger, W., Burge, M. J. (Eds.), 2008. Digital Image Processing: An algorithmic introduction using Java. Springer-Verlag, New York). Image colors are inverted to subtract background and integrated density of each dot recorded. Values are assigned + and − designations as follows: "++++"=>800000, "+++"=500000 to 800000, "++"=300000 to 499999, "+"=120000 to 299999, "+/−"=80000 to 119999 and "−"=<80000.

FIG. 18. RabG detection in cells infected with rCAV-2 p455 RabG: expression is detected in <1% of cells infected with original rCAV-2 CMVie RabG.

Figure 19:
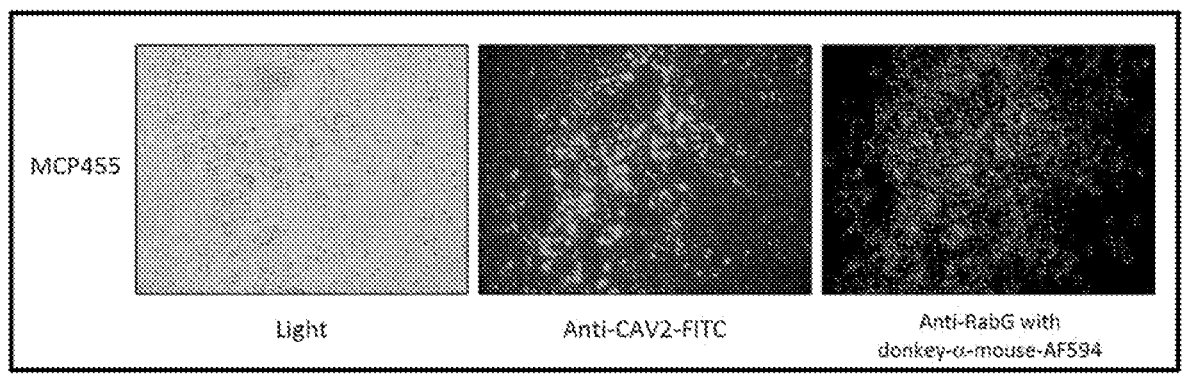

FIG. 19. RabG detection in cells infected with rCAV-2 p455 RabG: A) IFA for CPV VP2 expression in infected AI-ST 2015 cells; B) IFA for RabG expression in AI-ST 2015 cells; C) IFA for RabG expression in BIVI 2011 MDCK cells—dual stain for RabG and CAV-2.

Figure 20:
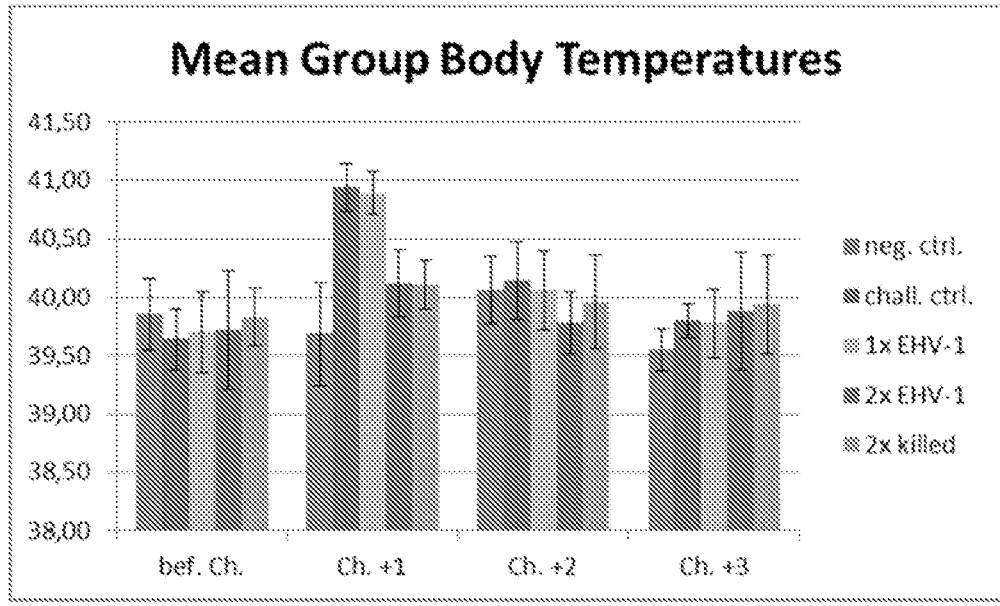

FIG. 20. Mean body temperatures of groups before and at 1, 2, and 3 days after challenge. Error bars, standard deviations. From left to right per study day: negative control group (neg. ctrl.), challenge control group (chall. ctrl.), animals vaccinated once with RacH-SE-70-p455-H3 (1× EHV-1), vaccinated twice with RacH-SE-70-p455-H3 (2× EHV-1), or twice with inactivated Swine IAV vaccine (2× killed).

FIG. 21. Mean lung scores of groups one and three days after challenge. Error bars, standard deviations. Negative control group (neg. ctrl.), challenge control group (chall. ctrl.), animals vaccinated once with RacH-SE-70-p455-H3 (1× EHV-1), vaccinated twice with RacH-SE-70-p455-H3 (2× EHV-1), or twice with inactivated Swine IAV vaccine (2× killed).

FIG. 22. Reciprocal serum neutralization (SN) titers of animal sera against Swine IAV H3 challenge strain R452-14 collected at day of challenge. 20, detection limit. Negative control group (neg. ctrl.), challenge control group (chall. ctrl.), animals vaccinated once with RacH-SE-70-p455-H3 (1× EHV-1), vaccinated twice with RacH-SE-70-p455-H3 (2× EHV-1), or twice with inactivated Swine IAV vaccine (2× killed).

Figure 23:
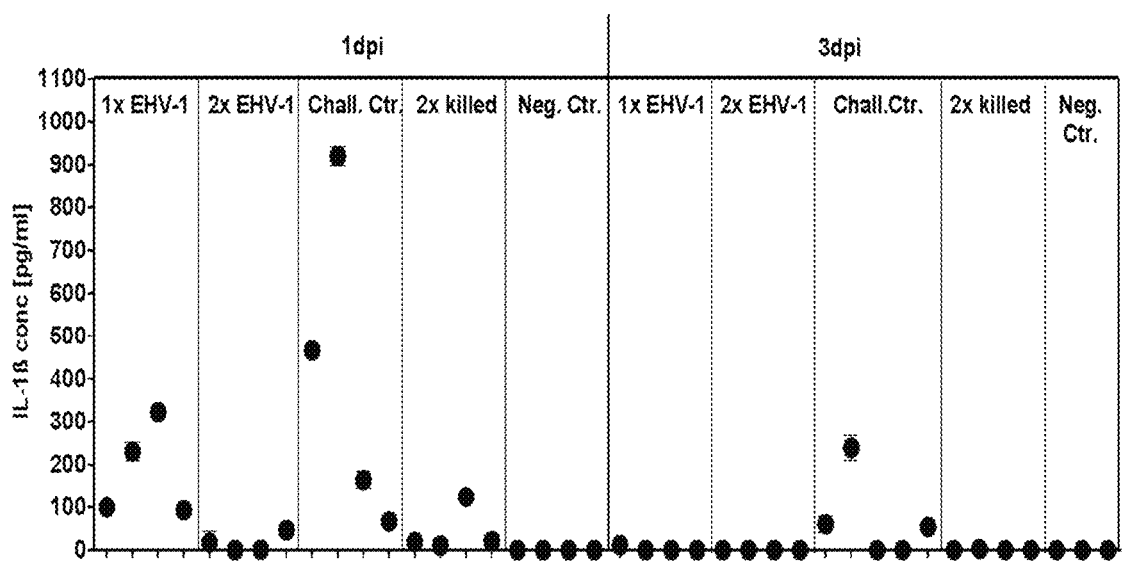

FIG. 23. Results from IL-1β from BALF taken one or two days after Swine IAV challenge application. Each dot represents the value determined per one animal. Negative control group (Neg. Ctr.), challenge control group (Chall. Ctr.), animals vaccinated once with RacH-SE-70-p455-H3 (1× EHV-1), vaccinated twice with RacH-SE-70-p455-H3 (2× EHV-1), or twice with inactivated Swine IAV vaccine (2× killed).

Figure 24:
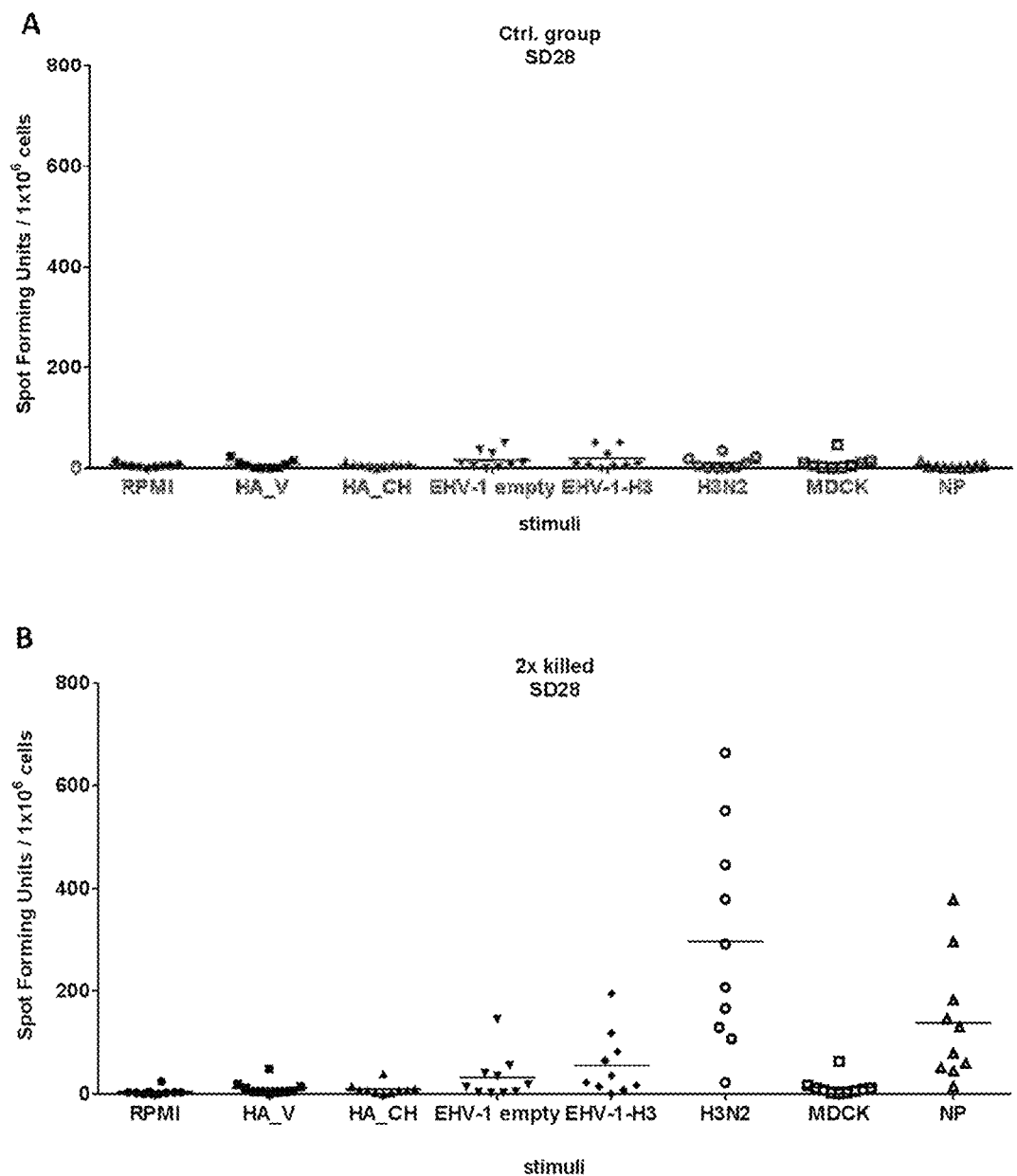
Figure 24:
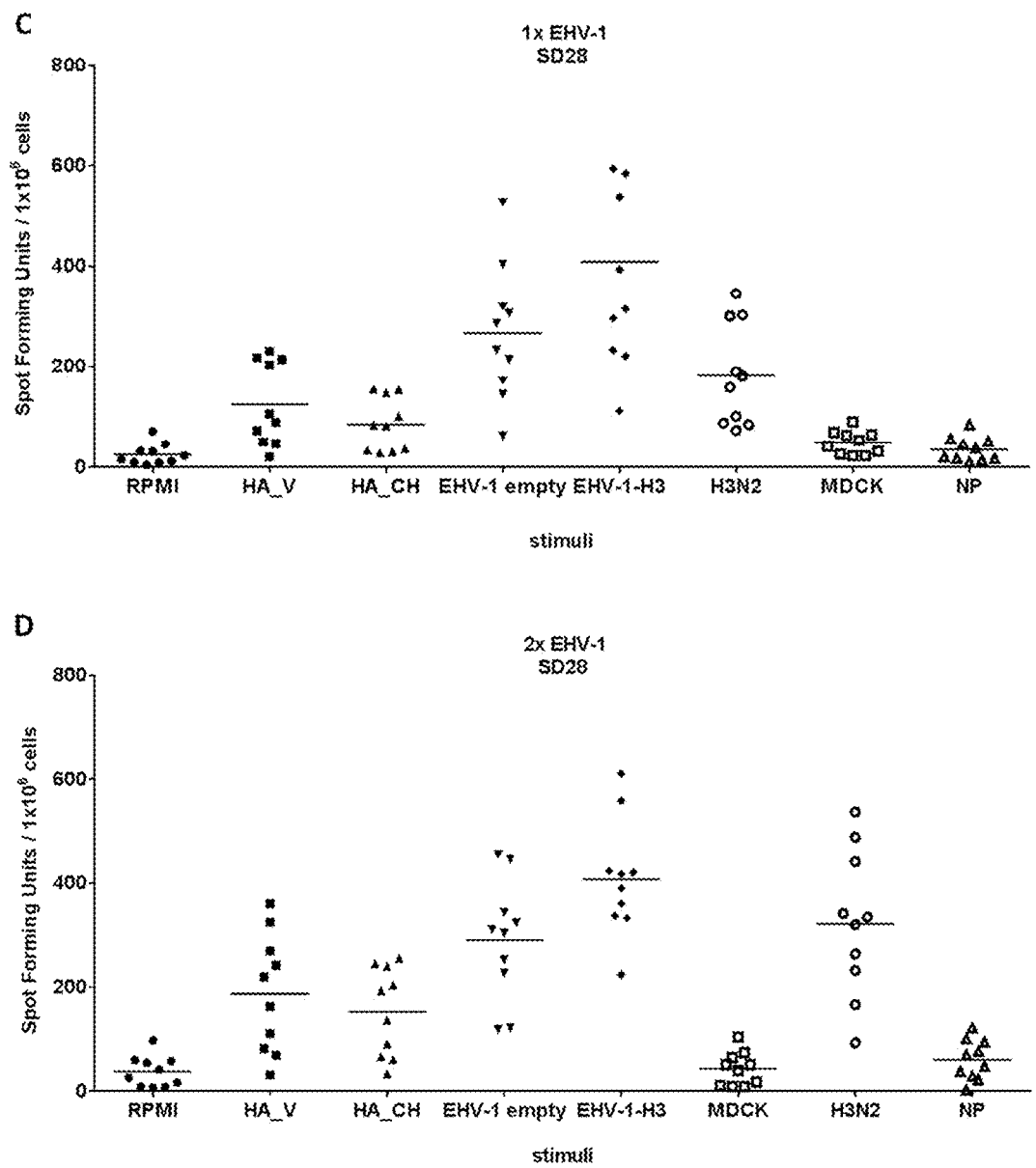

FIG. 24. Results from IFNγ-ELISpots of PBMCs restimulated 7 days after $2^{nd}$ vaccination. (A) unvaccinated control group; (B) vaccinated twice with inactivated Swine IAV vaccine; (C) vaccinated once with rEHV-1 RacH-SE-70-p455-H3; (D) vaccinated twice with rEHV-1 RacH-SE-70-p455-H3. For animals vaccinated only once with rEHV-1 RacH-SE-70-p455-H3 restimulation corresponds to 7 days after $1^{st}$ vaccination. Each dot represents the value determined per one animal for the given time point and after restimulation with the specific stimulus. For restimulation, recombinantly expressed Swine IAV HA corresponding to the H3 vaccine antigen in rEHV-1 RacH-SE-70-p455-H3 (HA_V), recombinantly expressed Swine IAV HA corresponding to the H3 of challenge strain R452-14 (HA_CH), the media to dilute HA_V and HA_CH (RPMI), empty EHV-1 vector RacH-SE (EHV-1 empty), vaccine RacH-SE-70-p455-H3 (EHV-1-H3), Swine IAV H3N2 challenge strain R452-14 (H3N2), cell supernatant from non-infected cells used to grow R452-14 (MDCK), or recombinantly expressed Swine IAV nucleoprotein (NP) were used.

FIG. 25. Schematic map of transfer plasmid pU1/3-p430-H1hu-BGHKBGH.

FIG. 26. Schematic map of transfer plasmid pU70-p455-H1pdm-71K71.

Figure 27:
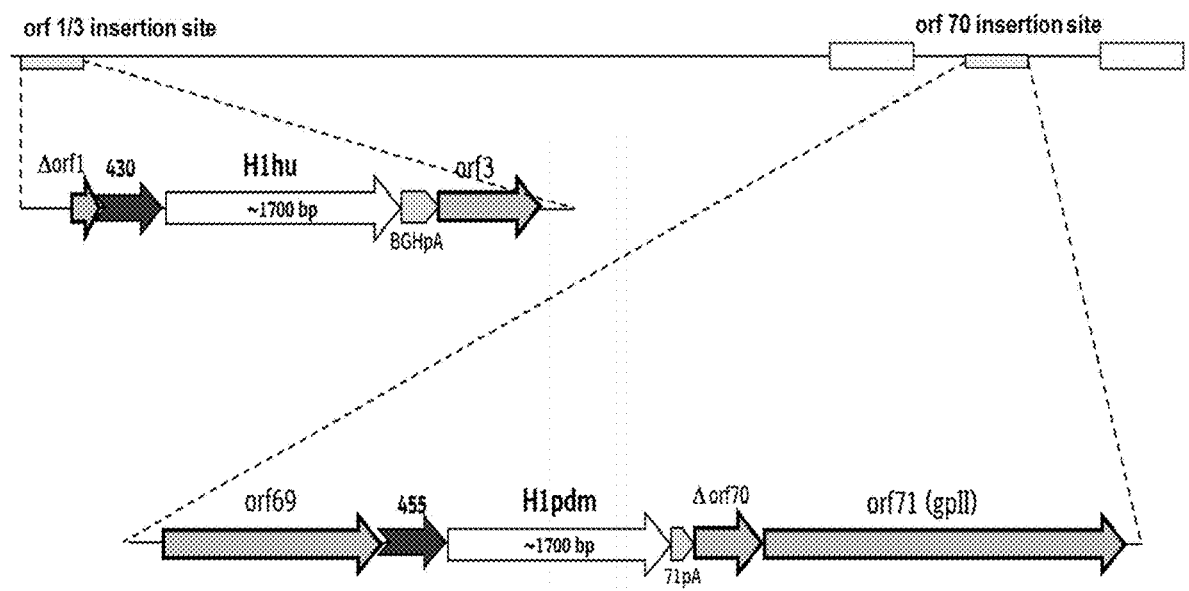

FIG. 27. The linear double-stranded DNA genome of rEHV-1 RacH-SE-1/3-p430-H1hu-70-p455-H1pdm (rEHV-1 RacH-SE_D) with the orf1/3 and orf70 insertion regions enlarged.

Figure 28:
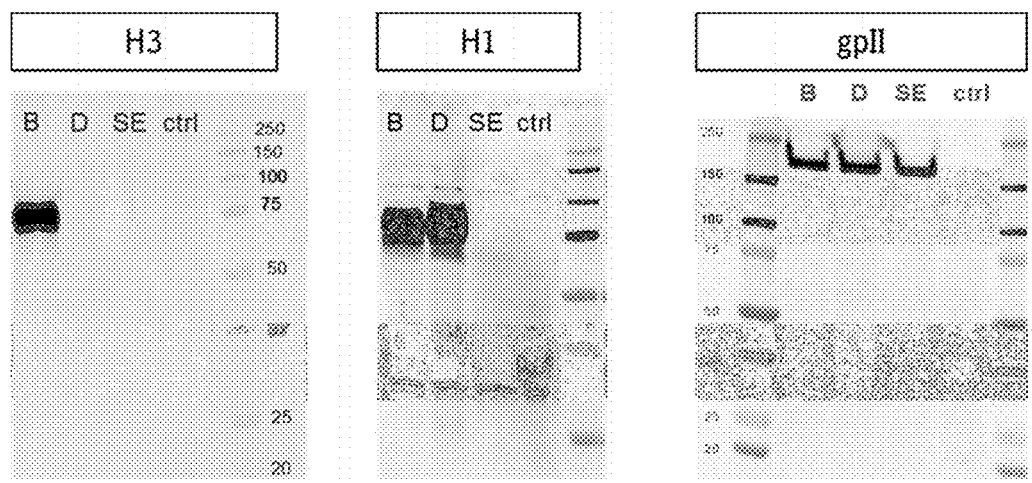

FIG. 28. Western blots of cells infected with rEHV-1 RacH-SE_B, RacH-SE_D, RacH-SE, or uninfected (ctrl). Replica blots were incubated either with a polyclonal rabbit hyperimmune serum directed against H3 (PA5-34930), a polyclonal rabbit hyperimmune serum directed against H1 (PA5-34929), or a monoclonal antibody (Ai2G7) against EHV-1 glycoprotein II (gpII). All antibodies produced the expected patterns confirming expression of the desired antigens H3 and H1 and comparable replication efficiency of the different viruses as judged from the very similar staining of EHV-1 gpII in all infected cells samples.

FIG. 29. Results of Influenza A virus neutralization tests of mice sera. *Error bars indicate standard deviation.

FIG. 30. Map of transfer plasmid pU70-455-SBVGc_71K71.

Figure 31:
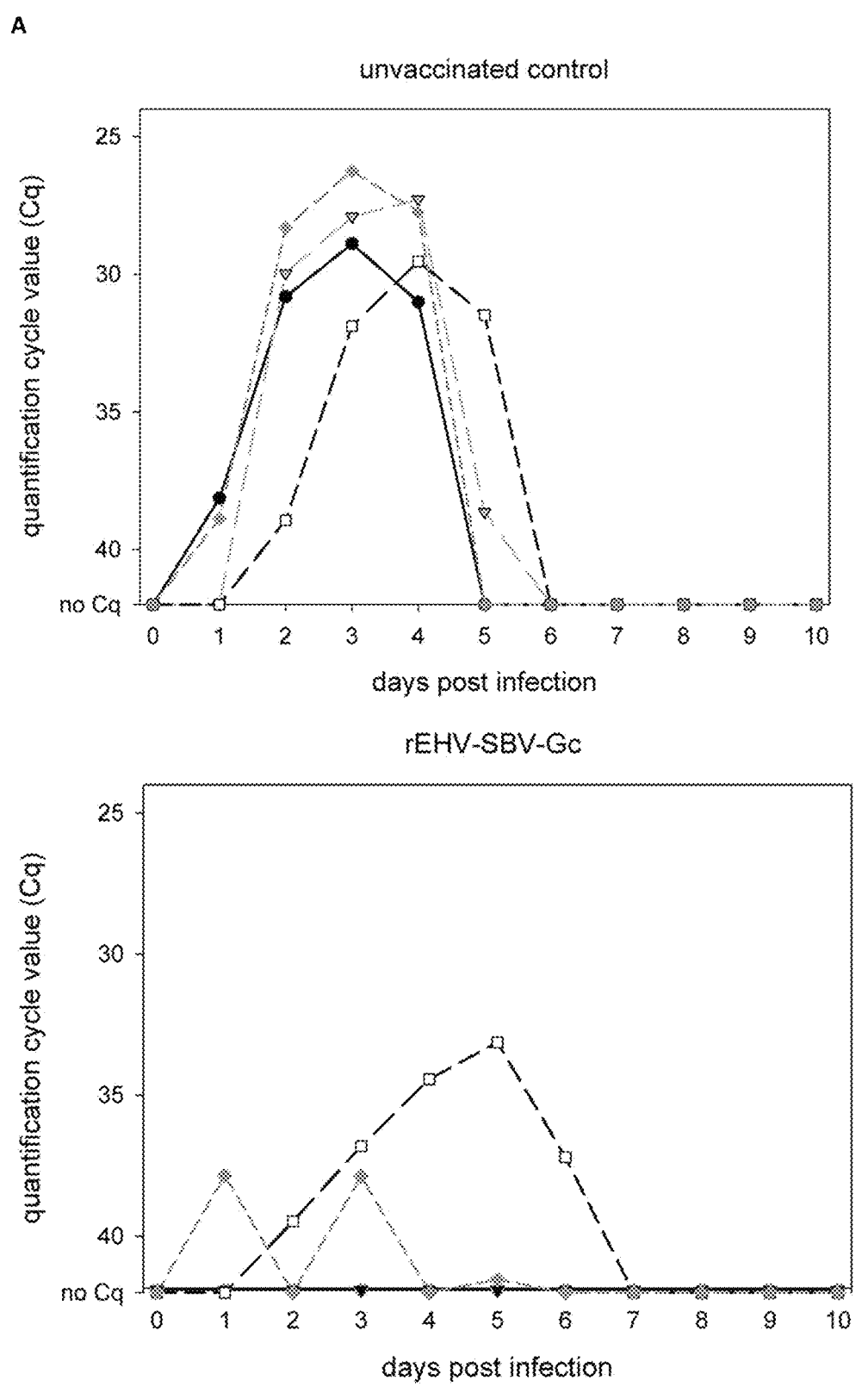
Figure 31:
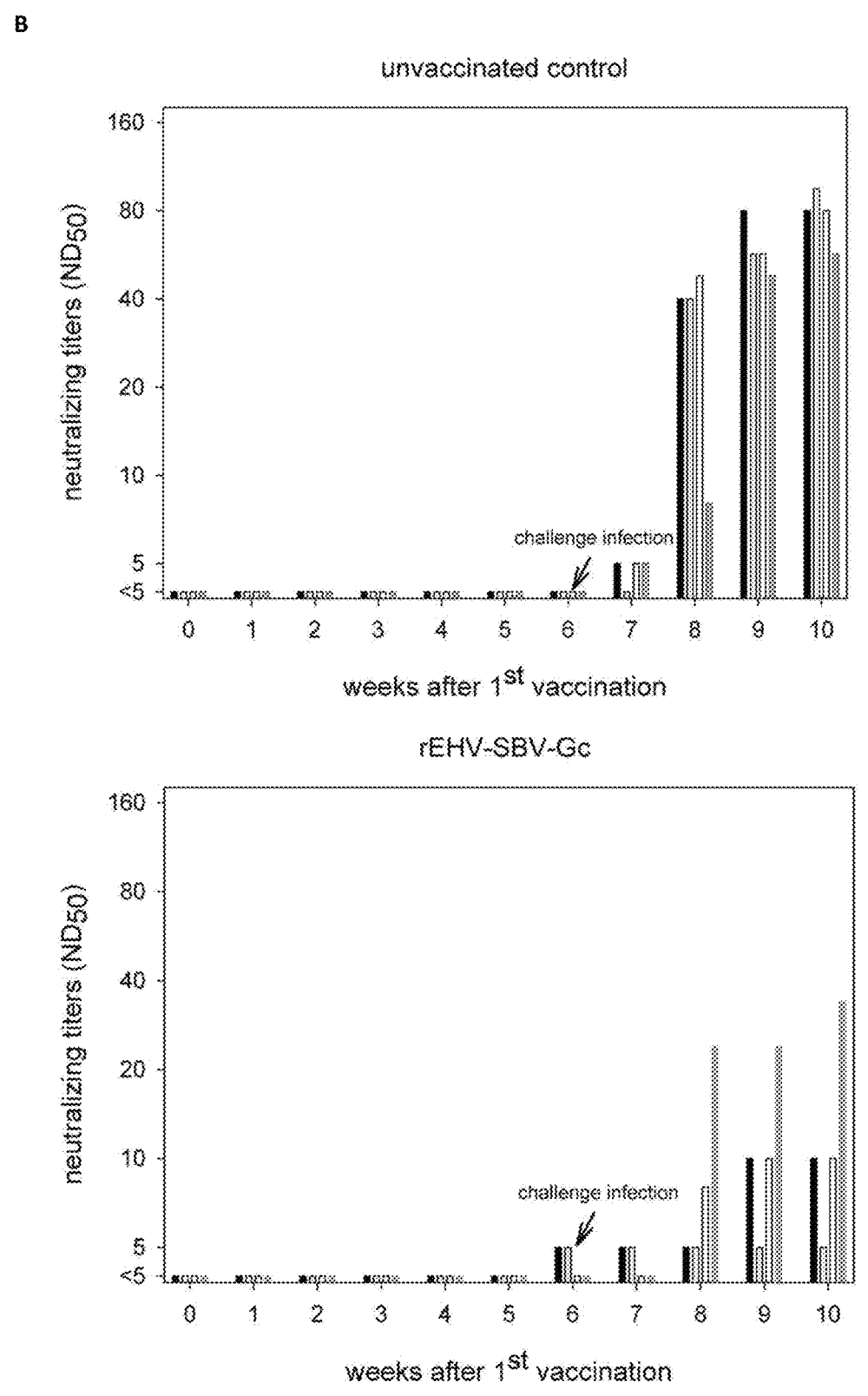

FIG. 31. A) Results of quantitative RT-PCR of unvaccinated control cattle (upper panel) and animals vaccinated twice with rEHV-SBV-Gc (lower panel) for detection of viral genome of SBV. Individual animals are identified by different types of lines and symbols for each group of animals unvaccinated and vaccinated, respectively. Animal 1 is depicted as black line with black filled circles (corresponds to black bar in FIG. 31, A). Animal 2 is depicted as broken grey line with grey filled triangles (corresponds to light grey bar in FIG. 31, B). Animal 3 is depicted as broken black line with unfilled squares (corresponds to white bar in FIG. 31, B). Animal 4 is depicted as broken grey line with grey filled diamonds (corresponds to dark grey bar in FIG. 31, B). B) Results of the serum neutralization tests of unvaccinated control cattle (upper panel) and animals vaccinated twice with rEHV-SBV-Gc (lower panel). Individual animals are identified by different bar colors/fillings (from black over light grey and dark grey to white) for each group of animals unvaccinated and vaccinated, respectively. Animal 1 is depicted as black bar (corresponds to black line with black filled circles in FIG. 31, A). Animal 2 is depicted as light grey bar (corresponds to broken grey line with grey filled triangles in FIG. 31, A). Animal 3 is depicted as white bar (corresponds to broken black line with unfilled squares in FIG. 31, A). Animal 4 is depicted as dark grey bar (corresponds to broken grey line with grey filled diamonds in FIG. 31, A).

Figure 32:
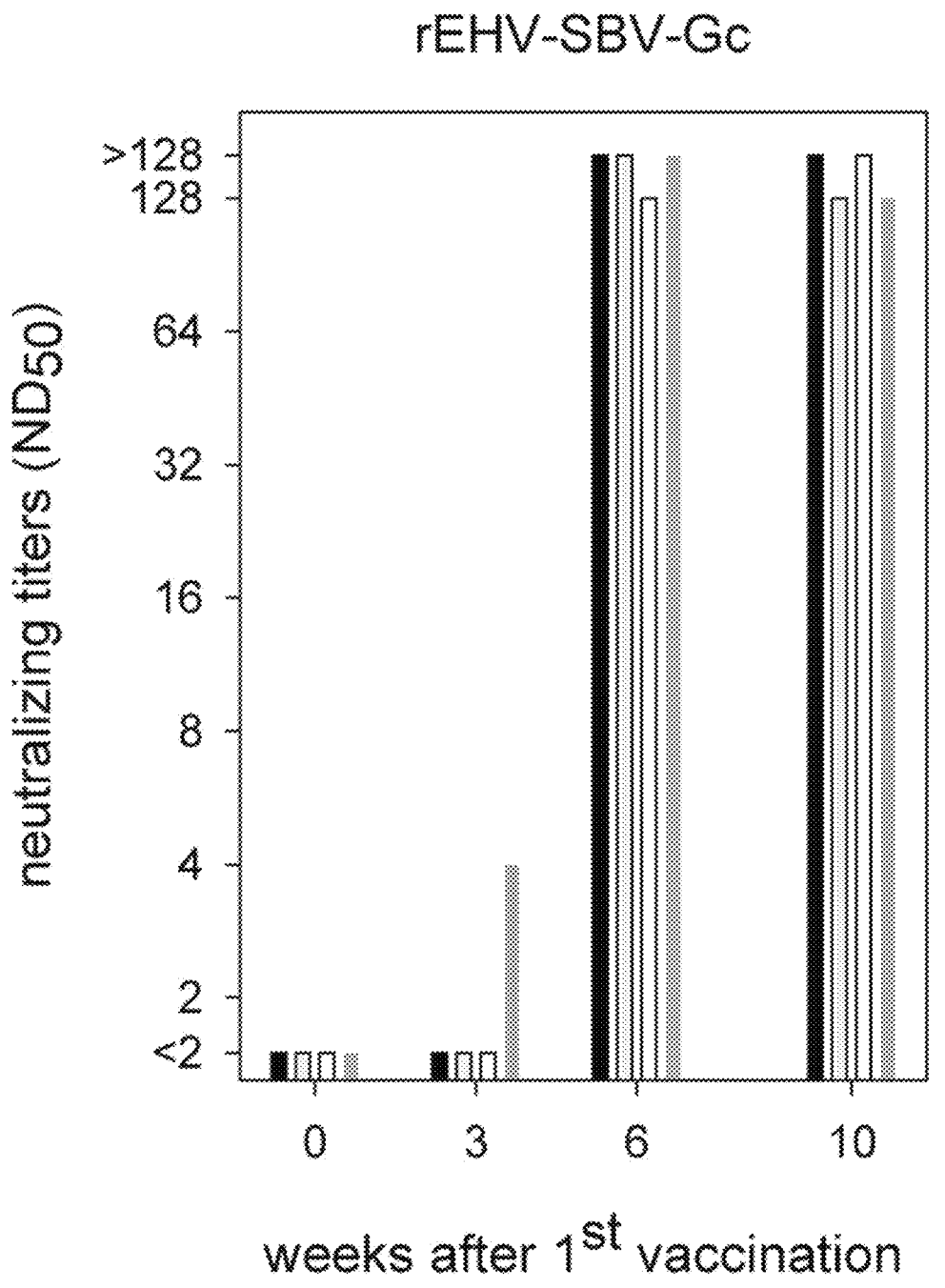

FIG. 32. EHV neutralization test. All results obtained from samples of the identical animal in a respective group are shown in the same shade of grey: one animal is represented by a black filled bar, another animal is represented by a light grey filled bar, a third animal is represented by a white bar, and a fourth animal is represented by a dark grey bar.

Figure 33:
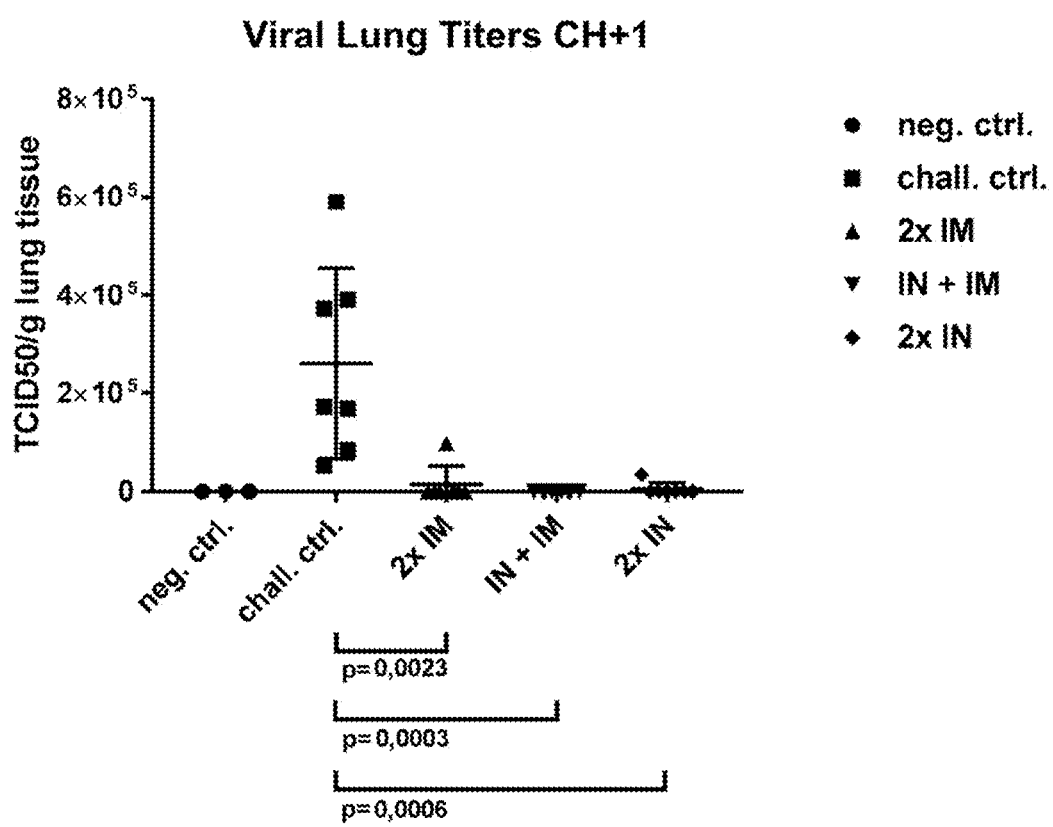

FIG. 33. Swine IAV lung titers determined as TCID50/g lung tissue for animals killed one day after challenge. neg. ctrl., negative control group; chall. ctrl., challenge control group; 2× IM, group vaccinated two times intramuscularly; IN+IM, group vaccinated first intranasally and second intramuscularly; 2× IN, group vaccinated two times intranasally. Data points indicate means obtained for individual animals. Middle horizontal lines indicate group means, respectively. Upper and lower horizontal lines indicate standard deviations, respectively. p values for pairwise statistical comparisons of groups are given below and were calculated by t-test using the Mann-Whitney test and GRAPHPAD PRISM® for Windows software 7.02, GraphPad Software, Inc., La Jolla, Calif. 92037, USA, using standard software settings, respectively.

Figure 34:
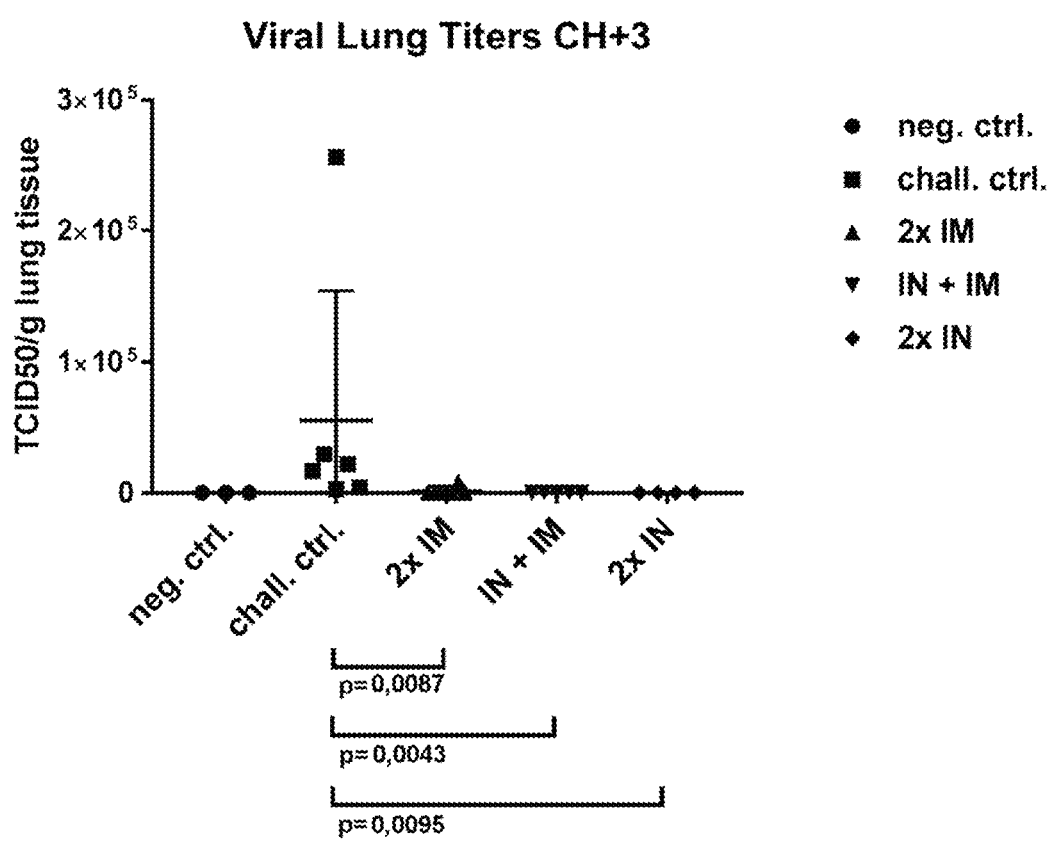

FIG. 34. Swine IAV lung titers determined as TCID50/g lung tissue for animals killed three days after challenge. neg. ctrl., negative control group; chall. ctrl., challenge control group; 2× IM, group vaccinated two times intramuscularly; IN+IM, group vaccinated first intranasally and second intramuscularly; 2× IN, group vaccinated two times intranasally. Data points indicate means obtained for individual animals. Middle horizontal lines indicate group means, respectively. Upper and lower horizontal lines indicate standard deviations, respectively. p values for pairwise statistical comparisons of groups are given below and were calculated by t-test using the Mann-Whitney test and GRAPHPAD PRISM® for Windows software 7.02, GraphPad Software, Inc., La Jolla, Calif. 92037, USA, using standard software settings, respectively.

Figure 35:
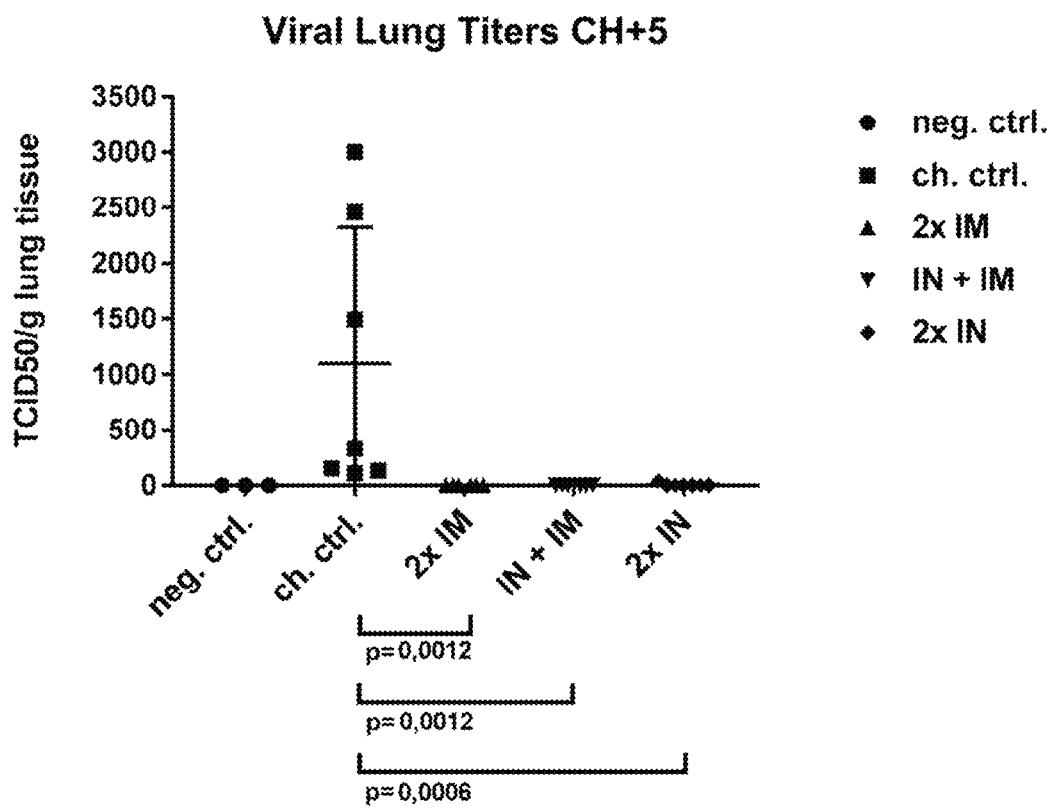

FIG. 35: Swine IAV lung titers determined as TCID50/g lung tissue for animals killed five days after challenge. neg. ctrl., negative control group; chall. ctrl., challenge control group; 2× IM, group vaccinated two times intramuscularly; IN+IM, group vaccinated first intranasally and second intramuscularly; 2× IN, group vaccinated two times intranasally. Data points indicate means obtained for individual animals. Middle horizontal lines indicate group means, respectively. Upper and lower horizontal lines indicate standard deviations, respectively. p values for pairwise statistical comparisons of groups are given below and were calculated by t-test using the Mann-Whitney test and GRAPHPAD PRISM® for Windows software 7.02, GraphPad Software, Inc., La Jolla, Calif. 92037, USA, using standard software settings, respectively.

Figure 36:
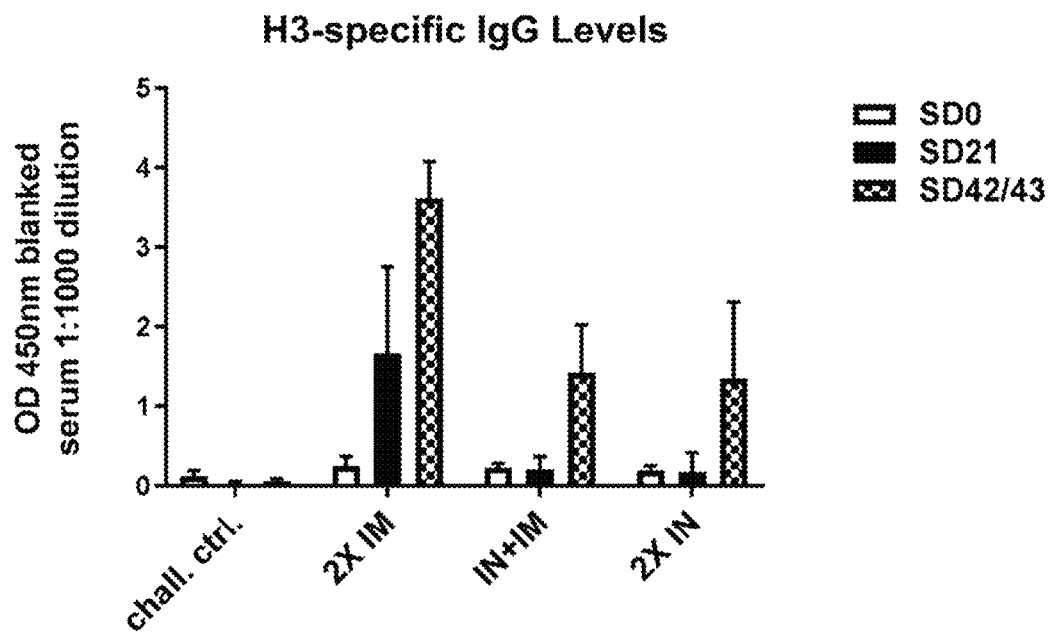

FIG. 36. Results from an enzyme-linked immunosorbent assay (ELISA) specific for swine immunoglobulin G (IgG) directed against a recombinantly expressed swine IAV hemagglutinin H3 antigen being homologous to the H3 expressed by vaccine strain rEHV-1 RacH-SE_B. For the test, each well was coated with 100 ng of recombinantly expressed H3. Samples were measured pairwise, sample means calculated from pairwise measurements, and group values were calculated from sample means, respectively. chall. ctrl., challenge control group (served as negative control); 2× IM, group vaccinated two times intramuscularly; 1N+IM, group vaccinated first intranasally and second intramuscularly; 2× IN, group vaccinated two times intranasally. Error bars indicate standard deviations. Study days (SD) are indicated in the legend to the right of the graph.

Figure 37:
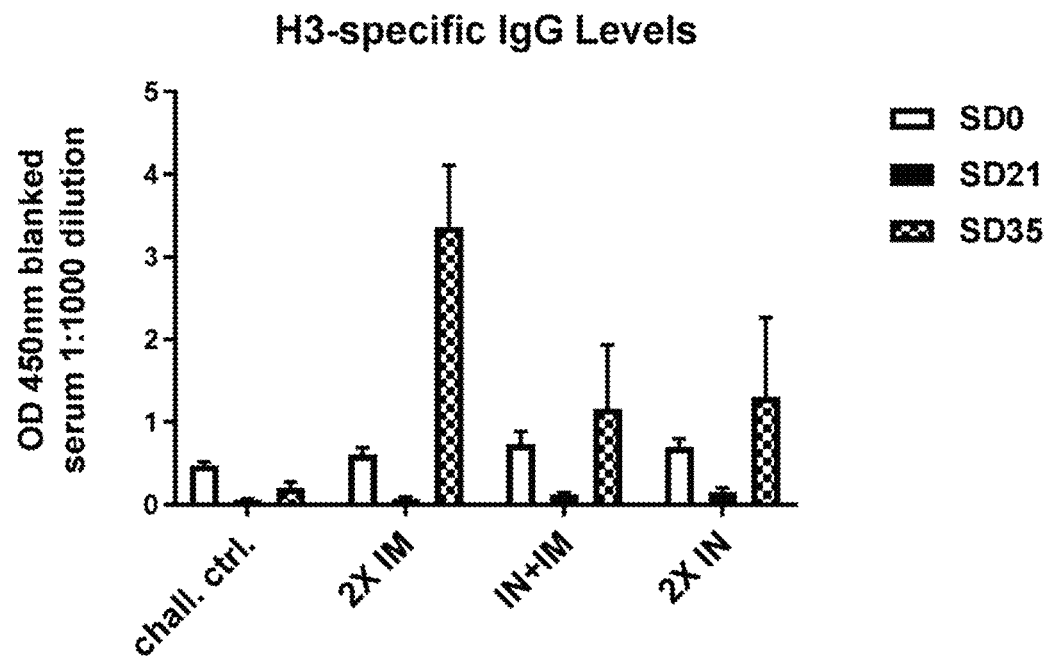

FIG. 37. Results from an enzyme-linked immunosorbent assay (ELISA) specific for swine immunoglobulin G (IgG) directed against a recombinantly expressed swine IAV hemagglutinin H3 antigen being homologous to the H3 expressed by vaccine strain rEHV-1 RacH-SE_B. For the test, each well was coated with 100 ng of recombinantly expressed H3. Samples were measured pairwise, sample means calculated from pairwise measurements, and group values were calculated from sample means, respectively. chall. ctrl., challenge control group (served as negative control); 2× IM, group vaccinated two times intramuscularly; 1N+IM, group vaccinated first intranasally and second intramuscularly; 2× IN, group vaccinated two times intranasally. Error bars indicate standard deviations. Study days (SD) are indicated in the legend to the right of the graph.

Figure 38:
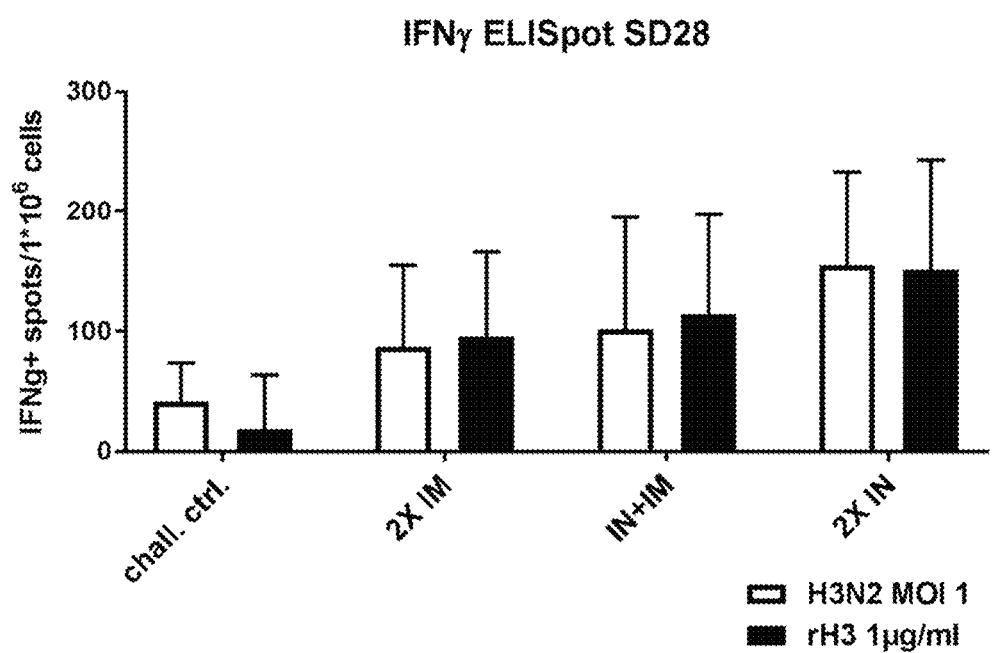

FIG. 38. Results from interferon gamma-specific enzyme-linked immunosorbent spot assay (IFNγ ELISpot). Peripheral blood mononuclear cells (PBMCs) were purified from blood taken from study animals at study day 28 (SD28). The PBMCs then were restimulated either with H3N2 swine IAV challenge strain R452-14 at a multiplicity on infection of 1 (H3N2 MOI 1) or with recombinantly expressed swine IAV H3 antigen being homologous to the H3 expressed by vaccine strain rEHV-1 RacH-SE_B at a concentration of 1 µg/ml (rH3 1 µg/ml). Using the restimulated PBMCs, an interferon gamma-specific enzyme-linked immunosorbent spot assay (IFNγ ELISpot) was performed, and the obtained values normalized to 10^6 cells and calculated as means per group, respectively. chall. ctrl., challenge control group (served as negative control); 2× IM, group vaccinated two times intramuscularly; IN+IM, group vaccinated first intranasally and second intramuscularly; 2× IN, group vaccinated two times intranasally. Error bars indicate standard deviations.

Figure 39:
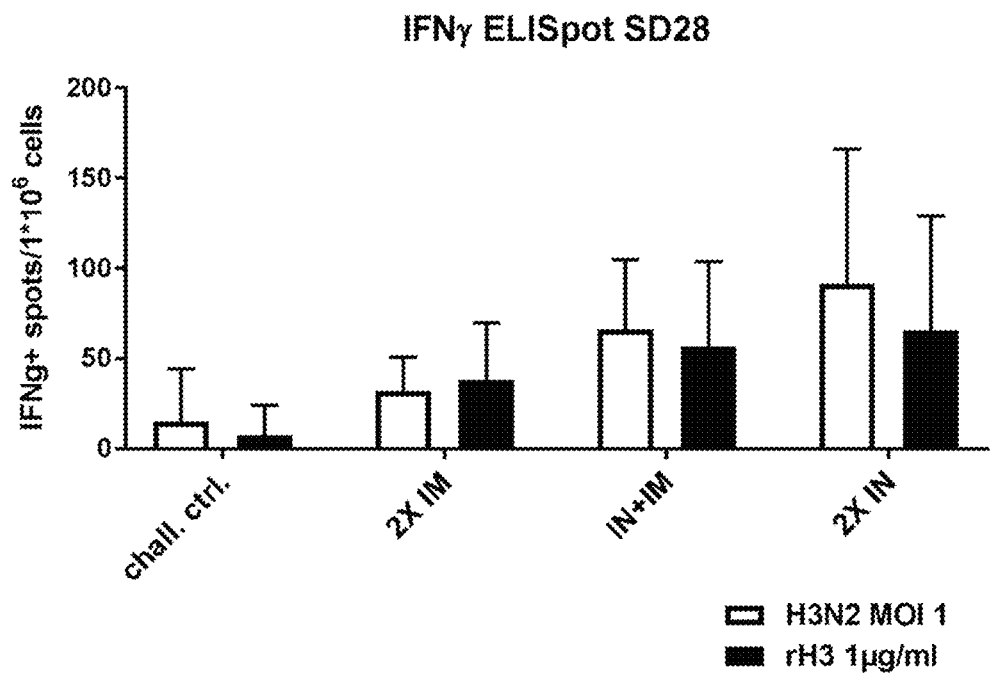

FIG. 39. Results from interferon gamma-specific enzyme-linked immunosorbent spot assay (IFNγ ELISpot). Peripheral blood mononuclear cells (PBMCs) were purified from blood taken from study animals at study day 28 (SD28). The PBMCs then were restimulated either with H3N2 swine IAV challenge strain R452-14 at a multiplicity on infection of 1 (H3N2 MOI 1) or with recombinantly expressed swine IAV H3 antigen being homologous to the H3 expressed by vaccine strain rEHV-1 RacH-SE_B at a concentration of 1 µg/ml (rH3 1 µg/ml). Using the restimulated PBMCs, an interferon gamma-specific enzyme-linked immunosorbent spot assay (IFNγ ELISpot) was performed, and the obtained values normalized to 10^6 cells and calculated as means per group, respectively. chall. ctrl., challenge control group (served as negative control); 2× IM, group vaccinated two times intramuscularly; IN+IM, group vaccinated first intranasally and second intramuscularly; 2× IN, group vaccinated two times intranasally. Error bars indicate standard deviations.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification and Construction of New Promoters

The strategy to identify suitable promoter sequences was as follows: 600 bp fragments of the EHV-4 sequence upstream of two known orfs were analyzed first by aligning them with the respective sequence fragments of the EHV-1 genome. The genes chosen were orf42 encoding the major capsid protein (MCP), and orf70 encoding glycoprotein G (gG). The major capsid protein is one of the most abundant constituents of the virion and needed for assembly of capsids in the cell nucleus as soon as newly synthesized viral DNA is ready for packaging. Its promoter is therefore expected to be active during early and late times in the viral replication cycle. For glycoprotein G it is known that its gene (orf70) is active also during early and late times in the replication cycle (Colle et al. 1995, Drummer et al. 1998). Sequence identity was 82.2% for the putative MCP-promoter and 82.3% for the putative gG-promoter. These differences were considered large enough to prevent homologous recombination on the one hand, and small enough to allow for transcriptional activation during EHV-1 replication on the other hand. In order to test for promoter activity, the 600 bp DNA fragments 4pgG600

```
                                                  (SEQ ID NO: 1)
GCAGACTTTGGAGCAGCACAATTTCCGGTTGTGGACCCCATGGACCTTGG

CTGGTACCGTGGAAACTAACGCTCCGGAAGTTTTGGCCAGAGCAAAATAC

TTTGGAATTCGAAGGTAGACATATGGAGCGCCGGAATAGTTCTGTTTGAA

ATGCTCGCATATCCATCAACTCTATTTGAGGACCCGCCGAGTACCCCACA

AGAGTATGTAAAAAGCTGTCATTCTCAACTACTGAGAATAATATCAAAGC

TAAAGATAAACCCTGAGGAGTTTCCACGGGAACCAGAGTCTAGGCTCGTG

CGCGGATACATCGAATACGCCAGCCTAGAGCGTAAGCCACATACGCGCTA

TCCTTGCTTCCAGCGCGTGAACCTACACATTGACGGGGAATTTTTGATCC

ATAAAATGCTAGCGTTCAATGCTGCGATGCGCCCATCCGCAGAAGAGTTG

TTGTCCTACCCAATGTTTATGAATCTGTAGGATGACTAACAGATTTGGGG

TGGAGACGGCGTGGGCGATACTGTATAAAGTTGTACTACTTACCAGCCCA

GTCAGTGTGCTGTAGTGCCACCACCTGTAAAGCTGTGATAAGCTGCAGTT
``` and 4pMCP600

(SEQ ID NO: 2)
AGCTGGGGGAGTTTGTACTATAGTGTATTACATGCGGCTTGCAATAACTG

CCTGGTTTATGTTTCGCAACATTCAAGCAGACATGCTACCGCTAAACACT

TTGCAACAATTTTTTATTGGGTGTTTGGCCTTTGGTAGAACTGTCGCGTT

TTTGGTGGTAGCATATACTACCTTATTTATACGCTCCGAGCTGTTTTTCA

GCATGCTAGCACCCAACGCCGAGCGAGAGTATATAACTCCCATCATTGCC

CACAAGCTTATGCCACTTATTAGCGTCCGCTCTGCCGTTTGCTTAGTCAT

AATATCTACCGCCGTTTACGCAGCAGACGCTATCTGCGACACAATTGGAT

TTGCGATACCGCGCATGTGGATGTGTATTTTAATGAGATCAACCTCCATG

AAGCGTAACTAGGGGGCCTCCCACTGAGGCACTACCGGCTTAGCAGCTGA

CTAACACAGTATAAAACGTGAGAAGAAATCAGTCTCATGCGCCATTAGCG

CTAGGCTAGTTAGCGTGGAGGACCGGAGCGCTACCGCCAGCAGTTTCATC

CGCCTGGTTACGGGTTTGTTAACACCTACCGGTGTTTTACCGCTACCATA were synthesized and cloned upstream of a reporter gene encoding the auto fluorescent protein mCherry (Shaner et al., 2004). As transcription termination signal and mRNA stabilizing function the bovine growth hormone polyadenylation sequence (BGHpA; Goodwin & Rottman, 1992) was cloned directly downstream at the 3'end of the reporter gene.

To be used as a positive control the CMV promoter was amplified from the commercially available plasmid pcDNA3.1 (Invitrogen) and cloned upstream of the mCherry reporter gene, here also the BGHpA was added at the 3'end of the reporter gene. Cell cultures were transfected with the three plasmids (pBlu-4pgGmCherry, pBlu-4pMCPmCherry, and pBlu-CMVmCherry) and inspected by fluorescence microscopy for mCherry fluorescence. Strong activity of the CMV promoter was obvious at different times after transfection. The 4pgG600 promoter was also active after transfection, activity of the 4pMCP600 promoter was also detectable, but weak in comparison with the 4pgG600 promoter and even more so when compared with the CMV-promoter even three days after transfection.

In order to investigate the effect of viral gene products on promoter activity, cell cultures transfected with either pBlu-4pgG600-mCherry or pBlu-4pMCP600-mCherry were superinfected one day after transfection with the green fluorescent EHV-1 RacHI-EF. The viral gene products obviously transactivated the 4pMCP600 promoter to significantly higher activity than in the absence of EHV-1 RacHI-EF replication. The effect was also present in cell cultures transfected with pBlu-4pgG600-mCherry and superinfected with EHV-1 RacHI-EF, albeit not so drastic since the initial activity in the absence of viral replication was higher than observed for pBlu-4pMCP600-mCherry. Still, for both 600 bp promoters a transactivating effect of viral replication on their activities in cell cultures was demonstrated.

This effect might be explained if the 600 bp sequences contain repressor elements, which are normally located upstream of the activator elements. Consequently, a shorter promoter might be more active in the absence of viral gene products. To test this both EHV-4 promoter sequences were truncated to approximately 75% of their original lengths and tested again.

In particular the 600 bp promoters were truncated to 430 bp for 4pgG, new name: p430:

(SEQ ID NO: 3)
TCTATTTGAGGACCCGCCGAGTACCCCACAAGAGTATGTAAAAAGCTGTC

ATTCTCAACTACTGAGAATAATATCAAAGCTAAAGATAAACCCTGAGGAG

TTTCCACGGGAACCAGAGTCTAGGCTCGTGCGCGGATACATCGAATACGC

CAGCCTAGAGCGTAAGCCACATACGCGCTATCCTTGCTTCCAGCGCGTGA

ACCTACACATTGACGGGGAATTTTTGATCCATAAAATGCTAGCGTTCAAT

GCTGCGATGCGCCCATCCGCAGAAGAGTTGTTGTCCTACCCAATGTTTAT

GAATCTGTAGGATGACTAACAGATTTGGGGTGGAGACGGCGTGGGCGATA

CTGTATAAAGTTGTACTACTTACCAGCCCAGTCAGTGTGCTGTAGTGCCA

CCACCTGTAAAGCTGTGATAAGCTGCAGTT and to 449 bp for 4pMCP, new name: p455:

(SEQ ID NO: 4)
TTGGTGGTAGCATATACTACCTTATTTATACGCTCCGAGCTGTTTTTCAG

CATGCTAGCACCCAACGCCGAGCGAGAGTATATAACTCCCATCATTGCCC

ACAAGCTTATGCCACTTATTAGCGTCCGCTCTGCCGTTTGCTTAGTCATA

ATATCTACCGCCGTTTACGCAGCAGACGCTATCTGCGACACAATTGGATT

TGCGATACCGCGCATGTGGATGTGTATTTTAATGAGATCAACCTCCATGA

AGCGTAACTAGGGGGCCTCCCACTGAGGCACTACCGGCTTAGCAGCTGAC

TAACACAGTATAAAACGTGAGAAGAAATCAGTCTCATGCGCCATTAGCGC

TAGGCTAGTTAGCGTGGAGGACCGGAGCGCTACCGCCAGCAGTTTCATCC

GCCTGGTTACGGGTTTGTTAACACCTACCGGTGTTTTACCGCTACCATA.

mCherry-reporter plasmids containing the shortened promoters were transfected in cell cultures and inspected by fluorescence microscopy. While the p430 activity was comparable to that of the 600 bp version (4pgG600), the activity of the p455 was significantly increased over the activity of the 4pMCP600. This result was in accordance with the results of the transfection/superinfection experiments using the 600 bp versions of the two promoters, namely, that presence of EHV-1 replication in the same cell provided a mechanism of transactivation of the 4pMCP600 promoter increasing its activity strongly while the transactivation of the 4pgG600 promoter was visible but less pronounced.

In addition to two new promoters also a new polyA sequence was needed for expression from the new orf70 insertion site. The element is called 71 pA. Its nucleotide sequence was synthesized and cloned downstream of the mCherry orf in a transfer plasmid containing the p455 targeted for the orf70 insertion site in pRacH-SE.

Next, rEHV-1 RacH-SE were generated to assay promoter activities in the background of viral replication (Table 1). The two EHV-4 promoters (p430 and p455), the CMV promoter and the mouse cytomegalovirus IE1 promoter (MCMV) were used to direct expression of mCherry in combination with a BGH polyA signal to increase mRNA stability. The MCMV IE1 promoter (enhancer) as described by Dorsch-Hasler et al. (1985) was synthesized and cloned in a plasmid vector from which it was subcloned into the transfer plasmid. In addition, the p455 was also cloned into the new insertion site in orf70 driving expression of mCherry in combination with the new polyA signal 71 pA.

As another control rEHV-1 RacHmC70 was included in the experiments. Cells infected with this recombinant virus express mCherry under control of the endogenous gG promoter (egGp) (Table 1).

TABLE 1

| name | promoter | reporter | polyA | Promoter | reporter | polyA |
|---|---|---|---|---|---|---|
| 1/3-CMV-mC | HCMV IE1 | mCherry | BGH | none | none | none |
| 1/3-MCMV-mC | MCMV IE1 | mCherry | BGH | none | none | none |
| 1/3-p455-mC | p455 | mCherry | BGH | none | none | none |
| 1/3-p430-mC | p430 | mCherry | BGH | none | none | none |
| 70-egGp-mC | none | none | none | endogenous gG | mCherry | BGH |
| 70-p455-mC | none | none | none | p455 | mCherry | 71pA |

VERO or PK/WRL cells were infected with all six mCherry expressing viruses at a m.o.i. of 1. Infected cells were collected at 0, 4, 8, and 12 hours p.i. and total RNA was prepared. Viral and cellular genomic DNA contaminating the RNA preparations was destroyed by DNAse I digestion. Integrity of the RNA and removal of viral DNA was shown by reverse transcription with and without addition of reverse transcriptase followed by PCR with a primer pair specific for orf72 (primers no 1130/1131, (TGTCTACCTTCAAGCTTATG (SEQ ID NO:5)/CTAGCGCAGTCGCGTTG (SEQ ID NO:6)) encoding the essential structural glycoprotein D of EHV-1. The expected 196 bp PCR product was amplified only from reverse transcribed samples (cDNA) where reverse transcriptase had been added, specifically the samples prepared at t1=4 h p.i., t2=8 h p.i., and t3=12 h p.i., not from the samples prepared at t0=0 h p.i. All samples where reverse transcriptase had not been added to the reaction did not produce any PCR product as expected. Thus it was shown that the samples (cDNA) that would be used as templates for qPCR did not contain viral genomic DNA.

The cDNAs obtained from the reverse transcription with added enzyme were then analyzed by qPCR using a primer pair specific for mCherry (primers no. 1079/1080, (GCGAGGAGGATAACATGG (SEQ ID NO:7)/ ACCCTTGGTCACCTTCAG (SEQ ID NO:8)) and the orf72 primer pair 1130/1131 (TGTCTACCTTCAAGCTTATG (SEQ ID NO:5)/CTAGCGCAGTCGCGTTG (SEQ ID NO:6)). Ct values for the orf72 qPCR were used to assess comparability of the different virus infections run in parallel and to normalize the Ct values for the mCherry qPCR. Thus, transcription of mCherry was quantified relative to the time after infection and to the different viruses (FIG. 3).

As shown in the left graph in FIG. 3 Ct values for orf72 transcripts were nearly identical for the six different viruses at the four different times after infection. Ideally all six viruses would produce identical values at the times investigated and only one line would be visible. Nearly identical lines confirmed sufficient quality of the experiment, also the 12 h p.i. time results are valid because the decrease as compared to 8 h p.i. indicates a further increase in the number of transcripts which is only possible when the replication has not yet passed its maximum. The statistical average of each time p.i. was calculated. The value of each virus at a certain time was divided by the average calculated for that time and used as a factor which with the Ct values of the mCherry qPCR were normalized to make them directly comparable. Normalized Ct values of the mCherry qPCR are graphically shown in the right graph in FIG. 3. Divergence of the lines indicates differences in the numbers of mCherry transcripts produced in the different virus-infected cells.

Figure 4:
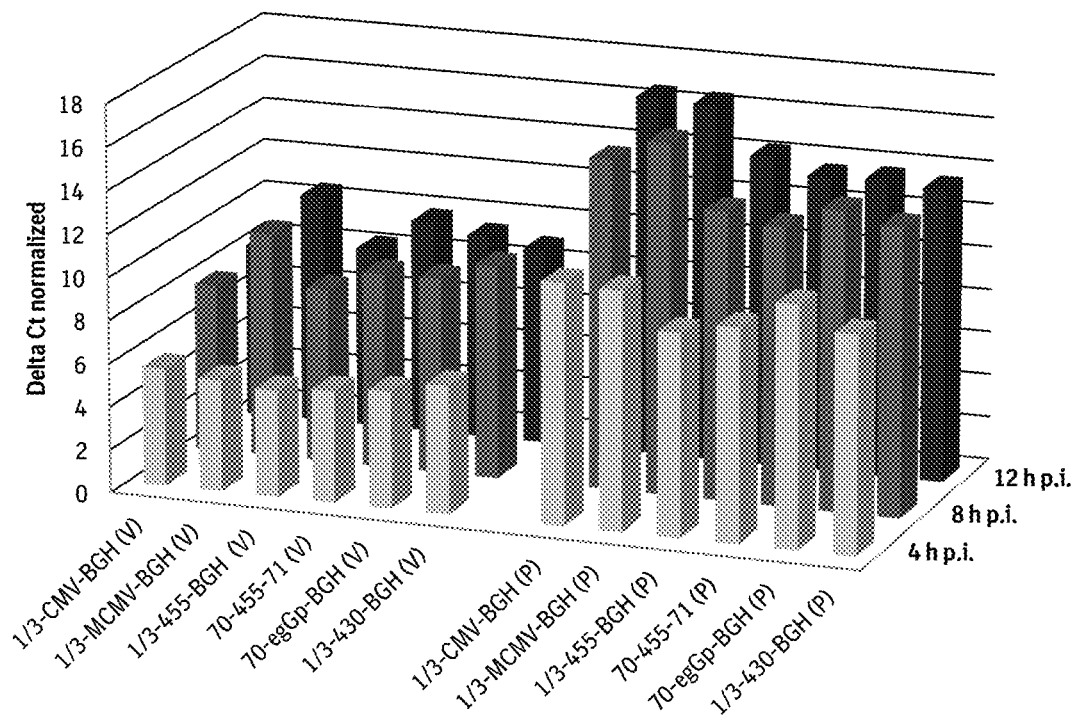
FIG. 4. qPCR results of two independent promoter kinetics experiments: Positive correlation of transcription activity and value depicted. Normalized Ct values of mCherry qPCR results at the different times after infection were subtracted from the corresponding average Ct value at t=0. Two experiments in two different cell lines are shown.

In a different type of graph two experiments, one using VERO-EU cells (V) and one using PK/WRL cells (P) were combined (FIG. 4). Quality of the RNA preparations and the viral replication over time was confirmed as described above by reverse transcription with and without reverse transcriptase followed by PCR with the orf72 primers. qPCR Ct values obtained for mCherry were normalized as described above on the basis of the qPCR Ct values for orf72. Normalized Ct values of t1=4 h p.i.; t2=8 h p.i., and t3=12 h p.i. were subtracted from the normalized Ct values at t0 (Delta normalized Ct) resulting in a positive correlation with transcription activity.

Although the two experiments in VERO (V) or PK/WRL (P) cells cannot directly be compared, the higher expression levels in PK/WRL cells most likely reflect the superior permissivity of PK/WRL cells for EHV-1 replication which routinely results in ten times higher titers of infectious virus. While activities of the EHV-derived promoters p430, p455 and egGp are almost the same at the respective times p.i. for the used cell line, irrespective of their insertion site or the used poly A (BGH or 71 pA), activities of the CMV- and MCMV promoters are higher in the PK/WRL cells. In VERO-EU cells, only the MCMV promoter was shown to have higher activity, the CMV promoter was not superior to the EHV-promoters.

From these experiments it was concluded that the EHV-4 promoters p430 and p455 were suitable to be used in the EHV-1 RacH backbone to drive expression of inserted transgenes from both the orf1/3 and the orf70 insertion sites.

Example 2

Use of the New p455 Promoter in Recombinant EHV-1 Vector Vaccines and Construction of a Recombinant Virus The p455 Promoter:

For a first animal experiment an Influenza hemagglutinin subtype H3 from a swine origin Influenza A virus (A/swine/Italy/7680/2001(H3N2), GenBank accession no.: ABS50302.2) was used. Its coding sequence was synthesized and subcloned generating the transfer vector pU70-p455-H3-71K71, placing H3 under control of the new p455 promoter and the new 71 pA polyadenylation signal and framing the cassette with the recombination regions for insertion into orf70 (FIG. 5).

By en-passant mutagenesis using the RED recombination system (Tischer et al. 2006) the expression cassette p455-H3-71 was inserted in orf70 of pRacH-SE to generate pRacH-SE70-p455-H3 (FIG. 6).

PK/WRL cells were transfected with pRacH-SE70-p455-H3, recombinant virus rEHV-1 RacH-SE70-p455-H3 was rescued and plaque-purified twice. Correct insertion of the expression cassette was verified by sequencing of a high-fidelity PCR product of the insertion region. Expression of the transgene in infected cells was analyzed by indirect immunofluorescence assay (IFA, FIG. 7).

Restoration of orf71 encoding EHV-1 gpII was confirmed by IFA (not shown) and Western blot (FIG. 8) using a monoclonal antibody Ai2G7 (owned by BI). Appearance of trimers of H3 on the plasma membrane of infected cells was assayed by a hemadsorption test using chicken erythrozyes (not shown). Peak titers determined as $TCID_{50}$/ml in PK/WRL cells were in the same range as titers of the parental virus rEHV-1 RacH-SE which indicates that transgene expression had no detrimental effect on viral replication (not shown). This was confirmed by passaging of rEHV-1 RacH-SE70-p455-H3 in PK/WRL cells up to passage 20 (P20) after rescue. At P5, P10, P15, and P20 the virus was characterized by titration, sequencing, and Western blot (FIG. 8), at P10 and P20 additionally by IFA, and HA expression and genetic stability of the HA encoding insert along with the promoter and polyA sequences were confirmed.

The two blots shown in FIG. 8 are replicas that were incubated with either the monoclonal antibody Ai2G7 (left) that specifically detects EHV-1 glycoprotein II (gpII) or with a commercial polyclonal antibody from rabbit (PA5-34930) raised against Influenza hemagglutinin subtype H3 (right). gpII was detected in all cell cultures infected with recombinant EHV-1 as expected. Full-length H3 was detected in all cells infected with the different passages of rEHV-1 RacH-SE-70-p455-H3 as expected. Specificity of the H3-antiserum was shown in the same Western blot, see lane gG430mC. Here only the gpII mab produced a reaction, as expected, while the anti-H3 antibody did not bind in the respective replica lane.

By double immunofluorescence assay (dIFA) of viral plaques in cells infected with P20 using a monoclonal anti-H3 antibody and a horse anti-EHV antiserum, it was confirmed that virtually all EHV-1 induced plaques also express H3 (not shown). All tests confirmed stability of the recombinant EHV-1 RacH-SE-70-p455-H3.

Example 3

Proof of Concept Animal Study (POC I) Using the p455 Promoter and Assessment of the Serological Response Test Animals: Inclusion Criteria and Experimental Design:

Five groups of ten piglets born from Influenza A-naive sows were included in the POC-I study as summarized in table 2.

TABLE 2

| Group | | No. of animals | Route | Dose |
|---|---|---|---|---|
| | Vaccine Treatment | | | |
| 1 | 1x NaCl; 1x EHV1 vector vaccine | 10 | i.m. | 2 ml NaCl; 2 ml EHV1, $1.00 \times 10^7$ $TCID_{50}$ |
| 2 | 2x EHV1 vector vaccine | 10 | i.m. | 2x 2 ml EHV1, $1.00 \times 10^7$ $TCID_{50}$ |
| 3 | 2x NaCl | 10 | i.m. | 2x 2 ml NaCl |
| 4 | 2x inactivated vaccine | 10 | i.m. | 2x 2 ml Inact. |
| 5 | 2x NaCl | 10 | i.m. | 2x 2 ml NaCl |

TABLE 2-continued

| Group | | No. of animals | Route | Dose |
|---|---|---|---|---|
| | Challenge Treatment | | | |
| 1 | H3N2 INFLUENZA A VIRUS FROM SWINE | 10 | Intra-tracheal | 8 ml; $1.00 \times 10^7$ $TCID_{50}$/ml |
| 2 | H3N2 INFLUENZA A VIRUS FROM SWINE | 10 | Intra-tracheal | 8 ml; $1.00 \times 10^7$ $TCID_{50}$/ml |
| 3 | H3N2 INFLUENZA A VIRUS FROM SWINE | 10 | Intra-tracheal | 8 ml; $1.00 \times 10^7$ $TCID_{50}$/ml |
| 4 | H3N2 INFLUENZA A VIRUS FROM SWINE | 10 | Intra-tracheal | 8 ml; $1.00 \times 10^7$ $TCID_{50}$/ml |
| 5 | cell culture medium (Negative Control) | 10 | Intra-tracheal | 8 ml |

An infectious dose of $1 \times 10^7$ TCID50 of rEHV-1 RacH-70-p455-H3 (EHV-1) was applied either once at five weeks of age or twice at two and five weeks of age. For comparison commercially available inactivated vaccine (Inact) was applied twice at two and five weeks of age. All piglets were free of maternally derived antibodies in order not to abolish the effect of the inactivated vaccine (Inact). Two groups were not vaccinated but received injections with physiological sodium chloride solution (NaCl) to serve as challenge control or strict negative control, respectively. 21 days after the second vaccination all groups except the strict negative control group were challenged with $1 \times 10^7$ $TCID_{50}$ of a heterologous Influenza A (IVA) strain (H3N2 INFLUENZA A VIRUS FROM SWINE R452-14, challenge isolate owned by BI). While in the non-vaccinated challenge control group (Chall ctrl) all pigs had high influenza virus titers in their lungs at one and three days after challenge infection, all pigs in the strict negative control group (neg ctrl) and the group that had been vaccinated twice (EHV 2x) with rEHV-1 RacH-SE-70-p455-H3 were negative for IVA at both days. In the group vaccinated twice with the inactivated control vaccine (Inact 2x), one of five animals had a low IVA titer at day three after challenge. In the group vaccinated once (EHV 1x) 21 days prior to challenge with rEHV-1 RacH-SE-70-455-H3, two of five animals had low IVA titers in their lungs one day after challenge infection and one of five at three days after challenge. (FIG. 9).

Two vaccinations with $1 \times 10^7$ TCID50 of rEHV-1 RacH-SE-70-p455-H3 completely protected pigs against challenge infection with a heterologous IAV, subtype H3N2.

It was demonstrated that the EHV-1 vector RacH-SE is suitable for vaccination of pigs and that the new promoter 455 is functional in driving immunogenic expression of IAV hemagglutinin in vaccinated pigs.

Example 4

Use of the New p430 Promoter in Recombinant EHV-1 Vector Vaccines and Construction of a Recombinant Virus The p430 Promoter:

The newly identified p430 promoter was used to drive expression of another Influenza hemagglutinin from an H1N1 virus ((A/swine/Gent/132/2005(H1N1), GenBank accession no.: AFR76623.1). Since the hemagglutinin gene in this virus isolate originated from an avian IAV it will be referred to as H1av. H1av was synthesized and subcloned in a transfer vector for the orf1/3 insertion region to generate pU1/3-p430-H1av-BGH_K_BGH. Expression of H1av was placed under control of the p430 promoter and the bovine growth hormone (BGH) polyA signal (FIG. 10).

By en-passant mutagenesis using the RED recombination system (Tischer et al. 2006) the expression cassette p430-H1av-BGH was inserted in orf1/3 of pRacH-SE to generate pRacH-SE1/3-p430-H1av (FIG. 11).

PK/WRL cells were transfected with pRacH-SE1/3-p430-H1av, recombinant virus rEHV-1 RacH-SE1/3-p430-H1av was rescued and plaque-purified twice. Correct insertion of the expression cassette was verified by sequencing of a high-fidelity PCR product of the insertion region. Expression of the transgene in infected cells was analyzed by indirect immunofluorescence assay (IFA) and Western blot using commercially available monoclonal and polyclonal antibodies (FIG. 12).

Restoration of orf71 encoding EHV-1 gpII was confirmed by IFA and Western blot using a monoclonal antibody Ai2G7 (owned by BI), (not shown). Correct processing and transport of H1av and localization in the plasma membrane of infected cells was assayed by a hemadsorption test using chicken erythrozytes (not shown). Peak titers determined as TCID50/ml in PK/WRL cells were in the same range as titers of the parental virus RacH-SE which indicates that transgene expression had no detrimental effect on viral replication (not shown).

Specific detection of a broad band migrating at 75 kDa by antibody PA-34929 is in concordance with the expected appearance of the recombinant HA glycoprotein as predicted from its sequence. Apparent staining of cellular membranes with the monoclonal antibody C102 is in line with the subcellular localization as expected (FIG. 12).

In order to test whether the expressed recombinant hemagglutinins were processed and transported as expected, VERO-cells were infected with rEHV-1 RacH-SE-1/3-p430-H1av, rEHV-1 RacH-SE-70-p455-H3, rEHV-1 RacH-SE (parent) at an m.o.i. of 0.01, or left uninfected. 24 h p.i. live infected and uninfected cells were incubated with a suspension of chicken erythrocytes in PBS, washed with PBS and stained with the fluorescent Hoechst 33342 nuclear stain. Since erythrocytes of birds contain cell nuclei they can be stained with Hoechst33342 and appear as tiny blue specks by fluorescence microscopy, Compared with cells that were infected with rEHV-1 RacH-SE that does not express hemagglutinin, adsorption of chicken erythrocytes was significantly increased on cells infected with either rEHV-1 RacH-SE-1/3-p430-H1av or rEHV-1 RacH-SE-70-p455-H3 (not shown). From this it can be concluded that the hemagglutinins were translated, processed and transported to the plasma membrane of vector virus infected cells in a manner as if they were produced by authentic influenza virus infection.

The clear phenotype of hemadsorption of infected cells supports the findings of the Western blots and immunofluorescence assays showing efficient expression of the transgenic proteins and suggesting formation of functional HA trimers on the cell surface of EHV-1 vector infected cells.

Example 5

Use of the Two New Promoters p455 and p430 in Recombinant EHV-1 Vector Vaccines in Two Insertion Sites in Parallel To show that the two new promoters can be used in parallel a recombinant EHV-1 RacH was generated expressing two different hemagglutinins of two different Influenza A virus subtypes.

Specificity and lack of cross-reactivity of the polyclonal commercial antibodies to H3 (PA5-34930) and H1 (PA5-34929) was verified by Western blots of infected cells infected with single-insert viruses rEHV-1 RacH-SE-70-p455-H3 and rEHV-1 RacH-SE-1/3-p430-H1av (not shown).

Starting with the recombinant BAC pRacH-SE-70-p455-H3, the expression cassette p430-H1av-BGH as assembled in the transfer vector pU1/3-p430-H1av-BGH_K_BGH (FIG. 10) was inserted into the orf1/3 insertion site by two-step RED recombination to generate pRacH-SE-1/3-p430-H1av-70-p455-H3. PK/WRL cells were transfected with pRacH-SE1/3-p430-H1av-70-p455-H3, and recombinant virus rEHV-1 RacH-SE1/3-p430-H1av-70-p455-H3 was rescued and plaque-purified twice (FIG. 13).

The short designation for this recombinant virus is rEHV-1 RacH-SE_B. Correct insertion of the expression cassette was verified by sequencing of high-fidelity PCR products of the insertion regions together with flanking sequences. Expression of the transgenes in infected cells was analyzed by indirect immunofluorescence assay (IFA, not shown) and Western blot using commercially available monoclonal and polyclonal antibodies (FIG. 14). Restoration of orf71 encoding EHV-1 gpII was confirmed by IFA (not shown) and Western blot using a monoclonal antibody Ai2G7 (owned by BI), (FIG. 14).

As shown in FIG. 14 both transgenes H3 and H1av were expressed in parallel in cell cultures infected with the dual insert recombinant rEHV-1 RacH-SE-1/3-p430-H1av-70-p455-H3 (B). Transgene expression was stable and did not impair viral titers tested until passage 11 in PK/WRL cells (not shown).

The two new promoters p430 and p455 were shown to be functional in the context of rEHV1-RacH replication in cell cultures. Activity levels during the viral replication cycle appear to be very similar as deduced from in vitro promoter kinetic experiments. These properties allow creation of recombinant vector vaccines based on EHV-1 RacH or other vector platforms expressing two different antigens in parallel with similar efficiency. If a vaccine target consists of two different pathogens application of the two new promoters in two insertion sites combined with two polyadenylation sequences can reduce cost of goods significantly and represents a clear advantage over a vector expressing only one antigenic component.

Example 6 rCAV-2 Vector Vaccines Using the New p455 and p430 Promoters

Methods
AI-ST 2015 cells infected with the following rCAV-2
1.CAV-2 CMVie BRSV (positive control for anti-CAV2; negative control for anti-VP2)
2.CAV-2 p430 CPV VP2 (Despliced A1-2-1)
3.CAV-2 p430 CPV VP2 (Gen 0.95 D1-5-1)
4.CAV-2 p455 CPV VP2 (Gen0.95 E1-8-1)
5.CAV-2 p430 RabG (n)
6.CAV-2 p455 RabG (n)
Immunofluorescence Analysis (IFA)
AI-ST 2015 cells are fixed with Cytofix/Cytoperm 72 h post-infection and stained with anti-CPV VP2-FITC (mAb), anti-RabG-FITC (mAb) and anti-CAV-2-FITC (porcine antisera) (VMRD).
Flow Cytometry (FC)
AI-ST 2015 cells are fixed with Cytofix/Cytoperm 48 & 72 h post-infection and cells stained with anti-CAV-2-FITC, anti-CPV VP2-FITC (VMRD), porcine hyperimmune sera against CPV (Benchmark) and anti-RabG-FITC (Novus).

Dot Blot for CPV VP2

Clarified (6000×g, 5 min) tissue culture supernatants/lysates (freeze/thaw) from infected E1B MDCK (for rCAV-2) cells are serially diluted with PBS before addition to apparatus and adsorbed to PVDF via aspiration. Subsequent steps are a 30 minute exposure to 5.0% BioRad Blotting Grade Blocker in TBST, 1.0 h exposure to 1° antibodies, three TBST washes, and a 1.0 h exposure to peroxidase-conjugated 2° antibodies (anti-mouse and anti-swine, Jackson ImmunoResearch) and visualization via TMB. For quantification, dot blots are analyzed using ImageJ software (Burger, W., Burge, M. J. (Eds.), 2008. Digital Image Processing: An algorithmic introduction using Java. Springer-Verlag, New York). Image colors are inverted to subtract background and integrated density of each dot recorded. Values are assigned + and − designations as follows: "++++"=>800000, "+++"=500000 to 800000, "++"=300000 to 499999, "+"=120000 to 299999, "+/−"=80000 to 119999 and "−"=<80000.

The CAV-2 VP2 Construct:

The generation of virus like particles (VLPs) by rCAV-2 vaccine virus infected cells can be a critical factor for canine adenovirus (CAV-2) vaccine efficacy. While rCAV-2 containing a CMVie-driven CPV VP2 expression cassette could be rescued, substantial VP2 expression (for VLP generation) in rCAV-2 CMVie CPV VP2 infected cells could not be achieved using the conventional CMVie promoter. A rCAV-2 VP2 virus containing the CMV5 promoter could not be rescued.

IFA, flow cytometry and Dot blots were employed to assess EHV-4 promoter-driven expression of CPV VP2 in rCAV-2-infected AI-ST 2015 cells. CAV-2 protein expression was probed with anti-CAV-2 FITC-conjugated porcine polyclonal antibodies (VMRD). CPV VP2 protein expression was probed with mouse monoclonal (VMRD) and porcine hyperimmune sera (Benchmark). CAV-2 and CPV VP2 proteins are readily visualized by IFA and detected by FC in a substantial proportion of AI-ST 2015 cells infected with rCAV-2 carrying two different nucleotide variants of CPV VP2 (Despl and Gen0.95, at 48 and 72 h post-infection). Substantial CPV VP2 protein was identified in tissue culture supernatants/lysates (after freeze/thaw) by Dot Blot (and very likely reflects the presence of assembled VLPs).

CPV VP2 expression in infected AI-ST 2015 cells was readily detected by IFA (see FIG. 19, A). CPV VP2 expression was detected in less than 3% of the cells infected with original rCAV-2 CMVie CPV VP2 (see FIG. 15). Therefore, rCAV-2 carrying CPV VP2 expression cassettes driven by the new EHV4 derived promoters p430 and p455 were rescued and tested to determine whether they could effectively drive the expression of CPV VP2 in infected cells. Surprisingly, CPV VP2 expression was detected in 14% to 36% of the infected cells (see FIG. 16). Additionally, and in contrast to the original rCAV-2 CMVie CPV VP2 (wherein dot blot analysis showed CMVie-driven CPV VP2 signal was at or below background levels—comparable with supernatants/lysates from CAV-2, rCAV-2 CMVie BRSV F-infected cells and cell culture supernatant/lysates from uninfected cells—data not shown), an abundant amount of CPV VP2 is detected in supernatants/lysates from infected AI-ST 2015 cells (see FIG. 17). FIG. 17 shows that the VP2 protein can be recognized in the supernatant and, therefore, is expected to be in the conformation required (VLPs) to be immunogenic. Importantly, the rescue of recombinant CAV-2 was not achieved when either the CAG or CMV5 promoter sequences were present in the expression cassettes located in the E3 region. This appears to be sequence-specific as the size of the expression cassettes had not exceeded observed experimental genome size limitations. Thus, the new EHV-4 derived promoter sequences of the present invention such as p430 and p455 not only facilitate transgene expression, but also support the crucial step of viral rescue.

In conclusion, IFA, FC and Dot Blot demonstrate robust EHV-4 promoter-driven expression of CPV VP2 transgene by rCAV-2 in infected AI ST 2015 cells. These results confirm the utility of the EHV-4 promoters in a vector other than EHV-1.

rCAV-2 RabG (n) Construct:

A second CAV-2 construct was generated using the new EHV-4 derived p455 promoter of the present invention. The rCAV-2 RabG(n) was chosen because expression by infected cells was not observed using the conventional CMVie promoter.

The objective of this experiment was to confirm the activity of the new EHV-4 promoter in the context of rCAV-2 with a second transgene, RabG (a membrane protein) by the measurement of EHV-4 promoter-driven RabG protein expression by rCAV-2 p455 RabG (n)-infected AI-ST 2015 cells.

IFA and flow cytometry were employed to assess EHV-4 promoter-driven expression of RabG in rCAV-2-infected AI-ST 2015 cells. CAV-2 protein expression was probed with anti-CAV-2 FITC-conjugated porcine polyclonal antibodies (VMRD). RabG protein expression was probed with mouse monoclonal antibodies (Novus). CAV-2 and RabG proteins are readily visualized by IFA and detected by FC in AI-ST 2015 cells infected with rCAV-2 carrying RabG (n) (at 72 h post-infection).

As a result: While RabG is readily detected in cells infected with rCAV-2 p455 RabG (see FIGS. 19, B and 19, C), expression is detected in <2.0% of cells infected with original rCAV-2 CMVie RabG (see FIG. 18). Minimal to no signal is seen in cells infected with rCAV-2 with a non-relevant transgene (see FIG. 19, B; CPV VP2, which is not relevant for the anti RabG antibody). As seen in the dual stain in FIG. 19, C many CAV-2 positive cells are also positive for RabG.

In conclusion, the IFA and FC data demonstrate EHV-4 promoter-driven expression of RabG transgene by rCAV-2 by infected AI ST cells. These results further confirm the utility of the EHV-4 promoters of the present invention in a vector other than EHV-1.

Example 7

Figure 1:
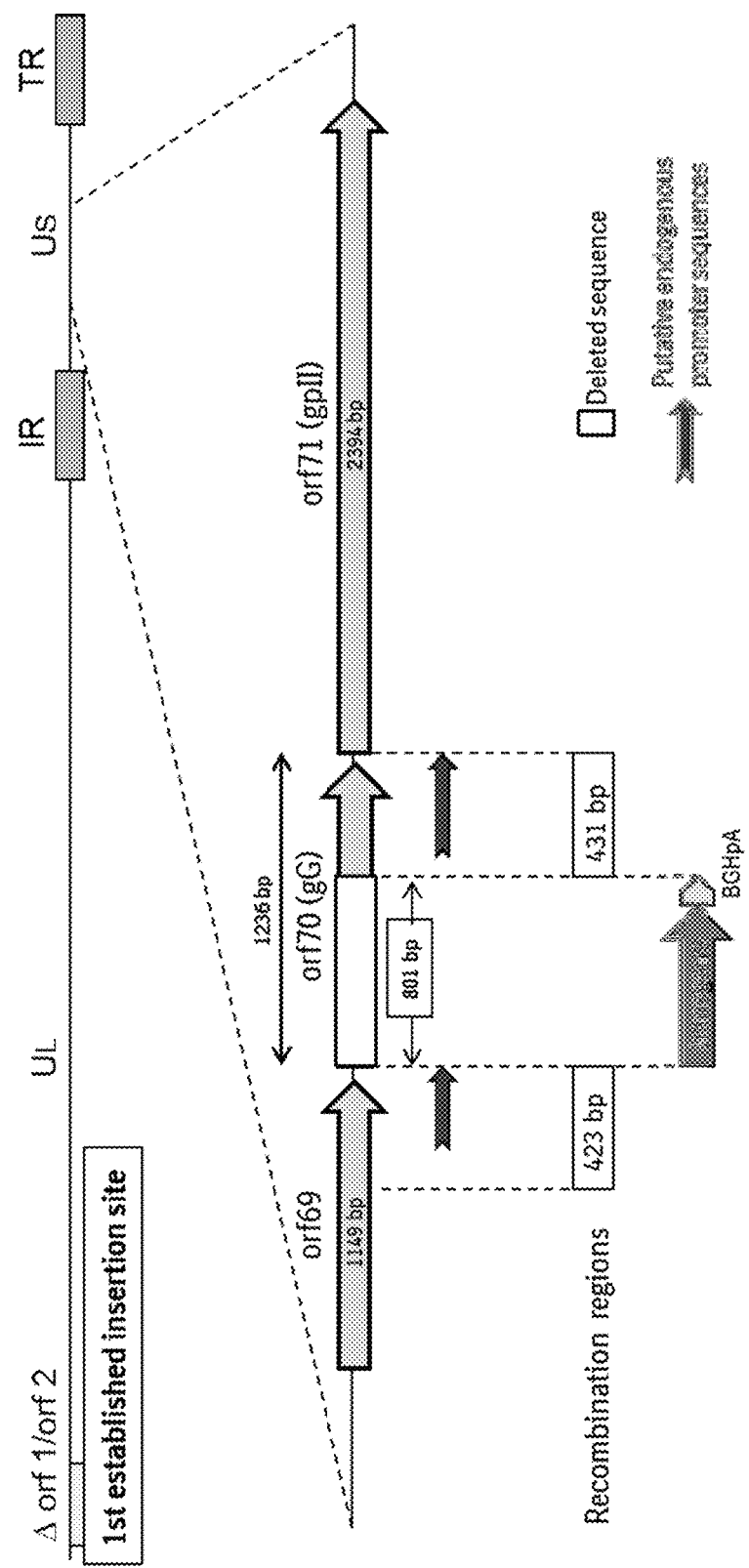
FIG. 1. Schematic drawing of the orf70 insertion site. UL=long unique segment; US=short unique segment; IR=inner inverted repeat; TR=terminal inverted repeat; gG=glycoprotein G; gpII=glycoprotein II; orf=open reading frame; bp=base pairs.
Figure 2:
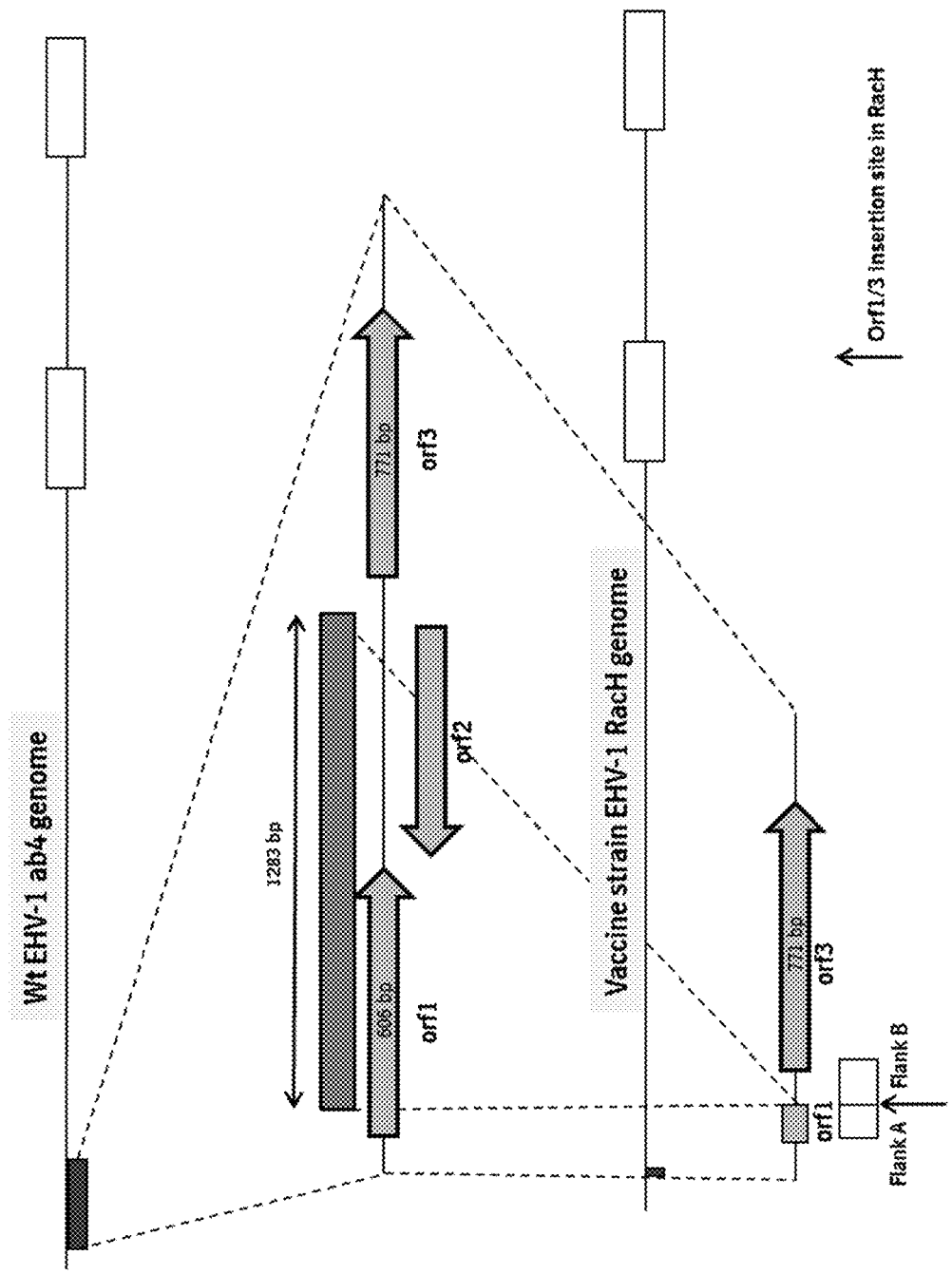
FIG. 2. Schematic illustration comparing the orf1/3 regions of wild-type (wt) EHV-1 strain ab4 and attenuated vaccine strain EHV-1 RacH.

Generation, In Vitro Characterization and In Vivo Testing of a Monovalent Ehv-1 Vectored Influenza A Virus Vaccine (H3 Vaccine) for Swine Swine IAV Influenza virus hemagglutinin of serotype H3 (SEQ ID NO 27) (A/swine/Italy/7680/2001(H3N2), GenBank accession no.: ABS50302.2) was chosen as antigen to be tested for vaccination study in pigs. This new vaccine against swine IAV provides a DIVA feature, e.g. by detection of antibodies against Swine IAV proteins NP or NA in animals that were infected by Swine IAV field strains but not in animals only vaccinated with the vaccine described here since it only expresses one Swine IAV HA protein. Its coding sequence was synthesized and subcloned generating the transfer vector pU70-p455-H3-71K71, placing H3 under control of the new p455 promoter and the new 71 pA polyadenylation signal and framing the cassette with the recombination regions for insertion into orf70 (FIG. 1 and FIG. 5).

By en-passant mutagenesis using the RED recombination system the expression cassette p455-H3-71 was inserted in orf70 of pRacH-SE to generate pRacH-SE70-p455-H3

PK/WRL cells were transfected with pRacH-SE70-p455-H3, recombinant virus rEHV-1 RacH-SE70-p455-H3 was rescued and plaque-purified twice. (FIG. 6).

Correct insertion of the expression cassette was verified by sequencing of a high-fidelity PCR product of the insertion region. Expression of the transgene in infected cells was analyzed by indirect immunofluorescence assay (IFA, FIG. 7) and Western blot (FIG. 8) using commercially available monoclonal and polyclonal antibodies.

Restoration of orf71 encoding EHV-1 gpII was confirmed by IFA (not shown) and Western blot (FIG. 8) using a monoclonal antibody Ai2G7 (owned by BI). Appearance of trimers of H3 on the plasma membrane of infected cells was assayed by a hemadsorption test using chicken erythrozytes (not shown). Peak titers determined as $TCID_{50}$/ml in PK/WRL cells were in the same range as titers of the parental virus RacH-SE which indicates that transgene expression had no detrimental effect on viral replication (not shown). This was confirmed by passaging of rEHV-1 RacH-SE70-p455-H3 in PK/WRL cells up to passage 20 (P20) after rescue. At P5, P10, P15, and P20 the virus was characterized by titration, sequencing, and Western blot (FIG. 8), at P10 and P20 additionally by IFA, and HA expression and genetic stability of the HA encoding insert along with the promoter and polyA sequences were confirmed.

The two blots shown in FIG. 8 are replicas that were incubated with either the monoclonal antibody Ai2G7 (left) that specifically detects EHV-1 glycoprotein II (gpII) or with a commercial polyclonal antibody from rabbit (PA5-34930) raised against Influenza hemagglutinin subtype H3 (right). gpII was detected in all cell cultures infected with recombinant EHV-1 as expected. Full-length H3 was detected in all cells infected with the different passages of rEHV-1 RacH-SE-70-p455-H3 as expected. Specificity of the H3-antiserum was also shown by Western blots of cells infected with other recombinant EHV-1 RacH-SE expressing Influenza hemagglutinins from H1 subtype viruses, FIG. 14.

By double immunofluorescence assay (dIFA) of viral plaques in cells infected with P20 using a monoclonal anti-H3 antibody and a horse anti-EHV antiserum, it was confirmed that virtually all EHV-1 induced plaques also express H3 (not shown). All tests confirmed stability of the recombinant EHV-1 RacH-SE-70-p455-H3.

To investigate its properties as a vectored vaccine in young piglets, rEHV-1 RacH-SE-70-p455-H3 was tested in a vaccination-challenge study. In detail, piglets without maternally derived immunity against Swine IAV (no maternal antibodies) were vaccinated twice with RacH-SE-70-p455-H3 at a dose of 1×10^7 TCID50 intramuscularly at an age of two and five weeks (two-shot vaccination, 2× EHV-1), or at an age of five weeks only (one-shot vaccination, 1× EHV-1). A non-vaccinated group served as negative control and a group of animals that were vaccinated at two and five weeks of age with a commercially available inactivated Swine IAV vaccine according to the manufacturer's instructions (but for the time points of vaccination) served as positive control (killed). At an age of 8 weeks, all animals but the negative control were challenged by an intratracheally applied dosage of 1×10^7 TCID50 of an H3N2 Swine IAV challenge strain (European field virus isolate R452-14 whose H3 is being heterologous to the H3 vaccine antigen used in RacH-SE-70-p455-H3). Non-vaccinated and unchallenged animals served as negative control, while non-vaccinated but challenged animals served as challenge control. At and after vaccinations and before and after challenge, body temperatures were measured and blood samples were taken at different time points. One day after challenge, half of the animals per group were killed and the lungs were scored for lesions typical for Swine IAV infection, three lung samples per left and right lung were taken per animal, respectively, to determine infectious Swine IAV titers in lung homogenates, and bronchi alveolar lavage fluid (BALF) was sampled. The same procedure was performed with the remaining half on animals per group three days after challenge.

When investigating the body temperature rise after Swine IAV challenge virus application, non-vaccinated animals showed a body temperature increase of about 1° C. 1 day after challenge. This body temperature increase 1 day after challenge was prevented for the group vaccinated twice with the RacH-SE-70-p455-H3 vaccine (FIG. 20).

Assessment of the lung scores from animals killed at 1 or 3 days after Swine IAV challenge virus application revealed that the negative control showed no lung lesions typical for Swine IAV infection, the challenge control showed lung lesions in the mean range of 6-7%, and that regarding the group mean values lung lesion scores were strongly reduced to one to less than 4% for the group vaccinated twice with the RacH-SE-70-p455-H3 vaccine (FIG. 21).

The mean Swine IAV lung titers from animals killed at 1 or 3 days after Swine IAV challenge virus application showed that the negative control showed no Swine IAV in lung samples, whereas the challenge control showed virus titers per g lung tissue in the range of more than 5 (day3) to more than 7 logs (day1). In stark contrast, the group mean values were strongly reduced to about two logs or less for the group vaccinated once with the RacH-SE-70-p455-H3 vaccine and reduced to undetectable levels for the group vaccinated twice with the RacH-SE-70-p455-H3 vaccine (FIG. 22).

When testing the induction of Swine IAV neutralizing antibodies after vaccination, sera from animals vaccinated once with the RacH-SE-70-p455-H3 vaccine showed reciprocal neutralization titers in the range of about 160 three weeks after first vaccination and sera from animals vaccinated twice with the RacH-SE-70-p455-H3 vaccine showed neutralizing titers of about 2560 three weeks after $2^{nd}$ vaccination, while sera from the non-vaccinated groups had no detectable Swine IAV neutralizing antibody levels (FIG. 22).

When determining the amounts of pro-inflammatory cytokine IL-1β in BALF from animals 1 or 3 days after Swine IAV challenge, IL-1 levels of more than 100 µg/ml up to 900 µg/ml were detectable in three of four animals tested at day 1, whereas these levels were reduced to 100-300 µg/ml IL-1β for BALFs from animals vaccinated once with the RacH-SE-70-p455-H3 vaccine and even further reduced to levels of 0 to less than 100 µg/ml IL-1β for all animals vaccinated twice with the RacH-SE-70-p455-H3 vaccine (FIG. 23). This shows that vaccination with the RacH-SE-70-p455-H3 vaccine had effectively prevented induction of the pro-inflammatory cytokine IL-1β after Swine IAV infection.

When testing restimulation of peripheral blood mononuclear cells (PBMCs) sampled at study day 28 and using different stimuli, stimulation of PBMCs from non-vaccinated animals showed less than 75/1×10^6 counts in IFNγ-ELISpot irrespective of the stimuli used (FIG. 24 A). PBMCs of animals that had received the inactivated vaccine twice (killed) showed about 150/1×10^6 counts when they were restimulated with recombinant Swine IAV nucleoprotein NP and about 3000/1×10^6 counts in IFNγ-ELISpot when they were restimulated with Swine IAV H3N2 challenge strain R452-14, but showed no restimulation of PBMCs (levels of 75/1×10^6 counts or lower) when recombinant Swine IAV HAs or EHV-1 viruses were used (FIG. 24 B). In contrast, animals vaccinated once or twice with RacH-SE-70-p455-H3 vaccine also showed about 200 (1× EHV-1) to 300 (2× EHV-1)/1×10^6 counts in IFNγ-ELISpot when they were restimulated with Swine IAV H3N2 challenge strain R452-14, but no restimulation of PBMCs (levels of 75/1×10^6 counts or lower) when recombinant Swine IAV NP was used (FIGS. 24 C and D). When EHV-1 viruses were used for restimulation, animals vaccinated once or twice with RacH-SE-70-p455-H3 vaccine showed about 300/1× 10^6 counts in IFNγ-ELISpot when they were restimulated with empty EHV-1 vaccine RacH-SE, and this value was further increased to more than 400/1×10^6 counts when RacH-SE-70-p455-H3 vaccine expressing a Swine IAV H3 was used, respectively (FIGS. 24 C and D). Accordingly, when recombinant Swine IAV HAs were used for restimulation, only animals vaccinated once or twice with RacH-SE-70-p455-H3 vaccine showed about 100-150 (1×EHV-1) to 150-200 (2× EHV-1)/1×10^6 counts in IFNγ-ELISpot (FIGS. 24 C and D).

Example 8

Generation, In Vitro Characterization and In Vivo Testing of a Tetravalent Ehv-1 Vectored Influenza A Virus Vaccine for Swine As described below, in the described invention the four Swine IAV hemagglutinin (HA) antigens as described derived from H1N2, H3N2, H1N1 avian, and H1N1 pandemic Swine IAV sub-/serotypes are expressed by two recombinant EHV-1 vector viruses. This new tetravalent vaccine against swine IAV provides a DIVA feature, e.g. by detection of antibodies against Swine IAV proteins NP or NA in animals that were infected by Swine IAV field strains but not in animals only vaccinated with the vaccine described here since it only expresses the Swine IAV HA proteins.

The new tetravalent Swine IAV vaccine was characterized in vitro and is tested in vivo for its efficacy against Swine IAV.

The newly identified p430 promoter was used to drive expression of Swine IAV HIN1 ((A/swine/Gent/132/2005 (H1N1), GenBank accession no.: AFR76623.1). Since the hemagglutinin gene in this virus isolate originated from an avian IAV it will be referred to as H1av. H1av was synthesized and subcloned in a transfer vector for the orf1/3 insertion region to generate pU1/3-p430-H1av-BGHKBGH. Expression of H1av was placed under control of the p430 promoter and the bovine growth hormone (BGH) polyA signal and framed with the recombination regions for insertion into orf1/3 (FIG. 10).

By en-passant mutagenesis using the RED recombination system the expression cassette p430-H1av-BGH was inserted in orf1/3 of pRacH-SE to generate pRacH-SE1/3-p430-H1av). PK/WRL cells were transfected with pRacH-SE1/3-p430-H1av, recombinant virus rEHV-1 RacH-SE1/3-p430-H1av FIG. 11 was rescued and plaque-purified twice. Correct insertion of the expression cassette was verified by sequencing of a high-fidelity PCR product of the insertion region. Expression of the transgene in infected cells was analyzed by indirect immunofluorescence assay (IFA) and Western blot using commercially available monoclonal and polyclonal antibodies (FIG. 12). Restoration of orf71 encoding EHV-1 gpII was confirmed by IFA and Western blot using a monoclonal antibody Ai2G7 (owned by BI), (not shown). Correct processing and transport of H1av and localization in the plasma membrane of infected cells was assayed by a hemadsorption test using chicken erythrozytes (not shown). Peak titers determined as TCID50/ml in PK/WRL cells were in the same range as titers of the parental virus RacH-SE which indicates that transgene expression had no detrimental effect on viral replication (not shown).

Specific detection of a broad band migrating at 75 kDa by antibody PA-34929 is in concordance with the expected appearance of the recombinant HA glycoprotein as predicted from its sequence. Apparent staining of cellular membranes with the monoclonal antibody C102 is in line with the subcellular localization as expected.

In order to test whether the expressed recombinant hemagglutinins were processed and transported as expected, VERO-cells were infected with rEHV-1 RacH-SE-1/3-p430-H1av, rEHV-1 RacH-SE-70-p455-H3, rEHV-1 RacH-SE (parent) at an m.o.i. of 0.01, or left uninfected. 24 h p.i. live infected and uninfected cells were incubated with a suspension of chicken erythrocytes in PBS, washed with PBS and stained with the fluorescent Hoechst 33342 nuclear stain. Since erythrocytes of birds contain cell nuclei they can be stained with Hoechst33342 and appear as tiny blue specks by fluorescence microscopy, compared with cells that were infected with rEHV-1 RacH-SE that does not express hemagglutinin, adsorption of chicken erythrocytes was significantly increased on cells infected with either rEHV-1 RacH-SE-1/3-p430-H1av or rEHV-1 RacH-SE-70-p455-H3 (not shown). From this it can be concluded that the hemagglutinins were translated, processed and transported to the plasma membrane of vector virus infected cells in a manner as if they were produced by authentic influenza virus replication. The phenotype of hemadsorption of infected cells supports the findings of the Western blots and immunofluorescence assays (for H1av, FIG. 12) showing efficient expression of the transgenic proteins and suggesting formation of functional HA trimers on the cell surface of EHV-1 vector infected cells.

Specificity and lack of cross-reactivity of the polyclonal commercial antibodies to H3 (PA5-34930) and H1 (PA5-34929) was verified by Western blots of infected cells infected with single-insert viruses rEHV-1 RacH-SE-70-p455-H3 and rEHV-1 RacH-SE-1/3-p430-H1av (not shown).

Next, a recombinant EHV-1 RacH-SE was generated expressing two different hemagglutinins of two different Influenza A virus sub-/serotypes.

Starting with the recombinant BAC pRacH-SE-70-p455-H3, the expression cassette p430-H1av-BGH as assembled in the transfer vector pU1/3-p430-H1av-BGH_K_BGH (FIG. 10) was inserted into the orf1/3 insertion site by two-step RED recombination to generate pRacH-SE-1/3-p430-H1av-70-p455-H3. PK/WRL cells were transfected with pRacH-SE1/3-p430-H1av-70-p455-H3, and recombinant virus rEHV-1 RacH-SE1/3-p430-H1av-70-p455-H3 was rescued and plaque-purified twice. The short designation for this recombinant virus is rEHV-1 RacH-SE_B (FIG. 13). Correct insertion of the expression cassette was verified by sequencing of high-fidelity PCR products of the insertion regions together with flanking sequences.

Expression of the transgenes in infected cells was analyzed by indirect immunofluorescence assay (IFA, not shown) and Western blot using commercially available monoclonal and polyclonal antibodies (FIG. 14). Restoration of orf71 encoding EHV-1 gpII was confirmed by IFA (not shown) and Western blot using a monoclonal antibody Ai2G7 (owned by BI), (FIG. 14).

Both transgenes H3 and H1av were expressed in parallel in cell cultures infected with the dual insert recombinant rEHV-1 RacH-SE_B. Transgene expression was stable and did not impair viral titers tested until passage 11 in PK/WRL cells.

The enhanced EHV-1 vector with two insertion sites and two new promoters was shown to express two Influenza virus hemagglutinins in parallel. Subcellular localization as determined by IFA and mobility in SDS-PAGE as determined by Western blot corresponded to authentic hemagglutinins expressed in Influenza A virus infected cells known from the literature.

Next, a second double-insert rEHV-1 RacH expressing hemagglutinins H1hu, SEQ ID NO:29, (A/swine/Italy/4675/2003(H1N2); GenBank accession no. ADK98476.1) and H1pdm, SEQ ID NO:26, (A/swine/Italy/116114/2010 (H1N2); GenBank accession no. ADR01746.1) was generated.

The coding sequence of H1hu was synthesized and subcloned in a transfer vector for the orf1/3 insertion region to generate pU1/3-p430-H1hu-BGHKBGH. Expression of H1hu was placed under control of the p430 promoter and the bovine growth hormone (BGH) polyA signal and framed with the recombination regions for insertion into orf1/3 (FIG. 25).

The coding sequence of H1pdm was synthesized and subcloned generating the transfer vector pU70-p455-H1pdm-71K71, placing H1pdm under control of the new p455 promoter and the new 71 pA polyadenylation signal and framing the cassette with the recombination regions for insertion into orf70 (FIG. 26).

Subsequently, the expression cassettes p430-H1av-BGH and p455-H1pdm-71 were inserted into pRacH-SE by en-passant mutagenesis using the RED recombination system, generating pRacH-SE-1/3-p430-H1hu first. Using this modified BAC as the target, p455-H1pdm-71 was inserted by en-passant mutagenesis using the RED recombination system, generating pRacH-SE-1/3-p430-H1hu-70-p455-H1pdm. pRacH-SE-1/3-p430-H1hu-70-p455-H1pdm was transfected in PK/WRL cells and rEHV-1 RacH-SE-1/3-p430-H1hu-70-p455-H1pdm was rescued and plaque purified three times. The short designation of the new recombinant vector virus is rEHV-1 RacH-SE_D (FIG. 27).

Expression of the transgenes in infected cells was analyzed by indirect immunofluorescence assay (IFA, not shown) and Western blot using commercially available monoclonal and polyclonal antibodies (FIG. 25). Restoration of orf71 encoding EHV-1 gpII was confirmed by IFA (not shown) and Western blot using a monoclonal antibody Ai2G7 (owned by BI), (FIG. 28).

Genetic and phenotypic stabilities of the recombinant rEHV-1 were shown by passaging in cell culture, determining viral titers every 5 passages. Sequences of the insertion regions were confirmed every ten passages as well as transgene expression by Western blot (not shown). Expression fidelity was assessed by double IFA of plaques under methocel-overlay, counting plaques stained with anti-EHV-antibodies and transgene-specific antibodies (not shown).

To investigate its properties as a vectored vaccine in young piglets, the tetravalent Swine IAV vaccine consisting of rEHV-1 RacH-SE_B and rEHV-1 RacH-SE_D is tested in a vaccination-challenge study. In detail, piglets with maternally derived immunity against Swine IAV (positive for maternal antibodies) are vaccinated twice with rEHV-1 RacH-SE_B and rEHV-1 RacH-SE_D at a dose of $1\times10^7$ TCID50 per vaccine strain intramuscularly at an age of one and four weeks (two-shot vaccination, 2× EHV-1) or at an age of four weeks only (one-shot vaccination, 1× EHV-1). A non-vaccinated group serves as negative control. At an age of 11 weeks, all animals but the negative control are challenged by an intratracheally applied dosage of $1\times10^6$ TCID50 of an H3N2 Swine IAV challenge strain (European field virus isolate R452-14 whose H3 is being heterologous to the H3 vaccine antigen used in rEHV-1 RacH-SE_B). Non-vaccinated and unchallenged animals serve as negative control, while non-vaccinated but challenged animals serve as challenge control. At and after vaccinations and before and after challenge, body temperatures are measured and blood samples are taken at different time points. One day after challenge, half of the animals per group are killed and the lungs are scored for lesions typical for Swine IAV infection, three lung samples per left and right lung are taken per animal, respectively, to determine infectious Swine IAV titers in lung homogenates, and bronchioalveolar lavage fluid (BALF) is sampled. The same procedure is performed with the remaining half on animals per group three days after challenge. Sample material and collected data is analyzed to determine, among others, body temperature changes after challenge, clinical signs after Swine IAV infection, lung scores, Swine IAV lung titers, histological changes in lung tissue, Swine IAV serum neutralization titers, cytokine levels in BALF, restimulation of PBMCS as measured by IFNγ-ELISpot, and B-cell activation.

Example 9

Induction of a Neutralizing Antibody Response Against Two Antigens in Mice Vaccinated with a Bivalent Rehv-1 Rach Vector Vaccine The rEHV-1 RacH SE B (rEHV-1 RacH-SE-1/3-p430-H1av-7-p455-H3 see FIG. 13) was used for immunization of Balb/c mice in order to demonstrate that the expressed transgenes are immunogenic in another species than swine and that neutralizing antibodies are induced against either one of the two antigens by intranasal application.

In detail, three groups of five Balb/c mice per group, 3-5 weeks of age, were intranasally inoculated on study days 0 and 21 either with 40 µl of rEHV-1 RacH SE B (rEHV-1 RacH-SE-1/3-430-H1av-7-455-H3, group 1), or 40 µl of empty vector (rEHV-1 RacH-SE, group 2, vector control), or 40 µl of tissue culture medium (group 3 negative control), respectively. For groups 1 and 2, infectious recombinant EHV-1 dosages were $1\times10^5$ TCID50/40 µl, respectively. Mice were bled on study days 0 (before $1^{st}$ inoculation), 7, 14, 21 (before $2^{nd}$ inoculation), 28, and 35. Serum was prepared from the blood samples and stored frozen at −80° C.

Immunofluorescence Assay for Detection of Antibodies Against the Vector Virus

AI-ST cells were infected at a multiplicity of infection (MOI) of 0.001 with rEHV-1 RacH-SE1212, a virus rescued from the empty vector BAC pRacH-SE1.2. 24 hours p.i.

distinctive plaques were observed and cells were processed for indirect immunofluorescence assay (IFA). Sera of all three groups of the final bleeds (obtained 14 days after the second vaccination) diluted 1:50 in PBS were tested. As positive control serum from an EHV-1 vaccinated horse was used in a dilution of 1:500. Secondary antibodies were commercially available FITC-conjugated rabbit anti-mouse IgG for the mice sera and Cy5-conjugated goat-anti horse IgG for the horse serum and used at 1:200 dilution. Antibody binding was evaluated by fluorescence microscopy. All vaccinated mice had developed antibodies reactive in IFA with rEHV-1 RacH-SE-infected cells. Uninfected cells were not bound by any of the tested sera. Sera from the negative control group of mice did not show any specific binding neither to infected nor to uninfected cells. Data are summarized in the table below.

TABLE 3

Fluorescence microscopy results of IFA for anti-EHV-1 antibodies

| Treatment | Mouse number | ID in experiment | dilution | Uninfected cells | Infected cells |
|---|---|---|---|---|---|
| Group 3 (Negative control) | 1 | 1 | 1:50 | neg | neg |
| | 2 | 2 | 1:50 | neg | neg |
| | 3 | 3 | 1:50 | neg | neg |
| | 4 | 4 | 1:50 | neg | neg |
| | 5 | 5 | 1:50 | neg | neg |
| Group 2 (Empty vector) | 1 | 6 | 1:50 | neg | pos |
| | 2 | 7 | 1:50 | neg | pos |
| | 3 | 8 | 1:50 | neg | pos |
| | 4 | 9 | 1:50 | neg | pos |
| | 5 | 10 | 1:50 | neg | pos |
| Group 1 (rEHV-1 RacH SE B) | 1 | 11 | 1:50 | neg | pos |
| | 2 | 12 | 1:50 | neg | pos |
| | 3 | 13 | 1:50 | neg | pos |
| | 4 | 14 | 1:50 | neg | pos |
| | 5 | 15 | 1:50 | neg | pos |
| Control antibody Horse serum | Specific for EHV-1 | 22 | 1:500 | neg | pos |
| Secondary antibodies FITC-goat anti- | Specific for mouse | 23 | 1:200 | neg | neg |
| Cy5 goat anti- | horse | 24 | 1:200 | neg | neg |

From this it can be concluded that inoculation of the rEHV-1 into the nostrils of the mice resulted in infection and viral replication, so that the mice immune systems were stimulated to produce anti-EHV-1 antibodies.

Virus Neutralization Tests (VNT)

In order to show induction of protective immunity against the expressed transgenes originating either from Influenza A virus (IAV) (A/swine/Italy/7680/2001(H3N2)) or (A/swine/Gent/132/2005(H1N1)) the mice sera were tested for neutralizing activity against the respective viruses (Allwinn et al. 2010; Trombetta et al. 2014). IAV used for neutralization tests were isolates from pigs in Germany from 2014, specifically A/swine/Germany/AR452/2014 (H3N2) and A/swine/Germany/AR1181/2014 (H1N1). As these are heterologous from the strains the vaccine targets were derived from, any neutralization of these viruses by the mouse sera will be indicative of broad and efficient induction of protective immunity by the rEHV-1 vaccination. As a negative control serum, a serum from a pig which had been shown to be negative for Influenza virus antibodies was used.

Influenza A Virus Neutralization Tests

MDCK cells for virus neutralization as well as back-titration in 96-well plates were incubated for two days at 37° C./5% $CO_2$ prior to use. The respective IAV stocks H3N2 and H1avN1 were thawed on ice and diluted in MEM containing Gentamycin and the double concentration of trypsin (MEM/Genta/2× trypsin).

Sera tested were from the final bleeds of group 1 (rEHV-1 RacH SE B), group 2 (empty vector), a positive control (serum from a pig vaccinated with inactivated multivalent IAV vaccine, and a negative control.

Sera were heat inactivated and in two and three independent tests, respectively, serially 1:2 diluted starting at 1:16 up to 1:4096. IAV was diluted to approximately 100 TCID50/neutralization reaction. Neutralization reactions were incubated for 2 hours at 37° C., 5% $CO_2$. Back-titration of used virus was done in quadruplicate. Growth medium was removed and MDCK-cells were washed with medium containing Gentamycin and trypsin before adding the neutralization reactions or the virus dilutions of the back-titrations. VNT and titration plates were incubated at 37° C./5% CO2 for 1 h after addition of neutralization reaction or virus dilutions to the MDCK-cells, respectively. Thereafter inocula were removed and cells were overlaid with fresh medium containing Gentamycin and trypsin. Five days p.i. CPE was monitored and documented. Actually used virus titer in the test was calculated as TCID50/ml according to Reed and Munch and dilutions at which the tested sera prevented induction of Influenza virus-typical CPE were reported, see tables below.

TABLE 4

Results Influenza H1avN1 VNT

| | H1avN1 | | | | | | | |
|---|---|---|---|---|---|---|---|---|
| | VNT#1 | | VNT#2 | | VNT#3 | | | |
| mouse | 146 TCID50/well Reciprocal neutralizing dilution | capacity | 32 TCID50/well Reciprocal neutralizing dilution | capacity | 181 TCID50/well Reciprocal neutralizing dilution | capacity | Average neutralizing capacity | SD (standard deviation) |
| rEHV-1 RacH SE B -1 | 32 | 4672 | 128 | 4096 | 32 | 5792 | 4853 | 862 |
| rEHV-1 RacH SE B -2 | 16 | 2336 | 64 | 2048 | neg | | 2192 | 204 |
| rEHV-1 RacH | 32 | 4672 | 128 | 4096 | 16 | 2896 | 3888 | 906 |

TABLE 4-continued Results Influenza H1avN1 VNT

| | H1avN1 | | | | | | | |
|---|---|---|---|---|---|---|---|---|
| | VNT#1 | | VNT#2 | | VNT#3 | | | |
| | 146 TCID50/well Reciprocal neutralizing | | 32 TCID50/well Reciprocal neutralizing | | 181 TCID50/well Reciprocal neutralizing | | Average neutralizing | SD (standard |
| mouse | dilution | capacity | dilution | capacity | dilution | capacity | capacity | deviation) |
| rEHV-1 RacH SE B -3 | 128 | 18688 | 512 | 16384 | 64 | 11584 | 15552 | 3624 |
| rEHV-1 RacH SE B -4 | 32 | 4672 | 256 | 8192 | 16 | 2896 | 5253 | 2695 |
| rEHV-1 RacH SE B -5 | n.d. | n/a | neg | n/a | neg | n/a | n/a | n/a |
| Empty vector-1 | n.d. | n/a | neg | n/a | neg | n/a | n/a | n/a |
| Empty vector-2 | n.d. | n/a | neg | n/a | neg | n/a | n/a | n/a |
| Empty vector-3 | neg | n/a | neg | n/a | neg | n/a | n/a | n/a |
| Empty vector-4 | n.d. | n/a | neg | n/a | neg | n/a | n/a | n/a |
| Empty vector-5 | 32 | n/a | n.d | n/a | n.d | n/a | n/a | n/a |
| Pos control Pig serum | | | | | | | | |

TABLE 5

Results Influenza H3N2 VNT

| | H3N2 | | | | | | | |
|---|---|---|---|---|---|---|---|---|
| | VNT#1 | | VNT#2 | | VNT#3 | | | |
| | 16 TCID50/well Reciprocal neutralizing | | 24 TCID50/well Reciprocal neutralizing | | 15 TCID50/well Reciprocal neutralizing | | Average neutralizing | SD (standard |
| mouse | dilution | capacity | dilution | capacity | dilution | capacity | capacity | deviation) |
| rEHV-1 RacH SE B -1 | 4096 | 65536 | 1024 | 24576 | 2048 | 30720 | 40277 | 22089 |
| rEHV-1 RacH SE B -2 | 1024 | 16384 | 512 | 12288 | 128 | 1920 | 10197 | 7455 |
| rEHV-1 RacH SE B -3 | 1024 | 16384 | 512 | 12288 | 256 | 3840 | 10837 | 6397 |
| rEHV-1 RacH SE B -4 | 256 | 4096 | 256 | 6144 | 64 | 960 | 3733 | 2611 |
| rEHV-1 RacH SE B -5 | 256 | 4096 | 128 | 3072 | 64 | 960 | 2709 | 1599 |
| Empty vector-1 | neg | n/a | neg | n/a | neg | n/a | n/a | n/

In order to compare results of independent tests neutralizing capacity was calculated by multiplication of the reciprocal serum dilution and the respective titer that was neutralized by it. Averages of three tests were then divided by 100 to reflect neutralization of 100 TCID50 (Tables 3, 4, and 5). Data are summarized and shown graphically in FIG. 29.

All mice vaccinated with rEHV-1 RacH SE B had developed neutralizing antibodies against the respective IAV, heterologous strains of subtypes H3N2 and H1avN1. Thus, twofold intranasal application of rEHV-1 RacH-SE expressing hemagglutinins of IAV from the orf70 insertion site under control of the p455 promoter (H3) and in parallel from the orf1/3 insertion site under control of the p430 promoter (H1av), successfully stimulated protective immune response in BALB/c mice.

It can be concluded that the vector rEHV-1 RacH-SE can be used for parallel expression of two different transgenes to stimulate immune response after intranasal vaccination.

Example 10

Generation, In Vitro Characterization and In Vivo Testing of an Ehv-1 Vectored Schmallenberg (Sbv) Virus Vaccine For Cattle One of the emerging bunyaviruses is Schmallenberg virus (SBV), the first European Simbu serogroup virus (genus *Orthobunyavirus*), which may cause abortions, stillbirth, and severe fetal malformation when pregnant animals are infected during a critical phase of gestation and which is by now more and more used as a model virus for studying orthobunyaviruses (Bilk et al., 2012). Since Simbu viruses are transmitted by insect vectors and treatment options are not available, vaccination is a major component of disease control. Against SBV and further Simbu viruses such as Akabane virus (AKAV) or Aino virus inactivated whole-virus vaccines are available and live attenuated vaccines against SBV have been developed (Anonymous, 2013, 2015; Kraatz et al., 2015; Wernike et al., 2013b), however, none of these vaccines allows differentiation between field-infected and vaccinated animals (DIVA principle). Only recently, DIVA-compatible subunit vaccines based on 234 amino acids (aa) from the amino-terminus of SBV glycoprotein Gc, were tested in a lethal small animal challenge model and in cattle (Wernike et al., 2017). When delivered as expression plasmids or expressed in a mammalian cell culture system the Gc domain conferred protection in up to 66% of the animals, while all animals immunized with the Gc domain of SBV linked to the corresponding domain of the related AKAV were fully protected (Wernike et al., 2017). In order to investigate the application of rEHV-1 RacH-SE as a vector vaccine in cattle the 234 amino-terminal aa of SBV-Gc were inserted into the orf70(US4) insertion site and expressed under control of the new p455 promoter and 71 pA poly A signal and tested in a vaccination-challenge trial in cattle.

Generation of Recombinant EHV-1 Expressing an Antigen Derived of Schmallenberg Virus (SBV) Glycoprotein c (Gc)

A 234 amino acid portion of the coding region of Schmallenberg virus (SBV) glycoprotein c (Gc) was codon-usage optimized for expression in EHV-1 and additionally modified to achieve efficient transport to and insertion in the plasma membranes of infected cells. To this end a signal peptide coding sequence derived from an Influenza A virus (IAV) hemagglutinin (HA) subtype H1N2 (A/swine/Italy/116114/2010 (H1N2), GenBank accession no. ADR01746.1) as well as the transmembrane anchor (TM) and a cytoplasmic C-terminus from that HA were attached to the 5' and 3'ends, respectively. In addition, a GS linker HMGGSGGGGSGGGGSGGGT (SEQ ID NO:30) was inserted between the Gc portion and the HA-TM-domain. The DNA (SEQ ID NO:31) was synthesized and subcloned into the NotI/KpnI sites of pU70-455-71K71, a transfer vector for insertion of transgene expression cassettes into orf70 (US4) of EHV-1 by RED-mediated recombination of the BAC pRacH-SE. The resulting plasmid pU70-455-SBVGc_71K71 (FIG. 30) was cut with XbaI to release a 3056 bp DNA fragment (SEQ ID NO:32), which was transformed into *E. coli* K12 GS1783 carrying pRacH-SE.

SEQ ID NO:31: Synthesized DNA sequence including restriction sites for subcloning

```
GCGGCCGCATGAAGGCGATCCTGGTTGTGCTGCTGTACACCTTTGCC

ACCGCCAACGCCGATACGCTGATCAACTGCAAGAACATCCAGAGCACCCA

GCTGACAATCGAGCACCTGAGCAAGTGCATGGCCTTCTACCAGAACAAGA

CCAGCAGCCCCGTCGTGATCAACGAGATCATCTCCGACGCCAGCGTGGAC

GAACAGGAACTGATTAAGTCTCTGAACCTGAACTGCAACGTGATCGACCG

GTTCATCAGCGAGTCCAGCGTGATCGAGACACAGGTGTACTACGAGTATA

TCAAGAGCCAGCTGTGTCCACTGCAAGTGCACGATATCTTCACCATCAAC

AGCGCCAGCAACATCCAGTGGAAGGCCCTGGCCCGCAGCTTTACCCTGGG

CGTGTGCAACACCAACCCCCACAAGCACATCTGCCGGTGCCTGGAATCCA

TGCAGATGTGTACCAGCACCAAGACCGACCACGCCAGAGAGATGAGCATC

TACTACGACGGCCACCCCGACAGATTCGAGCACGACATGAAGATTATCCT

GAATATCATGCGGTACATCGTGCCCGGCCTGGGCAGAGTGCTGCTGGACC

AGATCAAGCAGACCAAGGACTACCAGGCCCTGAGACACATCCAGGGCAAG

CTGAGCCCCAAGTCCCAGAGCAACCTGCAGCTGAAGGGCTTCCTGGAATT

CGTGGACTTCATCCTGGGCGCCAACGTGACCATTGAGAAAACCCCCCAGA

CCCTGACCACCCTGAGCCTGATTCATATGGGAGGTTCCGGAGGTGGAGGT

TCCGGAGGTGGAGGTTCCGGAGGTGGCACCATACTGGCCATTTACAGCAC

AGTTGCGAGCAGCCTGGTCCTGATCGTGAGCCTGGGTGCTATATCATTCT

GGATGTGCAGCAACGGCTCTCTCCAGTGCCGCATCTGTATCTGAGGTACC
```

SEQ ID NO:32: DNA fragment used for RED recombination to generate pRacH-SE-70-455-SBVGc Restriction enzyme cleavage positions indicated by asterisks (*)

```
T*CTAGACTCGAGCGCAAGCCCTACACGCGCTACCCCTGCTTTCAAC

GCGTCAACCTGCACATTGACGGGGAGTTTCTGGTTCACAAGATGCTAGCGTTCAA

TGCCGCGATGCGCCCATCGGCCGAGGAGCTGCTGTCATACCCAATGTTTGCTCAA
```

-continued

```
CTTTAGGATGACTAACCTGTTTCTGGGAGGAGACAGCGTGGGCGACGGTGTATA

AAGTTGGTCTGCTTTCAAGCCCTGCCACTGCGCTACAGTGCCACCAACTGTAAAG

CGGTAGTAAGCTGCAGTGGTCGACTGGTGGTAGCATATACTACCTTATTTATACG

CTCCGAGCTGTTTTTCAGCATGCTAGCACCCAACGCCGAGCGAGAGTATATAACT

CCCATCATTGCCCACAAGCTTATGCCACTTATTAGCGTCCGCTCTGCCGTTTGCTT

AGTCATAATATCTACCGCCGTTTACGCAGCAGACGCTATCTGCGACACAATTGGA

TTTGCGATACCGCGCATGTGGATGTGTATTTTAATGAGATCAACCTCCATGAAGC

GTAACTAGGGGGCCTCCCACTGAGGCACTACCGGCTTAGCAGCTGACTAACACA

GTATAAAACGTGAGAAGAAATCAGTCTCATGCGCCATTAGCGCTAGGCTAGTTA

GCGTGGAGGACCGGAGCGCTACCGCCAGCAGTTTCATCCGCCTGGTTACGGGTTT

GTTAACACCTACCGGTGTTTTACCGCTACCATAGGATCCGATCCATGGGCGGCCG

CATGAAGGCGATCCTGGTTGTGCTGCTGTACACCTTTGCCACCGCCAACGCCGAT

ACGCTGATCAACTGCAAGAACATCCAGAGCACCCAGCTGACAATCGAGCACCTG

AGCAAGTGCATGGCCTTCTACCAGAACAAGACCAGCAGCCCCGTCGTGATCAAC

GAGATCATCTCCGACGCCAGCGTGGACGAACAGGAACTGATTAAGTCTCTGAAC

CTGAACTGCAACGTGATCGACCGGTTCATCAGCGAGTCCAGCGTGATCGAGACA

CAGGTGTACTACGAGTATATCAAGAGCCAGCTGTGTCCACTGCAAGTGCACGAT

ATCTTCACCATCAACAGCGCCAGCAACATCCAGTGGAAGGCCCTGGCCCGCAGC

TTTACCCTGGGCGTGTGCAACACCAACCCCCACAAGCACATCTGCCGGTGCCTGG

AATCCATGCAGATGTGTACCAGCACCAAGACCGACCACGCCAGAGAGATGAGCA

TCTACTACGACGGCCACCCCGACAGATTCGAGCACGACATGAAGATTATCCTGA

ATATCATGCGGTACATCGTGCCCGGCCTGGGCAGAGTGCTGCTGGACCAGATCA

AGCAGACCAAGGACTACCAGGCCCTGAGACACATCCAGGGCAAGCTGAGCCCCA

AGTCCCAGAGCAACCTGCAGCTGAAGGGCTTCCTGGAATTCGTGGACTTCATCCT

GGGCGCCAACGTGACCATTGAGAAAACCCCCCAGACCCTGACCACCCTGAGCCT

GATTCATATGGGAGGTTCCGGAGGTGGAGGTTCCGGAGGTGGAGGTTCCGGAGG

TGGCACCATACTGGCCATTTACAGCACAGTTGCGAGCAGCCTGGTCCTGATCGTG

AGCCTGGGTGCTATATCATTCTGGATGTGCAGCAACGGCTCTCTCCAGTGCCGCA

TCTGTATCTGAGGTACCAATAAACGCGGTATGTCTACCTTCAAGCCTATGATGAA

CGGATGTTTGGTGTTTGCGGCTATTATAACGCTCTTGAGTTTTATGCTATCTCTGG

GAACATGCGAAAATTACAGGCGTGTGGTTCGGGATCCTAGGGATAACAGGGTAA

TCGATTTATTCAACAAAGCCACGTTGTGTCTCAAAATCTCTGATGTTACATTGCAC

AAGATAAAAATATATCATCATGAACAATAAAACTGTCTGCTTACATAAACAGTA

ATACAAGGGGTGTTATGAGCCATATTCAACGGGAAACGTCTTGCTCGAGGCCGC

GATTAAATTCCAACATGGATGCTGATTTATATGGGTATAAATGGGCTCGCGATAA

TGTCGGGCAATCAGGTGCGACAATCTATCGATTGTATGGGAAGCCCGATGCGCC

AGAGTTGTTTCTGAAACATGGCAAAGGTAGCGTTGCCAATGATGTTACAGATGA

GATGGTCAGACTAAACTGGCTGACGGAATTTATGCCTCTTCCGACCATCAAGCAT

TTTATCCGTACTCCTGATGATGCATGGTTACTCACCACTGCGATCCCCGGGAAAA

CAGCATTCCAGGTATTAGAAGAATATCCTGATTCAGGTGAAAATATTGTTGATGC
```

-continued
```
GCTGGCAGTGTTCCTGCGCCGGTTGCATTCGATTCCTGTTTGTAATTGTCCTTTTA

ACAGCGATCGCGTATTTCGTCTCGCTCAGGCGCAATCACGAATGAATAACGGTTT

GGTTGATGCGAGTGATTTTGATGACGAGCGTAATGGCTGGCCTGTTGAACAAGTC

TGGAAAGAAATGCATAAGCTTTTGCCATTCTCACCGGATTCAGTCGTCACTCATG

GTGATTTCTCACTTGATAACCTTATTTTTGACGAGGGGAAATTAATAGGTTGTATT

GATGTTGGACGAGTCGGAATCGCAGACCGATACCAGGATCTTGCCATCCTATGG

AACTGCCTCGGTGAGTTTTCTCCTTCATTACAGAAACGGCTTTTTCAAAAATATG

GTATTGATAATCCTGATATGAATAAATTGCAGTTTCATTTGATGCTCGATGAGTTT

TTCTAAAATAAACGCGGTATGTCTACCTTCAAGCCTATGATGAACGGATGTTTGG

TGTTTGCGGCTATTATAACGCTCTTGAGTTTTATGCTATCTCTGGGAACATGCGAA

AATTACAGGCGTGTGGTTCGGGATCCGACCCTGTTGGTGGGTGCGGTTGGACTCA

GAATCTTGGCGCAGGCATGGAAGTTTGTCGGTGACGAAACATACGACACCATCC

GCGCAGAAGCAAAGAATTTAGAGACCCACGTACCCTCAAGTGCTGCAGAGTCGT*CTAGA
```

Recombinant pRacH-SE-70-455-SBVGc DNA was prepared and correct insertion of the expression cassette and sequence identity was confirmed by high fidelity PCR using HERCULASE™ and Sanger sequencing of the PCR products. Used primers see table 6, SEQ ID NO: 33 to SEQ ID NO:37.

TABLE 6

Primers used for PCR and sequencing

| # | name | sequence | use |
|---|------|----------|-----|
| SEQ ID NO: 33 | up70_F | 5'-CGTGCGCGG ATACATCG-3' | PCR & sequencing |
| SEQ ID NO: 34 | up71_R | 5'-CGCTTCGCA GGTGGGC-3' | PCR & sequencing |
| SEQ ID NO: 35 | seq455-F1 | 5'-GACTGGTGGT AGCATATAC-3' | sequencing |
| SEQ ID NO: 36 | SBV Gc F1 | 5'-GATCAACGAG ATCATCTCC-3' | sequencing |
| SEQ ID NO: 37 | SBV Gc R1 | 5'-CTGGAGAGAG CCGTTGC-3' | sequencing |

Rescue and Characterization of Recombinant EHV-1 RacH-SE-70-455-SBVGc

BAC DNA was prepared from four different clones of pRacH-SE-70-455-SBVGc. AI-ST cells (Boehringer-Ingelheim proprietary swine testicular cell line) were seeded in 6-well plates (Corning Incorporated—Life Sciences, One Becton Circle, Durham, N.C. 27712, USA; REF 353046) at a density of $10^5$ cells/well in MEM (Sigma-Aldrich Chemie GmbH, Munich, Germany, SAFC62892-1000M3056) containing 10% FBS (Sigma-Aldrich Chemie GmbH, Munich, Germany, SAFC, Cat 12003C-1000 ml). When the cells were 60-70% confluent, usually the next day, they were transfected with 2 g of BAC DNA using the MIRUS™ mRNA transfection kit (Mirus Bio LLC, 545 Science Drive, Madison, Wis. 53711 USA) according to the instructions by the supplier. Briefly, 200 µl OPTIMEM™ (Thermo Fisher Scientific) medium were added to 5 ml polystyrene tubes. DNA was added and mixed. Next 3 µl of Boost reagent were added and mixed by swirling followed by addition of the same volume of Transfection reagent and again mixing by swirling. Mixtures were incubated for 3 minutes at room temperature and then added drop-wise directly into the cell cultures. Cells were incubated at 37° C./5% $CO_2$ for five days. Cells were rinsed into the medium and collected for storage at −80° C. Serial 1:10 dilutions of the rescued viruses were prepared in MEM and plated on confluent AI-ST cell monolayers in 6-well plates. After adsorption for 1 h at 37° C./5% $CO_2$, inocula were removed and cells were overlaid with semi-solid medium containing 0.5% Methocel (Methyl cellulose Ph. Eur., Fluka 64632-500G) and 5% FBS (MEM-Methocel). After incubation at 37° C./5% $CO_2$ for two to three days (passage 1), individual plaques located as distant from neighboring plaques as possible were aspirated in a volume of 10 µl and inoculated in new AI-ST cell cultures in 6-well plates. Infected cells were incubated for two to three days until massive CPE was observed (passage 2). Cells were rinsed into the medium and collected for storage at −80° C. This procedure of plaque purification was repeated twice. AI-ST cells infected with the three times plaque purified viruses were processed for indirect immunofluorescence assay (IFA) or Western blot, respectively.

Viral DNA prepared from infected cells was used as template for high fidelity PCR using HERCULASE™. Obtained PCR-products were analyzed by Sanger sequencing and identity of the insertion region with the theoretical sequence and the sequence of the corresponding PCR-product of the BAC were confirmed.

Indirect Immuno-Fluorescence Assay

AI-ST cells in 24-well plates (Corning Incorporated—Life Sciences, One Becton Circle, Durham, N.C. 27712, USA; REF 353047) were infected with three times plaque purified virus serially diluted in MEM. Growth medium was aspirated off the cells and cells were overlaid with 250 µL of diluted virus (dilutions $10^{-2}$ to $10^{-7}$). Cells were incubated for 1 h at 37° C./5% $CO_2$ for adsorption of virus, then the inocula were removed and cells were overlaid with 1000 µL MEM-Methocel/well and incubated at 37° C./5% $CO_2$ for two days. When plaque formation was observed microscopically, cells were processed for IFA. Medium was aspirated and cells were washed once with 1 ml PBS (Gibco Life Technologies, Paisley PA49RF, UK, DPBS (1×) REF 14190-136)/well. PBS was removed and cells were fixed by addition of 1 ml/well of −20° C. cold ethanol (Carl Roth GmbH, Schoemperlenstr. 3-5, D-76185 Karlsruhe, Art. Nr. 5054.1) and incubation for 30 min at RT. Ethanol was aspirated and cells were air-dried. After rehydration of the cells with 1 ml/well of PBS for 10 min at RT, primary antibodies diluted in PBS were added (150 µl/well) and incubated for 1 h at RT. Primary antibodies were removed and cells were washed three times for 2 min with 1 ml PBS/well before adding secondary antibody dilutions (150 µl/well). After 1 h incubation at RT protected from light, secondary antibody dilutions were removed and cells were washed three times for 2 min with 1 ml PBS/well and finally overlaid with 500 µl PBS/well for inspection by fluorescence microscopy. Used antibodies are listed in table 7.

TABLE 7

| Antibody | diluted |
| --- | --- |
| Horse anti-EHV-1 hyper-immune serum (Boehringer Ingelheim Veterinary Research Centre proprietary) | 1:400 |
| Anti SBV-Gc monoclonal antibody (Wernike et al., 2015a) | 1:50 |
| FITC-conjugated Goat anti-mouse IgG Jackson Immuno Research cat. no. 115-095-003 | 1:200 |
| Cy$^{TM}$5-conjugated Goat anti-horse IgG Jackson Immuno Research cat. no. 108-175-003 | 1:200 |

Western Blot

1. Infection: Three wells each of confluent monolayers of AI-ST cells in 6-well plates were infected at an M.O.I. of approximately 1 with two different plaque isolates of rEHV-1 RacH-SE-455-SBVGc (#121.131 P6 and #121.232 P6) and a plaque isolate of rEHV-1 RacH-SE1212 P9 (rescued from the parental empty BAC pRacH-SE1.2) by directly adding 50 µl and 10 µl, respectively, of thawed virus stocks to the growth medium. Three wells were left uninfected. Infected and uninfected cells were incubated for two days and then processed for Western blot.

2. Preparation of lysates: RIPA buffer supplemented with protease inhibitor cocktail (RIPA+PI) was prepared as follows: 0.7 ml 10× RIPA lysis buffer Millipore Cat #20-188 were added to 6.3 ml $H_2O$, Fisher Scientific Cat #BP2470-1, and 1 tablet COMPLETE™ Mini Protease inhibitor cocktail (Roche cat #11 836 153 001) was dissolved in 7 ml 1×RIPA buffer.

Uninfected controls were scraped into the medium and suspensions from the three replicate wells were pooled in 15 ml centrifuge tubes and placed on ice. Infected cells were rinsed off in the medium and the suspensions from the three replicate wells were pooled in 15 ml centrifuge tubes and placed on ice. Cells were sedimented by centrifugation at 1000×g 4° C. for 5 min. Supernatants were carefully aspirated and the cell pellets were resuspended in RIPA+PI (Uninfected cells in 300 μl, infected cells in 150 μl). Suspensions were incubated on ice for 30 min and vortexed every 10 min. Suspensions were transferred to 1.5 ml microfuge tubes and undissolved material was sedimented by centrifugation at 15000 rpm, 4° C., for 10 min in a micro centrifuge. Clear supernatants were transferred to new 1.5 ml microfuge tubes and stored at −80° C. until use.

3. SDS-PAGE and transfer on nylon membranes: Materials: BioRad Criterion TGX Stain Free Precast Gels, 4-20%, 26 well Cat #_567-8095; Bio Rad Precision Plus Dual Color Marker, Cat #161-0374; Bio Rad Precision Plus All Blue Marker, Cat #161-0373; Bio Rad Trans Blot Turbo transfer kit, Midi format Cat #170-4159; Bio Rad 4× Laemmli Sample Buffer (Cat no. 161-0747) (Bio Rad Laboratories GmbH, Heidemannstrasse 164, D-80939 München); TGS Running buffer (Sambrook et al.), Blocking Solution 1: 5% FBS in PBST (Sambrook et al.); PBST.

Samples were prepared without addition of a reducing agent. Samples were thawed on ice and mixed with 1 volume of 4× Lämmli buffer, boiled for 6 min at 96° C., and kept at RT until loading of the gel. Gel was run for 30 min at 230 mA and then assembled for electro transfer using the BioRad Trans Blot Turbo system. Transfer was set to 2.5 A 25 V 10 min. Membrane was rinsed in sterile distilled $H_2O$ and incubated with 25 mL Blocking Solution 5% FBS in PBST for 30 min at 4° C.

Antibody Incubation and Detection

Materials: Immun-Star WestemC Chemiluminecent Kit (Bio Rad Laboratories GmbH, Heidemannstrasse 164, D-80939 München) Cat #170-5070

Primary antibodies:

A: SBV-Gc-protein specific monoclonal antibody (Wernike et al., 2015a) 1:20

B: Mouse monoclonal antibody Ai2G7 to EHV-1 gpII (Boehringer Ingelheim proprietary)

Secondary Antibody: Peroxidase conjugated Goat anti-mouse, (Jackson Immune Research #115-035-146) 1:5000

All incubations were done in sufficient volume under constant agitation. Antibodies were diluted in 5% FBS/TBST. Primary antibodies were incubated over night at 4° C. Antibody solution was removed and blots were washed three times with TBST for 5-10 min. Diluted secondary antibody was incubated with the blots for 1 h at RT, removed and blots were washed three times with TBST for 5-10 min. Blots were placed on a clear plastic sheet protector. Peroxide and Lumino/Enhancer solutions were mixed 1 ml+1 ml (2 ml total for each blot), pipetted on the blots and incubated for 3 to 5 min. Thereafter the membranes were placed in the ChemiDocXRS imaging system (Bio Rad Laboratories GmbH, Heidemannstrasse 164, D-80939 München) and signals were recorded using Image Lab software.

Virus Titrations

AI-ST cells were seeded in 96-well plates (Corning Incorporated—Life Sciences, One Becton Circle, Durham, N.C. 27712, USA; REF 353072) at $2\times10^4$ cells/well in MEM supplemented with 10% FBS one day before infection. Virus stocks were quickly thawed and placed on ice. Ten serial 1:10 dilutions were prepared in MEM in 1.2 ml volume per dilution. 100 μl/well of the virus dilutions were added to the cells, 8 wells in one vertical row per dilution. Vertical rows 11 and 12 of each plate served as medium control by addition of 100 μl/well MEM. Titrations were done in triplicate and cells were incubated for 5 days at 37° C./5% $CO_2$. Cell cultures were inspected microscopically and wells where EHV-1 RacH typical CPE was observed were recorded. Titers were calculated as TCID50/ml according to the method by Reed and Muench (1938).

Characterization of Recombinant EHV-1 Used for Vaccination

Expression of the modified SBV Gc234 in infected cells was shown by Western blot and double immunofluorescence assay (DIFA) for plaque isolate of rEHV-1 RacH-SE-70-455-SBVGc 121.232. DIFA with a polyclonal horse-anti- EHV-antiserum and the monoclonal anti-SBV antibody confirmed expression of the transgene in apparently 100% of the rEHV-1 infected cells. When DIFA of cells infected with rEHV-1 RacH-SE-70-455-SBVGc_121.232 was performed, EHV-1 antigen-positive cells that were stained with a horse anti-EHV antiserum (purple) also bound a monoclonal antibody to SBV Gc. Western blots run under non-reducing conditions confirmed expression of the modified SBVGc234 in cells infected with recombinant EHV-1 RacH-SE-70-455-SBVGc. Western blots of lysates of infected or uninfected cells probed with a monoclonal antibody to SBV Gc or a monoclonal antibody to EHV-1 gpII were performed. While EHV-1 gpII was expressed in all infected cells, SBV Gc was only expressed in the cells infected with rEHV-1RacH-SE-70-455-SBVGc, not in those infected with the empty vector rEHV-1 RacH-SE1212. Neither viral protein was detected in lysates of mock-infected cells. Incubation of parallel blots with a monoclonal antibody against gpII of EHV-1 confirmed restoration of orf71 (US5) by the self-excision procedure during rescue of recombinant virus after transfection. A P7 virus stock raised from three times plaque purified isolate rEHV-1 RacH-SE-70-455-SBVGc_121.232 replicated to a very high titer of $1.85 \times 10^9$ TCID50/ml in AI-ST cells, indicating that expression of the transgene did not impair EHV-replication in this cell line. An average of six titrations of rEHV-1RacH-SE-70-455-SBVGc_121.232 as TCID50/ml resulted in $1.85 \times 10^9$ TCID50/ml with a standard deviation of $1.28 \times 10^9$ TCID50/ml.

Animals and Experimental Design

A number of 4 cattle of German domestic breeds were vaccinated twice three weeks apart with $10^8$ TCID$_{50}$ rEHV-SBV-Gc; 4 additional cattle were kept as unvaccinated controls. Three weeks after the second immunization all animals were inoculated subcutaneously with 2×0.5 ml of an SBV field strain which was passaged solely in cattle (Wernike et al., 2012). During the entire study, rectal body temperatures were measured daily and the animals were examined for clinical signs by veterinarians. Sera were taken at weekly intervals and analyzed by a commercially available N-based ELISA (ID Screen® Schmallenberg virus Competition, ID vet, France) and by a micro neutralization test against SBV isolate BH80/11 as described previously (Wernike et al., 2013a). Evaluation was done by assessment of the cytopathic effect after 3 days; all samples were tested in quadruplicate and the antibody titers were calculated as ND$_{50}$ according to Behrens and Kaerber. Sera taken at the days of immunization, challenge infection, and at the end of the study, respectively, were additionally analyzed by micro neutralization tests against EHV strain RacH (group rEHV-SBV-Gc and unvaccinated control animals).

During the first 10 days after challenge infection blood samples were additionally collected on a daily basis. From these samples, viral RNA was extracted using the King Fisher 96 Flex (Thermo Scientific, Braunschweig, Germany) in combination with the MagAttract Virus Mini M48 Kit (Qiagen, Hilden, Germany) according to the manufacturer's instructions and tested by an S-segment-based real-time RT-PCR (Bilk et al., 2012).

The experimental protocol has been reviewed by the responsible state ethics commission and was approved by the competent authority (State Office for Agriculture, Food Safety and Fisheries of Mecklenburg-Vorpommem, Rostock, Germany, ref. LALLF M-VTSD/7221.3-1.1-004/12).

Clinical Observation and Viral RNA Detection

None of the animals showed any relevant SBV-specific clinical signs during the entire study and the body temperatures remained within a normal range for all animals, when measured rectally.

Starting from day one or two post challenge infection, viral RNA was detectable in serum samples of each unvaccinated control animal for four consecutive days. All vaccinated animals from the rEHV-SBV-Gc group showed reduced viral RNA concentrations by quantitative RT-PCR (FIG. 31A) throughout the entire sampling period. Two animals of the rEHV-SBV-Gc group tested completely negative by quantitative RT-PCR (FIG. 31A) throughout the entire sampling period. In two animals immunized with rEHV-SBV-Gc the SBV genome was detected at reduced levels for three or five days, respectively.

Antibody Response

In the unvaccinated control animals no SBV-specific antibodies were detected by serum neutralization test before challenge infection. From one or two weeks after infection onwards high titers of neutralizing antibodies were detected in all unvaccinated animals (FIG. 31B).

In contrast to the unvaccinated control group, SBV-specific neutralizing antibodies were detectable at the day of challenge infection in two out of four cattle immunized with rEHV-SBV-Gc. In the remaining two animals of this group, no SBV-specific neutralizing antibodies were detected before challenge infection, but from two weeks after infection, neutralizing antibodies were present (FIG. 31B). Titers of SBV-specific neutralizing antibodies in all four vaccinated animals were lower than in the challenge control, indicating less efficient viral replication of the challenge virus, and thus supporting the quantitative RT-PCR data.

EHV Neutralization Test

Two-fold dilutions of sera were prepared in MEM, starting at 1:5. Fifty µl of MEM containing 100 TCID50 of SBV and 50 µl of the diluted sera were incubated in 96-well cell culture plates for 2 hours. Thereafter, 100 µl freshly prepared suspension of BHK-cells (in MEM containing 10% fetal calf serum) were added and cultures plates were incubated for 3-4 days at 37° C./5% CO$_2$. Cytopathic effect was evaluated by light microscopy. All sera were tested in duplicates, and the antibody titer was calculated as ND50 according to Kaerber (1931) as modified by Behrens (personal communication). The results as shown in FIG. 32 indicate that vaccination of cattle with rEHV-1 RacH-SE-70-455-SBVGc resulted in replication of the vector virus efficient enough to induce a specific immune response. In one out of four animal EHV-1 a very low titer of neutralizing antibodies (1:4) was detectable three weeks after primary vaccination. After two vaccinations, three weeks after the second application, all four cattle had produced neutralizing antibodies at a titer of 1:128. From this result it can be concluded that EHV-1 RacH might also be functional as a vaccine vector in cattle.

Example 11

Efficacy of Tetravalent Swine IAV Vaccine Consisting of rEHV-1 RacH-SE_B and rEHV-1 RacH-SE_D Against Swine IAV H3N2 Challenge in Piglets To investigate its properties as a vectored vaccine in young piglets, the tetravalent Swine IAV vaccine consisting of rEHV-1 RacH-SE_B (rEHV-1 RacH-SE-1/3-p430-H1av-70-p455-H3 see FIG. 13) and rEHV-1 RacH-SE_D (rEHV-1 RacH-SE-1/3-p430-H1hu-70-p455-H1pdm see FIG. 27) was tested in a second vaccination-challenge study.

In this second study, piglets from unvaccinated sows and tested serologically negative for swine IAV-specific antibodies by use of an H3-specific ELISA (FIG. 36) and by virus neutralization test (data not shown) at the time of first vaccination were vaccinated twice with the tetravalent vaccine consisting of rEHV-1 RacH-SE_B and rEHV-1 RacH-SE_D. Animals were vaccinated the first time in their first week of life (study day 0, SD0) and the second time in their fourth week of life (study day 21, SD21), respectively, either intramuscularly and then intramuscularly (2× IM), or first intranasally and then intramuscularly (IN+IM), or twice intranasally (2× IN), at a dose of 1×10^7 TCID50 in a 2 ml dose per vaccine strain, animal, and vaccination, respectively. A non-vaccinated group served as negative control and another non-vaccinated group served as challenge control at the eleventh week of life (study days 69 or 70, SD42/43), all animals but the negative control were challenged by an intratracheally applied dosage of 2×10^7 TCID50 of an H3N2 Swine IAV challenge strain (European field virus isolate R452-14 whose H3 is being heterologous to the H3 vaccine antigen used in rEHV-1 RacH-SE_B). Non-vaccinated and unchallenged animals served as negative control (neg. ctrl.), while non-vaccinated but challenged animals served as challenge control (chall. ctrl.). At and after vaccinations and before challenge, blood samples were taken at different time points.

One day after challenge, half of the animals per group were killed and three lung samples per left and per right lung were taken per animal, respectively. Then, infectious swine IAV titers per gram lung homogenate were determined for each animal as an average of the left and right lungs per animal that each were obtained from homogenates of the pooled three samples per left or right lung and that were normalized to the total weight of the three samples of the left or the right lung, respectively. The same procedure was performed with the remaining half of animals per group three days after challenge. For all vaccinated groups, the medians of titers of infectious swine IAV obtained from individual animals in the group were statistically significantly reduced for samples taken at day one after challenge (CH+1) when compared to the challenge control group, while all animals from the negative control group showed no infectious swine IAV virus titers in their lung homogenates (FIG. 33). Moreover, for all vaccinated groups, the medians of titers of infectious swine IAV obtained from individual animals in the group were statistically significantly reduced for samples taken at day 3 after challenge (CH+3) when compared to the challenge control group, while all animals from the negative control group showed no infectious swine IAV virus titers in their lung homogenates (FIG. 34). Thus, vaccination with the tetravalent swine IAV vaccine consisting of rEHV-1 RacH-SE_B and rEHV-1 RacH-SE_D statistically significantly reduced the swine IAV lung loads at one and three days after challenge with a heterologous swine IAV H3N2 strain in piglets, respectively. Consequently, the vaccine described here is efficacious against swine IAV in pigs.

Moreover, serum taken from study animals at study day 0 (SD0, before first vaccination), at study day 21 (SD21, before second vaccination), and at study days 42 or 43 (SD42/43, before application of challenge material) was analyzed by an enzyme-linked immunosorbent assay (ELISA) specific for swine immunoglobulin G (IgG) directed against a recombinantly expressed swine IAV H3 antigen being homologous to the H3 expressed by vaccine strain rEHV-1 RacH-SE_B. While mean OD values of sera from the negative control group gave only very low values for all time points measured, sera from vaccinated groups demonstrated a strong increase of OD values after two intramuscular applications (2× IM; SD21 and SD42/43), after first intranasal and then intramuscular application (IN+IM; SD42/43), and after two intranasal applications (2× IN; SD42/43); FIG. 36. Thus, vaccination with the tetravalent swine IAV vaccine consisting of rEHV-1 RacH-SE_B and rEHV-1 RacH-SE_D elicited a serological immune response in piglets against the swine IAV hemagglutinin H3 expressed by vaccine strain rEHV-1 RacH-SE_B, respectively.

In addition, peripheral blood mononuclear cells (PBMCs) were purified from blood taken from study animals at study day 28 (SD28). The PBMCs then were restimulated either with H3N2 swine IAV challenge strain R452-14 at a multiplicity on infection of 1 (H3N2 MOI 1) or with recombinantly expressed swine IAV H3 antigen being homologous to the H3 expressed by vaccine strain rEHV-1 RacH-SE_B at a concentration of 1 µg/ml (rH3 1 µg/ml). Using the restimulated PBMCs, an interferon gamma-specific enzyme-linked immunosorbent spot assay (IFNγ ELISpot) was performed, and the obtained values normalized to 10^6 cells and calculated as means per group, respectively (FIG. 38). While restimulated PBMCs from the challenge control group (served as negative control for this test, animals were not vaccinated) showed mean spots per group of below 45 after either of the restimulations, restimulated PBMCs from vaccinated animals showed mean spots per group of above 85 after two intramuscular applications, of more than 100 spots after first intranasal and then intramuscular application (IN+IM), and of more than 150 spots after two intranasal applications (2× IN), after either of the restimulations, respectively (FIG. 38). Thus, vaccination with the tetravalent swine IAV vaccine consisting of rEHV-1 RacH-SE_B and rEHV-1 RacH-SE_D elicited a cellular immune response in piglets both against the swine IAV hemagglutinin H3 expressed by vaccine strain rEHV-1 RacH-SE_B and against the swine IAV H3N2 R452-14 used for heterologous challenge virus infection, respectively.

Thus, vaccination of piglets with tetravalent Swine IAV vaccine consisting of rEHV-1 RacH-SE_B and rEHV-1 RacH-SE_D induced a detectable serological and cellular immune response in piglets and demonstrated vaccine efficacy by statistically significantly reducing swine IAV loads in lung homogenates one and three days after heterologous swine IAV challenge.

Example 12

Efficacy of Tetravalent Swine IAV Vaccine Consisting of rEHV-1 RacH-SE_B and rEHV-1 RacH-SE_D Against Swine IAV H3N2 Challenge in Piglets with Maternally Derived Antibodies To investigate its properties as a vectored vaccine in young piglets, the tetravalent Swine IAV vaccine consisting of rEHV-1 RacH-SE_B and rEHV-1 RacH-SE_D was tested in a third vaccination-challenge study.

In this third study, piglets born by and colostrum- and milk-fed by sows that were vaccinated twice during pregnancy with a commercially available inactivated vaccine against swine IAV were used. Piglets were tested serologically positive for swine IAV-specific antibodies by use of a H3-specific ELISA (FIG. 37) and by use of a commercially available swine IAV-specific antibody ELISA (*IDEXX Influenza A (Virus Antibody Test)*®; IDEXX, Westbrook, Me. 04092, USA) following the manufacturer's testing recommendations (data not shown) at the time of first vaccination were vaccinated twice with the tetravalent vaccine consisting of rEHV-1 RacH-SE_B and rEHV-1 RacH-SE_D. Animals were vaccinated the first time in their first week of life (study day 0, SD0) and the second time in their fourth week of life (study day 21, SD21), respectively, either intramuscularly and then intramuscularly (2× IM), or first intranasally and then intramuscularly (IN+IM), or twice intranasally (2× IN), at a dose of 1×10^7 TCID50 in a 2 ml dose per vaccine strain, animal, and vaccination, respectively. A non-vaccinated group served as negative control and another non-vaccinated group served as challenge control. In their eleventh week of life (study days 69 or 70, SD69/70), all animals but the negative control were challenged by an intratracheally applied dosage of 2×10^7 TCID50 of an H3N2 Swine IAV challenge strain (European field virus isolate R452-14 whose H3 is being heterologous to the H3 vaccine antigen used in rEHV-1 RacH-SE_B). Non-vaccinated and unchallenged animals served as negative control (neg. ctrl.), while non-vaccinated but challenged animals served as challenge control (chall. ctrl.). At and after vaccinations and before challenge, blood samples were taken at different time points.

Five days after challenge animals were killed and three lung samples per left and per right lung were taken per animal, respectively. Then, infectious swine IAV titers per gram lung homogenate were determined for each animal as an average of the left and right lungs per animal that each were obtained from homogenates of the pooled three samples per left or right lung and that were normalized to the total weight of the three samples of the left or the right lung, respectively. For all vaccinated groups, the medians of titers of infectious swine IAV obtained from individual animals in the group were statistically significantly reduced for samples taken at day five after challenge (CH+5) when compared to the challenge control group, while all animals from the negative control group showed no infectious swine IAV virus titers in their lung homogenates (FIG. 35). Thus, vaccination with the tetravalent swine IAV vaccine consisting of rEHV-1 RacH-SE_B and rEHV-1 RacH-SE_D statistically significantly reduced the swine IAV lung loads five days after challenge with a heterologous swine IAV H3N2 strain in piglets, respectively. Consequently, the vaccine described here is efficacious against swine IAV in pigs.

Moreover, serum taken from study animals at study day 0 (SD0, before first vaccination), at study day 21 (SD21, before second vaccination), and at study day 35 (SD35, two weeks after second vaccination) was analyzed by an enzyme-linked immunosorbent assay (ELISA) specific for swine immunoglobulin G (IgG) directed against a recombinantly expressed swine IAV H3 antigen being homologous to the H3 expressed by vaccine strain rEHV-1 RacH-SE_B. While mean OD values of sera from the negative control group gave only very low values for SD21 and SD35, sera from vaccinated groups demonstrated a strong increase of OD values after two intramuscular applications (2× IM; SD35), after first intranasal and then intramuscular application (IN+IM; SD35), and after two intranasal applications (2× IN; SD35); FIG. 37. Thus, vaccination with the tetravalent swine IAV vaccine consisting of rEHV-1 RacH-SE_B and rEHV-1 RacH-SE_D elicited a serological immune response in piglets against the swine IAV hemagglutinin H3 expressed by vaccine strain rEHV-1 RacH-SE_B, respectively.

In addition, peripheral blood mononuclear cells (PBMCs) were purified from blood taken from study animals at study day 28 (SD28). The PBMCs then were restimulated either with H3N2 swine IAV challenge strain R452-14 at a multiplicity on infection of 1 (H3N2 MOI 1) or with recombinantly expressed swine IAV H3 antigen being homologous to the H3 expressed by vaccine strain rEHV-1 RacH-SE_B at a concentration of 1 µg/ml (rH3 1 µg/ml). Using the restimulated PBMCs, an interferon gamma-specific enzyme-linked immunosorbent spot assay (IFNγ ELISpot) was performed, and the obtained values normalized to 10^6 cells and calculated as means per group, respectively (FIG. 39). While restimulated PBMCs from the challenge control group (served as negative control for this test, animals were not vaccinated) showed mean spots per group of below 15 after either of the restimulations, restimulated PBMCs from vaccinated animals showed mean spots per group of above 30 after two intramuscular applications, of more than 55 spots after first intranasal and then intramuscular application (IN+IM), and of more than 65 spots after two intranasal applications (2× IN), after either of the restimulations, respectively (FIG. 39). Thus, vaccination with the tetravalent swine IAV vaccine consisting of rEHV-1 RacH-SE_B and rEHV-1 RacH-SE_D elicited a cellular immune response in piglets both against the swine IAV hemagglutinin H3 expressed by vaccine strain rEHV-1 RacH-SE_B and against the swine IAV H3N2 R452-14 used for heterologous challenge virus infection, respectively.

Thus, vaccination of piglets with tetravalent Swine IAV vaccine consisting of rEHV-1 RacH-SE_B and rEHV-1 RacH-SE_D induced a detectable serological and cellular immune response in piglets and demonstrated vaccine efficacy by statistically significantly reducing swine IAV loads in lung homogenates five days after heterologous swine IAV challenge.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

REFERENCES

The following references, to the extent that they provide exemplary procedural or other details supplementary to those set forth herein, are specifically incorporated herein by reference.

1. Allwinn R, Geiler J, Berger A, Cinatl J, Doerr H W. 2010. Determination of serum antibodies against swine-origin influenza A virus H1N1/09 by immunofluorescence, haemagglutination inhibition, and by neutralization tests: how is the prevalence rate of protecting antibodies in humans? Med Microbiol Immunol. 199(2):117-21. doi: 10.1007/s00430-010-0143-4. Epub 2010 Feb. 17.
2. Anonymous (2013). VMD authorizes SBV vaccine for use in the UK. The Veterinary record 172, 543

3. Anonymous (2015). Schmallenberg virus vaccine. The Veterinary record 177, 321
4. Bilk S, Schulze C, Fischer M, Beer M, Hlinak A, Hoffmann B (2012). Organ distribution of Schmallenberg virus RNA in malformed newborns. Veterinary microbiology 159, 236-238
5. Boshart M, Weber F, Jahn G, Dorsch-Hasler K, Fleckenstein B, Schaffner W. 1985. A very strong enhancer is located upstream of an immediate early gene of human cytomegalovirus. Cell 41(2):521-30.
6. Bustin, S. 2000. Absolute quantification of mRNA using real-time reverse transcription polymerase chain reaction assays. Journal of Molecular Endocrinology 25(2): 169-193.
7. Charoensawan, V., Wilson, D., Teichmann, S. A. 2010. Genomic repertoires of DNA-binding transcription factors across the tree of life. Nucleic Acids Res. 38(21): 7364-77
8. Colle, C. F. 3rd, O'Callaghan, D. J. 1995. Transcriptional analyses of the unique short segment of EHV-1 strain Kentucky A. Virus Genes; 9(3):257-68.
9. Dorsch-Häsler, K., Keil, G. M., Weber, F., Jasin, M. Schaffner, W., and Koszinowski, U. H. 1985. A long and complex enhancer activates transcription of the gene coding for the highly abundant immediate early mRNA in murine cytomegalovirus. PNAS Vol. 82: 8325-8329.
10. Drummer, H. E., Studdert, M. J., Crabb, B. S. 1998. Equine herpesvirus-4 glycoprotein G is secreted as a disulphide-linked homodimer and is present as two homodimeric species in the virion. J. Gen. Virol. 79: 1205-1213
11. Fields, B, Knipe, D. M.; and Howley, P. M. 2013. Virology. 6$^{th}$ ed. Philadelphia; Wolters Kluwer Health/Lippincott Williams&Wilkins
12. Foecking, M. K., Hofstetter, H. 1986. Powerful and versatile enhancer-promoter unit for mammalian expression vectors. Gene 45(1):101-5.
13. Goodwin, E. C. & Rottman, F. M. 1992. The 3'flanking sequence of the bovine growth hormone gene contains novel elements required for efficient and accurate poly adenylation. J. Biol. Chem. 267: 16330-16334.
14. Hübert, P. H., Birkenmaier, S., Rziha, H.-J. and Osterrieder, N. (1996), Alterations in the Equine Herpesvirus Type-1 (EHV-1) Strain RacH During Attenuation. Journal of Veterinary Medicine, Series B, 43: 1-14. doi:10.1111/j.1439-0450.1996.tb00282.x
15. Karber, G (1931) Beitrag zur kollektiven Behandlung pharmakologischer Reihenversuche. Archiv f experiment Pathol u Pharmakol.; 162:480-483
16. Kim, D. W., Uetsuki, T., Kaziro, Y., Yamaguchi, N., Sugano, S. 1990. Use of the human elongation factor 1 alpha promoter as a versatile and efficient expression system. Gene 16; 91(2):217-23.
17. Kraatz F, Wernike K, Hechinger S, Konig P, Granzow H, Reimann I, Beer, M (2015). Deletion mutants of Schmallenberg virus are avirulent and protect from virus challenge. J Virol 89, 1825-1837
18. Luke, G A and Ryan, M D. 2013. The protein coexpression problem in biotechnology and biomedicine: virus 2A and 2A-like sequences provide a solution. Future Virology, Vol. 8, No. 10, Pages 983-996.
19. Ma, G., Eschbaumer, M., Said, A., Hoffmann, B., Beer, M., Osterrieder, N. 2012. An equine herpesvirus type 1 (EHV-1) expressing VP2 and VP5 of serotype 8 bluetongue virus (BTV-8) induces protection in a murine infection model. PLoS One. 2012; 7(4):e34425. doi: 10.1371/journal.pone.0034425. Epub 2012 Apr. 12.
20. Ma, G., Azab, W., Osterrieder, N. 2013. Equine herpesviruses type 1 (EHV-1) and 4 (EHV-4)—masters of co-evolution and a constant threat to equids and beyond. Vet Microbiol. 167(1-2):123-34.
21. Nolan, T. Rebecca E Hands, R. E., and Bustin S. A. 2006. Quantification of mRNA using real-time RT-PCR Nature Protocols 1: 1559-1582
22. Osterrieder, N., Neubauer, A., Brandmuller, C., Kaaden, O R., and O'Callaghan, D. J. 1996. The equine herpesvirus 1 IR6 protein influences virus growth at elevated temperature and is a major determinant of virulence. Virology 226:243-251.
23. Ptashne, M. 2014. *The Chemistry of Regulation of Genes and Other Things* The Journal of Biological Chemistry Vol. 289, (9) 5417-5435. Reed, L. J., and Muench, H. 1938. A simple method of estimating fifty percent endpoints. Am. J. Hyg. (27) 3; 493-497.
24. Reed L J and Muench H (1938). A simple method estimating fifty percent endpoints. The American Journal of Hygiene 27(3) 493-497
25. Rosas, C. T., Konig, P., Beer, M., Dubovi, E. J., Tischer, B. K., Osterrieder, N., 2007a. Evaluation of the vaccine potential of an equine herpesvirus type 1 vector expressing bovine viral diarrhea virus structural proteins. J. Gen. Virol. 88 (3), 748-757.
26. Rosas, C. T., B. K. Tischer, G. A. Perkins, B. Wagner, L. B. Goodman, N. Osterrieder. 2007b. Live-attenuated recombinant equine herpesvirus type 1 (EHV-1) induces a neutralizing antibody response against West Nile virus (WNV) Virus Research, 125, pp. 69-78.
27. Rosas, C. T., Van de Walle, G. R., Metzger, S. M., Loelzer, K., Dubovi, E. J., Kim, S. G., Parrish, C. R., Osterrieder, N., 2008. Evaluation of a vectored equine herpesvirus type 1 (EHV-1) vaccine expressing H3 hemagglutinin in the protection of dogs against canine influenza. Vaccine 26 (19), 2335-3234.
28. Said, A., Elke Lange, E., Beer, M. Damiani, A., Osterrieder, N. 2013. Recombinant equine herpesvirus 1 (EHV-1) vaccine protects pigs against challenge with influenza A(H1N1)pmd09 Virus Research 173: 371-376
29. Sambrook J and Russell D W (2001). Molecular Cloning, 3rd ed. Cold Spring harbor Laboratory Press, Cold Spring Harbor, N.Y.; ISBN 978-087969-577-4
30. Shaner, N. C., Campbell, R. E., Steinbach, P. A., Giepmans, B. N., Palmer, A. E., Tsien, R. Y. 2004. Improved monomeric red, orange and yellow fluorescent proteins derived from *Discosoma* sp. red fluorescent protein. Nat Biotechnol. December; 22(12):1567-72. Epub 2004 Nov. 21.
31. Tischer, B. K., von Einem, J., Kaufer, B., Osterrieder, N., 2006. Two-step red-mediated recombination for versatile high-efficiency markerless DNA manipulation in *Escherichia coli*. Biotechnol. Tech. 40, 191-197.
32. Tischer, B. K., Kaufer, B. B., Sommer, M., Wussow, F., Arvin, A., and Osterrieder, N. A Self-Excisable Infectious Bacterial Artificial Chromosome Clone of Varicella-Zoster Virus Allows Analysis of the Essential Tegument Protein Encoded by ORF9. J. Virol.81 (23), 2007, 13200-13208.
33. Tischer, B. K, Smith, G. A., and Osterrieder, N. in: Jeff Braman (ed.), In Vitro Mutagenesis Protocols: Third Edition, Methods in Molecular Biology, vol. 634, DOI 10.1007/978-1-60761-652-8_30, © Springer Science+Business Media, LLC 2010, Chapter 30: En Passant Mutagenesis: A Two Step Markerless Red Recombination System.

34. Thompson, S. R. 2012. Tricks an IRES uses to enslave ribosomes. Trends Microbiol. November; 20(11):558-66.
35. Trapp, S., von Einem, J., Hofmann, H., Kostler, J., Wild, J., Wagner, R., Beer, M., Osterrieder, N., 2005. Potential of equine herpesvirus 1 as a vector for immunization. J. Virol. 79, 5445-5454.
36. Trombetta C M, Perini D, Mather S, Temperton N, Montomoli E. 2014. Overview of Serological Techniques for Influenza Vaccine Evaluation: Past, Present and Future. Vaccines (Basel) 13; 2(4):707-34. doi: 10.3390/vaccines2040707.
37. Wellington, J. E., Allen, G. P., Gooley, A. A., Love, D. N., Packer, N. H., Yan, J. X., Whalley, J. M. 1996. The highly 0-glycosylated glycoprotein gp2 of equine herpesvirus 1 is encoded by gene 71. J Virol. 70(11):8195-8.
38. Wernike K, Aebischer A, Roman-Sosa G, Beer M, (2017). The N-terminal domain of Schmallenberg virus envelope protein Gc is highly immunogenic and can provide protection from infection. Scientific reports.2017 Feb. 13; 7:42500.
39. Wernike K, Eschbaumer M, Breithaupt A, Hoffmann B, Beer M (2012). Schmallenberg virus challenge models in cattle: infectious serum or culture-grown virus? Veterinary research 43, 84
40. Wernike K, Eschbaumer M, Schirrmeier H, Blohm U, Breithaupt A, Hoffmann B, Beer M, (2013a). Oral exposure, reinfection and cellular immunity to Schmallenberg virus in cattle. Veterinary microbiology 165, 155-159
41. Wernike K, Nikolin V M, Hechinger S, Hoffmann B, Beer M (2013b). Inactivated Schmallenberg virus prototype vaccines. Vaccine 31, 3558-3563

What is claimed is:

1. A promoter sequence comprising sequences having at least 95% sequence identity and/or homology to SEQ ID NO: 1 (4pgG600), SEQ ID NO. 2 (4pMCP600), SEQ ID NO. 3 (p430), SEQ ID NO: 4 (p455), or the complementary nucleotide sequences thereof, wherein said promoter sequence is operably linked to a heterologous nucleotide sequence of interest, a gene of interest, and/or an antigen encoding sequence of interest.

2. The promoter sequence of claim 1, wherein the promoter sequence is selected from the group consisting of SEQ ID NO: 3, SEQ ID NO: 4, and the complementary nucleotide sequences thereof.

3. An expression cassette comprising a promoter sequence selected from the group consisting of sequences having at least 95% sequence identity and/or homology to SEQ ID NO. 1 (4pgG600), SEQ ID NO. 2, (4pMCP600), SEQ ID NO. 3 (p430), SEQ ID NO: 4 (p455), and the complementary nucleotide sequences thereof,
  wherein the promoter sequence is operably linked to a nucleotide sequence of interest,
  wherein said promoter sequence leads to expression of the nucleotide sequence of interest,
  whereby said promoter sequence is a heterologous promoter sequence, and/or an exogenous promoter sequence.

4. The expression cassette of claim 3, wherein the promoter sequence selected from the group consisting of SEQ ID NO: 3, SEQ ID NO: 4, and the complementary nucleotide sequences thereof.

5. A vector comprising the expression cassette according to claim 3.

6. The vector according to claim 5, whereby said vector is a recombinant vector, and/or a heterologous vector, and/or an exogenous vector.

7. The vector according to claim 5, whereby said vector is a viral vector, selected from the group consisting of: Herpesviridae, Varicelloviruses, Adenoviridae (AdV), Adena-associated viridae, Baculoviridae, Lentiviridae.

8. The vector according to claim 5, whereby said viral vector is a member of the family Herpesviridae, and/or of the genus Alphaherpesvirinae, and/or of the subgenus *Varicellovirus*, and/or is Equid Alphaherpesvirus 1 (EHV-1).

9. The vector according to claim 5, whereby said vector comprises one or more further regulatory sequences, a polyadenylation signal, an IRES regulatory element, and/or a 2a peptide regulatory element.

10. An eukaryotic host cell line comprising a vector comprising a promoter sequence selected from the group consisting of sequences having at least 95% sequence identity and/or homology to SEQ ID NO. 1 (4pgG600), SEQ ID NO. 2 (4pMCP600), SEQ ID NO. 3 (p430), SEQ ID NO: 4 (p455), and the complementary nucleotide sequences thereof,
wherein the promoter sequence is operably linked to a nucleotide sequence of interest, selected from the group consisting of: a gene of interest, a heterologous and/or exogenous sequence of interest, or an antigen encoding sequence of interest,
wherein said promoter sequence leads to expression of the nucleotide sequence of interest,
whereby said promoter sequence is a heterologous promoter sequence, and/or an exogenous promoter sequence,
wherein said host cell line is a mammalian cell line or an insect cell line, selected from the group consisting of: a PK/WRL cell line, a RK13 cell line, a MDBK cell line, a ST cell line, an AI-ST cell line, a VERO cell line, a Sf9 cell line, a Sf21, a Sf plus cell line, a MDCK cell line, and/or derivatives thereof.

11. A kit comprising
a. a host cell(s),
b. optionally a transfection reagent(s),
c. an instruction leaflet, and
d. a vector comprising a promoter sequence selected from the group consisting of sequences having at least 95% sequence identity and/or homology to SEQ ID NO. 1 (4pgG600), SEQ ID NO. 2 (4pMCP600), SEQ ID NO. 3 (p430), SEQ ID NO: 4 (p455), and the complementary nucleotide sequences thereof,
wherein the promoter sequence is operably linked to a nucleotide sequence of interest, selected from the group consisting of: a gene of interest, a heterologous and/or exogenous sequence of interest, or antigen encoding sequence of interest,
wherein said promoter sequence leads to expression of the nucleotide sequence of interest,
whereby said promoter sequence is a heterologous promoter sequence, and/or an exogenous promoter sequence.

12. A method of producing a vector, comprising
a. providing a promoter sequence comprising SEQ ID NO: 1 (4pgG600), SEQ ID NO. 2 (4pMCP600), SEQ ID NO. 3 (p430), SEQ ID NO: 4 (p455), or the complementary nucleotide sequences thereof, wherein said promoter sequence leads to expression of a nucleotide sequence of interest, and/or an antigen encoding sequence of interest,
b. integrating said promoter sequence of step a) into a vector backbone derived from a virus, which is selected from the group consisting of: Herpesviridae, varicelloviruses, Adenoviridae (AdV), Parvoviridae like Adena-associated viruses, Baculoviridae, Retroviridae, and Poxviridae.

13. A method of preparing a host cell, comprising:
a) infecting a permissive eukaryotic host cell line with a vector comprising a promoter sequence selected from the group consisting of SEQ ID NO: 1 (4pgG600), SEQ ID NO: 2 (4pMCP600), SEQ ID NO: 3 (p430), SEQ ID NO: 4 (p455), and the complementary nucleotide sequences thereof and a functional and the complementary nucleotide sequences thereof,
wherein the promoter sequence is operably linked to a nucleotide sequence of interest, selected from the group consisting of: a gene of interest, a heterologous and/or exogenous sequence of interest, or antigen encoding sequence of interest,
wherein said promoter sequence leads to expression of the nucleotide sequence of interest, whereby said promoter sequence is a heterologous promoter sequence, and/or an exogenous promoter sequence,
b) cultivating the infected cells of a) under suitable conditions, and
c) optionally harvesting said host cell.

14. A method for the preparation of an immunogenic composition or a vaccine for reducing the incidence or the severity of one or more clinical signs associated with or caused by an infection, comprising the following steps:
a) infecting a permissive eukaryotic host cell line with a vector comprising a promoter sequence selected from the group consisting of SEQ ID NO: 1 (4pgG600), SEQ ID NO. 2 (4pMCP600), SEQ ID NO. 3 (p430), SEQ ID NO: 4 (p455), and the complementary nucleotide sequences thereof and a functional and the complementary nucleotide sequences thereof,
wherein the promoter sequence is operably linked to a nucleotide sequence of interest, selected from the group consisting of: a gene of interest, a heterologous and/or exogenous sequence of interest, or antigen encoding sequence of interest,
wherein said promoter sequence leads to expression of the nucleotide sequence of interest,
whereby said promoter sequence is a heterologous promoter sequence, and/or an exogenous promoter sequence,
b) cultivating the infected cells of a) under suitable conditions,
c) harvesting infected cells of b) and/or vector and/or virus components,
d) optionally purifying the harvest of step c), and
e) admixing said harvest with a pharmaceutically acceptable carrier.

* * * * *

SEQUENCE LISTING

```
<160> NUMBER OF SEQ ID NOS: 37

<210> SEQ ID NO 1
<211> LENGTH: 600
<212> TYPE: DNA
<213> ORGANISM: Equine herpesvirus 4

<400> SEQUENCE: 1
gcagactttg gagcagcaca atttccggtt gtggaccccca tggaccttgg tttggctggt      60
accgtggaaa ctaacgctcc ggaagttttg gccagagcaa aatacaattc gaaggtagac     120
atatggagcg ccggaatagt tctgtttgaa atgctcgcat atccatcaac tctatttgag     180
gacccgccga gtacccccaca agagtatgta aaaagctgtc attctcaact actgagaata     240
atatcaaagc taaagataaa ccctgaggag tttccacggg aaccagagtc taggctcgtg     300
cgcggataca tcgaatacgc cagcctagag cgtaagccac atacgcgcta tccttgcttc     360
cagcgcgtga acctacacat tgacggggaa ttttttgatcc ataaaatgct agcgttcaat     420
gctgcgatgc gcccatccgc agaagagttg ttgtcctacc caatgtttat gaatctgtag     480
gatgactaac agatttgggg tggagacggc gtgggcgata ctgtataaag ttgtactact     540
taccagccca gtcagtgtgc tgtagtgcca ccacctgtaa agctgtgata agctgcagtt     600

<210> SEQ ID NO 2
<211> LENGTH: 600
<212> TYPE: DNA
<213> ORGANISM: Equine herpesvirus 4

<400> SEQUENCE: 2
agctggggga gtttgtacta tagtgtatta catgcggctt gcaataactg cctggtttat      60
gtttcgcaac attcaagcag acatgctacc gctaaacact ttgcaacaat ttttattgg      120 gtgtttggcc tttggtagaa ctgtcgcgtt tttggtggta gcatatacta ccttatttat     180
acgctccgag ctgtttttca gcatgctagc acccaacgcc gagcgagagt atataactcc     240
catcattgcc cacaagctta tgccacttat tagcgtccgc tctgccgttt gcttagtcat     300
aatatctacc gccgtttacg cagcagacgc tatctgcgac acaattggat ttgcgatacc     360
gcgcatgtgg atgtgtattt taatgagatc aacctccatg aagcgtaact aggggggcctc     420 ccactgaggc actaccggct tagcagctga ctaacacagt ataaaacgtg agaagaaatc     480
agtctcatgc gccattagcg ctaggctagt tagcgtggag gaccggagcg ctaccgccag     540
cagtttcatc cgcctggtta cgggtttgtt aacacctacc ggtgttttac cgctaccata     600
```

<210> SEQ ID NO 3
<211> LENGTH: 430
<212> TYPE: DNA
<213> ORGANISM: Equine herpesvirus 4

<400> SEQUENCE: 3

```
tctatttgag acccgccga gtacccaca agagtatgta aaaagctgtc attctcaact      60
actgagaata atatcaaagc taaagataaa ccctgaggag tttccacggg aaccagagtc    120
taggctcgtg cgcggataca tcgaatacgc cagcctagag cgtaagccac atacgcgcta   180
tccttgcttc cagcgcgtga acctacacat tgacggggaa ttttttgatcc ataaaatgct   240
agcgttcaat gctgcgatgc gcccatccgc agaagagttg ttgtcctacc caatgtttat   300
gaatctgtag gatgactaac agatttgggg tggagacggc gtgggcgata ctgtataaag   360
ttgtactact taccagccca gtcagtgtgc tgtagtgcca ccacctgtaa agctgtgata   420
agctgcagtt                                                           430
```

<210> SEQ ID NO 4
<211> LENGTH: 449
<212> TYPE: DNA
<213> ORGANISM: Equine herpesvirus 4

<400> SEQUENCE: 4

```
ttggtggtag catatactac cttatttata cgctccgagc tgttttcag catgctagca     60
cccaacgccg agcgagagta taaactccc atcattgccc acaagcttat gccacttatt    120
agcgtccgct ctgccgtttg cttagtcata atatctaccg ccgtttacgc agcagacgct   180
atctgcgaca caattggatt tgcgataccg cgcatgtgga tgtgtatttt aatgagatca   240
acctccatga agcgtaacta gggggcctcc cactgaggca ctaccggctt agcagctgac   300
taacacagta taaaacgtga aagaaatca gtctcatgcg ccattagcgc taggctagtt    360
agcgtggagg accggagcgc taccgccagc agtttcatcc gcctggttac gggtttgtta   420
acacctaccg gtgtttacc gctaccata                                       449
```

<210> SEQ ID NO 5
<211> LENGTH: 20
<212> TYPE: DNA
<213> ORGANISM: Artificial Sequence
<220> FEATURE:
<223> OTHER INFORMATION: primer no 1130 specific for orf72

<400> SEQUENCE: 5

```
tgtctacctt caagcttatg                                                20
```

<210> SEQ ID NO 6
<211> LENGTH: 17
<212> TYPE: DNA
<213> ORGANISM: Artificial Sequence
<220> FEATURE:
<223> OTHER INFORMATION: primer no 1131 specific for orf72

<400> SEQUENCE: 6

```
ctagcgcagt cgcgttg                                                   17
```

<210> SEQ ID NO 7
<211> LENGTH: 18
<212> TYPE: DNA
<213> ORGANISM: Artificial Sequence
<220> FEATURE:
<223> OTHER INFORMATION: primer no. 1079 specific for mCherry

<400> SEQUENCE: 7
gcgaggagga taacatgg                                                    18

<210> SEQ ID NO 8
<211> LENGTH: 18
<212> TYPE: DNA
<213> ORGANISM: Artificial Sequence
<220> FEATURE:
<223> OTHER INFORMATION: primer no. 1080 specific for mCherry

<400> SEQUENCE: 8
acccttggtc accttcag                                                    18

<210> SEQ ID NO 9
<211> LENGTH: 22
<212> TYPE: DNA
<213> ORGANISM: Artificial Sequence
<220> FEATURE:
<223> OTHER INFORMATION: Artificial sequence nucleic acid PCR primer
      1017 for the orf70 insertion region

<400> SEQUENCE: 9
aggctcgtgc gcggatacat cg                                               22

<210> SEQ ID NO 10
<211> LENGTH: 22
<212> TYPE: DNA
<213> ORGANISM: Artificial Sequence
<220> FEATURE:
<223> OTHER INFORMATION: Artificial sequence nucleic acid PCR primer
      1018 for the orf70 insertion region

<400> SEQUENCE: 10
ttcggggctg ttagactcct cc                                               22

<210> SEQ ID NO 11
<211> LENGTH: 22
<212> TYPE: DNA
<213> ORGANISM: Artificial Sequence
<220> FEATURE:
<223> OTHER INFORMATION: Artificial sequence nucleic acid PCR primer
      1007 for the orf1/3 insertion region

<400> SEQUENCE: 11
ccaactcgcc gccatgagac cc                                               22

<210> SEQ ID NO 12
<211> LENGTH: 22
<212> TYPE: DNA
<213> ORGANISM: Artificial Sequence
<220> FEATURE:
<223> OTHER INFORMATION: Artificial sequence nucleic acid PCR primer
      1008 for the orf1/3 insertion region

<400> SEQUENCE: 12
agcgcgcccc gtacccagtg gg                                               22

<210> SEQ ID NO 13
<211> LENGTH: 417
<212> TYPE: DNA
<213> ORGANISM: Equine herpesvirus 1

<400> SEQUENCE: 13
ctccgagtac cccagaggag tatgtgaaa

```
caacgctcaa gataaatccg gaggagtttc ctcgagaccc cgggtcgagg ctcgtgcgcg    120
gatacatcga gtattctaga ctcgagcgca agccctacac gcgctacccc tgctttcaac    180
gcgtcaacct gcacattgac ggggagtttc tggttcacaa gatgctagcg ttcaatgccg    240
cgatgcgccc atcggccgag gagctgctgt catacccaat gtttgctcaa ctttaggatg    300
actaacctgt ttctgggagg agacagcgtg ggcgacggtg tataaagttg gtctgctttc    360
aagccctgcc actgcgctac agtgccacca actgtaaagc ggtagtaagc tgcagtg      417
```

<210> SEQ ID NO 14
<211> LENGTH: 431
<212> TYPE: DNA
<213> ORGANISM: Equine herpesvirus 1

<400> SEQUENCE: 14

```
gaccctgttg gtgggtgcgg ttggactcag aatcttggcg caggcatgga agtttgtcgg    60
tgacgaaaca tacgcacacca tccgcgcaga agcaaagaat ttagagaccc acgtaccctc   120
aagtgctgca gagtcgtctc tagaaaacca atcgacacag gaggagtcta acagcccga    180 agttgcccac ctgcgaagcg tcaacagcga tgacagtaca cacacggggg gtgcgtcgaa   240
cggcatccag gactgtgaca gtcagctcaa aactgtgtat gcctgcttgg ctctaattgg   300
actcggcaca tgtgccatga tagggttgat agtttacatt tgtgtattaa ggtcaaaact   360
gtcctctcgg aattttttcgc gcgcgcaaaa tgtaaaacat agaaattacc agcgacttga   420
gtacgttgct t                                                         431
```

<210> SEQ ID NO 15
<211> LENGTH: 417
<212> TYPE: DNA
<213> ORGANISM: Equine herpesvirus 1

<400> SEQUENCE: 15

```
ctccgagtac cccaga

```
gtacgttgct t 431

<210> SEQ ID NO 17
<211> LENGTH: 283
<212> TYPE: DNA
<213> ORGANISM: Equine herpesvirus 1

<400> SEQUENCE: 17
tctagactcg agcgcaagcc ctacacgcgc tacccctgct ttcaacgcgt caacctgcac 60
attgacgggg agtttctggt tcacaagatg ctagcgttca atgccgcgat gcgcccatcg 120
gccgaggagc tgctgtcata cccaatgttt gctcaacttt aggatgacta acctgtttct 180
gggaggagac agcgtgggcg acggtgtata aagttggtct gctttcaagc cctgccactg 240
cgctacagtg ccaccaactg taaagcggta gtaagctgca gtg 283

<210> SEQ ID NO 18
<211> LENGTH: 144
<212> TYPE: DNA
<213> ORGANISM: Equine herpesvirus 1

<400> SEQUENCE: 18
gaccctgttg gtgggtgcgg ttggactcag aatcttggcg caggcatgga agtttgtcgg 60
tgacgaaaca tacgacacca tccgcgcaga agcaaagaat ttagagaccc acgtaccctc 120
aagtgctgca gagtcgtctc taga 144

<210> SEQ ID NO 19
<211> LENGTH: 801
<212> TYPE: DNA
<213> ORGANISM: Equine herpesvirus 1

<400> SEQUENCE: 19
atgttgactg tcttagcagc cctgagtctg ctcagcttgc ttacgagcgc aaccggacgg 60
ctcgccccag atgaactctg ttatgccgaa ccccgcagaa ctggcagccc accaaacacc 120
cagcccgaac gcccacccgt aatatttgag cccccaacaa ttgcgattaa agctgaatcc 180
aagggttgtg agctaatttt attagatcca cccatagatg taagctatcg cagagaagat 240
aaggtgaatg cgtccattgc ttggtttttt gactttggcg cttgccggat gcccatcgca 300
tacagagagt attacggttg tattggcaat gctgttccct ccccagagac ttgtgatgcg 360
tactcattta cccttattag gaccgagggt atcgtggagt ttaccatcgt aaacatgagc 420
ctcctgtttc agcctggaat atacgatagt ggcaatttta tctacagcgt tctcctggac 480
taccacatat ttacaggacg tgtaacgttg gaagtggaaa aggacacaaa ctatccctgt 540
ggcatgattc atggactcac tgcttacgga aacatcaacg tagatgaaac catggacaac 600
gccagcccac acccgcgtgc cgtggggtgc tttcccgagc ccatcgacaa cgaagcgtgg 660
gcaaacgtta catttactga attggggata ccagacccaa actcatttct cgatgacgag 720
ggtgattacc cgaatatatc agactgtcac tcgtgggagt catacaccta cccaaatacg 780
ctgaggcagg ccacaggacc c 801

<210> SEQ ID NO 20
<211> LENGTH: 801
<212> TYPE: DNA
<213> ORGANISM: Equine herpesvirus 1

<400> SEQUENCE: 20

|  |  |
|---|---|
| atgttgactg tcttagcagc tctgagtctg ctcagcttgc ttacgagcgc aaccggacgg | 60 |
| ctcgccccag atgaactctg ttatgccgaa ccccgcagaa ctggcagccc accaaacacc | 120 |
| cagcccgaac gcccacccgt aatatttgag cccccaacaa ttgcgattaa agctgaatcc | 180 |
| aagggttgtg agctaatttt attagatcca cccatagatg taagctatcg cagagaagat | 240 |
| aaggtgaatg cgtccattgc ttggtttttt gactttggcg cttgccggat gcccatcgca | 300 |
| tacagagagt attacggttg tattggcaat gctgttccct ccccagagac ttgtgatgcg | 360 |
| tactcattta cccttattag gaccgagggt atcgtggagt ttaccatcgt aaacatgagc | 420 |
| ctcctgtttc agcctggaat atacgatagt ggcaatttta tctacagcgt tctcctggac | 480 |
| taccacatat ttacaggacg tgtaacgttg gaagtggaaa aggacacaaa ctatccctgt | 540 |
| ggcatgattc atggactcac tgcttacgga aacatcaacg tagatgaaac catggacaac | 600 |
| gccagcccac acccgcgtgc cgtggggtgc tttcccgagc ccatcgacaa cgaagcgtgg | 660 |
| gcaaacgtta catttactga attggggata ccagacccaa actcatttct cgatgacgag | 720 |
| ggtgattacc cgaatatatc agactgtcac tcgtgggagt catacaccta cccaaatacg | 780 |
| ctgaggcagg ccacaggacc c | 801 |

<210> SEQ ID NO 21
<211> LENGTH: 4435
<212> TYPE: DNA
<213> ORGANISM: Artificial Sequence
<220> FEATURE:
<223> OTHER INFORMATION: Nucleotide sequence of transfer plasmid pU-mC70-BGH

<400> SEQUENCE: 21

|  |  |
|---|---|
| tcgcgcgttt cggtgatgac ggtgaaaacc tctgacacat gcagctcccg gagacggtca | 60 |
| cagcttgtct gtaagcggat gccggagcca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cctccgagta ccccagagga | 420 |
| gtatgtgaaa agctgccact cgcaactact gaagataatt caacgctca agataaatcc | 480 |
| ggaggagttt cctcgagacc ccgggtcgag gctcgtgcgc ggatacatcg agtattctag | 540 |
| actcgagcgc aagccctaca cgcgctaccc ctgctttcaa cgcgtcaacc tgcacattga | 600 |
| cggggagttt ctggttcaca agatgctagc gttcaatgcc gcgatgcgcc catcggccga | 660 |
| ggagctgctg tcatacccaa tgtttgctca actttaggat gactaacctg tttctgggag | 720 |
| gagacagcgt gggcgacggt gtataaagtt ggtctgcttt caagccctgc cactgcgcta | 780 |
| cagtgccacc aactgtaaag cggtagtaag ctgcagtggt cgacatggtg agcaagggcg | 840 |
| aggaggataa catggccatc atcaaggagt tcatgcgctt caaggtgcac atggagggct | 900 |
| ccgtgaacgg ccacgagttc gagatcgagg gcgagggcga gggccgcccc tacgagggca | 960 |
| cccagaccgc caagctgaag gtgaccaagg gtggccccct gcccttcgcc tgggacatcc | 1020 |
| tgtcccctca gttcatgtac ggctccaagg cctacgtgaa gcaccccgcc gacatccccg | 1080 |
| actacttgaa gctgtccttc cccgagggct tcaagtggga gcgcgtgatg aacttcgagg | 1140 |
| acggcggcgt ggtgaccgtg acccaggact cctcccctgca ggacggcgag ttcatctaca | 1200 |

```
aggtgaagct gcgcggcacc aacttcccct ccgacggccc cgtaatgcag aagaagacca    1260
tgggctggga ggcctcctcc gagcggatgt accccgagga cggcgccctg aagggcgaga    1320
tcaagcagag gctgaagctg aaggacggcg ccactacga cgctgaggtc aagaccacct    1380
acaaggccaa gaagcccgtg cagctgcccg gcgcctacaa cgtcaacatc aagttggaca    1440
tcacctccca caacgaggac tacaccatcg tggaacagta cgaacgcgcc gagggccgcc    1500
actccaccgg cggcatggac gagctgtaca agtaactgtg ccttctagtt gccagccatc    1560
tgttgtttgc ccctcccccg tgccttcctt gaccctggaa ggtgccactc ccactgtcct    1620
ttcctaataa aatgaggaaa ttgcatcgca ttgtctgagt aggtgtcatt ctattctggg    1680
gggtggggtg gggcaggaca gcaaggggga ggattgggaa gacaatagca ggcatgctgg    1740
ggatgcggtg ggctctatgg atccgaccct gttggtgggt gcggttggac tcagaatctt    1800
ggcgcaggca tggaagtttg tcggtgacga acatacgac accatccgcg cagaagcaaa    1860
gaatttagag acccacgtac cctcaagtgc tgcagagtcg tctctagaaa accaatcgac    1920
acaggaggag tctaacagcc ccgaagttgc ccacctgcga agcgtcaaca gcgatgacag    1980
tacacacacg gggggtgcgt cgaacggcat ccaggactgt gacagtcagc tcaaaactgt    2040
gtatgcctgc ttggctctaa ttggactcgg cacatgtgcc atgatagggt tgatagttta    2100
catttgtgta ttaaggtcaa aactgtcctc tcggaattttt tcgcgcgcgc aaaatgtaaa    2160
acatagaaat taccagcgac ttgagtacgt tgcttaagct tggcgtaatc atggtcatag    2220
ctgtttcctg tgtgaaattg ttatccgctc acaattccac acaacatacg agccggaagc    2280
ataaagtgta aagcctgggg tgcctaatga gtgagctaac tcacattaat tgcgttgcgc    2340
tcactgcccg ctttccagtc gggaaacctg tcgtgccagc tgcattaatg aatcggccaa    2400
cgcgcgggga gaggcggttt gcgtattggg cgctcttccg cttcctcgct cactgactcg    2460
ctgcgctcgg tcgttcggct gcggcgagcg gtatcagctc actcaaaggc ggtaatacgg    2520
ttatccacag aatcagggga taacgcagga aagaacatgt gagcaaaagg ccagcaaaag    2580
gccaggaacc gtaaaaaggc cgcgttgctg gcgtttttcc ataggctccg ccccccctgac   2640 gagcatcaca aaaatcgacg ctcaagtcag aggtggcgaa acccgacagg actataaaga    2700
taccaggcgt ttccccctgg aagctccctc gtgcgctctc ctgttccgac cctgccgctt    2760
accggatacc tgtccgcctt tctcccttcg ggaagcgtgg cgctttctca tagctcacgc    2820
tgtaggtatc tcagttcggt gtaggtcgtt cgctccaagc tgggctgtgt gcacgaaccc    2880
cccgttcagc ccgaccgctg cgccttatcc ggtaactatc gtcttgagtc aacccggta    2940 agacacgact tatcgccact ggcagcagcc actggtaaca ggattagcag agcgaggtat    3000
gtaggcggtg ctacagagtt cttgaagtgg tggcctaact acggctacac tagaaggaca    3060
gtatttggta tctgcgctct gctgaagcca gttaccttcg aaaaagagt tggtagctct    3120 tgatccggca acaaaccac cgctggtagc ggtggttttt tgtttgcaa gcagcagatt    3180 acgcgcagaa aaaaggatc tcaagaagat cctttgatct tttctacggg gtctgacgct    3240
cagtggaacg aaaactcacg ttaagggatt ttggtcatga gattatcaaa aaggatcttc    3300
acctagatcc ttttaaatta aaatgaagt tttaaatcaa tctaaagtat atatgagtaa    3360
acttggtctg acagttacca atgcttaatc agtgaggcac ctatctcagc gatctgtcta    3420
tttcgttcat ccatagttgc ctgactcccc gtcgtgtaga taactacgat acgggagggc    3480
ttaccatctg gccccagtgc tgcaatgata ccgcgagacc cacgctcacc ggctccagat    3540
ttatcagcaa taaaccagcc agccggaagg gccgagcgca gaagtggtcc tgcaacttta    3600
```

```
tccgcctcca tccagtctat taattgttgc cgggaagcta gagtaagtag ttcgccagtt    3660
aatagtttgc gcaacgttgt tgccattgct acaggcatcg tggtgtcacg ctcgtcgttt    3720
ggtatggctt cattcagctc cggttcccaa cgatcaaggc gagttacatg atcccccatg    3780
ttgtgcaaaa aagcggttag ctccttcggt cctccgatcg ttgtcagaag taagttggcc    3840
gcagtgttat cactcatggt tatggcagca ctgcataatt ctcttactgt catgccatcc    3900
gtaagatgct tttctgtgac tggtgagtac tcaaccaagt cattctgaga atagtgtatg    3960
cggcgaccga gttgctcttg cccggcgtca atacgggata taccgcgcc acatagcaga     4020 actttaaaag tgctcatcat tggaaaacgt tcttcgggc gaaaactctc aaggatctta     4080
ccgctgttga gatccagttc gatgtaaccc actcgtgcac ccaactgatc ttcagcatct    4140
tttactttca ccagcgtttc tgggtgagca aaaacaggaa ggcaaaatgc cgcaaaaaag    4200
ggaataaggg cgacacggaa atgttgaata ctcatactct tccttttca atattattga     4260 agcatttatc agggttattg tctcatgagc ggatacatat ttgaatgtat ttagaaaaat    4320
aaacaaatag gggttccgcg cacatttccc cgaaaagtgc cacctgacgt ctaagaaacc    4380
attattatca tgacattaac ctataaaaat aggcgtatca cgaggccctt tcgtc         4435
```

<210> SEQ ID NO 22
<211> LENGTH: 5191
<212> TYPE: DNA
<213> ORGANISM: Artificial Sequence
<220> FEATURE:
<223> OTHER INFORMATION: Nucleotide sequence of transfer vector
      pU70-p455-71K71

<400> SEQUENCE: 22

```
caataaacgc ggtatgtcta ccttcaagcc tatgatgaac ggatgtttgg tgtttgcggc      60
tattataacg ctcttgagtt ttatgctatc tctgggaaca tgcgaaaatt acaggcgtgt     120
ggttcgggat cctagggata acagggtaat cgatttattc aacaaagcca cgttgtgtct    180
caaaatctct gatgttacat tgcacaagat aaaaatatat catcatgaac aataaaactg    240
tctgcttaca taaacagtaa tacaagggggt gttatgagcc atattcaacg ggaaacgtct    300
tgctcgaggc cgcgattaaa ttccaacatg gatgctgatt tatatgggta taaatgggct    360
cgcgataatg tcgggcaatc aggtgcgaca atctatcgat tgtatgggaa gcccgatgcg    420
ccagagttgt ttctgaaaca tggcaaaggt agcgttgcca atgatgttac agatgagatg    480
gtcagactaa actggctgac ggaatttatg cctcttccga ccatcaagca ttttatccgt    540
actcctgatg atgcatggtt actcaccact gcgatccccg gaaaacagc attccaggta     600 ttagaagaat atcctgattc aggtgaaaat attgttgatg cgctggcagt gttcctgcgc    660
cggttgcatt cgattcctgt ttgtaattgt ccttttaaca gcgatcgcgt atttcgtctc    720
gctcaggcgc aatcacgaat gaataacggt ttggttgatg cgagtgattt tgatgacgag    780
cgtaatggct ggcctgttga acaagtctgg aaagaaatgc ataagctttt gccattctca    840
ccggattcag tcgtcactca tggtgatttc tcacttgata accttatttt tgacgagggg    900
aaattaatag gttgtattga tgttggacga gtcggaatcg cagaccgata ccaggatctt    960
gccatcctat ggaactgcct cggtgagttt tctccttcat tacagaaacg ctttttcaa    1020 aaatatggta ttgataatcc tgatatgaat aaattgcagt ttcatttgat gctcgatgag    1080
tttttctaaa ataaacgcgg tatgtctacc ttcaagccta tgatgaacgg atgtttggtg    1140
tttgcggcta ttataacgct cttgagtttt atgctatctc tgggaacatg cgaaaattac    1200
```

```
aggcgtgtgg ttcgggatcc gaccctgttg gtgggtgcgg ttggactcag aatcttggcg    1260
caggcatgga agtttgtcgg tgacgaaaca tacgacacca tccgcgcaga agcaaagaat    1320
ttagagaccc acgtaccctc aagtgctgca gagtcgtctc tagaaaacca atcgacacag    1380
gaggagtcta acagcccga agttgccac ctgcgaagcg tcaacagcga tgacagtaca    1440 cacacgggg gtgcgtcgaa cggcatccag gactgtgaca gtcagctcaa aactgtgtat    1500
gcctgcttgg ctctaattgg actcggcaca tgtgccatga tagggttgat agtttacatt    1560
tgtgtattaa ggtcaaaact gtcctctcgg aattttcgc gcgcgcaaaa tgtaaaacat    1620
agaaattacc agcgacttga gtacgttgct taagcttggc gtaatcatgg tcatagctgt    1680
ttcctgtgtg aaattgttat ccgctcacaa ttccacacaa catacgagcc ggaagcataa    1740
agtgtaaagc ctggggtgcc taatgagtga gctaactcac attaattgcg ttgcgctcac    1800
tgcccgcttt ccagtcggga aacctgtcgt gccagctgca ttaatgaatc ggccaacgcg    1860
cggggagagg cggtttgcgt attgggcgct cttccgcttc ctcgctcact gactcgctgc    1920
gctcggtcgt tcggctgcgg cgagcggtat cagctcactc aaaggcggta atacggttat    1980
ccacagaatc aggggataac gcaggaaaga acatgtgagc aaaaggccag caaaaggcca    2040
ggaaccgtaa aaaggccgcg ttgctggcgt ttttccatag gctccgcccc cctgacgagc    2100
atcacaaaaa tcgacgctca agtcagaggt ggcgaaaccc gacaggacta taaagatacc    2160
aggcgtttcc ccctggaagc tccctcgtgc gctctcctgt tccgaccctg ccgcttaccg    2220
gatacctgtc cgcctttctc ccttcgggaa gcgtggcgct ttctcatagc tcacgctgta    2280
ggtatctcag ttcggtgtag tcgttcgct ccaagctggg ctgtgtgcac gaacccccg    2340 ttcagcccga ccgctgcgcc ttatccggta actatcgtct tgagtccaac ccggtaagac    2400
acgacttatc gccactggca gcagccactg gtaacaggat tagcagagcg aggtatgtag    2460
gcggtgctac agagttcttg aagtggtggc ctaactacgg ctacactaga aggacagtat    2520
ttggtatctg cgctctgctg aagccagtta ccttcggaaa aagagttggt agctcttgat    2580
ccggcaaaca aaccaccgct ggtagcggtg gttttttgt ttgcaagcag cagattacgc    2640
gcagaaaaaa aggatctcaa gaagatcctt tgatctttc tacggggtct gacgctcagt    2700
ggaacgaaaa ctcacgttaa gggattttgg tcatgagatt atcaaaaagg atcttcacct    2760
agatcctttt aaattaaaaa tgaagtttta atcaatcta agtatatat gagtaaactt    2820 ggtctgacag ttaccaatgc ttaatcagtg aggcacctat ctcagcgatc tgtctatttc    2880
gttcatccat agttgcctga ctccccgtcg tgtagataac tacgatacgg gagggcttac    2940
catctggccc cagtgctgca atgataccgc gagacccacg ctcaccggct ccagatttat    3000
cagcaataaa ccagccagcc ggaagggccg agcgcagaag tggtcctgca actttatccg    3060
cctccatcca gtctattaat tgttgccggg aagctagagt aagtagttcg ccagttaata    3120
gtttgcgcaa cgttgttgcc attgctacag gcatcgtggt gtcacgctcg tcgtttggta    3180
tggcttcatt cagctccggt tcccaacgat caaggcgagt tacatgatcc cccatgttgt    3240
gcaaaaaagc ggttagctcc ttcggtcctc cgatcgttgt cagaagtaag ttggccgcag    3300
tgttatcact catggttatg gcagcactgc ataattctct tactgtcatg ccatccgtaa    3360
gatgcttttc tgtgactggt gagtactcaa ccaagtcatt ctgagaatag tgtatgcggc    3420
gaccgagttg ctcttgcccg gcgtcaatac gggataatac cgcgccacat agcagaactt    3480
taaaagtgct catcattgga aaacgttctt cggggcgaaa actctcaagg atcttaccgc    3540
```

```
tgttgagatc cagttcgatg taacccactc gtgcacccaa ctgatcttca gcatctttta      3600
ctttcaccag cgtttctggg tgagcaaaaa caggaaggca aaatgccgca aaaaagggaa      3660
taagggcgac acggaaatgt tgaatactca tactcttcct ttttcaatat tattgaagca      3720
tttatcaggg ttattgtctc atgagcggat acatatttga atgtatttag aaaaataaac      3780 aaatagggt tccgcgcaca tttccccgaa aagtgccacc tgacgtctaa gaaaccatta      3840
ttatcatgac attaacctat aaaaataggc gtatcacgag gccctttcgt ctcgcgcgtt      3900
tcggtgatga cggtgaaaac ctctgacaca tgcagctccc ggagacggtc acagcttgtc      3960
tgtaagcgga tgccgggagc agacaagccc gtcagggcgc gtcagcgggt gttggcgggt      4020
gtcggggctg gcttaactat gcggcatcag agcagattgt actgagagtg caccatatgc      4080
ggtgtgaaat accgcacaga tgcgtaagga gaaaataccg catcaggcgc cattcgccat      4140
tcaggctgcg caactgttgg aagggcgat cggtgcgggc ctcttcgcta ttacgccagc      4200
tggcgaaagg gggatgtgct gcaaggcgat taagttgggt aacgccaggg ttttcccagt      4260
cacgacgttg taaaacgacg gccagtgaat tcctccgagt accccagagg agtatgtgaa      4320
aagctgccac tcgcaactac tgaagataat ttcaacgctc aagataaatc cggaggagtt      4380
tcctcgagac cccgggtcga ggctcgtgcg cggatacatc gagtattcta gactcgagcg      4440
caagccctac acgcgctacc cctgctttca acgcgtcaac ctgcacattg acgggagtt      4500 tctggttcac aagatgctag cgttcaatgc cgcgatgcgc ccatcggccg aggagctgct      4560 gtcatacccca atgtttgctc aactttagga tgactaacct gtttctggga ggagacagcg      4620
tgggcgacgg tgtataaagt tggtctgctt tcaagccctg ccactgcgct acagtgccac      4680
caactgtaaa gcggtagtaa gctgcagtgg tcgactggtg gtagcatata ctaccttatt      4740
tatacgctcc gagctgtttt tcagcatgct agcacccaac gccgagcgag agtatataac      4800
tcccatcatt gcccacaagc ttatgccact tattagcgtc cgctctgccg tttgcttagt      4860
cataatatct accgccgttt acgcagcaga cgctatctgc gacacaattg gatttgcgat      4920
accgcgcatg tggatgtgta ttttaatgag atcaacctcc atgaagcgta actaggggc      4980 ctcccactga gcactaccg gcttagcagc tgactaacac agtataaaac gtgagaagaa      5040
atcagtctca tgcgccatta gcgctaggct agttagcgtg gaggaccgga gcgctaccgc      5100
cagcagtttc atccgcctgg ttacgggttt gttaacacct accggtgttt taccgctacc      5160
ataggatccg atccatgggc ggccgcggta c                                    5191
```

<210> SEQ ID NO 23
<211> LENGTH: 6892
<212> TYPE: DNA
<213> ORGANISM: Artificial Sequence
<220> FEATURE:
<223> OTHER INFORMATION: Nucleotide sequence of transfer plasmid
      pU70-p455-H3-71K71

<400> SEQUENCE: 23

```
caataaacgc ggtatgtcta ccttcaagcc tatgatgaac ggatgtttgg tgtttgcggc        60
tattataacg ctcttgagtt ttatgctatc tctgggaaca tgcgaaaatt acaggcgtgt       120
ggttcgggat cctagggata acagggtaat cgatttattc aacaaagcca cgttgtgtct       180
caaaatctct gatgttacat tgcacaagat aaaaatatat catcatgaac aataaaactg       240
tctgcttaca taaacagtaa tacaaggggg gttatgagcc atattcaacg ggaaacgtct       300
tgctcgaggc cgcgattaaa ttccaacatg gatgctgatt tatatgggta taaatgggct       360
```

```
cgcgataatg tcgggcaatc aggtgcgaca atctatcgat tgtatgggaa gcccgatgcg      420
ccagagttgt ttctgaaaca tggcaaaggt agcgttgcca atgatgttac agatgagatg      480
gtcagactaa actggctgac ggaatttatg cctcttccga ccatcaagca tttttatccgt     540 actcctgatg atgcatggtt actcaccact gcgatccccg ggaaaacagc attccaggta      600
ttagaagaat atcctgattc aggtgaaaat attgttgatg cgctggcagt gttcctgcgc      660
cggttgcatt cgattcctgt ttgtaattgt ccttttaaca gcgatcgcgt atttcgtctc      720
gctcaggcgc aatcacgaat gaataacggt ttggttgatg cgagtgattt tgatgacgag      780
cgtaatggct ggcctgttga acaagtctgg aaagaaatgc ataagctttt gccattctca      840
ccggattcag tcgtcactca tggtgatttc tcacttgata accttatttt tgacgagggg      900
aaattaatag ttgtattga tgttggacga gtcggaatcg cagaccgata ccaggatctt       960
gccatcctat ggaactgcct cggtgagttt tctccttcat tacagaaacg gcttttttcaa    1020 aaatatggta ttgataatcc tgatatgaat aaattgcagt ttcatttgat gctcgatgag    1080 ttttttctaaa ataaacgcgg tatgtctacc ttcaagccta tgatgaacgg atgtttggtg   1140
tttgcggcta ttataacgct cttgagtttt atgctatctc tgggaacatg cgaaaattac    1200
aggcgtgtgg ttcgggatcc gaccctgttg gtgggtgcgg ttggactcag aatcttggcg    1260
caggcatgga agtttgtcgg tgacgaaaca tacgacacca tccgcgcaga agcaaagaat    1320
ttagagaccc acgtaccctc aagtgctgca gagtcgtctc tagaaaacca atcgacacag    1380
gaggagtcta acagccccga agttgcccac ctgcgaagcg tcaacagcga tgacagtaca    1440 cacacgggg gtgcgtcgaa cggcatccag gactgtgaca gtcagctcaa aactgtgtat     1500
gcctgcttgg ctctaattgg actcggcaca tgtgccatga tagggttgat agtttacatt    1560
tgtgtattaa ggtcaaaact gtcctctcgg aattttttcgc gcgcgcaaaa tgtaaaacat   1620
agaaattacc agcgacttga gtacgttgct taagcttggc gtaatcatgg tcatagctgt    1680
ttcctgtgtg aaattgttat ccgctcacaa ttccacacaa catacgagcc ggaagcataa    1740
agtgtaaagc ctggggtgcc taatgagtga gctaactcac attaattgcg ttgcgctcac    1800
tgcccgcttt ccagtcggga aacctgtcgt gccagctgca ttaatgaatc ggccaacgcg    1860
cggggagagg cggtttgcgt attgggcgct cttccgcttc ctcgctcact gactcgctgc    1920
gctcggtcgt tcggctgcgg cgagcggtat cagctcactc aaaggcggta atacggttat    1980
ccacagaatc aggggataac gcaggaaaga acatgtgagc aaaaggccag caaaaggcca    2040
ggaaccgtaa aaaggccgcg ttgctggcgt ttttccatag gctccgcccc cctgacgagc    2100
atcacaaaaa tcgacgctca agtcagaggt ggcgaaaccc gacaggacta taaagatacc    2160
aggcgtttcc ccctggaagc tccctcgtgc gctctcctgt tccgaccctg ccgcttaccg    2220
gatacctgtc cgcctttctc ccttcgggaa gcgtggcgct ttctcatagc tcacgctgta    2280
ggtatctcag ttcggtgtag tcgttcgct ccaagctggg ctgtgtgcac gaaccccccg     2340
ttcagcccga ccgctgcgcc ttatccggta actatcgtct tgagtccaac ccggtaagac    2400
acgacttatc gccactggca gcagccactg gtaacaggat tagcagagcg aggtatgtag    2460
gcggtgctac agagttcttg aagtggtggc ctaactacgg ctacactaga aggacagtat    2520
ttggtatctg cgctctgctg aagccagtta ccttcggaaa aagagttggt agctcttgat    2580
ccggcaaaca aaccaccgct ggtagcggtg gtttttttgt ttgcaagcag cagattacgc    2640
gcagaaaaaa aggatctcaa gaagatcctt tgatcttttc tacggggtct gacgctcagt    2700
ggaacgaaaa ctcacgttaa gggattttgg tcatgagatt atcaaaaagg atcttcacct    2760
```

```
agatcctttt aaattaaaaa tgaagtttta aatcaatcta aagtatatat gagtaaactt    2820
ggtctgacag ttaccaatgc ttaatcagtg aggcacctat ctcagcgatc tgtctatttc    2880
gttcatccat agttgcctga ctccccgtcg tgtagataac tacgatacgg gagggcttac    2940
catctggccc cagtgctgca atgataccgc gagacccacg ctcaccggct ccagatttat    3000
cagcaataaa ccagccagcc ggaagggccg agcgcagaag tggtcctgca actttatccg    3060
cctccatcca gtctattaat tgttgccggg aagctagagt aagtagttcg ccagttaata    3120
gtttgcgcaa cgttgttgcc attgctacag gcatcgtggt gtcacgctcg tcgtttggta    3180
tggcttcatt cagctccggt tcccaacgat caaggcgagt tacatgatcc cccatgttgt    3240
gcaaaaaagc ggttagctcc ttcggtcctc cgatcgttgt cagaagtaag ttggccgcag    3300
tgttatcact catggttatg gcagcactgc ataattctct tactgtcatg ccatccgtaa    3360
gatgcttttc tgtgactggt gagtactcaa ccaagtcatt ctgagaatag tgtatgcggc    3420
gaccgagttg ctcttgcccg gcgtcaatac gggataatac cgcgccacat agcagaactt    3480
taaaagtgct catcattgga aaacgttctt cggggcgaaa actctcaagg atcttaccgc    3540
tgttgagatc cagttcgatg taacccactc gtgcacccaa ctgatcttca gcatctttta    3600
ctttcaccag cgtttctggg tgagcaaaaa caggaaggca aaatgccgca aaaaagggaa    3660
taagggcgac acggaaatgt tgaatactca tactcttcct ttttcaatat tattgaagca    3720
tttatcaggg ttattgtctc atgagcggat acatatttga atgtatttag aaaaataaac    3780
aaataggggt tccgcgcaca tttccccgaa aagtgccacc tgacgtctaa gaaaccatta    3840
ttatcatgac attaacctat aaaaataggc gtatcacgag gccctttcgt ctcgcgcgtt    3900
tcggtgatga cggtgaaaac ctctgacaca tgcagctccc ggagacggtc acagcttgtc    3960
tgtaagcgga tgccgggagc agacaagccc gtcagggcgc gtcagcgggt gttggcgggt    4020 gtcgggctg gcttaactat gcggcatcag agcagattgt actgagagtg caccatatgc    4080
ggtgtgaaat accgcacaga tgcgtaagga gaaaataccg catcaggcgc cattcgccat    4140
tcaggctgcg caactgttgg gaagggcgat cggtgcgggc ctcttcgcta ttacgccagc    4200
tggcgaaagg gggatgtgct gcaaggcgat taagttgggt aacgccaggg ttttcccagt    4260
cacgacgttg taaaacgacg gccagtgaat tcctccgagt accccagagg agtatgtgaa    4320
aagctgccac tcgcaactac tgaagataat ttcaacgctc aagataaatc cggaggagtt    4380
tcctcgagac cccgggtcga ggctcgtgcg cggatacatc gagtattcta gactcgagcg    4440
caagccctac acgcgctacc cctgctttca acgcgtcaac ctgcacattg acgggagtt    4500 tctggttcac aagatgctag cgttcaatgc cgcgatcgcg ccatcggccg aggagctgct    4560 gtcatacccca atgtttgctc aactttagga tgactaacct gtttctggga ggagacagcg    4620
tgggcgacgg tgtataaagt tggtctgctt tcaagccctg ccactgcgct acagtgccac    4680
caactgtaaa gcggtagtaa gctgcagtgg tcgactggtg gtagcatata ctaccttatt    4740
tatacgctcc gagctgtttt tcagcatgct agcacccaac gccgagcgag agtatataac    4800
tcccatcatt gcccacaagc ttatgccact tattagcgtc cgctctgccg tttgcttagt    4860
cataatatct accgccgttt acgcagcaga cgctatctgc gacacaattg gatttgcgat    4920
accgcgcatg tggatgtgta ttttaatgag atcaacctcc atgaagcgta actaggggc    4980 ctcccactga ggcactaccg gcttagcagc tgactaacac agtataaaac gtgagaagaa    5040
atcagtctca tgcgccatta gcgctaggct agttagcgtg gaggaccgga gcgctaccgc    5100
```

| | |
|---|---:|
| cagcagtttc atccgcctgg ttacgggttt gttaacacct accggtgttt taccgctacc | 5160 |
| ataggatccg atccatgggc ggccgcatga agaccgtgat cgccctgagt tacatcttct | 5220 |
| gcctggtgtt tgggcaggac ctccctggta aaggcaacaa cacggccacg ctgtgccttg | 5280 |
| ggcaccacgc cgtgccgaac ggcacccttg tgaaaactat taccgacgat cagatcgagg | 5340 |
| tgaccaacgc caccgaactg gttcagaatt ttagcatggg caaaatttgc aataacccgc | 5400 |
| accgcattct ggacggggcc aactgcacgc tgatcgattc attgctgggt gatccccact | 5460 |
| gcgatggctt tcaaaacgaa agtgggact tgttcatcga acgcagcaag gcattcagca | 5520 |
| actgctaccc atacgacgtg cccgaataca ccagcctgcg aagcctgatc gcgagctctg | 5580 |
| ggaccctgga gttcaccaat gagaacttca attggaccgg agtgacccaa aacggtggct | 5640 |
| ccagcgcctg taaaggggga cccaataaca gcttctttag caagttgaat tggctttaca | 5700 |
| agagcggcaa tacttacccg atgttgaatg tgaccatgcc caacagtgac gactttgata | 5760 |
| aactgtacat atggggcgtg caccatccca gcacggaccg cgaacagata aacctgtacg | 5820 |
| tgcaggccag cggaagata atcgtgagca ccaagcgcag ccagcagacc atcattccca | 5880 |
| acattggcag ccgaccgtgg gtgcgcggtc tgagctcccg catcagcata tactggacca | 5940 |
| ttgtcaagcc gggagacatc ctgatcatca actctaatgg caatcttatc gccccacgcg | 6000 |
| gctacttcaa gatgcagacc ggcaaaagca gtgtgatgag gagcgacgcc cccatcgaca | 6060 |
| cctgcaatag cgaatgcatc accccaatg gcagcatccc caacgacaag cctttccaga | 6120 |
| acgtgaataa gatcacctac ggcgcgtgcc ccaagtacat caagcagaac accctgaagc | 6180 |
| tggccaccgg catgcgcaac atccccgagc gacagacacg gggcattttt ggcgcaatcg | 6240 |
| cagggttcat tgagaatggc tgggagggaa tggttaacgg ctggtacggc ttccgccatc | 6300 |
| agaactctga aggaatcggc caagctgcgg atctgaagtc cacgcaagca gccatcaacc | 6360 |
| agatcaacgg caagcttaac cgcgtgattg aaaagacgaa cgagaaattc caccaaatag | 6420 |
| agaaagaatt cagcgaggtg gagggccgca tccaagacct cgagcgctac gtggaggaca | 6480 |
| ccaagatcga cctgtggagc tacaatgccg agctcctggt cgccttggaa aaccaacaca | 6540 |
| ccattgacct gaccgacagc gagatgaata aactcttcga gaagacccgg aagcaactcc | 6600 |
| gagagaacgc cgaagacatg ggtaatgggt gttttaagat ctaccacaag tgcgacaata | 6660 |
| gctgcatgga gagcatccga aacggaacct acgaccacaa cgtaccgc gatgaggcag | 6720 |
| ttaataaccg cttccaaatc aaaagcgtgg aactgaagag tggctataag gactggatac | 6780 |
| tgtggatcag ctttgccata agctgcttcc tgctgtgcgc cgtttggttg ggtttcatca | 6840 |
| tgtgggcctg tcaaaagggc aatattcgct gtaacatctg catttgaggt ac | 6892 |

<210> SEQ ID NO 24
<211> LENGTH: 4977
<212> TYPE: DNA
<213> ORGANISM: Artificial Sequence
<220> FEATURE:
<223> OTHER INFORMATION: Nucleotide sequence of transfer vector
      pU-1-3-p430-BGHKBGH

<400> SEQUENCE: 24

| | |
|---|---:|
| cctgtgcctt ctagttgcca gccatctgtt gtttgcccct cccccgtgcc ttccttgacc | 60 |
| ctggaaggtg ccactcccac tgtccttttc ctaataaatg aggaaattgc atcgcattgt | 120 |
| ctgagtaggt gtcattctat tctggggggt ggggtgggc aggacagcaa ggggaggat | 180 |
| tgggaagaca atagcaggca tgctggggat gcggtgggct ctatggatcc tagggataac | 240 |

```
agggtaatcg atttattcaa caaagccacg ttgtgtctca aaatctctga tgttacattg      300
cacaagataa aaatatatca tcatgaacaa taaaactgtc tgcttacata aacagtaata      360 caagggtgt tatgagccat attcaacggg aaacgtcttg ctcgaggccg cgattaaatt       420
ccaacatgga tgctgattta tatgggtata aatgggctcg cgataatgtc gggcaatcag      480
gtgcgacaat ctatcgattg tatgggaagc ccgatgcgcc agagttgttt ctgaaacatg      540
gcaaaggtag cgttgccaat gatgttacag atgagatggt cagactaaac tggctgacgg      600
aatttatgcc tcttccgacc atcaagcatt ttatccgtac tcctgatgat gcatggttac      660
tcaccactgc gatccccggg aaaacagcat tccaggtatt agaagaatat cctgattcag      720
gtgaaaatat tgttgatgcg ctggcagtgt tcctgcgccg gttgcattcg attcctgttt      780
gtaattgtcc ttttaacagc gatcgcgtat ttcgtctcgc tcaggcgcaa tcacgaatga      840
ataacggttt ggttgatgcg agtgattttg atgacgagcg taatggctgg cctgttgaac      900
aagtctggaa agaaatgcat aagcttttgc cattctcacc ggattcagtc gtcactcatg      960
gtgatttctc acttgataac cttatttttg acgaggggaa attaataggt tgtattgatg     1020
ttggacgagt cggaatcgca gaccgatacc aggatcttgc catcctatgg aactgcctcg     1080
gtgagttttc tccttcatta cagaaacggc tttttcaaaa atatggtatt gataatcctg     1140
atatgaataa attgcagttt catttgatgc tcgatgagtt tttctaacca tggctgtgcc     1200
ttctagttgc cagccatctg ttgtttgccc ctcccccgtg ccttccttga ccctggaagg     1260
tgccactccc actgtccttt cctaataaaa tgaggaaatt gcatcgcatt gtctgagtag     1320
gtgtcattct attctggggg gtggggtggg gcaggacagc aaggggagg attgggaaga      1380 caatagcagg catgctgggg atgcggtggg ctctatggat ccgaccctcc ccggggctaa     1440
aaagctgcgt cttcacgccc gaggcgctta ttgcccactg gtacggggc gcgcttttat      1500 atgtgtaacg tcccaccggt gtgacgcacg tactacggtt gttctaaata gctgtccccg     1560
tgattgcctc ggctgcacac atcgcctagg tttccgccgt gcctggtgtc gagggcccac     1620
ccctgtaacc aacatcgatg ggggcctgct gctccttcgc taccttagga ccgttatagt     1680
tacgtcaagc ttggcgtaat catggtcata gctgtttcct gtgtgaaatt gttatccgct     1740
cacaattcca cacaacatac gagccggaag cataaagtgt aaagcctggg gtgcctaatg     1800
agtgagctaa ctcacattaa ttgcgttgcg ctcactgccc gctttccagt cgggaaacct     1860
gtcgtgccag ctgcattaat gaatcggcca acgcgcgggg agaggcggtt tgcgtattgg     1920
gcgctcttcc gcttcctcgc tcactgactc gctgcgctcg tcgttcggc tgcggcgagc      1980 ggtatcagct cactcaaagg cggtaatacg gttatccaca gaatcagggg ataacgcagg     2040
aaagaacatg tgagcaaaag gccagcaaaa ggccaggaac cgtaaaaagg ccgcgttgct     2100
ggcgtttttc cataggctcc gccccctga cgagcatcac aaaaatcgac gctcaagtca      2160
gaggtggcga aacccgacag gactataaag ataccaggcg tttccccctg gaagctccct     2220
cgtgcgctct cctgttccga ccctgccgct taccggatac ctgtccgcct ttctcccttc     2280
gggaagcgtg gcgctttctc atagctcacg ctgtaggtat ctcagttcgg tgtaggtcgt     2340
tcgctccaag ctgggctgtg tgcacgaacc ccccgttcag cccgaccgct gcgccttatc     2400
cggtaactat cgtcttgagt ccaacccggt aagacacgac ttatcgccac tggcagcagc     2460
cactggtaac aggattagca gagcgaggta tgtaggcggt gctacagagt tcttgaagtg     2520
gtggcctaac tacggctaca ctagaaggac agtatttggt atctgcgctc tgctgaagcc     2580
agttaccttc ggaaaaagag ttggtagctc ttgatccggc aaacaaacca ccgctggtag     2640
```

```
cggtggtttt tttgtttgca agcagcagat tacgcgcaga aaaaaaggat ctcaagaaga   2700
tcctttgatc ttttctacgg ggtctgacgc tcagtggaac gaaaactcac gttaagggat   2760
tttggtcatg agattatcaa aaaggatctt cacctagatc cttttaaatt aaaaatgaag   2820
ttttaaatca atctaaagta tatatgagta aacttggtct gacagttacc aatgcttaat   2880
cagtgaggca cctatctcag cgatctgtct atttcgttca tccatagttg cctgactccc   2940
cgtcgtgtag ataactacga tacgggaggg cttaccatct ggccccagtg ctgcaatgat   3000
accgcgagac ccacgctcac cggctccaga tttatcagca ataaaccagc cagccggaag   3060
ggccgagcgc agaagtggtc ctgcaacttt atccgcctcc atccagtcta ttaattgttg   3120
ccgggaagct agagtaagta gttcgccagt taatagtttg cgcaacgttg ttgccattgc   3180
tacaggcatc gtggtgtcac gctcgtcgtt tggtatggct tcattcagct ccggttccca   3240
acgatcaagg cgagttacat gatccccat gttgtgcaaa aaagcggtta gctccttcgg   3300
tcctccgatc gttgtcagaa gtaagttggc cgcagtgtta tcactcatgg ttatggcagc   3360
actgcataat tctcttactg tcatgccatc cgtaagatgc ttttctgtga ctggtgagta   3420
ctcaaccaag tcattctgag aatagtgtat gcggcgaccg agttgctctt gcccggcgtc   3480
aatacgggat aataccgcgc cacatagcag aactttaaaa gtgctcatca ttggaaaacg   3540
ttcttcgggg cgaaaactct caaggatctt accgctgttg agatccagtt cgatgtaacc   3600
cactcgtgca cccaactgat cttcagcatc ttttactttc accagcgttt ctgggtgagc   3660
aaaaacagga aggcaaaatg ccgcaaaaaa gggaataagg gcgacacgga aatgttgaat   3720
actcatactc ttcctttttc aatattattg aagcatttat cagggttatt gtctcatgag   3780
cggatacata tttgaatgta tttagaaaaa taaacaaata ggggttccgc gcacatttcc   3840
ccgaaaagtg ccacctgacg tctaagaaac cattattatc atgacattaa cctataaaaa   3900
taggcgtatc acgaggccct ttcgtctcgc gcgtttcggt gatgacggtg aaaacctctg   3960
acacatgcag ctcccggaga cggtcacagc ttgtctgtaa gcggatgccg ggagcagaca   4020
agcccgtcag ggcgcgtcag cgggtgttgg cgggtgtcgg ggctggctta actatgcggc   4080
atcagagcag attgtactga gagtgcacca tatgcggtgt gaaataccgc acagatgcgt   4140
aaggagaaaa taccgcatca ggcgccattc gccattcagg ctgcgcaact gttgggaagg   4200
gcgatcggtg cgggcctctt cgctattacg ccagctggcg aaagggggat gtgctgcaag   4260
gcgattaagt tgggtaacgc cagggttttc ccagtcacga cgttgtaaaa cgacggccag   4320
tgaattcgac gtaactataa cggtcctaag gtagcgaatt tttccattgg ccccctccct   4380
tttggctctg ggtatttagc ttccctccca cttctcattc cactttctcc acctgcacct   4440
tttccatctc ctctccaact cgccgccatg agacccgagg gagtttcgcg gggccgcgcc   4500
tcctctgtct ccatctccaa ctagtgtcga cctctatttg aggacccgcc gagtacccca   4560
caagagtatg taaaaagctg tcattctcaa ctactgagaa taatatcaaa gctaaagata   4620
aaccctgagg agtttccacg ggaaccagag tctaggctcg tgcgcggata catcgaatac   4680
gccagcctag agcgtaagcc acatacgcgc tatccttgct tccagcgcgt gaacctacac   4740
attgacgggg aattttgat ccataaatg ctagcgttca atgctgcgat gcgcccatcc   4800
gcagaagagt tgttgtccta cccaatgttt atgaatctgt aggatgacta acagatttgg   4860
ggtggagacg cgctgggcga tactgtataa agttgtacta cttaccagcc cagtcagtgt   4920
gctgtagtgc caccacctgt aaagctgtga taagctgcag ttgcggccgc cgggtac     4977
```

<210> SEQ ID NO 25
<211> LENGTH: 6678
<212> TYPE: DNA
<213> ORGANISM: Artificial Sequence
<220> FEATURE:
<223> OTHER INFORMATION: Nucleotide sequence of transfer plasmid
     pU1-3-p430-H1av-BGHKBGH

<400> SEQUENCE: 25

| | | | | | |
|---|---|---|---|---|---|
| cctgtgcctt | ctagttgcca | gccatctgtt | gtttgcccct | ccccgtgcc | ttccttgacc | 60 |
| ctggaaggtg | ccactcccac | tgtcctttcc | taataaaatg | aggaaattgc | atcgcattgt | 120 |
| ctgagtaggt | gtcattctat | tctgggggt | ggggtgggc | aggacagcaa | ggggaggat | 180 |
| tgggaagaca | atagcaggca | tgctggggat | gcggtgggct | ctatggatcc | tagggataac | 240 |
| agggtaatcg | atttattcaa | caaagccacg | ttgtgtctca | aaatctctga | tgttacattg | 300 |
| cacaagataa | aaatatatca | tcatgaacaa | taaaactgtc | tgcttacata | aacagtaata | 360 |
| caaggggtgt | tatgagccat | attcaacggg | aaacgtcttg | ctcgaggccg | cgattaaatt | 420 |
| ccaacatgga | tgctgattta | tatgggtata | aatgggctcg | cgataatgtc | gggcaatcag | 480 |
| gtgcgacaat | ctatcgattg | tatgggaagc | ccgatgcgcc | agagttgttt | ctgaaacatg | 540 |
| gcaaaggtag | cgttgccaat | gatgttacag | atgagatggt | cagactaaac | tggctgacgg | 600 |
| aatttatgcc | tcttccgacc | atcaagcatt | ttatccgtac | tcctgatgat | gcatggttac | 660 |
| tcaccactgc | gatccccggg | aaaacagcat | tccaggtatt | agaagaatat | cctgattcag | 720 |
| gtgaaaatat | tgttgatgcg | ctggcagtgt | tcctgcgccg | gttgcattcg | attcctgttt | 780 |
| gtaattgtcc | ttttaacagc | gatcgcgtat | tcgtctcgc | tcaggcgcaa | tcacgaatga | 840 |
| ataacggttt | ggttgatgcg | agtgattttg | atgacgagcg | taatggctgg | cctgttgaac | 900 |
| aagtctggaa | agaaatgcat | aagcttttgc | cattctcacc | ggattcagtc | gtcactcatg | 960 |
| gtgatttctc | acttgataac | cttatttttg | acgaggggaa | attaataggt | tgtattgatg | 1020 |
| ttggacgagt | cggaatcgca | gaccgatacc | aggatcttgc | catcctatgg | aactgcctcg | 1080 |
| gtgagttttc | tccttcatta | cagaaacggc | ttttttcaaaa | atatggtatt | gataatcctg | 1140 |
| atatgaataa | attgcagttt | catttgatgc | tcgatgagtt | tttctaacca | tggctgtgcc | 1200 |
| ttctagttgc | cagccatctg | ttgttttgccc | ctccccgtg | ccttccttga | ccctggaagg | 1260 |
| tgccactccc | actgtccttt | cctaataaaa | tgaggaaatt | gcatcgcatt | gtctgagtag | 1320 |
| gtgtcattct | attctggggg | gtggggtggg | gcaggacagc | aagggggagg | attgggaaga | 1380 |
| caatagcagg | catgctgggg | atgcggtggg | ctctatggat | ccgacccctcc | ccggggctaa | 1440 |
| aaagctgcgt | cttcacgccc | gaggcgctta | ttgcccactg | ggtacggggc | gcgcttttat | 1500 |
| atgtgtaacg | tcccaccggt | gtgacgcacg | tactacggtt | gttctaaata | gctgtccccg | 1560 |
| tgattgcctc | ggctgcacac | atcgcctagg | tttccgccgt | gcctggtgtc | gagggcccac | 1620 |
| ccctgtaacc | aacatcgatg | ggggcctgct | gctccttcgc | tacctaggga | ccgttatagt | 1680 |
| tacgtcaagc | ttggcgtaat | catggtcata | gctgtttcct | gtgtgaaatt | gttatccgct | 1740 |
| cacaattcca | cacaacatac | gagccggaag | cataaagtgt | aaagcctggg | gtgcctaatg | 1800 |
| agtgagctaa | ctcacattaa | ttgcgttgcg | ctcactgccc | gctttccagt | cgggaaacct | 1860 |
| gtcgtgccag | ctgcattaat | gaatcggcca | acgcgcgggg | agaggcggtt | tgcgtattgg | 1920 |
| gcgctcttcc | gcttcctcgc | tcactgactc | gctgcgctcg | gtcgttcggc | tgcggcgagc | 1980 |
| ggtatcagct | cactcaaagg | cggtaatacg | gttatccaca | gaatcagggg | ataacgcagg | 2040 |

```
aaagaacatg tgagcaaaag gccagcaaaa ggccaggaac cgtaaaaagg ccgcgttgct    2100 ggcgttttc cataggctcc gccccctga cgagcatcac aaaaatcgac gctcaagtca      2160
gaggtggcga aacccgacag gactataaag ataccaggcg tttccccctg gaagctccct    2220
cgtgcgctct cctgttccga ccctgccgct taccggatac ctgtccgcct ttctcccttc    2280
gggaagcgtg gcgctttctc atagctcacg ctgtaggtat ctcagttcgg tgtaggtcgt    2340
tcgctccaag ctgggctgtg tgcacgaacc ccccgttcag cccgaccgct gcgccttatc    2400
cggtaactat cgtcttgagt ccaacccggt aagacacgac ttatcgccac tggcagcagc    2460
cactggtaac aggattagca gagcgaggta tgtaggcggt gctacagagt tcttgaagtg    2520
gtggcctaac tacggctaca ctagaaggac agtatttggt atctgcgctc tgctgaagcc    2580
agttaccttc ggaaaaagag ttggtagctc ttgatccggc aaacaaacca ccgctggtag    2640
cggtggtttt tttgtttgca agcagcagat tacgcgcaga aaaaaaggat ctcaagaaga    2700
tcctttgatc ttttctacgg ggtctgacgc tcagtggaac gaaaactcac gttaagggat    2760
tttggtcatg agattatcaa aaaggatctt cacctagatc cttttaaatt aaaaatgaag    2820
ttttaaatca atctaaagta tatatgagta aacttggtct gacagttacc aatgcttaat    2880
cagtgaggca cctatctcag cgatctgtct atttcgttca tccatagttg cctgactccc    2940
cgtcgtgtag ataactacga tacgggaggg cttaccatct ggccccagtg ctgcaatgat    3000
accgcgagac ccacgctcac cggctccaga tttatcagca ataaaccagc cagccggaag    3060
ggccgagcgc agaagtggtc ctgcaacttt atccgcctcc atccagtcta ttaattgttg    3120
ccgggaagct agagtaagta gttcgccagt taatagtttg cgcaacgttg ttgccattgc    3180
tacaggcatc gtggtgtcac gctcgtcgtt tggtatggct tcattcagct ccggttccca    3240
acgatcaagg cgagttacat gatccccat gttgtgcaaa aaagcggtta gctccttcgg     3300
tcctccgatc gttgtcagaa gtaagttggc cgcagtgtta tcactcatgg ttatggcagc    3360
actgcataat tctcttactg tcatgccatc cgtaagatgc ttttctgtga ctggtgagta    3420
ctcaaccaag tcattctgag aatagtgtat gcggcgaccg agttgctctt gcccggcgtc    3480
aatacgggat aataccgcgc cacatagcag aactttaaaa gtgctcatca ttggaaaacg    3540
ttcttcgggg cgaaaactct caaggatctt accgctgttg agatccagtt cgatgtaacc    3600
cactcgtgca cccaactgat cttcagcatc ttttactttc accagcgttt ctgggtgagc    3660
aaaaacagga aggcaaaatg ccgcaaaaaa gggaataagg gcgacacgga aatgttgaat    3720
actcatactc ttccttttc aatattattg aagcatttat cagggttatt gtctcatgag     3780
cggatacata tttgaatgta tttagaaaaa taaacaaata ggggttccgc gcacatttcc    3840
ccgaaaagtg ccacctgacg tctaagaaac cattattatc atgacattaa cctataaaaa    3900
taggcgtatc acgaggccct ttcgtctcgc gcgtttcggt gatgacggtg aaaacctctg    3960
acacatgcag ctcccggaga cggtcacagc ttgtctgtaa gcggatgccg ggagcagaca    4020
agcccgtcag ggcgcgtcag cgggtgttgg cgggtgtcgg ggctggctta actatgcggc    4080
atcagagcag attgtactga gagtgcacca tatgcggtgt gaaataccgc acagatgcgt    4140
aaggagaaaa taccgcatca ggcgccattc gccattcagg ctgcgcaact gttgggaagg    4200
gcgatcggtg cgggcctctt cgctattacg ccagctggcg aaagggggat gtgctgcaag    4260
gcgattaagt tgggtaacgc cagggttttc ccagtcacga cgttgtaaaa cgacggccag    4320
tgaattcgac gtaactataa cggtcctaag gtagcgaatt tttccattgg gcccctccct    4380
tttggctctg ggtatttagc ttccctccca cttctcattc cactttctcc acctgcacct    4440
```

```
tttccatctc ctctccaact cgccgccatg agacccgagg gagtttcgcg gggccgcgcc      4500
tcctctgtct ccatctccaa ctagtgtcga cctctatttg aggacccgcc gagtacccca      4560
caagagtatg taaaaagctg tcattctcaa ctactgagaa taatatcaaa gctaaagata      4620
aaccctgagg agtttccacg ggaaccagag tctaggctcg tgcgcggata catcgaatac      4680
gccagcctag agcgtaagcc acatacgcgc tatccttgct tccagcgcgt gaacctacac      4740
attgacgggg aattttttgat ccataaaatg ctagcgttca atgctgcgat gcgcccatcc     4800
gcagaagagt tgttgtccta cccaatgttt atgaatctgt aggatgacta acagatttgg      4860
ggtggagacg gcgtgggcga tactgtataa agttgtacta cttaccagcc cagtcagtgt      4920
gctgtagtgc caccacctgt aaagctgtga taagctgcag ttgcggccgc cgatggaggc      4980
aaaattgttc gtgctgttct gcgccttcac tgctctgaag gcagacacca tctgcgtggg      5040
ttaccacgcc aataattcca ccgacacggt ggataccatc ctggagaaga acgtgaccgt      5100
gactcattcc gtgaacctct ggagaactc acacaatggt aaattgtgca gccttaacgg       5160 caaagcccg ctgcaattgg ggaattgtaa cgtggccgga tggatactgg ggaaccccga       5220
gtgcgacctt ctcctgaccg ccaacagttg gtcctacatc attgagacga gcaacagcaa      5280
gaatggcgcc tgctatcctg gggagttcgc tgactacgag gagctgcgcg agcagttgtc      5340
tacagtcagc agcttcgaaa gattcgagat cttcccaaag gccactagct ggcccaacca      5400
cgatactacc aagggcacta cagtgagttg cagccacagc ggtgccaata gcttctaccg      5460
caacctgctg tggatcgtga agaagggtaa cagctacccc aagctgagca atcttacac      5520 aaacaacaaa ggcaaagagg tgttggttat ctggggcgtg catcatcccc caaccgactc      5580
cgatcagcaa accctgtacc agaacaacca cacctacgtg agcgtcggta gctctaagta      5640
ttaccagcgc ttcaccccg aaatcgtcgc acgaccgaag gtgagagggc aggccgggag      5700
aatgaactac tactgacccc tgctggatca aggcgacact attaccttcg aggctaccgg      5760
caacttgatc gccccgtggc acgcgttcgc cctcaataaa ggatctaata gcggcataat      5820
gatgagtgat gcccacgtgc ataactgcac cacgaagtgc cagaccctc acggcgcact      5880 gaaaagcaat ctgcccttc agaatgtgca ccccatcacc atcggcgagt gcccaagta     5940 tgttaaaagc actcagctcc gcatggccac cggactgcgc aacatcccga gcatccaatc      6000
ccgcggactg ttcggcgcaa tcgcgggctt tatagagggc ggctgaccg gcatgatcga      6060 cggctggtac ggctaccacc atcaaaatga gcaaggttcc ggctacgccg cagaccagaa      6120
gagcacccaa atagcaatcg atggcatctc caacaaggtg aacagcgtga tcgaaaagat      6180
gaacatccag ttcacaagcg tggggaagga gttcaataac ctggaaaagc gcatcgagaa      6240
tctgaacaag aaggttgacg atgggttcct cgatgtctgg acctataacg ccgagctcct      6300
gatactgctt gagaacgagc gcaccctgga cttccacgac ttcaacgtga aaaacctgta      6360
cgaaaaggtc aagtcacagt tgcgaaacaa tgcgaaggag ataggcaacg gctgcttcga      6420
gttctatcac aagtgtgaca acgagtgcat ggagagcgtc aagaacggca cttacaacta      6480
cccgcgctac tctgaggaga gtaagctcaa ccgcgaagag attgacggcg tgaaactgga      6540
aagcgttggt gtccatcaga tcctggccat ctacagcacc gtggctagct ctctggttct      6600
gttggtgagc ctgggcgcta aagctttttg gatgtgttct aatgggagcc tgcagtgccg      6660
catctgcatc tgaggtac                                                    6678
```

<210> SEQ ID NO 26

```
<211> LENGTH: 566
<212> TYPE: PRT
<213> ORGANISM: Influenza A virus

<400> SEQUENCE: 26

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Thr Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Lys Ala Gly Ser Gly Ile Ile Ile Ser Asp Thr Pro
        275                 280                 285

Val His Asp Cys Asn Thr Thr Cys Gln Thr Pro Lys Gly Ala Ile Asn
290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
370                 375                 380

Thr Gln Asn Ala Ile Asp Glu Ile Thr Asn Lys Val Asn Ser Val Ile
```

```
385                 390                 395                 400
Glu Lys Met Asn Thr Gln Phe Thr Ala Val Gly Lys Glu Phe Asn His
                405                 410                 415
Leu Glu Lys Arg Ile Glu Asn Leu Asn Lys Lys Val Asp Asp Gly Phe
                420                 425                 430
Leu Asp Ile Trp Thr Tyr Asn Ala Glu Leu Leu Val Leu Leu Glu Asn
                435                 440                 445
Glu Arg Thr Leu Asp Tyr His Asp Ser Asn Val Lys Asn Leu Tyr Glu
            450                 455                 460
Lys Val Arg Ser Gln Leu Lys Asn Asn Ala Lys Glu Ile Gly Asn Gly
465                 470                 475                 480
Cys Phe Glu Phe Tyr His Lys Cys Asp Asn Thr Cys Met Glu Ser Val
                485                 490                 495
Lys Asn Gly Thr Tyr Asp Tyr Pro Lys Tyr Ser Glu Glu Ala Lys Leu
                500                 505                 510
Asn Arg Glu Glu Ile Asp Gly Val Lys Leu Glu Ser Thr Arg Ile Tyr
            515                 520                 525
Gln Ile Leu Ala Ile Tyr Ser Thr Val Ala Ser Ser Leu Val Leu Ile
            530                 535                 540
Val Ser Leu Gly Ala Ile Ser Phe Trp Met Cys Ser Asn Gly Ser Leu
545                 550                 555                 560
Gln Cys Arg Ile Cys Ile
                565

<210> SEQ ID NO 27
<211> LENGTH: 566
<212> TYPE: PRT
<213> ORGANISM: Influenza A virus

<400> SEQUENCE: 27

Met Lys Thr Val Ile Ala Leu Ser Tyr Ile Phe Cys Leu Val Phe Gly
1               5                   10                  15
Gln Asp Leu Pro Gly Lys Gly Asn Asn Thr Ala Thr Leu Cys Leu Gly
                20                  25                  30
His His Ala Val Pro Asn Gly Thr Leu Val Lys Thr Ile Thr Asp Asp
            35                  40                  45
Gln Ile Glu Val Thr Asn Ala Thr Glu Leu Val Gln Asn Phe Ser Met
        50                  55                  60
Gly Lys Ile Cys Asn Asn Pro His Arg Ile Leu Asp Gly Ala Asn Cys
65                  70                  75                  80
Thr Leu Ile Asp Ser Leu Leu Gly Asp Pro His Cys Asp Gly Phe Gln
                85                  90                  95
Asn Glu Lys Trp Asp Leu Phe Ile Glu Arg Ser Lys Ala Phe Ser Asn
                100                 105                 110
Cys Tyr Pro Tyr Asp Val Pro Glu Tyr Thr Ser Leu Arg Ser Leu Ile
            115                 120                 125
Ala Ser Ser Gly Thr Leu Glu Phe Thr Asn Glu Asn Phe Asn Trp Thr
        130                 135                 140
Gly Val Thr Gln Asn Gly Gly Ser Ser Ala Cys Lys Arg Gly Pro Asn
145                 150                 155                 160
Asn Ser Phe Phe Ser Lys Leu Asn Trp Leu Tyr Lys Ser Gly Asn Thr
                165                 170                 175
Tyr Pro Met Leu Asn Val Thr Met Pro Asn Ser Asp Asp Phe Asp Lys
                180                 185                 190
```

Leu Tyr Ile Trp Gly Val His His Pro Ser Thr Asp Arg Glu Gln Ile
195                 200                 205

Asn Leu Tyr Val Gln Ala Ser Gly Lys Ile Ile Val Ser Thr Lys Arg
210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
            245                 250                 255

Asp Ile Leu Ile Ile Asn Ser Asn Gly Asn Leu Ile Ala Pro Arg Gly
            260                 265                 270

Tyr Phe Lys Met Gln Thr Gly Lys Ser Ser Val Met Arg Ser Asp Ala
            275                 280                 285

Pro Ile Asp Thr Cys Asn Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Lys Tyr Ile Lys Gln Asn Thr Leu Lys Leu Ala Thr Gly Met
            325                 330                 335

Arg Asn Ile Pro Glu Arg Gln Thr Arg Gly Ile Phe Gly Ala Ile Ala
            340                 345                 350

Gly Phe Ile Glu Asn Gly Trp Glu Gly Met Val Asn Gly Trp Tyr Gly
            355                 360                 365

Phe Arg His Gln Asn Ser Glu Gly Ile Gly Gln Ala Ala Asp Leu Lys
            370                 375                 380

Ser Thr Gln Ala Ala Ile Asn Gln Ile Asn Gly Lys Leu Asn Arg Val
385                 390                 395                 400

Ile Glu Lys Thr Asn Glu Lys Phe His Gln Ile Glu Lys Glu Phe Ser
            405                 410                 415

Glu Val Glu Gly Arg Ile Gln Asp Leu Glu Arg Tyr Val Glu Asp Thr
            420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ser Cys Met Glu Ser
            485                 490                 495

Ile Arg Asn Gly Thr Tyr Asp His Asn Glu Tyr Arg Asp Glu Ala Val
            500                 505                 510

Asn Asn Arg Phe Gln Ile Lys Ser Val Glu Leu Lys Ser Gly Tyr Lys
            515                 520                 525

Asp Trp Ile Leu Trp Ile Ser Phe Ala Ile Ser Cys Phe Leu Leu Cys
            530                 535                 540

Ala Val Trp Leu Gly Phe Ile Met Trp Ala Cys Gln Lys Gly Asn Ile
545                 550                 555                 560

Arg Cys Asn Ile Cys Ile
            565

<210> SEQ ID NO 28
<211> LENGTH: 566
<212> TYPE: PRT
<213> ORGANISM: Influenza A virus

<400> SEQUENCE

-continued

```
Met Glu Ala Lys Leu Phe Val Leu Phe Cys Ala Phe Thr Ala Leu Lys
1               5                   10                  15

Ala Asp Thr Ile Cys Val Gly Tyr His Ala Asn Asn Ser Thr Asp Thr
            20                  25                  30

Val Asp Thr Ile Leu Glu Lys Asn Val Thr Val Thr His Ser Val Asn
            35                  40                  45

Leu Leu Glu Asn Ser His Asn Gly Lys Leu Cys Ser Leu Asn Gly Lys
50                  55                  60

Ala Pro Leu Gln Leu Gly Asn Cys Asn Val Ala Gly Trp Ile Leu Gly
65                  70                  75                  80

Asn Pro Glu Cys Asp Leu Leu Leu Thr Ala Asn Ser Trp Ser Tyr Ile
                85                  90                  95

Ile Glu Thr Ser Asn Ser Lys Asn Gly Ala Cys Tyr Pro Gly Glu Phe
                100                 105                 110

Ala Asp Tyr Glu Glu Leu Arg Glu Gln Leu Ser Thr Val Ser Ser Phe
            115                 120                 125

Glu Arg Phe Glu Ile Phe Pro Lys Ala Thr Ser Trp Pro Asn His Asp
130                 135                 140

Thr Thr Lys Gly Thr Thr Val Ser Cys Ser His Ser Gly Ala Asn Ser
145                 150                 155                 160

Phe Tyr Arg Asn Leu Leu Trp Ile Val Lys Lys Gly Asn Ser Tyr Pro
                165                 170                 175

Lys Leu Ser Lys Ser Tyr Thr Asn Asn Lys Gly Lys Glu Val Leu Val
                180                 185                 190

Ile Trp Gly Val His His Pro Pro Thr Asp Ser Asp Gln Gln Thr Leu
                195                 200                 205

Tyr Gln Asn Asn His Thr Tyr Val Ser Val Gly Ser Ser Lys Tyr Tyr
210                 215                 220

Gln Arg Phe Thr Pro Glu Ile Val Ala Arg Pro Lys Val Arg Gly Gln
225                 230                 235                 240

Ala Gly Arg Met Asn Tyr Tyr Trp Thr Leu Leu Asp Gln Gly Asp Thr
                245                 250                 255

Ile Thr Phe Glu Ala Thr Gly Asn Leu Ile Ala Pro Trp His Ala Phe
                260                 265                 270

Ala Leu Asn Lys Gly Ser Asn Ser Gly Ile Met Met Ser Asp Ala His
            275                 280                 285

Val His Asn Cys Thr Thr Lys Cys Gln Thr Pro His Gly Ala Leu Lys
        290                 295                 300

Ser Asn Leu Pro Phe Gln Asn Val His Pro Ile Thr Ile Gly Glu Cys
305                 310                 315                 320

Pro Lys Tyr Val Lys Ser Thr Gln Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Ile Ala Ile Asp Gly Ile Ser Asn Lys Val Asn Ser Val Ile
385                 390                 395                 400

Glu Lys Met Asn Ile Gln Phe Thr Ser Val Gly Lys Glu Phe Asn Asn
                405                 410                 415
```

```
Leu Glu Lys Arg Ile Glu Asn Leu Asn Lys Lys Val Asp Asp Gly Phe
            420                 425                 430
Leu Asp Val Trp Thr Tyr Asn Ala Glu Leu Leu Ile Leu Leu Glu Asn
        435                 440                 445
Glu Arg Thr Leu Asp Phe His Asp Phe Asn Val Lys Asn Leu Tyr Glu
    450                 455                 460
Lys Val Lys Ser Gln Leu Arg Asn Asn Ala Lys Glu Ile Gly Asn Gly
465                 470                 475                 480
Cys Phe Glu Phe Tyr His Lys Cys Asp Asn Glu Cys Met Glu Ser Val
                485                 490                 495
Lys Asn Gly Thr Tyr Asn Tyr Pro Arg Tyr Ser Glu Glu Ser Lys Leu
            500                 505                 510
Asn Arg Glu Glu Ile Asp Gly Val Lys Leu Glu Ser Val Gly Val His
        515                 520                 525
Gln Ile Leu Ala Ile Tyr Ser Thr Val Ala Ser Ser Leu Val Leu Leu
    530                 535                 540
Val Ser Leu Gly Ala Ile Ser Phe Trp Met Cys Ser Asn Gly Ser Leu
545                 550                 555                 560
Gln Cys Arg Ile Cys Ile
                565

<210> SEQ ID NO 29
<211> LENGTH: 564
<212> TYPE: PRT
<213> ORGANISM: Influenza A virus

<400> SEQUENCE: 29

Met Lys Ala Lys Leu Leu Ile Leu Trp Cys Ala Leu Ser Ala Thr Asp
1               5                  10                  15
Ala Asp Thr Ile Cys Ile Gly Tyr His Ala Asn Asn Ser Thr Asp Thr
            20                  25                  30
Val Asp Thr Val Leu Glu Lys Asn Val Thr Val Thr His Ser Val Asn
        35                  40                  45
Leu Leu Glu Asp Asn His Asn Gly Lys Leu Cys Lys Leu Lys Gly Val
    50                  55                  60
Ala Pro Leu Gln Leu Gly Lys Cys Ser Ile Ala Gly Trp Ile Leu Gly
65                  70                  75                  80
Asn Pro Glu Cys Glu Ser Leu Phe Ser Lys Lys Ser Trp Ser Tyr Ile
                85                  90                  95
Ala Glu Thr Pro Asn Ala Glu Asn Gly Ile Cys Tyr Pro Gly Tyr Phe
            100                 105                 110
Ser Asp Tyr Glu Glu Leu Arg Glu Gln Leu Ser Ser Val Ser Ser Phe
        115                 120                 125
Glu Arg Phe Glu Ile Phe Pro Lys Glu Ser Ser Trp Pro Lys His Ser
    130                 135                 140
Ile Gly Ala Thr Ala Ser Cys Ser Lys Gln Gly Arg Ser Ser Phe Tyr
145                 150                 155                 160
Arg Asn Leu Leu Trp Leu Thr Glu Lys Asn Gly Ser Tyr Pro Asn Leu
                165                 170                 175
Ser Lys Ser Tyr Val Asn Asp Lys Glu Arg Glu Val Leu Val Leu Trp
            180                 185                 190
Gly Val His His Pro Ser Asn Ile Glu Asp Gln Arg Ala Ile Tyr Arg
        195                 200                 205
Lys Glu Thr Ala Tyr Val Ser Val Met Ser Ser Leu Tyr Asn Arg Arg
    210                 215                 220
```

```
Phe Thr Pro Glu Ile Ala Lys Arg Pro Lys Ile Arg Asn Gln Glu Gly
225                 230                 235                 240

Arg Ile Asn Tyr Tyr Trp Thr Leu Leu Glu Pro Lys Asp Thr Ile Ile
                245                 250                 255

Phe Glu Ala Asn Gly Asn Leu Ile Ala Pro Trp Tyr Ala Phe Ala Leu
            260                 265                 270

Ser Arg Gly Phe Glu Ser Gly Ile Ile Val Ser Asn Ala Ser Met Asp
            275                 280                 285

Glu Cys Asp Ala Lys Cys Gln Thr Pro Gln Gly Ala Ile Asn Ser Ser
        290                 295                 300

Leu Pro Phe Gln Asn Val His Pro Val Thr Ile Gly Glu Cys Pro Lys
305                 310                 315                 320

Tyr Val Lys Ser Thr Lys Leu Lys Met Ala Thr Gly Leu Arg Asn Ile
                325                 330                 335

Pro Ser Ile Gln Thr Arg Gly Leu Phe Gly Ala Ile Ala Gly Phe Ile
            340                 345                 350

Glu Gly Gly Trp Thr Gly Met Ile Asp Gly Trp Tyr Gly Tyr His His
            355                 360                 365

Gln Asn Glu Gln Gly Ser Gly Tyr Ala Ala Asp Gln Lys Ser Thr Gln
370                 375                 380

Asn Ala Ile Asn Gly Ile Thr Asn Lys Val Asn Ser Val Ile Asp Lys
385                 390                 395                 400

Met Asn Thr Gln Phe Thr Ala Val Gly Lys Glu Phe Asn Lys Leu Glu
                405                 410                 415

Lys Arg Met Glu Asn Leu Asn Lys Lys Val Asp Asp Gly Phe Leu Asp
            420                 425                 430

Ile Trp Thr Tyr Asn Ala Glu Leu Leu Val Leu Leu Glu Asn Glu Arg
            435                 440                 445

Thr Leu Asp Phe His Asp Ser Asn Val Lys Ser Leu Tyr Glu Lys Val
450                 455                 460

Lys Gly Gln Leu Lys Asn Asn Ala Lys Glu Ile Gly Asn Gly Cys Phe
465                 470                 475                 480

Glu Phe Tyr His Lys Cys Asn Asn Glu Cys Met Asp Ser Val Lys Asn
                485                 490                 495

Gly Thr Tyr Asp Tyr Pro Arg Tyr Ser Glu Glu Ser Lys Leu Asn Arg
            500                 505                 510

Glu Lys Ile Asp Gly Val Glu Leu Lys Ser Met Gly Val Tyr Gln Ile
            515                 520                 525

Leu Ala Ile Tyr Ser Thr Val Ala Ser Ser Leu Val Leu Leu Val Ser
            530                 535                 540

Leu Gly Ala Thr Ser Phe Trp Met Cys Ser Asn Gly Ser Leu Gln Cys
545                 550                 555                 560

Arg Ile Cys Ile

<210> SEQ ID NO 30
<211> LENGTH: 19
<212> TYPE: PRT
<213> ORGANISM: Artificial Sequence
<220> FEATURE:
<223> OTHER INFORMATION: GS linker

<400> SEQUENCE: 30

His Met Gly Gly Ser Gly Gly Gly Ser Gly Gly Gly Gly Ser Gly
1               5                   10                  15
```

Gly Gly Thr

<210> SEQ ID NO 31
<211> LENGTH: 947
<212> TYPE: DNA
<213> ORGANISM: Artificial Sequence
<220> FEATURE:
<223> OTHER INFORMATION: Synthesized DNA sequence of truncated
      glycoprotein c (Gc) including restriction sites for subcloning

<400> SEQUENCE: 31

| | | | | | |
|---|---|---|---|---|---|
| gcggccgcat | gaaggcgatc | ctggttgtgc | tgctgtacac | ctttgccacc | gccaacgccg | 60 |
| atacgctgat | caactgcaag | aacatccaga | gcacccagct | gacaatcgag | cacctgagca | 120 |
| agtgcatggc | cttctaccag | aacaagacca | gcagccccgt | cgtgatcaac | gagatcatct | 180 |
| ccgacgccag | cgtggacgaa | caggaactga | ttaagtctct | gaacctgaac | tgcaacgtga | 240 |
| tcgaccggtt | catcagcgag | tccagcgtga | tcgagacaca | ggtgtactac | gagtatatca | 300 |
| agagccagct | gtgtccactg | caagtgcacg | atatcttcac | catcaacagc | gccagcaaca | 360 |
| tccagtggaa | ggccctggcc | cgcagcttta | ccctgggcgt | gtgcaacacc | aaccccccaca | 420 |
| agcacatctg | ccggtgcctg | gaatccatgc | agatgtgtac | cagcaccaag | accgaccacg | 480 |
| ccagagagat | gagcatctac | tacgacggcc | accccgacag | attcgagcac | gacatgaaga | 540 |
| ttatcctgaa | atcatgcgg | tacatcgtgc | ccggcctggg | cagagtgctg | ctggaccaga | 600 |
| tcaagcagac | caaggactac | caggccctga | cacacatcca | gggcaagctg | agccccaagt | 660 |
| cccagagcaa | cctgcagctg | aagggcttcc | tggaattcgt | ggacttcatc | ctgggcgcca | 720 |
| acgtgaccat | tgagaaaacc | ccccagaccc | tgaccaccct | gagcctgatt | catatgggag | 780 |
| gttccggagg | tggaggttcc | ggaggtggag | gttccggagg | tggcaccata | ctggccattt | 840 |
| acagcacagt | tgcgagcagc | ctggtcctga | tcgtgagcct | gggtgctata | tcattctgga | 900 |
| tgtgcagcaa | cggctctctc | cagtgccgca | tctgtatctg | aggtacc | | 947 |

<210> SEQ ID NO 32
<211> LENGTH: 3060
<212> TYPE: DNA
<213> ORGANISM: Artificial Sequence
<220> FEATURE:
<223> OTHER INFORMATION: DNA fragment used for RED recombination to
      generate pRacH-SE-70-455-SBVGc,

<400> SEQUENCE: 32

| | | | | | |
|---|---|---|---|---|---|
| tctagactcg | agcgcaagcc | ctacacgcgc | taccctgct | ttcaacgcgt | caacctgcac | 60 |
| attgacgggg | agtttctggt | tcacaagatg | ctagcgttca | atgccgcgat | gcgcccatcg | 120 |
| gccgaggagc | tgctgtcata | cccaatgttt | gctcaacttt | aggatgacta | acctgttcct | 180 |
| gggaggagac | agcgtgggcg | acggtgtata | aagttggtct | gctttcaagc | cctgccactg | 240 |
| cgctacagtg | ccaccaactg | taaagcggta | gtaagctgca | gtggtcgact | ggtggtagca | 300 |
| tatactacct | tatttatacg | ctccgagctg | tttttcagca | tgctagcacc | caacgccgag | 360 |
| cgagagtata | taactcccat | cattgcccac | aagcttatgc | cacttattag | cgtccgctct | 420 |
| gccgtttgct | tagtcataat | atctaccgcc | gtttacgcag | cagacgctat | ctgcgacaca | 480 |
| attggatttg | cgataccgcg | catgtggatg | tgtattttaa | tgagatcaac | ctccatgaag | 540 |
| cgtaactagg | gggcctccca | ctgaggcact | accggcttag | cagctgacta | acacagtata | 600 |
| aaacgtgaga | agaaatcagt | ctcatgcgcc | attagcgcta | ggctagttag | cgtggaggac | 660 |
| cggagcgcta | ccgccagcag | tttcatccgc | ctggttacgg | gtttgttaac | acctaccggt | 720 |

| | |
|---|---|
| gttttaccgc taccatagga tccgatccat gggcggccgc atgaaggcga tcctggttgt | 780 |
| gctgctgtac acctttgcca ccgccaacgc cgatacgctg atcaactgca agaacatcca | 840 |
| gagcacccag ctgacaatcg agcacctgag caagtgcatg gccttctacc agaacaagac | 900 |
| cagcagcccc gtcgtgatca acgagatcat ctccgacgcc agcgtggacg aacaggaact | 960 |
| gattaagtct ctgaacctga actgcaacgt gatcgaccgg ttcatcagcg agtccagcgt | 1020 |
| gatcgagaca caggtgtact acgagtatat caagagccag ctgtgtccac tgcaagtgca | 1080 |
| cgatatcttc accatcaaca gcgccagcaa catccagtgg aaggccctgg cccgcagctt | 1140 |
| tacccctggg cgtgtgcaaca ccaacccccca caagcacatc tgccggtgcc tggaatccat | 1200 |
| gcagatgtgt accagcacca agaccgacca cgccagagag atgagcatct actacgacgg | 1260 |
| ccaccccgac agattcgagc acgacatgaa gattatcctg aatatcatgc ggtacatcgt | 1320 |
| gcccggcctg ggcagagtgc tgctggacca gatcaagcag accaaggact accaggccct | 1380 |
| gagacacatc cagggcaagc tgagcccaa gtcccagagc aacctgcagc tgaagggctt | 1440 |
| cctggaattc gtggacttca tcctgggcgc caacgtgacc attgagaaaa cccccagac | 1500 |
| cctgaccacc ctgagcctga ttcatatggg aggttccgga ggtggaggtt ccggaggtgg | 1560 |
| aggttccgga ggtggcacca tactggccat ttacagcaca gttgcgagca gcctggtcct | 1620 |
| gatcgtgagc ctgggtgcta tatcattctg gatgtgcagc aacggctctc tccagtgccg | 1680 |
| catctgtatc tgaggtacca ataaacgcgg tatgtctacc ttcaagccta tgatgaacgg | 1740 |
| atgtttggtg tttgcggcta ttataacgct cttgagtttt atgctatctc tgggaacatg | 1800 |
| cgaaaattac aggcgtgtgg ttcgggatcc tagggataac agggtaatcg atttattcaa | 1860 |
| caaagccacg ttgtgtctca aaatctctga tgttacattg cacaagataa aaatatatca | 1920 |
| tcatgaacaa taaaactgtc tgcttacata aacagtaata caagggggtgt tatgagccat | 1980 |
| attcaacggg aaacgtcttg ctcgaggccg cgattaaatt ccaacatgga tgctgattta | 2040 |
| tatgggtata atgggctcg cgataatgtc gggcaatcag gtgcgacaat ctatcgattg | 2100 |
| tatgggaagc ccgatgcgcc agagttgttt ctgaaacatg gcaaaggtag cgttgccaat | 2160 |
| gatgttacag atgagatggt cagactaaac tggctgacgg aatttatgcc tcttccgacc | 2220 |
| atcaagcatt ttatccgtac tcctgatgat gcatggttac tcaccactgc gatccccggg | 2280 |
| aaaacagcat tccaggtatt agaagaatat cctgattcag gtgaaaatat tgttgatgcg | 2340 |
| ctggcagtgt tcctgcgccg gttgcattcg attcctgttt gtaattgtcc ttttaacagc | 2400 |
| gatcgcgtat ttcgtctcgc tcaggcgcaa tcacgaatga ataacggttt ggttgatgcg | 2460 |
| agtgattttg atgacgagcg taatggctgg cctgttgaac aagtctggaa agaaatgcat | 2520 |
| aagcttttgc cattctcacc ggattcagtc gtcactcatg gtgatttctc acttgataac | 2580 |
| cttattttg acgaggggaa attaataggt tgtattgatg ttggacgagt cggaatcgca | 2640 |
| gaccgatacc aggatcttgc catcctatgg aactgcctcg gtgagttttc tccttcatta | 2700 |
| cagaaacggc ttttttcaaaa atatggtatt gataatcctg atatgaataa attgcagttt | 2760 |
| catttgatgc tcgatgagtt tttctaaaat aaacgcggta tgtctacctt caagcctatg | 2820 |
| atgaacggat gtttggtgtt tgcggctatt ataacgctct tgagttttat gctatctctg | 2880 |
| ggaacatgcg aaaattacag gcgtgtggtt cgggatccga ccctgttggt gggtgcggtt | 2940 |
| ggactcagaa tcttggcgca ggcatggaag tttgtcggtg acgaaacata cgacaccatc | 3000 |
| cgcgcagaag caaagaattt agagacccac gtaccctcaa gtgctgcaga gtcgtctaga | 3060 |

```
<210> SEQ ID NO 33
<211> LENGTH: 17
<212> TYPE: DNA
<213> ORGANISM: Artificial Sequence
<220> FEATURE:
<223> OTHER INFORMATION: primer

<400> SEQUENCE: 33
cgtgcgcgga tacatcg                                                  17

<210> SEQ ID NO 34
<211> LENGTH: 16
<212> TYPE: DNA
<213> ORGANISM: Artificial Sequence
<220> FEATURE:
<223> OTHER INFORMATION: primer

<400> SEQUENCE: 34
cgcttcgcag gtgggc                                                   16

<210> SEQ ID NO 35
<211> LENGTH: 19
<212> TYPE: DNA
<213> ORGANISM: Artificial Sequence
<220> FEATURE:
<223> OTHER INFORMATION: primer

<400> SEQUENCE: 35
gactggtggt agcatatac                                                19

<210> SEQ ID NO 36
<211> LENGTH: 19
<212> TYPE: DNA
<213> ORGANISM: Artificial Sequence
<220> FEATURE:
<223> OTHER INFORMATION: primer

<400> SEQUENCE: 36
gatcaacgag atcatctcc                                                19

<210> SEQ ID NO 37
<211> LENGTH: 17
<212> TYPE: DNA
<213> ORGANISM: Artificial Sequence
<220> FEATURE:
<223> OTHER INFORMATION: primer

<400> SEQUENCE: 37
ctggagagag ccgttgc                                                  17
```